United States Patent [19]
Dahlberg et al.

[11] Patent Number: 5,888,780
[45] Date of Patent: Mar. 30, 1999

[54] RAPID DETECTION AND IDENTIFICATION OF NUCLEIC ACID VARIANTS

[75] Inventors: James E. Dahlberg; Victor I. Lyamichev; Mary Ann D. Brow; Mary C. Oldenburg, all of Madison, Wis.

[73] Assignee: Third Wave Technologies, Inc., Madison, Wis.

[21] Appl. No.: 802,233

[22] Filed: Feb. 19, 1997

Related U.S. Application Data

[63] Continuation of Ser. No. 402,601, Mar. 9, 1995, abandoned, which is a continuation-in-part of Ser. No. 337,164, Nov. 9, 1994, abandoned, which is a continuation-in-part of Ser. No. 254,359, Jun. 6, 1994, Pat. No. 5,614,402, which is a continuation-in-part of Ser. No. 73,384, Jun. 4, 1993, Pat. No. 5,541,311, which is a continuation-in-part of Ser. No. 986,330, Dec. 7, 1992, Pat. No. 5,422,253.

[51] Int. Cl.$^6$ ................................................. C12P 19/34
[52] U.S. Cl. ....................... 435/91.53; 435/975; 435/199
[58] Field of Search ............................. 435/91.53, 6, 19, 435/199, 925

[56] References Cited

U.S. PATENT DOCUMENTS

| | | | |
|---|---|---|---|
| 4,511,502 | 4/1985 | Builder et al. ...................... | 260/112 R |
| 4,511,503 | 4/1985 | Olson et al. ........................ | 260/112 R |
| 4,512,922 | 4/1985 | Jones et al. ........................ | 260/112 R |
| 4,518,526 | 5/1985 | Olson ................................. | 260/112 R |
| 4,683,195 | 7/1987 | Mullis et al. ............................... | 435/6 |
| 4,683,202 | 7/1987 | Mullis ....................................... | 435/91 |
| 5,108,892 | 4/1992 | Burke et al. .............................. | 435/6 |
| 5,144,019 | 9/1992 | Rossi ........................................ | 536/27 |
| 5,210,015 | 5/1993 | Gelfand et al. ........................... | 435/6 |
| 5,382,510 | 1/1995 | Levine et al. ............................. | 435/6 |
| 5,422,253 | 6/1995 | Dahlberg et al. ........................ | 435/91 |
| 5,455,170 | 10/1995 | Abramson et al. ................... | 435/252.3 |

FOREIGN PATENT DOCUMENTS

| | | |
|---|---|---|
| 0 482 714 A1 | 4/1992 | European Pat. Off. . |
| WO 90/01609 | 2/1990 | WIPO .............................. C12Q 1/68 |
| WO 91/09950 | 7/1991 | WIPO . |
| WO 92/02638 | 2/1992 | WIPO . |
| WO 92/06200 | 4/1992 | WIPO . |

OTHER PUBLICATIONS

J. Marmur and D. Lane, "Strand Separation and Specific Recombination in Deoxyribonucleic Acids: Biological Studies," Proc. Natl. Acad. Sci. USA 46:453 (1960).
P. Doty et al., "Strand Separation and Specific Recombination in Deoxyribonucleic Acids: Physical Chemical Studies," Proc. Natl. Acad. Sci. USA 46:461 (1960).
M. Hayashi et al., "Restriction of In Vivo Genetic Transcription to One of the Complementary Strands of DNA," Proc. Natl. Acad. Sci. USA 50:664 (1963).
H. O. Smith and K. W. Wilcox, "A Restriction Enzyme from *Hemophilus influenza,*" J. Mol. Biol. 51:379 (1970).
E. M. Southern, "Detection of Specific Sequences Among DNA Fragments Separated by Gel Electrophoresis," J. Mol. Biol. 98:503 (1975).

R. B. Wallace et al., "Application of Synthetic Oligonucleotides to the Diagnosis of Human Genetic Diseases," Biochimie 67:755 (1985).
A. B. Studencki and R. B. Wallace, "Allele–Specific Hybridization Using Oligonucleotide Probes of Very High Specific Activity: Discrimination of the Human $\beta^A$–and $\beta^S$–Globin Genes," DNA 3:7 (1984).
A.B. Studencki et al., "Discrimination among the Human $\beta^A$, $\beta^S$, and $\beta^C$–Globin Genes Using Allele–Specific Oligonucleotide Hybridization Probes," Am. J. Human Genetics 37:42 (1985).
R.K. Saiki, *PCR Technology—Principles and Applications for DNA Amplification* (H.A. Erlich, Ed.), Stockton Press, New York, pp. 7–16 (1989).
P. M. Holland et al., "Detection of Specific Polymerase Chain Reaction Product by Utilizing the 5'–3' Exonuclease Activity of *Thermus aquaticus* DNA Polymerase," Proc. Natl. Acad. Sci. USA 88:7276 (1991).
R. B. Wallace et al., "Hybridization of Synthetic Oligodeoxyribonucleotides to $\Phi_x$ 174 DNA: the Effect of Single Base Pair Mismatch," Nucl. Acids Res. 6:3543 (1979).
R. B. Wallace et al., "The Use of Oligonucleotides as Hybridization Probes. II. Hybridization of Oligonucleotides of Mixed Sequence to Rabbit β–Globin DNA," Nucl. Acids Res. 9:879 (1981).
R. K. Saiki et al., "Analysis of Enzymatically Amplified β–Globin and HLA–DQα DNA with Allele–Specific Oligonucleotide Probes," Nature 324:163 (1986).
S. Kwok et al., "Effects of Primer–Template Mismatches on the Polymerase Chain Reaction: Human Immunodeficiency Virus Type 1 Model Studies," Nucl. Acids Res. 18:999 (1990).
A. Kornberg, *DNA Replication*, W.H. Freeman and Co., San Francisco, pp. 127–139 (1980).
K.R. Tindall and T.A. Kunkel, "Fidelity of DNA Synthesis by the *Thermus aquaticus* DNA Polymerase," Biochem. 27:6008 (1988).
D. Brutlag et al., "An Active Fragment of DNA Polymerase Produced by Proteolytic Cleavage," Biochem. Biophys. Res. Commun. 37:982 (1969).
H.A. Erlich et al., "Recent Advances in the Polymerase Chain Reaction," Science 252:1643 (1991).
P. Setlow and A. Kornberg, "Deoxyribonucleic Acid Polymerase: Two Distinct Enzymes in One Polypeptide—II. A Proteolytic Fragment Containing the 5'–3' Exonuclease Function. Restoration of Intact Enzyme Functions from the Two Proteolytic Fragments," J. Biol. Chem. 247:232 (1972).

(List continued on next page.)

*Primary Examiner*—Charles L. Patterson, Jr.
*Attorney, Agent, or Firm*—Medlen & Carroll, LLP

[57] ABSTRACT

The present invention relates to means for cleaving a nucleic acid cleavage structure in a site-specific manner. Enzymes, including 5' nucleases and 3' exonucleases, are used to screen for known and unknown mutations, including single base changes, in nucleic acids. Methods are provided which allow for the identification of genetic mutations and the identification bacterial and viral strains and species in a sample.

18 Claims, 80 Drawing Sheets

OTHER PUBLICATIONS

D.H. Gelfand, *PCR Technology—Principles and Applications for DNA Amplification* (H.A. Erlich, Ed.), Stockton Press, New York, p. 17 (1989).

F.C. Lawyer et al., "Isolation, Characterization, and Expression in *Escherichia coli* of the DNA Polymerase Gene from *Thermus aquaticus*," J. Biol. Chem. 264:6427 (1989).

A.A. Akhmetzjanov and V.A. Vakhitov, "Molecular Cloning and Nucleotide Sequence of the DNA Polymerase Gene from *Thermus flavus*," Nucl. Acids Res. 20:5839 (1992).

P. Setlow et al., "Deoxyribonucleic Acid Polymerase: Two Distinct Enzymes in One Polypeptide—I. A Proteolytic Fragment Containing the Polymerase and 3'–5' Exonuclease Functions," J. Biol. Chem. 247:224 (1972).

R.K. Saiki et al., "Primer–Directed Enzymatic Amplification of DNA with a Thermostable DNA Polymerase," Science 239:487 (1988).

K.B. Mullis and F.A. Faloona, "Specific Synthesis of DNA in Vitro via a Polymerase–Catalyzed Chain Reaction," *Methods in Enzymology* 155:335 (1987).

M. Bargseid et al., "A High Fidelity Thermostable DNA Polymerase Isolated from *Pyrococcus furiosus*," Strategies (Stratagene, LaJolla, CA) 4:34 (1991).

F.B. Perler et al., "Intervening Sequences in an Archaea DNA Polymerase Gene," Proc. Natl. Acad. Sci. USA 89:5577 (1992).

A.S. Kaledin et al., "Isolation and Properties of DNA Polymerase from the Extremely Thermophilic Bacterium *Thermus flavus*," Biokhimiya 46:1276 (1981).

N. Carballeira et al., "Purification of a Thermostable DNA Polymerase from *Thermus thermophilus* HB8, Useful in the Polymerase Chain Reaction," BioTechniques 9:276 (1990).

T.W. Myers and D.H. Gelfand, "Reverse Transcription and DNA Amplification by a *Thermus thermophilus* DNA Polymerase," Biochem. 30:7661 (1991).

J. Ito and D.K. Braithwaite, "Compilation and Alignment of DNA Polymerase Sequences," Nucl. Acids Res. 19:4045 (1991).

E.J. Mathur et al., "The DNA Polymerase Gene from the Hyperthermophilic Marine Archaebacterium, *Pyrococcus furiosus*, Shows Sequence Homology with α–like DNA Polymerases," Nucl. Acids. Res. 19:6952 (1991).

J.J. Dunn and F. W. Studier, "Complete Nucleotide Sequence of Bacteriophage T7 DNA and the Location of T7 Genetic Elements," J. Mol. Biol. 166:477 (1983).

V.P. Antao et al., "A Thermodynamic Study of Unusually Stable RNA and DNA Hairpins," Nucl. Acids Res. 19:5901 (1991).

M.J.R. Stark, "Multicopy Expression Vectors Carrying the lac Repressor Gene for Regulated High–Level Expression of Genes in *Escherichia coli*," Gene 5:255 (1987).

F.W. Studier and B.A. Moffatt, "Use of Bacteriophage T7 RNA Polymerase to Direct Selective High–level Expression of Cloned Genes," J. Mol. Biol. 189:113 (1986).

D.R. Englke et al., "Purification of *Thermus aquaticus* DNA Polymerase Expressed in *Escherichia coli*," Anal. Biochem 191:396 (1990).

C.G. Copley and C. Boot, "Exonuclease Cycling Assay: An Amplified Assay for the Detection of Specific DNA Sequences," BioTechniques 13:888 (1992).

M. Ortia et al., "Rapid and Simple Detection of Point Mutations and DNA Polymorphisms Using the Polymorphisms Using the Polymerase Chain Reaction," Genomics 5:874 (1989).

K. Hayaski, "PCR–SSCP: A Simple and Sensistive Method for Detection of Mutations in the Genomic DNA," PCR Meth. and Appl. 1:34 (1991).

R.B. Kelley, et al., "Excision of Thymine Dimers and Other Mismatched Sequences by DNA Polymerase of *Escherichia coli*," Nature 244:495 (1969).

A. Kornberg et al., "Enzymatic Synthesis of Deoxyribonucleic Acid, XVL Oligonucleotides as Templates and the Mechanism of Their Replication," Biochemistry 51:315 (1961).

A. Kornberg, "DNA Polymerase—A Perspective," The Enzymes, vol. XIV:3.

I.R. Lehman, "DNA Polymerase I of *Escherichia coli*," The Enzymes, vol. XIV:15.

P. Lopez et al., "Characterization of the polA Gene of *Streptococcus pneumoniae* and Comparison of the DNA Polymerase I It Encodes to Homologous Enzymes from *Escherichia coli* and Phage T7," J. Biol. Chem. 264:4255 (1989).

H.K. Schachman, et al., "Enzymatic Synthesis of Deoxyribonucleic Acid," J. Biol. Chem. 235:3242 (1960).

R.C. Lundquist, et al., "Transient Generation of Displaced Single–Stranded DNA During Nick Translation," Cell 31:53 (1982).

M.A. Innis, et al., "DNA Sequencing with *Thermus aquaticus* DNA Polymerase and Direct Sequencing of Polymerase Chain Reaction–Amplified DNA," Proc. Natl. Acad. Sci. USA 85:9436 (1988).

Perkin Elmer Cetus, Product Analysis: "AmpliTaq DNA Polymerase".

Promega, Product Analysis: "Taq DNA Polymerase", Certificate of Analysis.

M.J. Longley et al., "Characterization of the 5' to 3' Exonuclease Associated with *Thermus aquatics* DNA Polymerase," Nucl. Acids Res. 18:7317 (1990).

Y. Li, et al., "Targeted Cleavage of mRNA in vitro by RNase P from *Escherichia coli*," Proc. Natl. Acad. Sci. USA 89:3185 (1992).

A.J. Podhajska et al., "Conversion of the FokI Endonuclease to a Universal Restriction Enzyme: Cleavage of Phage M13mp7 DNA at Predetermined Sites," Gene 40:175 (1985).

R.H. Symons, "Small Catalytic RNAs," Annu. Rev. Biochem. 61:641 (1992).

D.M.J. Lilley, et al., "Cruciform–Resolvase Interactions in Supercoiled DNA," Cell 36:413 (1984).

S.A. Chow, et al., "Reversal of Integration and DNA Splicing Mediated by Integrase of Human Immunodeficiency Virus," Science 255:723 (1992).

F.C. Lawyer et al., "High–level Expression, Purification, and Enzymatic Characterization of Full–length *Thermus aquaticus* DNA Polymerase and a Truncated Form Deficient in 5' to 3' Exonuclease Activity," PCR Meth. and Appl. 2:275 (1993).

V. Lyamichev et al., "Structure–Specific Endonucleolytic Cleavage of Nucleic Acids by Eubacterial DNA Polymerases," Science 260:778 (1993).

D.R. Duckett et al., "The Structure of DNA Junctions and their Interaction with Enzymes," Eur. J. Biochem. 207:285 (1992).

T.R. Cech et al., "Secondary Structure of the Tetrahymena ribosomal RNA intervening sequence, Structural homology with fungal mitochondrial intervening sequences," *Proc. Natl. Acad. Sci. USA* 80:3903 (1983).

D.S. Sigman, "Chemical Nucleases," *Chemical Reviews* (1993) 93, 2295–2316.

C.R. Woese, "Detailed Analysis of the Higher Order Structure of 16S–LikeRibosomal Ribonucleic Acids," *Microbiology Reviews* 47:621 (1983).

R. Youil et al., "Screening for Mutations by Enzyme Mismatch Cleavage with T4 Endonuclease VII," *Proc. Natl. Acad. Sci. USA* (1995).

Hoheisel et al., "On The Activities of *Escherichia coli* Exonuclease III," *Anal. Biochem.* 209:238–246 (1993).

Tabor, S., et al., (1989) Proc. Natl. Acad. Sci., USA 86, 4076–4080.

Longley, M. J., et al. (1990) Nucl. Acids Res. 18 (24), 7317–7322.

Barany, "Genetic disease detection and DNA amplification using cloned thermostable ligase," *Proc. Natl. Acad. Sci.* 88:189 (1991).

Barany, F., "The Ligase Chain Reaction in a PCR World," *PCR Methods and Applic.* 1:5–16 (1991).

Wu and Wallace, "The Ligation Amplification Reaction (LAR)—Amplification of Specific DNA Sequences Using Sequential Rounds of Template–Dependent Ligation," *Genomics* 4:560 (1989).

Guatelli et al., "Isothermal, in vitro amplification of nucleic acids by a multienzyme reaction modeled after retroviral replication," *Proc. Natl. Acad. Sci.* 87:1874–1878 (1990).

Kwoh et al., "Transcription–based amplification system and detection of amplified human immunodeficiency virus type 1 with a bead–based sandwich hybridization format," *Proc. Natl. Acad. Sci.* 86:1173–1177 (1989).

Fahy et al., "Self–sustained Sequence Replication (3SR): An Isothermal Transcription–based Amplification System Alternative to PCR," *PCR Meth. Appl.* 1:25–33 (1991).

Landgren, "Molecular mechanisms of nucleic acid sequence amplification," *Trends in Genetics* 9:199 (1993).

Mullis, "The Polymerase Chain Reaction in an Anemic Mode: How to Avoid Cold Oligodeoxyribonuclear Fusion," *PCR Methods Applic.* 1:1 (1991).

Duck et al., "Probe Amplifier System Based on Chimeric Cycling Oligonucleotides," *BioTech.* 9:142 (1990).

Urdea et al., "A novel method for the rapid detection of specific nucleotide sequences in crude biological samples without blotting or radioactivity; application to the analysis of hepatitis B virus in human serum," *Gene* 61:253–264 (1987).

Gogos et al., "Detection of single base mismatches of thymine and cytosine residues by potassium permanganate and hydroxylamine in the presence of tetralkylammonium salts," *Nucl. Acids Res.*, 18:6807–6817 (1990).

Barlow and Lehrach, "Genetics by gel electrophoresis: the impact of pulsed field gel electrophoresis on mammalian genetics," *Trends Genet.* 3:167 (1987).

Perlman and Butow, "Mobile Introns and Intron–Encoded Proteins," *Science* 246:1106 (1989).

Conner et al., "Detection of sickle cell $\beta^S$–globin allele by hybridization with synthetic oligonucleotides," *Proc. Natl. Acad. Sci.*, 80:278–282 (1983).

Vogelstein et al., "Genetic Alterations During Colorectal–Tumor Development," *N. Eng. J. Med.*, 319:525–532 (1988).

Farr et al., "Analysis of RAS gene mutations in acute myeloid leukemia by polymerase chain reaction and oligonucleotide probes," *Proc. Natl. Acad. Sci.*, 85:1629–1633 (1988).

Lyons et al., "Two G Protein Oncogenes in Human Endocrine Tumors," *Science* 249:655–659 (1990).

Abrams et al., "Comprehensive Detection of Single Base Changes in Human Genomic DNA Using Denaturing Gradient Gel Electrophoresis and a GC Clamp," *Genomics* 7:463–475 (1990).

Sheffield et al., "Attachment of a 40–base–pair G+C–rich sequence (GC–clamp) to genomic DNA fragments by the polymerase chain reaction results in improved detection of single–base changes," *Proc. Natl. Acad. Sci.*, 86:232–236 (1989).

Lerman and Silverstein, "Computational Simulation of DNA Melting and Its Application to Denaturing Gradient Gel Electrophoresis," *Meth. Enzymol.*, 155:482–501 (1987).

Wartell et al., "Detecting base pair substitutions in DNA fragments by temperature–gradient gel electrophoresis," *Nucl. Acids Res.*, 18:2699–2701 (1990).

Smith et al., "Novel Method of Detecting Single Base Substitutions in RNA Molecules by Differential Melting Behavior in Solution," *Genomics* 3:217–223 (1988).

K. Hayashi, "PCR–SSCP: A Simple and Sensitive Method for Detection of Mutations in the Genomic DNA," *PCR Meth. Appl.*, 1:34–38, [1991].

M. Orita, et al., "Rapid and Simple Detection of Point Mutations and DNA Polymorphisms Using the Polymerase Chain Reaction," Genomics 5:874–879, [1989].

R. B. Wallace et al., "Application of Synthetic Oligonucleotides to the Diagnosis of Human Genetic Diseases," *Biochimie* 67:755 (1985).

A. B. Studencki and R. B. Wallace, "Allele–Specific Hybridization Using Oligonucleotide Probes of Very High Specific Activity: Discrimination of the Human $\beta^A$–and $\beta^S$–Globin Genes," *DNA* 3(1)(1984), pp. 7–15.

Harrington, J.J. and Lieber, "Functional domains within FEN–1 and RAD2 define a family of structure–specific endonucleases: implications for nucleotide excision repair," *Genes and Develop.* 8:1344 (1994).

Murante, R.S., et al., "The Calf 5'–to 3'–Exonuclease Is Also an Endonuclease with Both Activities Dependent on Primers Annealed Upstream of the Point of Cleavage," *J. Biol. Chem.* 269:1191 (1994).

J. Sambrook, et al., *Molecular Cloning,* Cold Spring Harbor Laboratory Press, Cold Spring Harbor, pp. 1.63–1.69 (1989).

King, R.A., et al., "Non–random Distribution of Missense Mutations Within the Human Tyrosinase Gene in Type 1 (Tyrosinase–related) Oculocutaneous Albinism," *Mol. Biol. Med.* 8:19 (1991).

Geibel, L.B., et al., "Organization and Nucleotide Sequences of the Human Tyrosinase Gene and a Truncated Tyrosinase–Related Segment," *Genomics* 9:435 (1991).

Spritz, R.A., "Molecular genetics of oculocutaneous albinism," *Human Molecular Genetics* 3:1469 (1994).

Giebel, L.B., et al., "A Tyrosinase Gene Missense Mutation in Temperature–sensitive Type 1 Oculocutaneous Albinism," J. Clin. Invest. 87:1119 (1991).

Bouchard, B., et al., "Induction of Pigmentation in Mouse Fibroblasts by Expression of Human Tyrosinase cDNA," *J. Exp. Med.* 169:2029 (1989).

Orkin, S.H. and Kazazian, H.H., Jr., "The Mutation and Polymorphism of the Human $\beta$–Globin Gene and its Surrounding DNA," *Annu. Rev. Genet.* 18:131 (1984).

Collins, F.S. and Weissman, S.M., *The Molecular Genetics of Human Hemoglobin, Prog. Nucleic Acid Res. Mol. Biol.* 31:315 (1984).

Lawn, R.M., et al., "The Nucleotide Sequence of the Human β–Globin Gene," *Cell* 21:647 (1980).

Orkin, S.H. and Goff, S.C., "Nonsense and Frameshift Mutations in β⁰–Thalassemia Detected in Cloned β–Globin Genes," *J. Biol. Chem.* 256:9782 (1981).

Goldsmith, M.E., et al., "'Silent' nucleotide substitution in a β⁺–thalassemia globin gene activates splice site in coding sequence RNA," *Proc. Natl. Acad. Sci. USA* 80:2318 (1983).

Giddings, M., et al., "An adaptive, object oriented strategy for base calling in DNA sequence analysis," *Nucl. Acids Res.* 21:4530 (1993).

Trivedi, P. et al., "Selective Amplification of Simian Immunodeficiency Virus Genotypes after Intrarectal Inoculation of Rhesus Monkeys," *Journal of Virology* 68:7649 (1994).

Nugent, M. et al., "Characterization of the Apurinic Endonuclease Activity of Drosophila Rrp1," *Biochemistry* 32:11445–11452 (1993).

Bardwell, A.J. et al., "Specific Cleavage of Model Recombination and Repair Intermediates by the Yeast Rad1–Rad10 DNA Endonuclease," *Science* 265:2082 (1994).

Orkin, S.H. et al., "Abnormal RNA processing due to the exon mutation of β$^E$–globin gene," *Nature* 300:768 (1982).

Spritz, R.A. et al., "Base substitution in an intervening sequence of a β⁺–thalassemic human globin gene," *Proc. Natl. Acad. Sci. USA* 78:2455 (1981).

A. Kornberg, et al., DNA Replication (2d ed.) W.H. Freeman and Co., San Francisco, pp. 403–414 (1992).

M. Orita et al., "Rapid and Simple Detection of Point Mutations and DNA Polymorphisms Using the Polymerase Chain Reaction," *Genomics* 5:874 (1989).

K. Hayaski, "PCR–SSCP: A Simple and Sensitive Method for Detection of Mutations in the Genomic DNA," *PCR Meth. and Appl.* 1:34 (1991).

A. Kornberg, "DNA Polymerases—A Perspective," *The Enzymes* vol. XIV:3 (1981).

I.R. Lehman, "DNA Polymerase I of *Escherichia coli*," *The Enzymes* vol. XIV:15 (1981).

P. Lopez et al., "Characterization of the polA Gene of *Steptococcus pneumoniae* and Comparison of the DNA Polymerase I It Encodes to Homologous Enzymes from *Escherichia coli* Phage T7," *J. Biol. Chem.* 264:4255 (1989).

Perkin Elmer Cetus, Product Analysis: "AmpliTaq DNA Polymerase" (1990).

Promega, Product Analysis: "Taq DNA Polymerase," Certificate of Analysis (No date given).

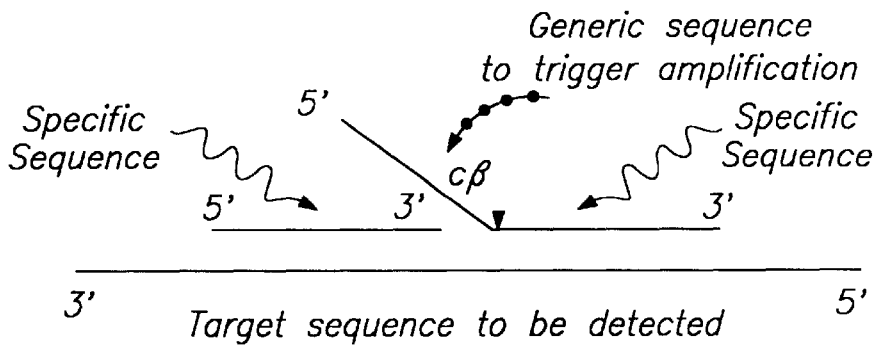
FIG. 1B PART ONE: TRIGGER REACTION
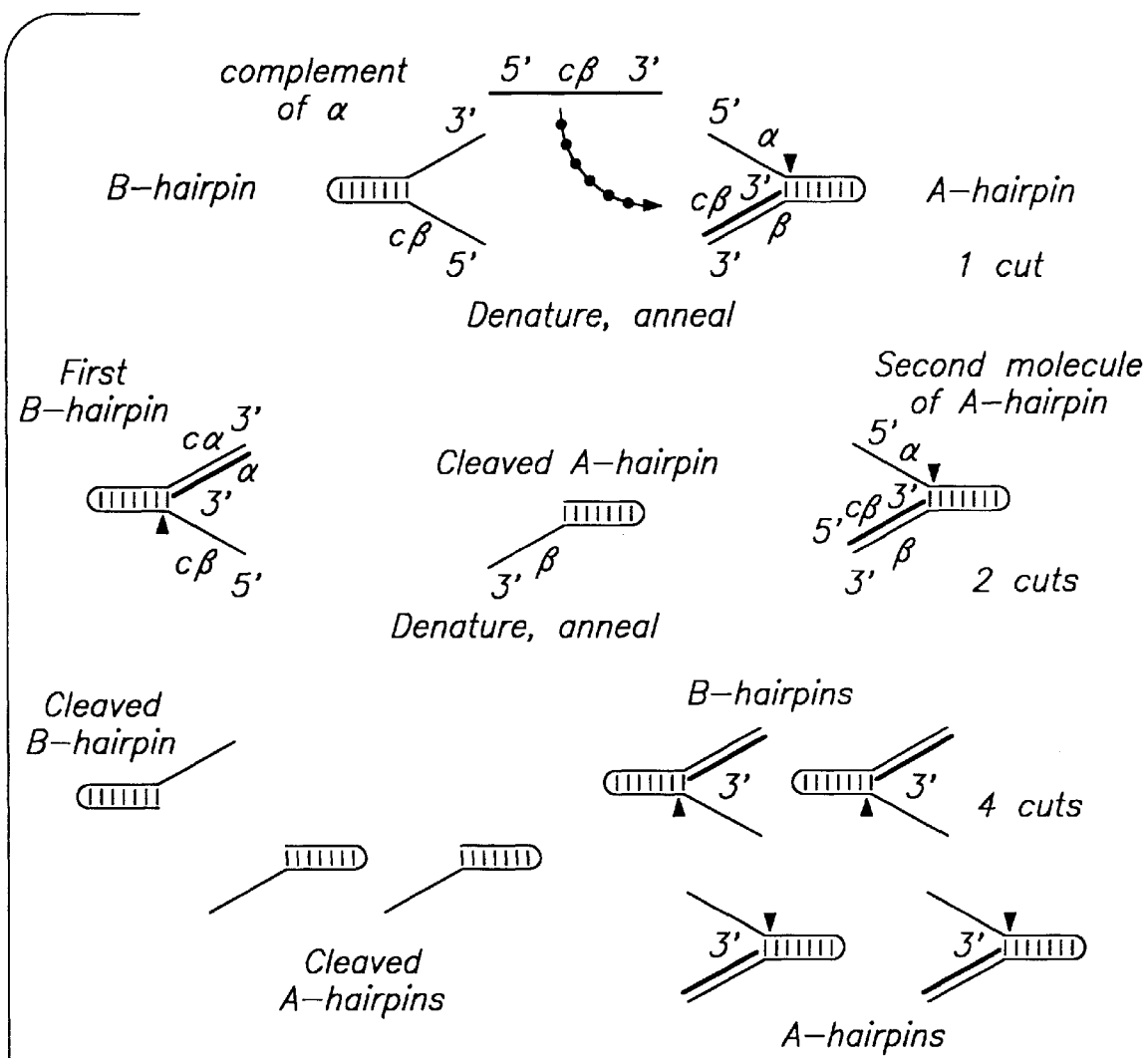
FIG. 1C PART TWO: DETECTION REACTION

```
MAJORITY [SEQ ID NO:7]  CGAGGGCGGACCACCTXCTGGCCACCCTGGCCAAGAAGGGCGAAAAGGAGGGGTACCGAGGTGCCGCATCCTC  417

DNAPTAQ  [SEQ ID NO:1]  ..........................C..........G.....................C...........  414
DNAPTFL  [SEQ ID NO:2]  T.........................G..........CG....................C...........
DNAPTTH  [SEQ ID NO:3]  ..........................T..C.......................................... 420

MAJORITY                ACCGCCGACCCGGACCCTCTACCAGCTCCTTTCCGACCCGCCATCGCCGTCCTCCACCCCGAGGGGTACCTCA  487

DNAPTAQ                 ....T.......AAA.....T.........................CA........................  484
DNAPTFL                 ..T...................................G..G...........A.........T........
DNAPTTH                 .....................A..G.C..............G..................CC.......... 490

MAJORITY                TCACCCCGGCGTGGCTTTGGGAGAAGTACGGGCCTGAGGCCGAGCAGTGGGTGGACTACCGGGCCCTGGC    557

DNAPTAQ                 ................C........A............................CC.............A.  554
DNAPTFL                 .................AC...............C.............C.C....................
DNAPTTH                 ................A........................................T...C.....C.T  560

MAJORITY                GGGGACCCCTCCGACAACCTCCCCGGGTCAAGGGCATCGGGGAGAAGACCCCCXGAAGCTCCTCXAG      627

DNAPTAQ                 C........GAG......T.........T...............................G..GAG....T..GG..   624
DNAPTFL                 .................G..T...A..................G...................A..G...A..CGC
DNAPTTH                 ...........A...................................................TC........A.. 630

MAJORITY                GAGTGGGGGAGCCTGGAAAAACCTCCTCAAGAACCTGGACCCGGGTGAAGCCCCC---CXTCGGGGAGAAGA  694

DNAPTAQ                 ..........................GC.................C.........A...........A..  691
DNAPTFL                 .....................................T.C.C...A.....T....A......T.G....C 700
DNAPTTH                 ...........A..............................A.....A.AAAA..A.AAAA.G.......
```

```
MAJORITY [SEQ ID NO:7]  GGAGATCCCGCCCCTCGAGGAGGAGGTCTTCCGCCTGGCCGGGCCACCCCTTCAACTCCCGGGAC   1464

DNAPTAQ [SEQ ID NO:1]   ..........GC.........CC.........................................   1461
DNAPTFL [SEQ ID NO:2]   ......G.G....AG..G...............................C..............   1470
DNAPTTH [SEQ ID NO:3]   .............................................T....G.............   1470

MAJORITY                CAGCTGGAAAGGGTGCTCTTTGACCAGCTXGGGCTTCCCGCCATCGGCAAGACGGAGAAGACXGGCAAGC   1534

DNAPTAQ                 ..................C..........A........................C.........   1531
DNAPTFL                 .................GC..........G.C..G..T..............G.G....A....   1540
DNAPTTH                 ..........................TA..........T.G..G......C.A.....A.....

MAJORITY                GCTCCACCAGCGGCGCGTGCTGGAGGCCCTXCCXGAGGCCCACCCCATCGTGGAGAAGATCCTGCAGTA   1604

DNAPTAQ                 ...............C.......C.C.......................................   1601
DNAPTFL                 ................T......G.A..................CCGC.................   1610
DNAPTTH                 ......G..........A.G..............................C.....C........

MAJORITY                CCGGGAGCTCACCAAGCTCAAGAACACCTACATXGACCCCCTGCCXGXCCTCGTCCACCCCAGGACGGGC   1674

DNAPTAQ                 ...............G........G....T...T......G.A....A.................   1677
DNAPTFL                 .................T........................C.C...G....A..C.......   1680
DNAPTTH                 ..................G...........C..AAG............G................

MAJORITY                CGCCTCCACACCCGCTTCAACCAGACAGGGCCACGGGCCAGGCTTAGTAGCTCCGACCCCAACCTGC   1744

DNAPTAQ                 ...............................................A........T......C.   1741
DNAPTFL                 ..G.............................C..............TCC...............   1750
DNAPTTH                 ...........................................G....................
```

```
MAJORITY [SEQ ID NO:7]   AGCTTCCCCAAGGTGCGGGCCTGGATTGAGAAGACCCTGGAGGAGGGCAGGAGGGGGGTACGTGGAGA   2164

DNAPTAQ  [SEQ ID NO:1]   ..........................................C.CC......T............    2161
DNAPTFL  [SEQ ID NO:2]   .........A...................GG......................G...A...C...    2161
DNAPTTH  [SEQ ID NO:3]   ..................................A..A...............G...A....A..   2170

MAJORITY                 CCCTCTTCGGCCCCCGGGCGCTACGTGCCCGACCTCAACGCCCCGGGTGAAGACCGTGCCGGAGCCCCGGA    2234

DNAPTAQ                  ..........................C..........A....AG.G......................    2231
DNAPTFL                  .....................T............................CA................    2231
DNAPTTH                  ...............AA.AA.................................C...............   2240

MAJORITY                 GCGCATGGCCTTCAACATGCCCGTCCAGGGCACCCCCGACCTCATGAAGCTGGCCATGGTGAAGCTC     2304

DNAPTAQ                  .....................................................T............    2301
DNAPTFL                  .......................G..............................................   2301
DNAPTTH                  ..................................G........................C..........  2310

MAJORITY                 TTCCCCCGGCTXCAGGAAATGGGGGCCAGGATGCTCCTXCAGGTCCACGACGAGCTGGTCCTCGAGCCCC     2374

DNAPTAQ                  ....A...GG......................T............TT.G.......CG...T......    2371
DNAPTFL                  .........T.....C..........G...........................CC.....G......    2371
DNAPTTH                  ......C.C.G..G..........C.C..........................C............    2380

MAJORITY                 CCAAAGAGGGCGGGAGGXGGTGCCCCTTTGCCCAAGGAGGTCATGGAGGGGTCTATCCCCTGGCCGT     2444

DNAPTAQ                  .A........A.............CC..CCGGC...........G.............G.....    2441
DNAPTFL                  ...G..C....AG..A........A...G............................GG....CAG....   2441
DNAPTTH                  ..C..C....C..............A......................AA..C................   2450
```

FIG. 2H

```
MAJORITY [SEQ ID NO:7]  GCCCCTGGAGGTGGAGGTGGGGATGGGGAGGACTGGCTCTCCGCCAAGGAGTAG

DNAPTAQ  [SEQ ID NO:1]  ..............................A.....................GA
DNAPTFL  [SEQ ID NO:2]  ...........................CC........................
DNAPTTH  [SEQ ID NO:3]  ...........................................T......GT..
```

FIG. 3A

```
MAJORITY  [SEQ ID NO:8]  MXAMLPLFEPKGRVLLVDGHHLAYRTFFALKGLTTSRGEPVQAVYGFAKSLLKALKEDG-DAVXVVFDAK

TAQ PRO   [SEQ ID NO:4]  ..RG................H................................I...........      69
TFL PRO   [SEQ ID NO:5]  ....................................................V.V..........      68
TTH PRO   [SEQ ID NO:6]  ..E..........................................................YK.F...      70

MAJORITY  APSFRHEAYEAYKAGRAPTPEDFPRQLALIKELVDLLGLXRLEVPGYEADDVLATLAKKAEKEGYEVRIL

TAQ PRO   ......GG...................................A.........S..............      139
TFL PRO   .........................................V...F.....................R      138
TTH PRO   ...........................................FT......................      140

MAJORITY  TADRDLYQLLSDRIAVLHPEGYLITPAWLWEKYGLRPEQWDYRALXGDPSDNLPGVKGIGEKTAXKLLX

TAQ PRO   ...K...............H......................D.A....T.E............R..E     209
TFL PRO   ........E...I........................Y...........A....I......QR.IR     208
TTH PRO   ........V..V......H...E.............................F..V.........L..K     210

MAJORITY  EWGSLENLLKNLDRVKP-XXREKIXAHMEDLXLSXXLSXVRTDLPLEVDFAXRREPDREGLRAFLERLEF

TAQ PRO   ......A.......AI...L....D.K..L...D.K.WD.AK.........K......R........     278
TFL PRO   ...........FQH.Q...SL...LQ.G..A.A..RK..Q.H......GR..T.NL............     277
TTH PRO   ............ENV....K.L...R..LE..R............L.QG..................     280

MAJORITY  GSLLHEFGLLEXPKALEEAPWPPPEGAFVGFVLSRPEPMWAELLALAAARXGRVHRAXDPLXGLRDLKEV

TAQ PRO   ............S.....................K....D...........G......PE.YKA....A     348
TFL PRO   ..G....A..........................L.SF............G.WE..L...Q..R....G.     347
TTH PRO   ..A.AP.........................................K...C.D...A..A..K...     350
```

FIG. 3B

```
MAJORITY [SEQ ID NO:8]  RGLLAKDLAVLALREGLDLXPGDDPMLLAYLLDPSNTTPEGVARRYGGEWTEDAGERALLSERLFXNLXX

TAQ PRO  [SEQ ID NO:4]  ..............S................G.P...........E......A.......A...WG  418
TFL PRO  [SEQ ID NO:5]  ..I.......................F.E................A......QT.KE         417
TTH PRO  [SEQ ID NO:6]  ..................S.......V..................AH......HR..LK         420

MAJORITY   RLEGEERLLWLYXEVEKPLSRVLAHMEATGVRLDVAYLQALSLEVAEEIRRLEEVFRLAGHPFNLNSRD

TAQ PRO    ..........R...R...A...............R................A...A.........   488
TFL PRO    ..K.......E.......R...............................EA.V.Q..........  487
TTH PRO    ......K...H...................................L....................  490

MAJORITY   QLERVLFDELGLPAIGKTEKTGKRSTSAAVLEALREAHPIVEKILQYRELTKLKNTYIDPLPXLVHPRTG

TAQ PRO    .............................................S......D.I............   558
TFL PRO    ........................DR...........................A....K........  557
TTH PRO    ....R..L..Q...........................H............V...S............  560

MAJORITY   RLHTRFNQTATATGRLSSSDPNLQNIPVRTPLGQRIRRAFVAEEGWXLVALDYSQIELRVLAHLSGDENL

TAQ PRO    ..........................................I.....L..................   628
TFL PRO    ..........................................V..V.....................  627
TTH PRO    .............................................A.A...................  630

MAJORITY   IRVFQEGRDIHTQTASWMFGVPPEAVDPLMRRAAKTINFGVLYGMSAHRLSQELAIPYEEAVAFIERYFQ

TAQ PRO    .............E.............R.........................Q.............   698
TFL PRO    ...................S..G..............................G.S............  697
TTH PRO    ....K......................................V........................  700
```

FIG. 3C

```
MAJORITY [SEQ ID NO:8]  SFPKVRAWIEKTLEEGRRRGYVETLFGRRRYVPDLNARVKSVREAAERMAFNMPVQGTAADLMKLAMVKL

TAQ PRO  [SEQ ID NO:4]  ..........................................E..........................  768
TFL PRO  [SEQ ID NO:5]  .Y............G...........................................R..........  767
TTH PRO  [SEQ ID NO:6]  ........................K.............................................  770

MAJORITY                FPRLXEMGARMLLQVHDELVLEAPKXRAEXVAALAKEVMEGVYPLAVPLEVEVGXGEDWLSAKEX

TAQ PRO                 ....E............E...A..R..................I...........................  833
TFL PRO                 ....Q.L..........D...R.............W..Q....L...........................  831
TTH PRO                 ....R...........QA.....E.........A..KA............M...............G....  835
```

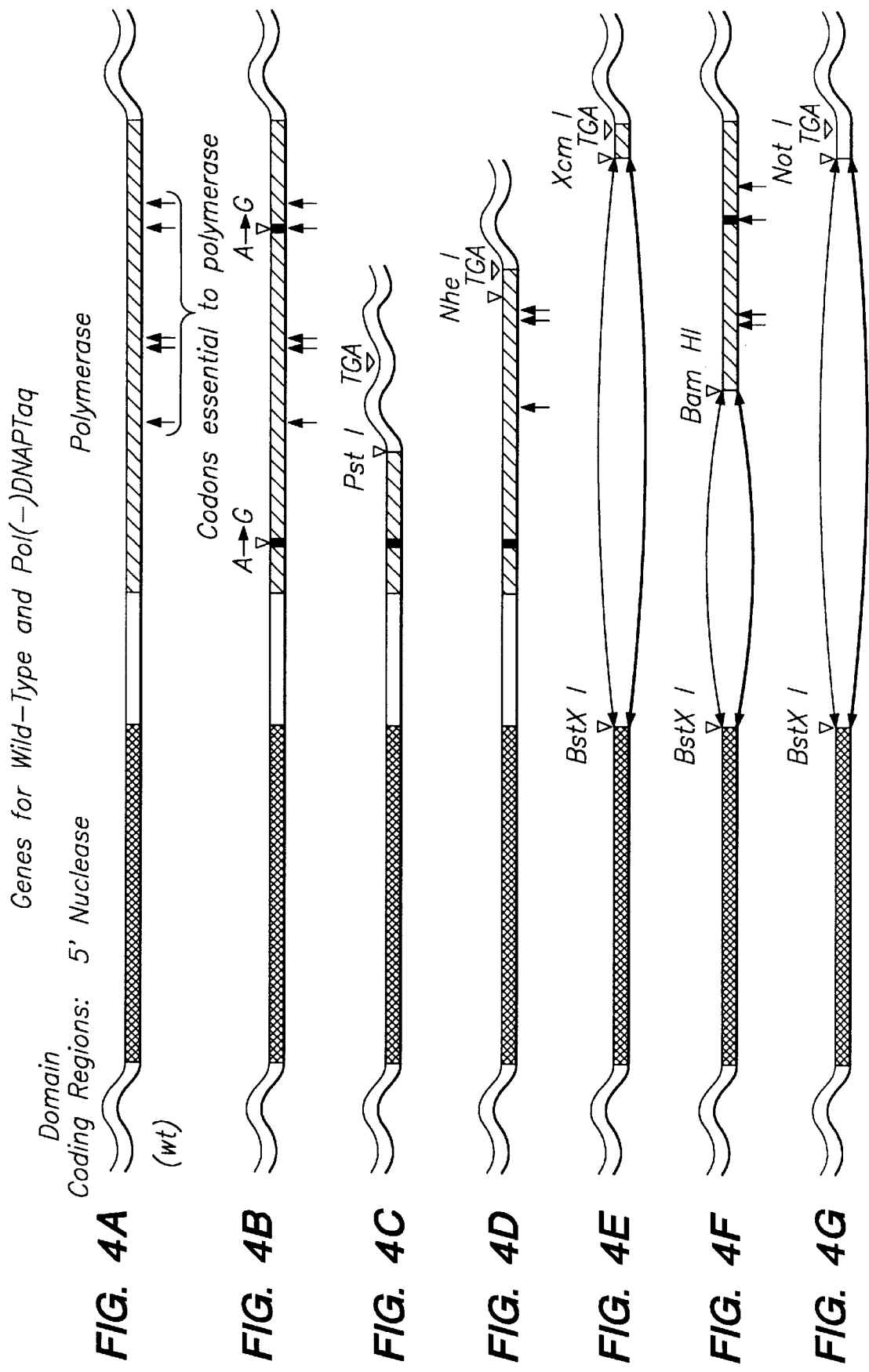

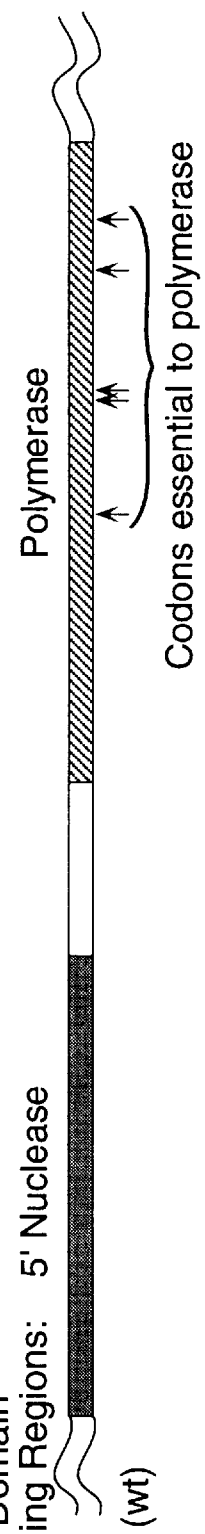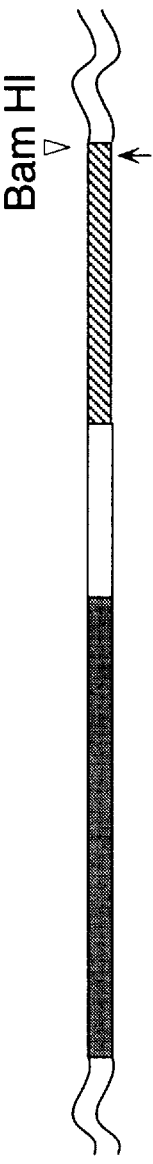
FIG. 5A
FIG. 5B

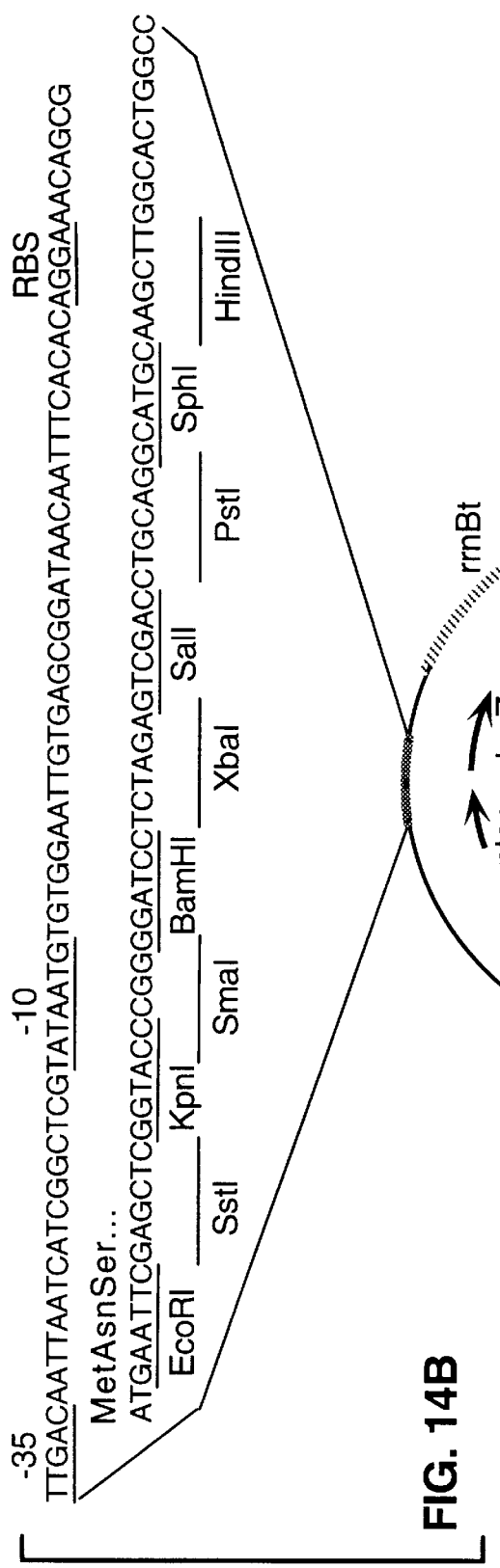

-35
TTGACAATTAATCATCGGCTCGTATAATGTGTGGAATTGTGAGCGGATAACAATTTCACACAGGAAACAGCG

RBS

MetAsnSer...
ATGAATTCGAGCTCGGTACCCGGGGATCCTCTAGAGTCGACCTGCAGGCATGCAAGCTTGGCACTGGCC

EcoRI  SstI  KpnI  SmaI  BamHI  XbaI  SalI  PstI  SphI  HindIII

FIG. 14B

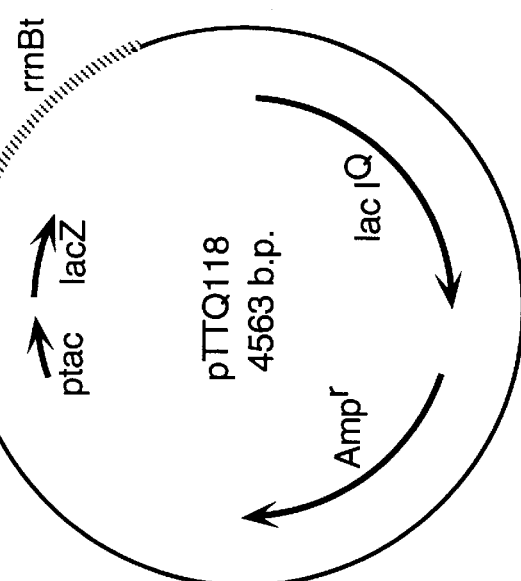

FIG. 14A

RBS: Ribosome binding site       lacZ: Beta-galactosidase alpha fragment
ptac: Synthetic tac promoter     rrnBt: E. coli rrnB transcription terminator
lac IQ: Lac repressor gene

FIG. 14C

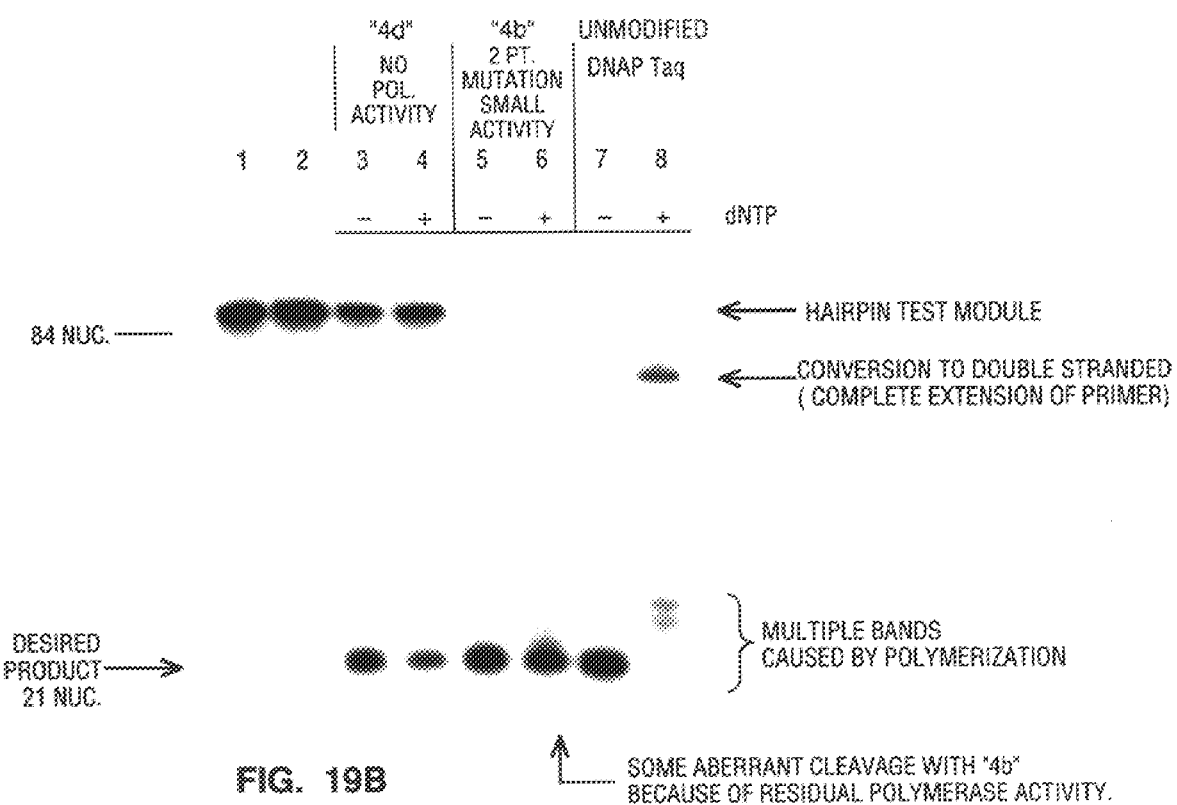

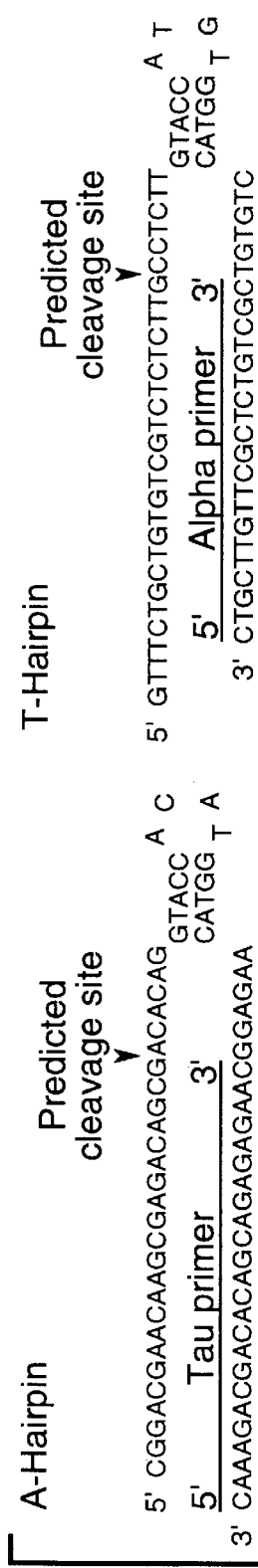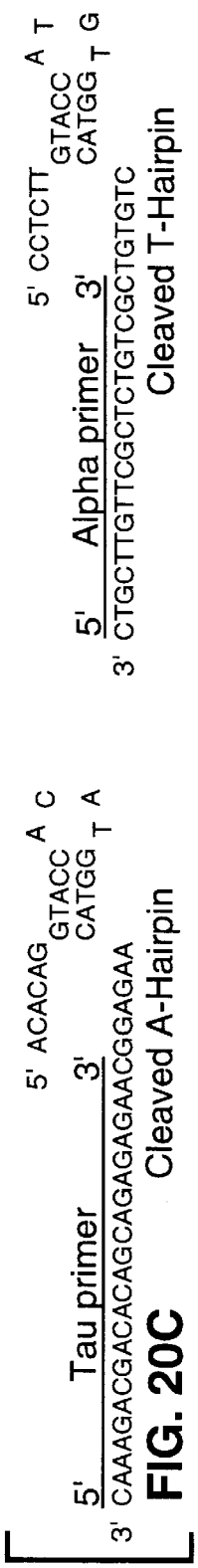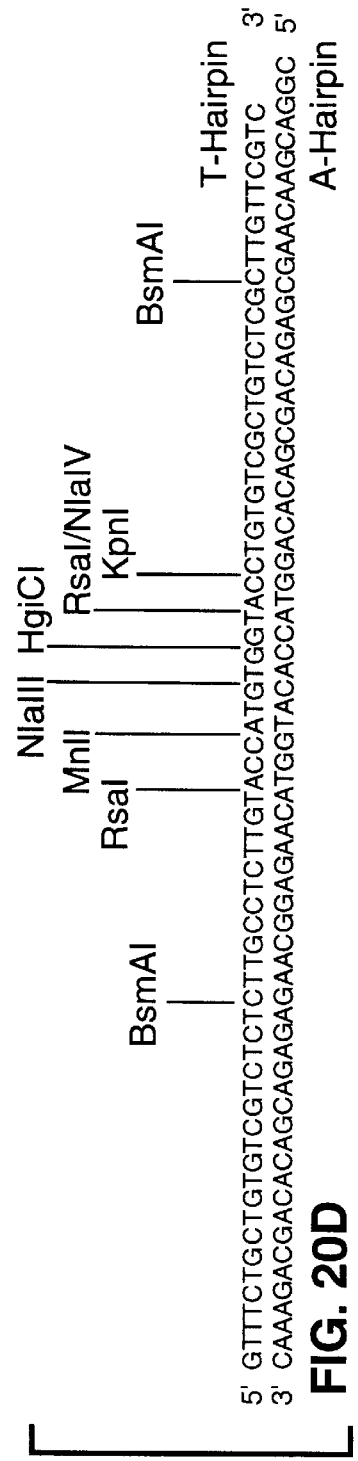

```
                                     50                                              100
L.100.8-1       5' GGCTGACAAGAAGGAAACTCGCTGAGACAGCAGGGACTTTCCACAAGGGG ATGTTACGGGGAGGTACTGGGAGGAGCCGGTCGGGAACGCCCACTCTCT
(SEQ ID NO:76)  3' CCGACTGTTCTTCCTTTGAGCGACTCTGTCGTCCCTGAAAGGTGTTCCCC TACAATGCCCCTCCATGACCCCTCCGGCCAGCCCTTGCGGGTGAGAGA

L.46.16-10      5' GGCTGACAAGAAGGAAACTCGCTGAGATAGCAGGGACTTTCCACAAGGGG ATGTTATGGGGAGG---------AGCCGGTCGGGAACACCCACTTTCT
(SEQ ID NO:77)  3' CCGACTGTTCTTCCTTTGAGCGACTCTATCGTCCCTGAAAGGTGTTCCCC TACAATACCCCTCC---------TCGGCCAGCCCTTGTGGGTGAAAGA

L.46.16-12      5' GGCTGACAAGAAGGAAACTCGCTGAGATAGCAGGGACTTTCCACAAGGGG ATGTTATGGGGAGG---------AGCCGGTCGGGAACACCCACTTTCT
(SEQ ID NO:78)  3' CCGACTGTTCTTCCTTTGAGCGACTCTATCGTCCCTGAAAGGTGTTCCCC TACAATACCCCTCC---------TCGGCCAGCCCTTGTGGGTGAAAGA

L.19.16-3       5' GGCTGACAAGAAGGAAACTCGCTGAGACAGCAGGGACTTTCCACAAGGGG ATGTTACGGGGAGGTACTGGGAGGAGCCGGTCGGGAACGCCCCTCTCT
(SEQ ID NO:79)  3' CCGACTGTTCTTCCTTTGAGCGACTCTGTCCCTGAAAGGTGTTCCCC TACAATGCCCCTCCATGACCCCTCCGGCCAGCCCTTGCGGGGAGAGA

L.CEM/251       5' GGCTGACAAGAAGAAACTCGCTGAAACAGCAGGGACTTTCCGAAAGGGG ATGTTACGGGGAGGTACTGGGAAGAGCCGGTCGGGAACGCCCACTTTCT
(SEQ ID NO:80)  3' CCGACTGTTCTTCCTTTGAGCGACTTTGTCGTCCCTGAAAGGTGTTCCCC TACAATGCCCCTCCATGACCCTTCCTCGGCCAGCCCTTGCGGGTGAAAGA

L.36.8-3        5' GGCTGACAAGAAGGAAACTCGCTGAGACAGCAGGGACTTTCCACAAGGGG ATGTTACGGGGAGGTACTGGGAGGAGCCGGTCGGGAACGCCCACTCTCT
(SEQ ID NO:81)  3' CCGACTGTTCTTCCTTTGAGCGACTCTGTCGTCCCTGAAAGGTGTTCCCC TACAATGCCCCTCCATGACCCCTCCGGCCAGCCCTTGCGGGTGAGAGA 150                                             200
L.100.8-1       5' TGATGTATAAATATCACTGCATTTCGCTCTGTATTCAGTCGCTCTGCGA GAGGCTGGCAGATTGAGCCTGGAGTTCTCTCCAGCACTAGCAGGTAG
                3' ACTACATATTTATAGTGACGTAAAGCGAGACATAAGTCAGCGAGACGCT CTCCGACCGTCTAACTCGGACCTCAAGAGAGGTCGTGATCGTCCATC

L.46.16-10      5' TGATGTATAAATATCACTGCATTTCGCTCTGTATTCAGTCGCTCTGCGA GAGGCTGGCAGATTGAGCCTGGAGTTCTCTCCAGCACTAGCAGGTAG
                3' ACTACATATTTATAGTGACGTAAAGCGAGCATAAGTCAGCGAGACGCCT CTCGACCGTCTAACTCGGACCTCAAGAGAGGTCGTGATCGTCCATC

L.46.16-12      5' TGGTGTATAAATATCACTGCATTTCGCTCTGTATTCAGTCGCTCTGCGA GAGGCTGGCAGATTGAGCCTGGAGTTCTCTCCAGCACTAGCAGGTAG
                3' ACCACATATTTATAGTGACGTAAAGCGAGACATAAGTCAGCGAGACGCT CTCCGACCGTCTAACTCGGACCTCAAGAGAGGTCGTGATCGTCCATC

L.19.16-3       5' TGATGTATAAATATCACTGCATTTCGCTCTGTATTCAGTCGCTCTGCGA GAGGCTGGCAGATTGAGCCTGGAGTTCTCTCCAGCACTAGCAGGTAG
                3' ACTACATATTTATAGTGACGTAAAGCGAGACATAAGTCAGCGAGACGCT CTCCGACCGTCTAACTCGGACCTCAAGAGAGGTCGTGATCGTCCATC

L.CBM/251       5' TGATGTATAAATATCACTGCATTTCGCTCTGTATTCAGTCGCTCTGCGA GAGGCTGGCAGATTGAGCCCTGGAGGTTCTCTCCAGGAGGTTCTCTCCAGCTAGCAGGTAG
                3' ACTACATATTTATAGTGACGTAAAGCGAGACATAAGTCAGCGAGACGCT CTCCGACCGTCTAACTCGGGACCCTCCAGGATGGATTCCTAAGAGAGGTCGTGATCGTCCATC

L.36.8-3        5' TGATGTATAAATTATAGTGACGTAAAGCGAGACATAAGTCAGCGAGACGCT GAGGCTGGCAGATTGAGCCTGGAGTTCTCTCCAGCACTAGCAGGTAG
                3' ACTACATATTTATAGTGACGTAAAGCGAGACATAAGTCAGCGAGACGCT CTCCGACCGTCTAACTCGGATCCTCCAAGAGAGGTCGTGATCGTCCATC
```

1/2

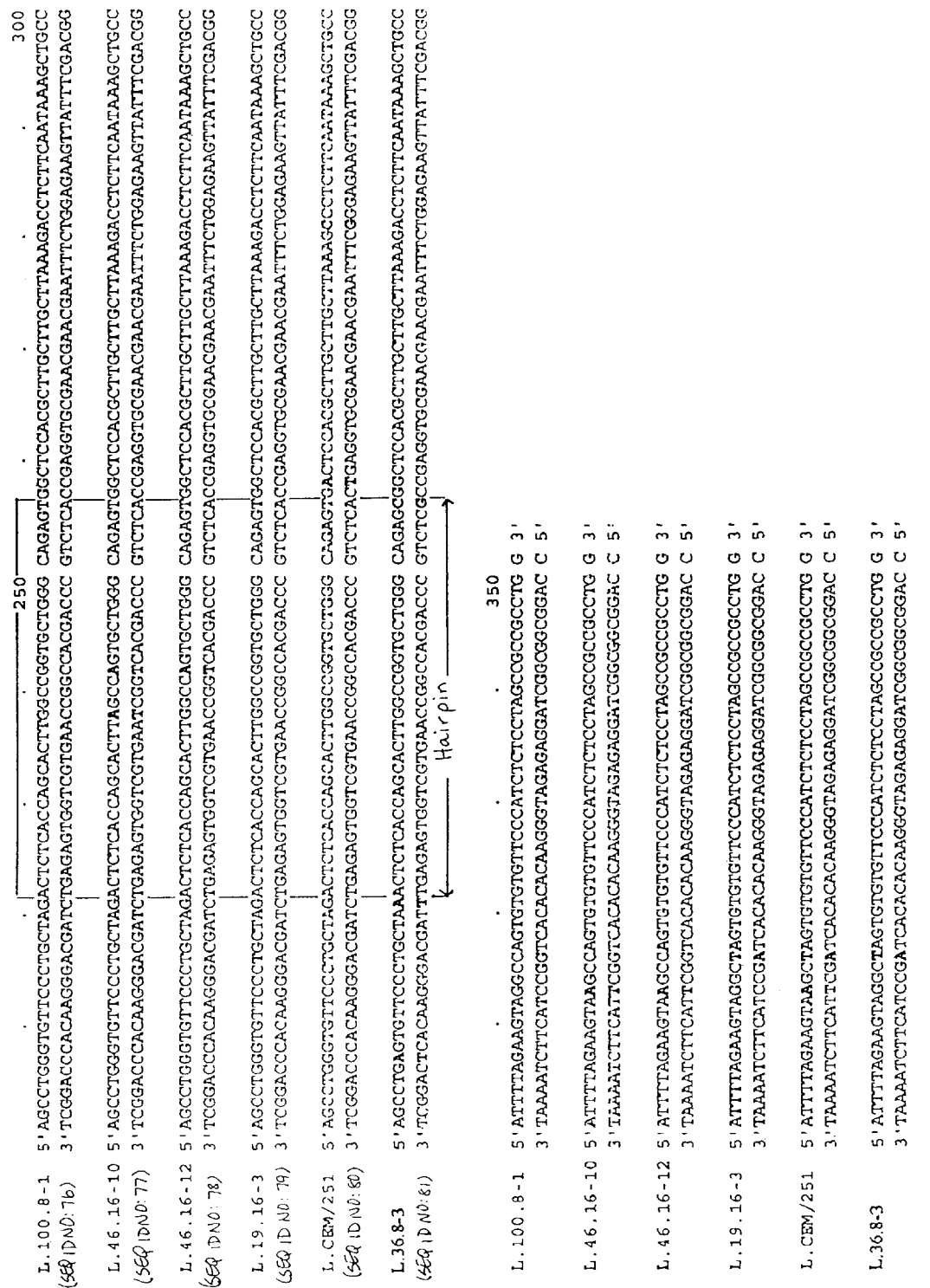

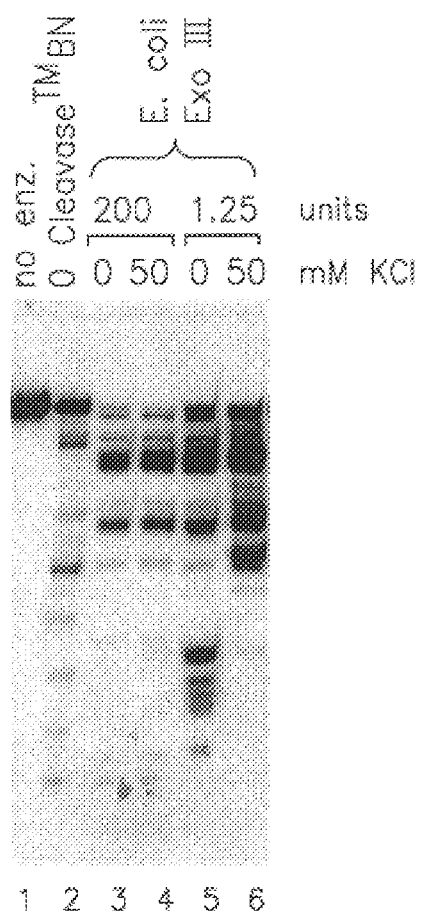
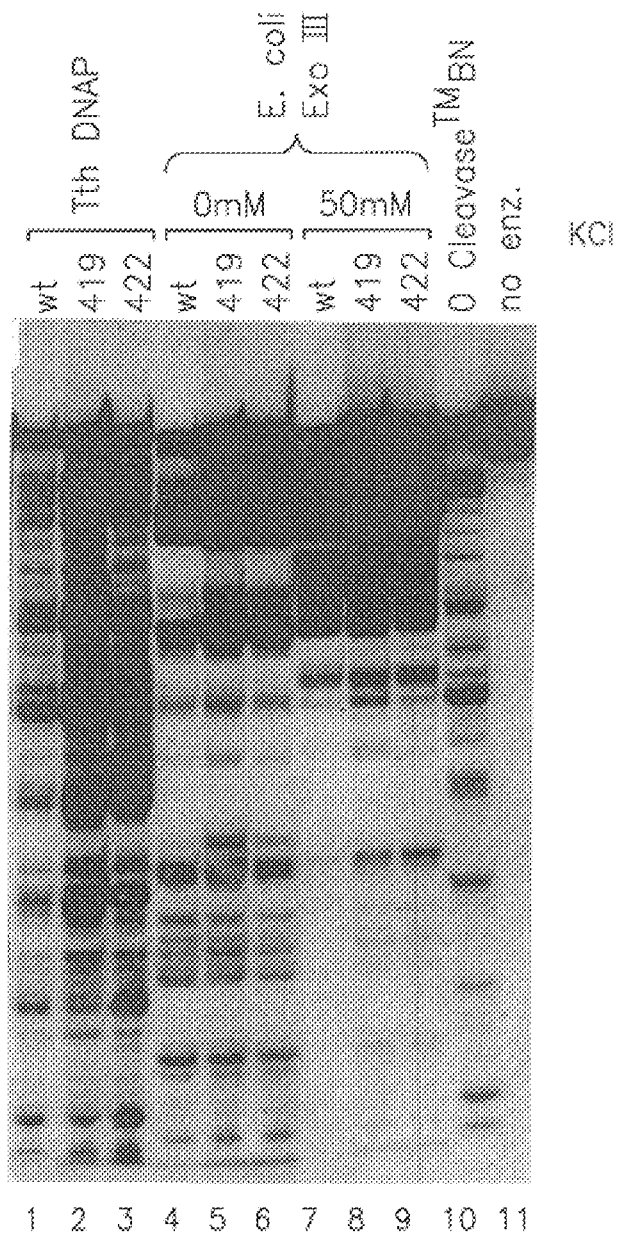
FIG. 69
FIG. 70

FIGURE 71
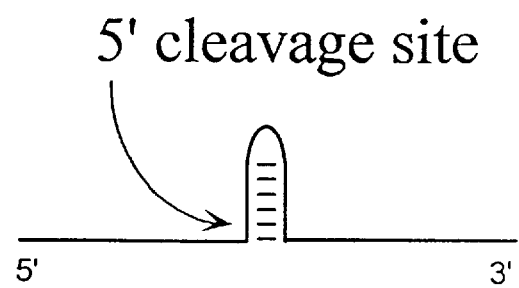
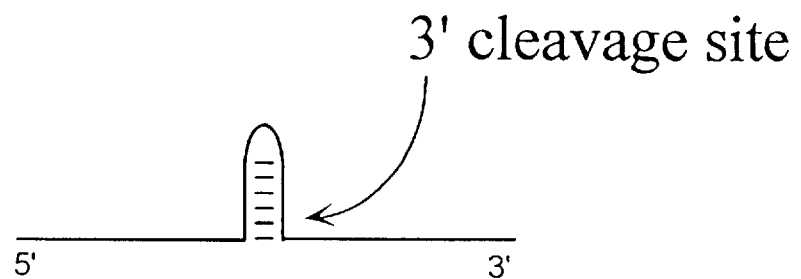

5,888,780

SEQUENCE LISTING ( 1 ) GENERAL INFORMATION:

( i i i ) NUMBER OF SEQUENCES: 91

( 2 ) INFORMATION FOR SEQ ID NO:1:

( i ) SEQUENCE CHARACTERISTICS:
        ( A ) LENGTH: 2506 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGAGGGGGA  TGCTGCCCCT  CTTTGAGCCC  AAGGGCCGGG  TCCTCCTGGT  GGACGGCCAC      60

CACCTGGCCT  ACCGCACCTT  CCACGCCCTG  AAGGGCCTCA  CCACCAGCCG  GGGGGAGCCG     120

GTGCAGGCGG  TCTACGGCTT  CGCCAAGAGC  CTCCTCAAGG  CCCTCAAGGA  GGACGGGGAC     180

GCGGTGATCG  TGGTCTTTGA  CGCCAAGGCC  CCCTCCTTCC  GCCACGAGGC  CTACGGGGGG     240

TACAAGGCGG  GCCGGGCCCC  CACGCCGGAG  GACTTTCCCC  GGCAACTCGC  CCTCATCAAG     300

GAGCTGGTGG  ACCTCCTGGG  GCTGGCGCGC  CTCGAGGTCC  CGGGCTACGA  GGCGGACGAC     360

GTCCTGGCCA  GCCTGGCCAA  GAAGGCGGAA  AAGGAGGGCT  ACGAGGTCCG  CATCCTCACC     420

GCCGACAAAG  ACCTTTACCA  GCTCCTTTCC  GACCGCATCC  ACGTCCTCCA  CCCCGAGGGG     480

TACCTCATCA  CCCCGGCCTG  GCTTTGGGAA  AAGTACGGCC  TGAGGCCCGA  CCAGTGGGCC     540

GACTACCGGG  CCCTGACCGG  GGACGAGTCC  GACAACCTTC  CCGGGGTCAA  GGGCATCGGG     600
```

-continued

| | | | | | |
|---|---|---|---|---|---|
| GAGAAGACGG | CGAGGAAGCT | TCTGGAGGAG | TGGGGGAGCC | TGGAAGCCCT | CCTCAAGAAC | 660 |
| CTGGACCGGC | TGAAGCCCGC | CATCCGGGAG | AAGATCCTGG | CCCACATGGA | CGATCTGAAG | 720 |
| CTCTCCTGGG | ACCTGGCCAA | GGTGCGCACC | GACCTGCCCC | TGGAGGTGGA | CTTCGCCAAA | 780 |
| AGGCGGGAGC | CCGACCGGGA | GAGGCTTAGG | GCCTTTCTGG | AGAGGCTTGA | GTTTGGCAGC | 840 |
| CTCCTCCACG | AGTTCGGCCT | TCTGGAAAGC | CCCAAGGCCC | TGGAGGAGGC | CCCCTGGCCC | 900 |
| CCGCCGGAAG | GGGCCTTCGT | GGGCTTTGTG | CTTTCCCGCA | AGGAGCCCAT | GTGGGCCGAT | 960 |
| CTTCTGGCCC | TGGCCGCCGC | CAGGGGGGGC | CGGGTCCACC | GGGCCCCCGA | GCCTATAAA | 1020 |
| GCCCTCAGGG | ACCTGAAGGA | GGCGCGGGGG | CTTCTCGCCA | AAGACCTGAG | CGTTCTGGCC | 1080 |
| CTGAGGGAAG | GCCTTGGCCT | CCCGCCCGGC | GACGACCCCA | TGCTCCTCGC | CTACCTCCTG | 1140 |
| GACCCTTCCA | ACACCACCCC | CGAGGGGGTG | GCCCGGCGCT | ACGGCGGGGA | GTGGACGGAG | 1200 |
| GAGGCGGGGG | AGCGGGCCGC | CCTTTCCGAG | AGGCTCTTCG | CCAACCTGTG | GGGGAGGCTT | 1260 |
| GAGGGGGAGG | AGAGGCTCCT | TTGGCTTTAC | CGGGAGGTGG | AGAGGCCCCT | TTCCGCTGTC | 1320 |
| CTGGCCCACA | TGGAGGCCAC | GGGGGTGCGC | CTGGACGTGG | CCTATCTCAG | GGCCTTGTCC | 1380 |
| CTGGAGGTGG | CCGAGGAGAT | CGCCCGCCTC | GAGGCCGAGG | TCTTCCGCCT | GGCCGGCCAC | 1440 |
| CCCTTCAACC | TCAACTCCCG | GGACCAGCTG | GAAAGGGTCC | TCTTTGACGA | GCTAGGGCTT | 1500 |
| CCCGCCATCG | GCAAGACGGA | GAAGACCGGC | AAGCGCTCCA | CCAGCGCCGC | CGTCCTGGAG | 1560 |
| GCCCTCCGCG | AGGCCCACCC | CATCGTGGAG | AAGATCCTGC | AGTACCGGGA | GCTCACCAAG | 1620 |
| CTGAAGAGCA | CCTACATTGA | CCCCTTGCCG | GACCTCATCC | ACCCCAGGAC | GGGCCGCCTC | 1680 |
| CACACCCGCT | TCAACCAGAC | GGCCACGGCC | ACGGGCAGGC | TAAGTAGCTC | CGATCCCAAC | 1740 |
| CTCCAGAACA | TCCCCGTCCG | CACCCCGCTT | GGGCAGAGGA | TCCGCCGGGC | CTTCATCGCC | 1800 |
| GAGGAGGGGT | GGCTATTGGT | GGCCCTGGAC | TATAGCCAGA | TAGAGCTCAG | GGTGCTGGCC | 1860 |
| CACCTCTCCG | GCGACGAGAA | CCTGATCCGG | GTCTTCCAGG | AGGGGCGGGA | CATCCACACG | 1920 |
| GAGACCGCCA | GCTGGATGTT | CGGCGTCCCC | CGGGAGGCCG | TGGACCCCCT | GATGCGCCGG | 1980 |
| GCGGCCAAGA | CCATCAACTT | CGGGGTCCTC | TACGGCATGT | CGGCCCACCG | CCTCTCCCAG | 2040 |
| GAGCTAGCCA | TCCCTTACGA | GGAGGCCCAG | GCCTTCATTG | AGCGCTACTT | TCAGAGCTTC | 2100 |
| CCCAAGGTGC | GGGCCTGGAT | TGAGAAGACC | CTGGAGGAGG | GCAGGAGGCG | GGGGTACGTG | 2160 |
| GAGACCCTCT | TCGGCCGCCG | CCGCTACGTG | CCAGACCTAG | AGGCCCGGGT | GAAGAGCGTG | 2220 |
| CGGGAGGCGG | CCGAGCGCAT | GGCCTTCAAC | ATGCCCGTCC | AGGGCACCGC | CGCCGACCTC | 2280 |
| ATGAAGCTGG | CTATGGTGAA | GCTCTTCCCC | AGGCTGGAGG | AAATGGGGGC | CAGGATGCTC | 2340 |
| CTTCAGGTCC | ACGACGAGCT | GGTCCTCGAG | GCCCCAAAAG | AGAGGGCGGA | GGCCGTGGCC | 2400 |
| CGGCTGGCCA | AGGAGGTCAT | GGAGGGGGTG | TATCCCCTGG | CCGTGCCCCT | GGAGGTGGAG | 2460 |
| GTGGGGATAG | GGAGGACTG | GCTCTCCGCC | AAGGAGTGAT | ACCACC | | 2506 |

( 2 ) INFORMATION FOR SEQ ID NO:2:

( i ) SEQUENCE CHARACTERISTICS:
        ( A ) LENGTH: 2496 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | |
|---|---|---|---|---|---|
| ATGGCGATGC | TTCCCCTCTT | TGAGCCCAAA | GGCCGCGTGC | TCCTGGTGGA | CGGCCACCAC | 60 |
| CTGGCCTACC | GCACCTTCTT | TGCCCTCAAG | GGCCTCACCA | CCAGCCGCGG | CGAACCCGTT | 120 |

-continued

```
CAGGCGGTCT ACGGCTTCGC CAAAAGCCTC CTCAAGGCCC TGAAGGAGGA CGGGGACGTG      180
GTGGTGGTGG TCTTTGACGC CAAGGCCCCC TCCTTCCGCC ACGAGGCCTA CGAGGCCTAC      240
AAGGCGGGCC GGGCCCCCAC CCCGGAGGAC TTTCCCCGGC AGCTGGCCCT CATCAAGGAG      300
TTGGTGGACC TCCTAGGCCT TGTGCGGCTG GAGGTTCCCG GCTTTGAGGC GGACGACGTG      360
CTGGCCACCC TGGCCAAGCG GGCGGAAAAG GAGGGGTACG AGGTGCGCAT CCTCACTGCC      420
GACCGCGACC TCTACCAGCT CCTTTCGGAG CGCATCGCCA TCCTCCACCC TGAGGGGTAC      480
CTGATCACCC CGGCGTGGCT TTACGAGAAG TACGGCCTGC GCCCGGAGCA GTGGGTGGAC      540
TACCGGGCCC TGGCGGGGGA CCCCTCGGAT AACATCCCCG GGGTGAAGGG CATCGGGGAG      600
AAGACCGCCC AGAGGCTCAT CCGCGAGTGG GGGAGCCTGG AAAACCTCTT CCAGCACCTG      660
GACCAGGTGA AGCCCTCCTT GCGGGAGAAG CTCCAGGCGG GCATGGAGGC CCTGGCCCTT      720
TCCCGGAAGC TTTCCCAGGT GCACACTGAC CTGCCCCTGG AGGTGGACTT CGGGAGGCGC      780
CGCACACCCA ACCTGGAGGG TCTGCGGGCT TTTTTGGAGC GGTTGGAGTT TGGAAGCCTC      840
CTCCACGAGT TCGGCCTCCT GGAGGGGCCG AAGGCGGCAG AGGAGGCCCC CTGGCCCCCT      900
CCGGAAGGGG CTTTTTTGGG CTTTTCCTTT TCCCGTCCCG AGCCCATGTG GGCCGAGCTT      960
CTGGCCCTGG CTGGGGCGTG GGAGGGGCGC CTCCATCGGG CACAAGACCC CCTTAGGGGC     1020
CTGAGGGACC TTAAGGGGGT GCGGGGAATC CTGGCCAAGG ACCTGGCGGT TTTGGCCCTG     1080
CGGGAGGGCC TGGACCTCTT CCCAGAGGAC GACCCCATGC TCCTGGCCTA CCTTCTGGAC     1140
CCCTCCAACA CCACCCCTGA GGGGGTGGCC CGGCGTTACG GGGGGGAGTG GACGGAGGAT     1200
GCGGGGGAGA GGGCCCTCCT GGCCGAGCGC CTCTTCCAGA CCCTAAAGGA GCGCCTTAAG     1260
GGAGAAGAAC GCCTGCTTTG GCTTTACGAG GAGGTGGAGA AGCCGCTTTC CCGGGTGTTG     1320
GCCCGGATGG AGGCCACGGG GGTCCGGCTG GACGTGGCCT ACCTCCAGGC CCTCTCCCTG     1380
GAGGTGGAGG CGGAGGTGCG CCAGCTGGAG GAGGAGGTCT TCCGCCTGGC CGGCCACCCC     1440
TTCAACCTCA ACTCCCGCGA CCAGCTGGAG CGGGTGCTCT TTGACGAGCT GGGCCTGCCT     1500
GCCATCGGCA AGACGGAGAA GACGGGGAAA CGCTCCACCA GCGCTGCCGT GCTGGAGGCC     1560
CTGCGAGAGG CCCACCCCAT CGTGGACCGC ATCCTGCAGT ACCGGGAGCT CACCAAGCTC     1620
AAGAACACCT ACATAGACCC CCTGCCCGCC CTGGTCCACC CCAAGACCGG CCGGCTCCAC     1680
ACCCGCTTCA ACCAGACGGC CACCGCCACG GGCAGGCTTT CCAGCTCCGA CCCCAACCTG     1740
CAGAACATCC CCGTGCGCAC CCCTCTGGGC CAGCGCATCC GCCGAGCCTT CGTGGCCGAG     1800
GAGGGCTGGG TGCTGGTGGT CTTGGACTAC AGCCAGATTG AGCTTCGGGT CCTGGCCCAC     1860
CTCTCCGGGG ACGAGAACCT GATCCGGGTC TTTCAGGAGG GGAGGGACAT CCACACCCAG     1920
ACCGCCAGCT GGATGTTCGG CGTTTCCCCC GAAGGGGTAG ACCCTCTGAT GCGCCGGGCG     1980
GCCAAGACCA TCAACTTCGG GGTGCTCTAC GGCATGTCCG CCCACCGCCT CTCCGGGGAG     2040
CTTTCCATCC CCTACGAGGA GGCGGTGGCC TTCATTGAGC GCTACTTCCA GAGCTACCCC     2100
AAGGTGCGGG CCTGGATTGA GGGGACCCTC GAGGAGGGCC GCCGGCGGGG GTATGTGGAG     2160
ACCCTCTTCG GCCGCCGGCG CTATGTGCCC GACCTCAACG CCCGGGTGAA GAGCGTGCGC     2220
GAGGCGGCGG AGCGCATGGC CTTCAACATG CCGGTCCAGG GCACCGCCGC CGACCTCATG     2280
AAGCTGGCCA TGGTGCGGCT TTTCCCCCGG CTTCAGGAAC TGGGGGCGAG GATGCTTTTG     2340
CAGGTGCACG ACGAGCTGGT CCTCGAGGCC CCCAAGGACC GGGCGGAGAG GGTAGCCGCT     2400
TTGGCCAAGG AGGTCATGGA GGGGGTCTGG CCCCTGCAGG TGCCCCTGGA GGTGGAGGTG     2460
GGCCTGGGGG AGGACTGGCT CTCCGCCAAG GAGTAG                               2496
```

( 2 ) INFORMATION FOR SEQ ID NO:3:

( i ) SEQUENCE CHARACTERISTICS:
        ( A ) LENGTH: 2504 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
ATGGAGGCGA   TGCTTCCGCT   CTTTGAACCC   AAAGGCCGGG   TCCTCCTGGT   GGACGGCCAC      60
CACCTGGCCT   ACCGCACCTT   CTTCGCCCTG   AAGGGCCTCA   CCACGAGCCG   GGGCGAACCG     120
GTGCAGGCGG   TCTACGGCTT   CGCCAAGAGC   CTCCTCAAGG   CCCTGAAGGA   GGACGGGTAC     180
AAGGCCGTCT   TCGTGGTCTT   TGACGCCAAG   GCCCCCTCCT   TCCGCCACGA   GGCCTACGAG     240
GCCTACAAGG   CGGGGAGGGC   CCCGACCCCC   GAGGACTTCC   CCCGGCAGCT   CGCCCTCATC     300
AAGGAGCTGG   TGGACCTCCT   GGGGTTTACC   CGCCTCGAGG   TCCCCGGCTA   CGAGGCGGAC     360
GACGTTCTCG   CCACCCTGGC   CAAGAAGGCG   GAAAAGGAGG   GGTACGAGGT   GCGCATCCTC     420
ACCGCCGACC   GCGACCTCTA   CCAACTCGTC   TCCGACCGCG   TCGCCGTCCT   CCACCCCGAG     480
GGCCACCTCA   TCACCCCGGA   GTGGCTTTGG   GAGAAGTACG   GCCTCAGGCC   GGAGCAGTGG     540
GTGGACTTCC   GCGCCCTCGT   GGGGGACCCC   TCCGACAACC   TCCCCGGGGT   CAAGGGCATC     600
GGGGAGAAGA   CCGCCCTCAA   GCTCCTCAAG   GAGTGGGGAA   GCCTGGAAAA   CCTCCTCAAG     660
AACCTGGACC   GGGTAAAGCC   AGAAAACGTC   CGGGAGAAGA   TCAAGGCCCA   CCTGGAAGAC     720
CTCAGGCTCT   CCTTGGAGCT   CTCCCGGGTG   CGCACCGACC   TCCCCCTGGA   GGTGGACCTC     780
GCCCAGGGGC   GGGAGCCCGA   CCGGGAGGGG   CTTAGGGCCT   TCCTGGAGAG   GCTGGAGTTC     840
GGCAGCCTCC   TCCACGAGTT   CGGCCTCCTG   GAGGCCCCCG   CCCCCCTGGA   GGAGGCCCCC     900
TGGCCCCCGC   CGGAAGGGGC   CTTCGTGGGC   TTCGTCCTCT   CCCGCCCCGA   GCCCATGTGG     960
GCGGAGCTTA   AAGCCCTGGC   CGCCTGCAGG   GACGGCCGGG   TGCACCGGGC   AGCAGACCCC    1020
TTGGCGGGGC   TAAAGGACCT   CAAGGAGGTC   CGGGGCCTCC   TCGCCAAGGA   CCTCGCCGTC    1080
TTGGCCTCGA   GGGAGGGGCT   AGACCTCGTG   CCCGGGACG    ACCCCATGCT   CCTCGCCTAC    1140
CTCCTGGACC   CCTCCAACAC   CACCCCCGAG   GGGGTGGCGC   GGCGCTACGG   GGGGGAGTGG    1200
ACGGAGGACG   CCGCCCACCG   GGCCCTCCTC   TCGGAGAGGC   TCCATCGGAA   CCTCCTTAAG    1260
CGCCTCGAGG   GGGAGGAGAA   GCTCCTTTGG   CTCTACCACG   AGGTGGAAAA   GCCCCTCTCC    1320
CGGGTCCTGG   CCCACATGGA   GGCCACCGGG   GTACGGCTGG   ACGTGGCCTA   CCTTCAGGCC    1380
CTTTCCCTGG   AGCTTGCGGA   GGAGATCCGC   CGCCTCGAGG   AGGAGGTCTT   CCGCTTGGCG    1440
GGCCACCCCT   TCAACCTCAA   CTCCCGGGAC   CAGCTGGAAA   GGGTGCTCTT   TGACGAGCTT    1500
AGGCTTCCCG   CCTTGGGGAA   GACGCAAAAG   ACAGGCAAGC   GCTCCACCAG   CGCCGCGGTG    1560
CTGGAGGCCC   TACGGGAGGC   CCACCCCATC   GTGGAGAAGA   TCCTCCAGCA   CCGGGAGCTC    1620
ACCAAGCTCA   AGAACACCTA   CGTGGACCCC   CTCCCAAGCC   TCGTCCACCC   GAGGACGGGC    1680
CGCCTCCACA   CCCGCTTCAA   CCAGACGGCC   ACGGCCACGG   GGAGGCTTAG   TAGCTCCGAC    1740
CCCAACCTGC   AGAACATCCC   CGTCCGCACC   CCCTTGGGCC   AGAGGATCCG   CCGGGCCTTC    1800
GTGGCCGAGG   CGGGTTGGGC   GTTGGTGGCC   CTGGACTATA   GCCAGATAGA   GCTCCGCGTC    1860
CTCGCCCACC   TCTCCGGGGA   CGAAAACCTG   ATCAGGGTCT   TCCAGGAGGG   AAGGACATC     1920
CACACCCAGA   CCGCAAGCTG   GATGTTCGGC   GTCCCCCCGG   AGGCCGTGGA   CCCCCTGATG    1980
```

```
CGCCGGGCGG CCAAGACGGT GAACTTCGGC GTCCTCTACG GCATGTCCGC CCATAGGCTC    2040

TCCCAGGAGC TTGCCATCCC CTACGAGGAG GCGGTGGCCT TTATAGAGGC TACTTCCAAA    2100

GCTTCCCCAA GGTGCGGGCC TGGATAGAAA AGACCCTGGA GGAGGGGAGG AAGCGGGGCT    2160

ACGTGGAAAC CCTCTTCGGA AGAAGGCGCT ACGTGCCCGA CCTCAACGCC CGGGTGAAGA    2220

GCGTCAGGGA GGCCGCGGAG CGCATGGCCT TCAACATGCC CGTCCAGGGC ACCGCCGCCG    2280

ACCTCATGAA GCTCGCCATG GTGAAGCTCT TCCCCCGCCT CCGGGAGATG GGGGCCCGCA    2340

TGCTCCTCCA GGTCCACGAC GAGCTCCTCC TGGAGGCCCC CCAAGCGCGG GCCGAGGAGG    2400

TGGCGGCTTT GGCCAAGGAG GCCATGGAGA AGGCCTATCC CCTCGCCGTG CCCCTGGAGG    2460

TGGAGGTGGG GATGGGGGAG GACTGGCTTT CCGCCAAGGG TTAG                     2504
```

( 2 ) INFORMATION FOR SEQ ID NO:4:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Met Arg Gly Met Leu Pro Leu Phe Glu Pro Lys Gly Arg Val Leu Leu
 1               5                  10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Asp Ala Val Ile Val
    50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125

Ala Glu Lys Glu Gly Tyr Glu Val Arg Ile Leu Thr Ala Asp Lys Asp
    130                 135                 140

Leu Tyr Gln Leu Leu Ser Asp Arg Ile His Val Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Leu Ala Lys Val Arg Thr Asp Leu Pro Leu Glu Val
                245                 250                 255
```

-continued

```
Asp  Phe  Ala  Lys  Arg  Arg  Glu  Pro  Asp  Arg  Glu  Arg  Leu  Arg  Ala  Phe
          260                      265                      270

Leu  Glu  Arg  Leu  Glu  Phe  Gly  Ser  Leu  Leu  His  Glu  Phe  Gly  Leu  Leu
          275                      280                      285

Glu  Ser  Pro  Lys  Ala  Leu  Glu  Ala  Pro  Trp  Pro  Pro  Glu  Gly
290                           295                      300

Ala  Phe  Val  Gly  Phe  Val  Leu  Ser  Arg  Lys  Glu  Pro  Met  Trp  Ala  Asp
305                      310                      315                      320

Leu  Leu  Ala  Leu  Ala  Ala  Ala  Arg  Gly  Gly  Arg  Val  His  Arg  Ala  Pro
                    325                      330                      335

Glu  Pro  Tyr  Lys  Ala  Leu  Arg  Asp  Leu  Lys  Glu  Ala  Arg  Gly  Leu  Leu
               340                      345                      350

Ala  Lys  Asp  Leu  Ser  Val  Leu  Ala  Leu  Arg  Glu  Gly  Leu  Gly  Leu  Pro
          355                      360                      365

Pro  Gly  Asp  Asp  Pro  Met  Leu  Leu  Ala  Tyr  Leu  Leu  Asp  Pro  Ser  Asn
370                      375                      380

Thr  Thr  Pro  Glu  Gly  Val  Ala  Arg  Arg  Tyr  Gly  Gly  Glu  Trp  Thr  Glu
385                      390                      395                      400

Glu  Ala  Gly  Glu  Arg  Ala  Ala  Leu  Ser  Glu  Arg  Leu  Phe  Ala  Asn  Leu
                    405                      410                      415

Trp  Gly  Arg  Leu  Glu  Gly  Glu  Glu  Arg  Leu  Leu  Trp  Leu  Tyr  Arg  Glu
                    420                      425                      430

Val  Glu  Arg  Pro  Leu  Ser  Ala  Val  Leu  Ala  His  Met  Glu  Ala  Thr  Gly
          435                      440                      445

Val  Arg  Leu  Asp  Val  Ala  Tyr  Leu  Arg  Ala  Leu  Ser  Leu  Glu  Val  Ala
     450                      455                      460

Glu  Glu  Ile  Ala  Arg  Leu  Glu  Ala  Glu  Val  Phe  Arg  Leu  Ala  Gly  His
465                      470                      475                      480

Pro  Phe  Asn  Leu  Asn  Ser  Arg  Asp  Gln  Leu  Glu  Arg  Val  Leu  Phe  Asp
               485                      490                      495

Glu  Leu  Gly  Leu  Pro  Ala  Ile  Gly  Lys  Thr  Glu  Lys  Thr  Gly  Lys  Arg
               500                      505                      510

Ser  Thr  Ser  Ala  Ala  Val  Leu  Glu  Ala  Leu  Arg  Glu  Ala  His  Pro  Ile
          515                      520                      525

Val  Glu  Lys  Ile  Leu  Gln  Tyr  Arg  Glu  Leu  Thr  Lys  Leu  Lys  Ser  Thr
530                      535                      540

Tyr  Ile  Asp  Pro  Leu  Pro  Asp  Leu  Ile  His  Pro  Arg  Thr  Gly  Arg  Leu
545                      550                      555                      560

His  Thr  Arg  Phe  Asn  Gln  Thr  Ala  Thr  Ala  Thr  Gly  Arg  Leu  Ser  Ser
               565                      570                      575

Ser  Asp  Pro  Asn  Leu  Gln  Asn  Ile  Pro  Val  Arg  Thr  Pro  Leu  Gly  Gln
               580                      585                      590

Arg  Ile  Arg  Arg  Ala  Phe  Ile  Ala  Glu  Glu  Gly  Trp  Leu  Leu  Val  Ala
          595                      600                      605

Leu  Asp  Tyr  Ser  Gln  Ile  Glu  Leu  Arg  Val  Leu  Ala  His  Leu  Ser  Gly
     610                      615                      620

Asp  Glu  Asn  Leu  Ile  Arg  Val  Phe  Gln  Glu  Gly  Arg  Asp  Ile  His  Thr
625                      630                      635                      640

Glu  Thr  Ala  Ser  Trp  Met  Phe  Gly  Val  Pro  Arg  Glu  Ala  Val  Asp  Pro
                    645                      650                      655

Leu  Met  Arg  Arg  Ala  Ala  Lys  Thr  Ile  Asn  Phe  Gly  Val  Leu  Tyr  Gly
               660                      665                      670

Met  Ser  Ala  His  Arg  Leu  Ser  Gln  Glu  Leu  Ala  Ile  Pro  Tyr  Glu  Glu
          675                      680                      685
```

```
Ala  Gln  Ala  Phe  Ile  Glu  Arg  Tyr  Phe  Gln  Ser  Phe  Pro  Lys  Val  Arg
     690            695                      700

Ala  Trp  Ile  Glu  Lys  Thr  Leu  Glu  Glu  Gly  Arg  Arg  Arg  Gly  Tyr  Val
705                      710                      715                      720

Glu  Thr  Leu  Phe  Gly  Arg  Arg  Arg  Tyr  Val  Pro  Asp  Leu  Glu  Ala  Arg
                    725                 730                           735

Val  Lys  Ser  Val  Arg  Glu  Ala  Ala  Arg  Met  Ala  Phe  Asn  Met  Pro
               740                 745                      750

Val  Gln  Gly  Thr  Ala  Ala  Asp  Leu  Met  Lys  Leu  Ala  Met  Val  Lys  Leu
          755                 760                           765

Phe  Pro  Arg  Leu  Glu  Glu  Met  Gly  Ala  Arg  Met  Leu  Leu  Gln  Val  His
     770                 775                      780

Asp  Glu  Leu  Val  Leu  Glu  Ala  Pro  Lys  Glu  Arg  Ala  Glu  Ala  Val  Ala
785                      790                 795                           800

Arg  Leu  Ala  Lys  Glu  Val  Met  Glu  Gly  Val  Tyr  Pro  Leu  Ala  Val  Pro
                    805                 810                           815

Leu  Glu  Val  Glu  Val  Gly  Ile  Gly  Glu  Asp  Trp  Leu  Ser  Ala  Lys  Glu
               820                 825                      830
```

( 2 ) INFORMATION FOR SEQ ID NO:5:

( i ) SEQUENCE CHARACTERISTICS:
       ( A ) LENGTH: 831 amino acids
       ( B ) TYPE: amino acid
       ( C ) STRANDEDNESS: single
       ( D ) TOPOLOGY: linear ( i i ) MOLECULE TYPE: protein ( x i ) SEQUENCE DESCRIPTION: SEQ ID NO:5:

```
Met  Ala  Met  Leu  Pro  Leu  Phe  Glu  Pro  Lys  Gly  Arg  Val  Leu  Leu  Val
1                   5                      10                      15

Asp  Gly  His  His  Leu  Ala  Tyr  Arg  Thr  Phe  Phe  Ala  Leu  Lys  Gly  Leu
               20                 25                      30

Thr  Thr  Ser  Arg  Gly  Glu  Pro  Val  Gln  Ala  Val  Tyr  Gly  Phe  Ala  Lys
          35                      40                      45

Ser  Leu  Leu  Lys  Ala  Leu  Lys  Glu  Asp  Gly  Asp  Val  Val  Val  Val  Val
     50                      55                      60

Phe  Asp  Ala  Lys  Ala  Pro  Ser  Phe  Arg  His  Glu  Ala  Tyr  Glu  Ala  Tyr
65                       70                 75                           80

Lys  Ala  Gly  Arg  Ala  Pro  Thr  Pro  Glu  Asp  Phe  Pro  Arg  Gln  Leu  Ala
                    85                 90                           95

Leu  Ile  Lys  Glu  Leu  Val  Asp  Leu  Leu  Gly  Leu  Val  Arg  Leu  Glu  Val
               100                 105                      110

Pro  Gly  Phe  Glu  Ala  Asp  Asp  Val  Leu  Ala  Thr  Leu  Ala  Lys  Arg  Ala
          115                      120                      125

Glu  Lys  Glu  Gly  Tyr  Glu  Val  Arg  Ile  Leu  Thr  Ala  Asp  Arg  Asp  Leu
     130                      135                      140

Tyr  Gln  Leu  Leu  Ser  Glu  Arg  Ile  Ala  Ile  Leu  His  Pro  Glu  Gly  Tyr
145                      150                           155                 160

Leu  Ile  Thr  Pro  Ala  Trp  Leu  Tyr  Glu  Lys  Tyr  Gly  Leu  Arg  Pro  Glu
                    165                 170                           175

Gln  Trp  Val  Asp  Tyr  Arg  Ala  Leu  Ala  Gly  Asp  Pro  Ser  Asp  Asn  Ile
               180                 185                      190

Pro  Gly  Val  Lys  Gly  Ile  Gly  Glu  Lys  Thr  Ala  Gln  Arg  Leu  Ile  Arg
          195                      200                      205
```

```
Glu  Trp  Gly  Ser  Leu  Glu  Asn  Leu  Phe  Gln  His  Leu  Asp  Gln  Val  Lys
     210                213                          220

Pro  Ser  Leu  Arg  Glu  Lys  Leu  Gln  Ala  Gly  Met  Glu  Ala  Leu  Ala  Leu
225                      230                235                          240

Ser  Arg  Lys  Leu  Ser  Gln  Val  His  Thr  Asp  Leu  Pro  Leu  Glu  Val  Asp
                    245                     250                          255

Phe  Gly  Arg  Arg  Arg  Thr  Pro  Asn  Leu  Glu  Gly  Leu  Arg  Ala  Phe  Leu
               260                     265                270

Glu  Arg  Leu  Glu  Phe  Gly  Ser  Leu  Leu  His  Glu  Phe  Gly  Leu  Leu  Glu
          275                     280                     285

Gly  Pro  Lys  Ala  Ala  Glu  Glu  Ala  Pro  Trp  Pro  Pro  Glu  Gly  Ala
     290                     295                     300

Phe  Leu  Gly  Phe  Ser  Phe  Ser  Arg  Pro  Glu  Pro  Met  Trp  Ala  Glu  Leu
305                      310                     315                          320

Leu  Ala  Leu  Ala  Gly  Ala  Trp  Glu  Gly  Arg  Leu  His  Arg  Ala  Gln  Asp
                    325                     330                          335

Pro  Leu  Arg  Gly  Leu  Arg  Asp  Leu  Lys  Gly  Val  Arg  Gly  Ile  Leu  Ala
               340                     345                     350

Lys  Asp  Leu  Ala  Val  Leu  Ala  Leu  Arg  Glu  Gly  Leu  Asp  Leu  Phe  Pro
          355                     360                     365

Glu  Asp  Asp  Pro  Met  Leu  Leu  Ala  Tyr  Leu  Leu  Asp  Pro  Ser  Asn  Thr
     370                     375                     380

Thr  Pro  Glu  Gly  Val  Ala  Arg  Arg  Tyr  Gly  Gly  Glu  Trp  Thr  Glu  Asp
385                      390                     395                          400

Ala  Gly  Glu  Arg  Ala  Leu  Leu  Ala  Glu  Arg  Leu  Phe  Gln  Thr  Leu  Lys
                    405                     410                          415

Glu  Arg  Leu  Lys  Gly  Glu  Glu  Arg  Leu  Leu  Trp  Leu  Tyr  Glu  Glu  Val
               420                     425                     430

Glu  Lys  Pro  Leu  Ser  Arg  Val  Leu  Ala  Arg  Met  Glu  Ala  Thr  Gly  Val
          435                     440                     445

Arg  Leu  Asp  Val  Ala  Tyr  Leu  Gln  Ala  Leu  Ser  Leu  Glu  Val  Glu  Ala
     450                     455                     460

Glu  Val  Arg  Gln  Leu  Glu  Glu  Glu  Val  Phe  Arg  Leu  Ala  Gly  His  Pro
465                      470                     475                          480

Phe  Asn  Leu  Asn  Ser  Arg  Asp  Gln  Leu  Glu  Arg  Val  Leu  Phe  Asp  Glu
                    485                     490                          495

Leu  Gly  Leu  Pro  Ala  Ile  Gly  Lys  Thr  Glu  Lys  Thr  Gly  Lys  Arg  Ser
               500                     505                     510

Thr  Ser  Ala  Ala  Val  Leu  Glu  Ala  Leu  Arg  Glu  Ala  His  Pro  Ile  Val
          515                     520                     525

Asp  Arg  Ile  Leu  Gln  Tyr  Arg  Glu  Leu  Thr  Lys  Leu  Lys  Asn  Thr  Tyr
     530                     535                     540

Ile  Asp  Pro  Leu  Pro  Ala  Leu  Val  His  Pro  Lys  Thr  Gly  Arg  Leu  His
545                      550                     555                          560

Thr  Arg  Phe  Asn  Gln  Thr  Ala  Thr  Ala  Thr  Gly  Arg  Leu  Ser  Ser  Ser
                    565                     570                          575

Asp  Pro  Asn  Leu  Gln  Asn  Ile  Pro  Val  Arg  Thr  Pro  Leu  Gly  Gln  Arg
               580                     585                     590

Ile  Arg  Arg  Ala  Phe  Val  Ala  Glu  Glu  Gly  Trp  Val  Leu  Val  Val  Leu
          595                     600                     605

Asp  Tyr  Ser  Gln  Ile  Glu  Leu  Arg  Val  Leu  Ala  His  Leu  Ser  Gly  Asp
     610                     615                     620

Glu  Asn  Leu  Ile  Arg  Val  Phe  Gln  Glu  Gly  Arg  Asp  Ile  His  Thr  Gln
625                      630                     635                          640
```

| | | | | | | | | | | | | | | |
|---|---|---|---|---|---|---|---|---|---|---|---|---|---|---|
| Thr | Ala | Ser | Trp | Met<br>645 | Phe | Gly | Val | Ser | Pro<br>650 | Glu | Gly | Val | Asp<br>655 | Pro | Leu |
| Met | Arg | Arg | Ala<br>660 | Ala | Lys | Thr | Ile | Asn<br>665 | Phe | Gly | Val | Leu | Tyr<br>670 | Gly | Met |
| Ser | Ala | His<br>675 | Arg | Leu | Ser | Gly | Glu<br>680 | Leu | Ser | Ile | Pro | Tyr<br>685 | Glu | Glu | Ala |
| Val | Ala<br>690 | Phe | Ile | Glu | Arg | Tyr<br>695 | Phe | Gln | Ser | Tyr | Pro<br>700 | Lys | Val | Arg | Ala |
| Trp<br>705 | Ile | Glu | Gly | Thr | Leu<br>710 | Glu | Glu | Gly | Arg | Arg<br>715 | Arg | Gly | Tyr | Val | Glu<br>720 |
| Thr | Leu | Phe | Gly | Arg<br>725 | Arg | Arg | Tyr | Val | Pro<br>730 | Asp | Leu | Asn | Ala | Arg<br>735 | Val |
| Lys | Ser | Val | Arg<br>740 | Glu | Ala | Ala | Glu | Arg<br>745 | Met | Ala | Phe | Asn | Met<br>750 | Pro | Val |
| Gln | Gly | Thr<br>755 | Ala | Ala | Asp | Leu | Met<br>760 | Lys | Leu | Ala | Met | Val<br>765 | Arg | Leu | Phe |
| Pro | Arg<br>770 | Leu | Gln | Glu | Leu | Gly<br>775 | Ala | Arg | Met | Leu | Leu<br>780 | Gln | Val | His | Asp |
| Glu<br>785 | Leu | Val | Leu | Glu | Ala<br>790 | Pro | Lys | Asp | Arg | Ala<br>795 | Glu | Arg | Val | Ala | Ala<br>800 |
| Leu | Ala | Lys | Glu | Val<br>805 | Met | Glu | Gly | Val | Trp<br>810 | Pro | Leu | Gln | Val | Pro<br>815 | Leu |
| Glu | Val | Glu | Val<br>820 | Gly | Leu | Gly | Glu | Asp<br>825 | Trp | Leu | Ser | Ala | Lys<br>830 | Glu | |

( 2 ) INFORMATION FOR SEQ ID NO:6:

( i ) SEQUENCE CHARACTERISTICS:
      ( A ) LENGTH: 834 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:6:

| | | | | | | | | | | | | | | |
|---|---|---|---|---|---|---|---|---|---|---|---|---|---|---|
| Met<br>1 | Glu | Ala | Met | Leu<br>5 | Pro | Leu | Phe | Glu | Pro<br>10 | Lys | Gly | Arg | Val | Leu<br>15 | Leu |
| Val | Asp | Gly | His<br>20 | His | Leu | Ala | Tyr | Arg<br>25 | Thr | Phe | Phe | Ala | Leu<br>30 | Lys | Gly |
| Leu | Thr | Thr<br>35 | Ser | Arg | Gly | Glu | Pro<br>40 | Val | Gln | Ala | Val | Tyr<br>45 | Gly | Phe | Ala |
| Lys | Ser<br>50 | Leu | Leu | Lys | Ala | Leu<br>55 | Lys | Glu | Asp | Gly | Tyr<br>60 | Lys | Ala | Val | Phe |
| Val<br>65 | Val | Phe | Asp | Ala | Lys<br>70 | Ala | Pro | Ser | Phe | Arg<br>75 | His | Glu | Ala | Tyr | Glu<br>80 |
| Ala | Tyr | Lys | Ala | Gly<br>85 | Arg | Ala | Pro | Thr | Pro<br>90 | Glu | Asp | Phe | Pro | Arg<br>95 | Gln |
| Leu | Ala | Leu | Ile<br>100 | Lys | Glu | Leu | Val | Asp<br>105 | Leu | Leu | Gly | Phe | Thr<br>110 | Arg | Leu |
| Glu | Val | Pro<br>115 | Gly | Tyr | Glu | Ala | Asp<br>120 | Asp | Val | Leu | Ala | Thr<br>125 | Leu | Ala | Lys |
| Lys | Ala<br>130 | Glu | Lys | Glu | Gly | Tyr<br>135 | Glu | Val | Arg | Ile | Leu<br>140 | Thr | Ala | Asp | Arg |
| Asp<br>145 | Leu | Tyr | Gln | Leu | Val<br>150 | Ser | Asp | Arg | Val | Ala<br>155 | Val | Leu | His | Pro | Glu<br>160 |

```
Gly His Leu Ile Thr Pro Glu Trp Leu Trp Glu Lys Tyr Gly Leu Arg
                165             170             175

Pro Glu Gln Trp Val Asp Phe Arg Ala Leu Val Gly Asp Pro Ser Asp
            180             185             190

Asn Leu Pro Gly Val Lys Gly Ile Gly Glu Lys Thr Ala Leu Lys Leu
        195             200             205

Leu Lys Glu Trp Gly Ser Leu Glu Asn Leu Leu Lys Asn Leu Asp Arg
    210             215             220

Val Lys Pro Glu Asn Val Arg Glu Lys Ile Lys Ala His Leu Glu Asp
225             230             235             240

Leu Arg Leu Ser Leu Glu Leu Ser Arg Val Arg Thr Asp Leu Pro Leu
                245             250             255

Glu Val Asp Leu Ala Gln Gly Arg Glu Pro Asp Arg Glu Gly Leu Arg
            260             265             270

Ala Phe Leu Glu Arg Leu Glu Phe Gly Ser Leu Leu His Glu Phe Gly
        275             280             285

Leu Leu Glu Ala Pro Ala Pro Leu Glu Glu Ala Pro Trp Pro Pro Pro
    290             295             300

Glu Gly Ala Phe Val Gly Phe Val Leu Ser Arg Pro Glu Pro Met Trp
305             310             315             320

Ala Glu Leu Lys Ala Leu Ala Ala Cys Arg Asp Gly Arg Val His Arg
                325             330             335

Ala Ala Asp Pro Leu Ala Gly Leu Lys Asp Leu Lys Glu Val Arg Gly
            340             345             350

Leu Leu Ala Lys Asp Leu Ala Val Leu Ala Ser Arg Glu Gly Leu Asp
        355             360             365

Leu Val Pro Gly Asp Asp Pro Met Leu Leu Ala Tyr Leu Leu Asp Pro
    370             375             380

Ser Asn Thr Thr Pro Glu Gly Val Ala Arg Arg Tyr Gly Gly Glu Trp
385             390             395             400

Thr Glu Asp Ala Ala His Arg Ala Leu Leu Ser Glu Arg Leu His Arg
                405             410             415

Asn Leu Leu Lys Arg Leu Glu Gly Glu Glu Lys Leu Leu Trp Leu Tyr
            420             425             430

His Glu Val Glu Lys Pro Leu Ser Arg Val Leu Ala His Met Glu Ala
        435             440             445

Thr Gly Val Arg Leu Asp Val Ala Tyr Leu Gln Ala Leu Ser Leu Glu
    450             455             460

Leu Ala Glu Glu Ile Arg Arg Leu Glu Glu Glu Val Phe Arg Leu Ala
465             470             475             480

Gly His Pro Phe Asn Leu Asn Ser Arg Asp Gln Leu Glu Arg Val Leu
                485             490             495

Phe Asp Glu Leu Arg Leu Pro Ala Leu Gly Lys Thr Gln Lys Thr Gly
            500             505             510

Lys Arg Ser Thr Ser Ala Ala Val Leu Glu Ala Leu Arg Glu Ala His
        515             520             525

Pro Ile Val Glu Lys Ile Leu Gln His Arg Glu Leu Thr Lys Leu Lys
    530             535             540

Asn Thr Tyr Val Asp Pro Leu Pro Ser Leu Val His Pro Arg Thr Gly
545             550             555             560

Arg Leu His Thr Arg Phe Asn Gln Thr Ala Thr Ala Thr Gly Arg Leu
                565             570             575

Ser Ser Ser Asp Pro Asn Leu Gln Asn Ile Pro Val Arg Thr Pro Leu
            580             585             590
```

| | | | | | | | | | | | | | | |
|---|---|---|---|---|---|---|---|---|---|---|---|---|---|---|
|Gly|Gln|Arg<br>595|Ile|Arg|Arg|Ala|Phe<br>600|Val|Ala|Glu|Ala|Gly<br>605|Trp|Ala|Leu|
|Val|Ala|Leu<br>610|Asp|Tyr|Ser|Gln<br>615|Ile|Glu|Leu|Arg|Val<br>620|Leu|Ala|His|Leu|
|Ser<br>625|Gly|Asp|Glu|Asn|Leu<br>630|Ile|Arg|Val|Phe|Gln<br>635|Glu|Gly|Lys|Asp|Ile<br>640|
|His|Thr|Gln|Thr|Ala<br>645|Ser|Trp|Met|Phe|Gly<br>650|Val|Pro|Pro|Glu|Ala|Val<br>655|
|Asp|Pro|Leu|Met<br>660|Arg|Arg|Ala|Ala|Lys<br>665|Thr|Val|Asn|Phe|Gly<br>670|Val|Leu|
|Tyr|Gly|Met<br>675|Ser|Ala|His|Arg|Leu<br>680|Ser|Gln|Glu|Leu|Ala<br>685|Ile|Pro|Tyr|
|Glu|Glu<br>690|Ala|Val|Ala|Phe|Ile<br>695|Glu|Arg|Tyr|Phe|Gln<br>700|Ser|Phe|Pro|Lys|
|Val<br>705|Arg|Ala|Trp|Ile|Glu<br>710|Lys|Thr|Leu|Glu|Glu<br>715|Gly|Arg|Lys|Arg|Gly<br>720|
|Tyr|Val|Glu|Thr|Leu<br>725|Phe|Gly|Arg|Arg|Arg<br>730|Tyr|Val|Pro|Asp|Leu<br>735|Asn|
|Ala|Arg|Val|Lys<br>740|Ser|Val|Arg|Glu|Ala<br>745|Ala|Glu|Arg|Met|Ala<br>750|Phe|Asn|
|Met|Pro|Val<br>755|Gln|Gly|Thr|Ala|Ala<br>760|Asp|Leu|Met|Lys|Leu<br>765|Ala|Met|Val|
|Lys|Leu|Phe|Pro<br>770|Arg|Leu|Arg|Glu|Met<br>775|Gly|Ala|Arg|Met<br>780|Leu|Leu|Gln|
|Val|His|Asp|Glu<br>785|Leu|Leu|Leu<br>790|Glu|Ala|Pro|Gln|Ala<br>795|Arg|Ala|Glu|Glu<br>800|
|Val|Ala|Ala|Leu|Ala<br>805|Lys|Glu|Ala|Met|Glu<br>810|Lys|Ala|Tyr|Pro|Leu<br>815|Ala|
|Val|Pro|Leu|Glu<br>820|Val|Glu|Val|Gly|Met<br>825|Gly|Glu|Asp|Trp|Leu<br>830|Ser|Ala|
|Lys|Gly| | | | | | | | | | | | | | |

( 2 ) INFORMATION FOR SEQ ID NO:7:

( i ) SEQUENCE CHARACTERISTICS:
        ( A ) LENGTH: 2502 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

```
ATGNNGGCGA  TGCTTCCCCT  CTTTGAGCCC  AAAGGCCGGG  TCCTCCTGGT  GGACGGCCAC      60
CACCTGGCCT  ACCGCACCTT  CTTCGCCCTG  AAGGGCCTCA  CCACCAGCCG  GGGCGAACCG     120
GTGCAGGCGG  TCTACGGCTT  CGCCAAGAGC  CTCCTCAAGG  CCCTGAAGGA  GGACGGGGAC     180
NNGGCGGTGN  TCGTGGTCTT  TGACGCCAAG  GCCCCCTCCT  TCCGCCACGA  GGCCTACGAG     240
GCCTACAAGG  CGGGCCGGGC  CCCCACCCCG  GAGGACTTTC  CCCGGCAGCT  CGCCCTCATC     300
AAGGAGCTGG  TGGACCTCCT  GGGGCTTGCG  CGCCTCGAGG  TCCCCGGCTA  CGAGGCGGAC     360
GACGTNCTGG  CCACCCTGGC  CAAGAAGGCG  GAAAAGGAGG  GGTACGAGGT  GCGCATCCTC     420
ACCGCCGACC  GCGACCTCTA  CCAGCTCCTT  TCCGACCGCA  TCGCCGTCCT  CCACCCCGAG     480
GGGTACCTCA  TCACCCCGGC  GTGGCTTTGG  GAGAAGTACG  GCCTGAGGCC  GGAGCAGTGG     540
GTGGACTACC  GGGCCCTGGC  GGGGGACCCC  TCCGACAACC  TCCCCGGGGT  CAAGGGCATC     600
```

| | | | | | |
|---|---|---|---|---|---|
| GGGGAGAAGA | CCGCCCNGAA | GCTCCTCNAG | GAGTGGGGGA | GCCTGGAAAA | CCTCCTCAAG | 660 |
| AACCTGGACC | GGGTGAAGCC | CGCCNTCCGG | GAGAAGATCC | AGGCCCACAT | GGANGACCTG | 720 |
| ANGCTCTCCT | GGGAGCTNTC | CCAGGTGCGC | ACCGACCTGC | CCCTGGAGGT | GGACTTCGCC | 780 |
| AAGNGGCGGG | AGCCCGACCG | GGAGGGGCTT | AGGGCCTTTC | TGGAGAGGCT | GGAGTTTGGC | 840 |
| AGCCTCCTCC | ACGAGTTCGG | CCTCCTGGAG | GGCCCCAAGG | CCCTGGAGGA | GGCCCCCTGG | 900 |
| CCCCCGCCGG | AAGGGGCCTT | CGTGGGCTTT | GTCCTTTCCC | GCCCCGAGCC | CATGTGGGCC | 960 |
| GAGCTTCTGG | CCCTGGCCGC | CGCCAGGGAG | GGCCGGGTCC | ACCGGGCACC | AGACCCCTTT | 1020 |
| ANGGGCCTNA | GGGACCTNAA | GGAGGTGCGG | GGNCTCCTCG | CCAAGGACCT | GGCCGTTTTG | 1080 |
| GCCCTGAGGG | AGGGCCTNGA | CCTCNTGCCC | GGGGACGACC | CCATGCTCCT | CGCCTACCTC | 1140 |
| CTGGACCCCT | CCAACACCAC | CCCCGAGGGG | GTGGCCCGGC | GCTACGGGGG | GGAGTGGACG | 1200 |
| GAGGANGCGG | GGGAGCGGGC | CCTCCTNTCC | GAGAGGCTCT | TCCNGAACCT | NNNGCAGCGC | 1260 |
| CTTGAGGGGG | AGGAGAGGCT | CCTTTGGCTT | TACCAGGAGG | TGGAGAAGCC | CCTTTCCCGG | 1320 |
| GTCCTGGCCC | ACATGGAGGC | CACGGGGGTN | CGGCTGGACG | TGGCCTACCT | CCAGGCCCTN | 1380 |
| TCCCTGGAGG | TGGCGGAGGA | GATCCGCCGC | CTCGAGGAGG | AGGTCTTCCG | CCTGGCCGGC | 1440 |
| CACCCCTTCA | ACCTCAACTC | CCGGGACCAG | CTGGAAAGGG | TGCTCTTTGA | CGAGCTNGGG | 1500 |
| CTTCCCGCCA | TCGGCAAGAC | GGAGAAGACN | GGCAAGCGCT | CCACCAGCGC | CGCCGTGCTG | 1560 |
| GAGGCCCTNC | GNGAGGCCCA | CCCCATCGTG | GAGAAGATCC | TGCAGTACCG | GGAGCTCACC | 1620 |
| AAGCTCAAGA | ACACCTACAT | NGACCCCCTG | CCNGNCCTCG | TCCACCCCAG | GACGGGCCGC | 1680 |
| CTCCACACCC | GCTTCAACCA | GACGGCCACG | GCCACGGGCA | GGCTTAGTAG | CTCCGACCCC | 1740 |
| AACCTGCAGA | ACATCCCCGT | CCGCACCCCN | CTGGGCCAGA | GGATCCGCCG | GGCCTTCGTG | 1800 |
| GCCGAGGAGG | GNTGGGTGTT | GGTGGCCCTG | GACTATAGCC | AGATAGAGCT | CCGGGTCCTG | 1860 |
| GCCCACCTCT | CCGGGGACGA | GAACCTGATC | CGGGTCTTCC | AGGAGGGGAG | GGACATCCAC | 1920 |
| ACCCAGACCG | CCAGCTGGAT | GTTCGGCGTC | CCCCCGGAGG | CCGTGGACCC | CCTGATGCGC | 1980 |
| CGGGCGGCCA | AGACCATCAA | CTTCGGGGTC | CTCTACGGCA | TGTCCGCCCA | CCGCCTCTCC | 2040 |
| CAGGAGCTTG | CCATCCCCTA | CGAGGAGGCG | GTGGCCTTCA | TTGAGCGCTA | CTTCCAGAGC | 2100 |
| TTCCCCAAGG | TGCGGGCCTG | GATTGAGAAG | ACCCTGGAGG | AGGGCAGGAG | GCGGGGGTAC | 2160 |
| GTGGAGACCC | TCTTCGGCCG | CCGGCGCTAC | GTGCCCGACC | TCAACGCCCG | GGTGAAGAGC | 2220 |
| GTGCGGGAGG | CGGCGGAGCG | CATGGCCTTC | AACATGCCCG | TCCAGGGCAC | CGCCGCCGAC | 2280 |
| CTCATGAAGC | TGGCCATGGT | GAAGCTCTTC | CCCCGGCTNC | AGGAAATGGG | GGCCAGGATG | 2340 |
| CTCCTNCAGG | TCCACGACGA | GCTGGTCCTC | GAGGCCCCCA | AAGAGCGGGC | GGAGGNGGTG | 2400 |
| GCCGCTTTGG | CCAAGGAGGT | CATGGAGGGG | GTCTATCCCC | TGGCCGTGCC | CCTGGAGGTG | 2460 |
| GAGGTGGGGA | TGGGGGAGGA | CTGGCTCTCC | GCCAAGGAGT | AG | | 2502 |

(2) INFORMATION FOR SEQ ID NO:8:

(i) SEQUENCE CHARACTERISTICS:
(A) LENGTH: 833 amino acids
(B) TYPE: amino acid
(C) STRANDEDNESS: single
(D) TOPOLOGY: unknown (ii) MOLECULE TYPE: peptide (xi) SEQUENCE DESCRIPTION: SEQ ID NO:8:

| Met | Xaa | Ala | Met | Leu | Pro | Leu | Phe | Glu | Pro | Lys | Gly | Arg | Val | Leu | Leu |
|---|---|---|---|---|---|---|---|---|---|---|---|---|---|---|---|
| 1 | | | | 5 | | | | | 10 | | | | | 15 | |

| | | | | | | | | | | | | | |
|---|---|---|---|---|---|---|---|---|---|---|---|---|---|
|Val|Asp|Gly|His 20|His|Leu|Ala|Tyr 25|Arg|Thr|Phe|Phe 30|Ala|Leu|Lys|Gly|
|Leu|Thr|Thr 35|Ser|Arg|Gly|Glu|Pro 40|Val|Gln|Ala|Val 45|Tyr|Gly|Phe|Ala|
|Lys|Ser 50|Leu|Leu|Lys|Ala|Leu 55|Lys|Glu|Asp|Gly|Asp 60|Ala|Val|Xaa|Val|
|Val 65|Phe|Asp|Ala|Lys|Ala 70|Pro|Ser|Phe|Arg|His 75|Glu|Ala|Tyr|Glu|Ala 80|
|Tyr|Lys|Ala|Gly|Arg 85|Ala|Pro|Thr|Pro|Glu 90|Asp|Phe|Pro|Arg|Gln 95|Leu|
|Ala|Leu|Ile|Lys 100|Glu|Leu|Val|Asp|Leu 105|Leu|Gly|Leu|Xaa|Arg 110|Leu|Glu|
|Val|Pro|Gly 115|Tyr|Glu|Ala|Asp|Asp 120|Val|Leu|Ala|Thr|Leu 125|Ala|Lys|Lys|
|Ala|Glu 130|Lys|Glu|Gly|Tyr|Glu 135|Val|Arg|Ile|Leu|Thr 140|Ala|Asp|Arg|Asp|
|Leu 145|Tyr|Gln|Leu|Leu|Ser 150|Asp|Arg|Ile|Ala|Val 155|Leu|His|Pro|Glu|Gly 160|
|Tyr|Leu|Ile|Thr|Pro 165|Ala|Trp|Leu|Trp|Glu 170|Lys|Tyr|Gly|Leu|Arg 175|Pro|
|Glu|Gln|Trp|Val 180|Asp|Tyr|Arg|Ala|Xaa 185|Gly|Asp|Pro|Ser 190|Asp|Asn|
|Leu|Pro|Gly 195|Val|Lys|Gly|Ile|Gly 200|Glu|Lys|Thr|Ala|Xaa 205|Lys|Leu|Leu|
|Xaa 210|Glu|Trp|Gly|Ser|Leu 215|Glu|Asn|Leu|Leu|Lys 220|Asn|Leu|Asp|Arg|Val|
|Lys 225|Pro|Xaa|Xaa|Arg|Glu 230|Lys|Ile|Xaa|Ala|His 235|Met|Glu|Asp|Leu|Xaa 240|
|Leu|Ser|Xaa|Xaa|Leu 245|Ser|Xaa|Val|Arg|Thr 250|Asp|Leu|Pro|Leu|Glu 255|Val|
|Asp|Phe|Ala|Xaa 260|Arg|Arg|Glu|Pro|Asp 265|Arg|Glu|Gly|Leu|Arg 270|Ala|Phe|
|Leu|Glu|Arg 275|Leu|Glu|Phe|Gly|Ser 280|Leu|Leu|His|Glu|Phe 285|Gly|Leu|Leu|
|Glu|Xaa 290|Pro|Lys|Ala|Leu|Glu 295|Ala|Pro|Trp|Pro 300|Pro|Glu|Gly|
|Ala 305|Phe|Val|Gly|Phe|Val 310|Leu|Ser|Arg|Pro|Glu 315|Pro|Met|Trp|Ala|Glu 320|
|Leu|Leu|Ala|Leu|Ala 325|Ala|Ala|Arg|Xaa|Gly 330|Arg|Val|His|Arg|Ala|Xaa 335|
|Asp|Pro|Leu|Xaa 340|Gly|Leu|Arg|Asp|Leu 345|Lys|Glu|Val|Arg|Gly 350|Leu|Leu|
|Ala|Lys|Asp 355|Leu|Ala|Val|Leu|Ala 360|Leu|Arg|Glu|Gly|Leu 365|Asp|Leu|Xaa|
|Pro|Gly 370|Asp|Asp|Pro|Met|Leu 375|Leu|Ala|Tyr|Leu|Leu 380|Asp|Pro|Ser|Asn|
|Thr 385|Thr|Pro|Glu|Gly|Val 390|Ala|Arg|Arg|Tyr|Gly 395|Gly|Glu|Trp|Thr|Glu 400|
|Asp|Ala|Gly|Glu|Arg 405|Ala|Leu|Leu|Ser|Glu 410|Arg|Leu|Phe|Xaa|Asn 415|Leu|
|Xaa|Xaa|Arg|Leu 420|Glu|Gly|Glu|Glu|Arg 425|Leu|Leu|Trp|Leu|Tyr 430|Xaa|Glu|

| | | | | | | | | | | | | | | |
|---|---|---|---|---|---|---|---|---|---|---|---|---|---|---|
|Val|Glu|Lys|Pro|Leu|Ser|Arg|Val|Leu|Ala|His|Met|Glu|Ala|Thr|Gly|
| | |435| | | | |440| | | |445| | | |
|Val|Arg|Leu|Asp|Val|Ala|Tyr|Leu|Gln|Ala|Leu|Ser|Leu|Glu|Val|Ala|
| |450| | | | |455| | | |460| | | | | |
|Glu|Glu|Ile|Arg|Arg|Leu|Glu|Glu|Val|Phe|Arg|Leu|Ala|Gly|His|
|465| | | | |470| | | |475| | | | |480|
|Pro|Phe|Asn|Leu|Asn|Ser|Arg|Asp|Gln|Leu|Glu|Arg|Val|Leu|Phe|Asp|
| | | | |485| | | | |490| | | | |495| |
|Glu|Leu|Gly|Leu|Pro|Ala|Ile|Gly|Lys|Thr|Glu|Lys|Thr|Gly|Lys|Arg|
| | | |500| | | |505| | | |510| | | | |
|Ser|Thr|Ser|Ala|Ala|Val|Leu|Glu|Ala|Leu|Arg|Glu|Ala|His|Pro|Ile|
| | |515| | | |520| | | |525| | | | | |
|Val|Glu|Lys|Ile|Leu|Gln|Tyr|Arg|Glu|Leu|Thr|Lys|Leu|Lys|Asn|Thr|
| |530| | | |535| | | |540| | | | | | |
|Tyr|Ile|Asp|Pro|Leu|Pro|Xaa|Leu|Val|His|Pro|Arg|Thr|Gly|Arg|Leu|
|545| | | |550| | | | |555| | | | |560| |
|His|Thr|Arg|Phe|Asn|Gln|Thr|Ala|Thr|Ala|Thr|Gly|Arg|Leu|Ser|Ser|
| | | |565| | | |570| | | | |575| | | |
|Ser|Asp|Pro|Asn|Leu|Gln|Asn|Ile|Pro|Val|Arg|Thr|Pro|Leu|Gly|Gln|
| | |580| | | |585| | | |590| | | | | |
|Arg|Ile|Arg|Arg|Ala|Phe|Val|Ala|Glu|Glu|Gly|Trp|Xaa|Leu|Val|Ala|
| |595| | | |600| | | |605| | | | | | |
|Leu|Asp|Tyr|Ser|Gln|Ile|Glu|Leu|Arg|Val|Leu|Ala|His|Leu|Ser|Gly|
| |610| | | |615| | | |620| | | | | | |
|Asp|Glu|Asn|Leu|Ile|Arg|Val|Phe|Gln|Glu|Gly|Arg|Asp|Ile|His|Thr|
|625| | | |630| | | |635| | | | | |640| |
|Gln|Thr|Ala|Ser|Trp|Met|Phe|Gly|Val|Pro|Pro|Glu|Ala|Val|Asp|Pro|
| | | |645| | | |650| | | |655| | | | |
|Leu|Met|Arg|Arg|Ala|Ala|Lys|Thr|Ile|Asn|Phe|Gly|Val|Leu|Tyr|Gly|
| | |660| | | |665| | | |670| | | | | |
|Met|Ser|Ala|His|Arg|Leu|Ser|Gln|Glu|Leu|Ala|Ile|Pro|Tyr|Glu|Glu|
| | |675| | | |680| | | |685| | | | | |
|Ala|Val|Ala|Phe|Ile|Glu|Arg|Tyr|Phe|Gln|Ser|Phe|Pro|Lys|Val|Arg|
|690| | | |695| | | |700| | | | | | | |
|Ala|Trp|Ile|Glu|Lys|Thr|Leu|Glu|Glu|Gly|Arg|Arg|Arg|Gly|Tyr|Val|
|705| | | |710| | | |715| | | | | |720| |
|Glu|Thr|Leu|Phe|Gly|Arg|Arg|Arg|Tyr|Val|Pro|Asp|Leu|Asn|Ala|Arg|
| | | |725| | | |730| | | |735| | | | |
|Val|Lys|Ser|Val|Arg|Glu|Ala|Ala|Glu|Arg|Met|Ala|Phe|Asn|Met|Pro|
| | |740| | | |745| | | |750| | | | | |
|Val|Gln|Gly|Thr|Ala|Ala|Asp|Leu|Met|Lys|Leu|Ala|Met|Val|Lys|Leu|
| |755| | | | |760| | | |765| | | | | |
|Phe|Pro|Arg|Leu|Xaa|Glu|Met|Gly|Ala|Arg|Met|Leu|Leu|Gln|Val|His|
| |770| | | |775| | | |780| | | | | | |
|Asp|Glu|Leu|Val|Leu|Glu|Ala|Pro|Lys|Xaa|Arg|Ala|Glu|Xaa|Val|Ala|
|785| | | |790| | | |795| | | | | |800| |
|Ala|Leu|Ala|Lys|Glu|Val|Met|Glu|Gly|Val|Tyr|Pro|Leu|Ala|Val|Pro|
| | | |805| | | |810| | | |815| | | | |
|Leu|Glu|Val|Glu|Val|Gly|Xaa|Gly|Glu|Asp|Trp|Leu|Ser|Ala|Lys|Glu|
| | |820| | | |825| | | |830| | | | | |
|Xaa| | | | | | | | | | | | | | | |

( 2 ) INFORMATION FOR SEQ ID NO:9:

( i ) SEQUENCE CHARACTERISTICS:
  ( A ) LENGTH: 1647 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:9:

| | | | | | | |
|---|---|---|---|---|---|---|
| ATGAATTCGG | GGATGCTGCC | CCTCTTTGAG | CCCAAGGGCC | GGGTCCTCCT | GGTGGACGGC | 60 |
| CACCACCTGG | CCTACCGCAC | CTTCCACGCC | CTGAAGGGCC | TCACCACCAG | CCGGGGGGAG | 120 |
| CCGGTGCAGG | CGGTCTACGG | CTTCGCCAAG | AGCCTCCTCA | AGGCCCTCAA | GGAGGACGGG | 180 |
| GACGCGGTGA | TCGTGGTCTT | TGACGCCAAG | GCCCCTCCT | TCCGCCACGA | GGCCTACGGG | 240 |
| GGGTACAAGG | CGGGCCGGGC | CCCCACGCCG | GAGGACTTTC | CCCGGCAACT | CGCCCTCATC | 300 |
| AAGGAGCTGG | TGGACCTCCT | GGGGCTGGCG | CGCCTCGAGG | TCCCGGGCTA | CGAGGCGGAC | 360 |
| GACGTCCTGG | CCAGCCTGGC | CAAGAAGGCG | GAAAAGGAGG | GCTACGAGGT | CCGCATCCTC | 420 |
| ACCGCCGACA | AAGACCTTTA | CCAGCTCCTT | TCCGACCGCA | TCCACGTCCT | CCACCCCGAG | 480 |
| GGGTACCTCA | TCACCCCGGC | CTGGCTTTGG | GAAAAGTACG | GCCTGAGGCC | CGACCAGTGG | 540 |
| GCCGACTACC | GGGCCCTGAC | CGGGGACGAG | TCCGACAACC | TTCCCGGGGT | CAAGGGCATC | 600 |
| GGGGAGAAGA | CGGCGAGGAA | GCTTCTGGAG | GAGTGGGGGA | GCCTGGAAGC | CCTCCTCAAG | 660 |
| AACCTGGACC | GGCTGAAGCC | CGCCATCCGG | GAGAAGATCC | TGGCCCACAT | GGACGATCTG | 720 |
| AAGCTCTCCT | GGGACCTGGC | CAAGGTGCGC | ACCGACCTGC | CCCTGGAGGT | GGACTTCGCC | 780 |
| AAAAGGCGGG | AGCCCGACCG | GGAGAGGCTT | AGGGCCTTTC | TGGAGAGGCT | TGAGTTTGGC | 840 |
| AGCCTCCTCC | ACGAGTTCGG | CCTTCTGGAA | AGCCCCAAGG | CCCTGGAGGA | GGCCCCCTGG | 900 |
| CCCCCGCCGG | AAGGGGCCTT | CGTGGGCTTT | GTGCTTTCCC | GCAAGGAGCC | CATGTGGGCC | 960 |
| GATCTTCTGG | CCCTGGCCGC | CGCCAGGGGG | GGCCGGGTCC | ACCGGGCCCC | CGAGCCTTAT | 1020 |
| AAAGCCCTCA | GGGACCTGAA | GGAGGCGCGG | GGGCTTCTCG | CCAAAGACCT | GAGCGTTCTG | 1080 |
| GCCCTGAGGG | AAGGCCTTGG | CCTCCCGCCC | GGCGACGACC | CCATGCTCCT | CGCCTACCTC | 1140 |
| CTGGACCCTT | CCAACACCAC | CCCCGAGGGG | GTGGCCCGGC | GCTACGGCGG | GGAGTGGACG | 1200 |
| GAGGAGGCGG | GGGAGCGGGC | CGCCCTTTCC | GAGAGGCTCT | TCGCCAACCT | GTGGGGGAGG | 1260 |
| CTTGAGGGGG | AGGAGAGGCT | CCTTTGGCTT | TACCGGGAGG | TGGAGAGGCC | CCTTTCCGCT | 1320 |
| GTCCTGGCCC | ACATGGAGGC | CACGGGGGTG | CGCCTGGACG | TGGCCTATCT | CAGGGCCTTG | 1380 |
| TCCCTGGAGG | TGGCCGGGGA | GATCGCCCGC | CTCGAGGCCG | AGGTCTTCCG | CCTGGCCGGC | 1440 |
| CACCCCTTCA | ACCTCAACTC | CCGGGACCAG | CTGGAAAGGG | TCCTCTTTGA | CGAGCTAGGG | 1500 |
| CTTCCCGCCA | TCGGCAAGAC | GGAGAAGACC | GGCAAGCGCT | CCACCAGCGC | CGCCGTCCTG | 1560 |
| GAGGCCCTCC | GCGAGGCCCA | CCCCATCGTG | GAGAAGATCC | TGCAGGCATG | CAAGCTTGGC | 1620 |
| ACTGGCCGTC | GTTTTACAAC | GTCGTGA | | | | 1647 |

( 2 ) INFORMATION FOR SEQ ID NO:10:

( i ) SEQUENCE CHARACTERISTICS:
  ( A ) LENGTH: 2088 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:10:

| | | | | | | |
|---|---|---|---|---|---|---|
| ATGAATTCGG | GGATGCTGCC | CCTCTTTGAG | CCCAAGGGCC | GGGTCCTCCT | GGTGGACGGC | 60 |

| | | | | | | |
|---|---|---|---|---|---|---|
| CACCACCTGG | CCTACCGCAC | CTTCCACGCC | CTGAAGGGCC | TCACCACCAG | CCGGGGGGAG | 120 |
| CCGGTGCAGG | CGGTCTACGG | CTTCGCCAAG | AGCCTCCTCA | AGGCCCTCAA | GGAGGACGGG | 180 |
| GACGCGGTGA | TCGTGGTCTT | TGACGCCAAG | GCCCCCTCCT | TCCGCCACGA | GGCCTACGGG | 240 |
| GGGTACAAGG | CGGGCCGGGC | CCCCACGCCG | GAGGACTTTC | CCCGGCAACT | CGCCCTCATC | 300 |
| AAGGAGCTGG | TGGACCTCCT | GGGGCTGGCG | CGCCTCGAGG | TCCCGGGCTA | CGAGGCGGAC | 360 |
| GACGTCCTGG | CCAGCCTGGC | CAAGAAGGCG | GAAAAGGAGG | GCTACGAGGT | CCGCATCCTC | 420 |
| ACCGCCGACA | AAGACCTTTA | CCAGCTCCTT | TCCGACCGCA | TCCACGTCCT | CCACCCCGAG | 480 |
| GGGTACCTCA | TCACCCCGGC | CTGGCTTTGG | GAAAAGTACG | GCCTGAGGCC | CGACCAGTGG | 540 |
| GCCGACTACC | GGGCCCTGAC | CGGGGACGAG | TCCGACAACC | TTCCCGGGGT | CAAGGGCATC | 600 |
| GGGGAGAAGA | CGGCGAGGAA | GCTTCTGGAG | GAGTGGGGGA | GCCTGGAAGC | CCTCCTCAAG | 660 |
| AACCTGGACC | GGCTGAAGCC | CGCCATCCGG | GAGAAGATCC | TGGCCCACAT | GGACGATCTG | 720 |
| AAGCTCTCCT | GGGACCTGGC | CAAGGTGCGC | ACCGACCTGC | CCCTGGAGGT | GGACTTCGCC | 780 |
| AAAAGGCGGG | AGCCCGACCG | GGAGAGGCTT | AGGGCCTTTC | TGGAGAGGCT | TGAGTTTGGC | 840 |
| AGCCTCCTCC | ACGAGTTCGG | CCTTCTGGAA | AGCCCCAAGG | CCCTGGAGGA | GGCCCCTGG | 900 |
| CCCCCGCCGG | AAGGGGCCTT | CGTGGGCTTT | GTGCTTTCCC | GCAAGGAGCC | CATGTGGGCC | 960 |
| GATCTTCTGG | CCCTGGCCGC | CGCCAGGGGG | GGCCGGGTCC | ACCGGGCCCC | CGAGCCTTAT | 1020 |
| AAAGCCCTCA | GGGACCTGAA | GGAGGCGCGG | GGGCTTCTCG | CCAAAGACCT | GAGCGTTCTG | 1080 |
| GCCCTGAGGG | AAGGCCTTGG | CCTCCCGCCC | GGCGACGACC | CCATGCTCCT | CGCCTACCTC | 1140 |
| CTGGACCCTT | CCAACACCAC | CCCCGAGGGG | GTGGCCCGGC | GCTACGGCGG | GGAGTGGACG | 1200 |
| GAGGAGGCGG | GGGAGCGGGC | CGCCCTTTCC | GAGAGGCTCT | TCGCCAACCT | GTGGGGGAGG | 1260 |
| CTTGAGGGGG | AGGAGAGGCT | CCTTTGGCTT | TACCGGGAGG | TGGAGAGGCC | CCTTTCCGCT | 1320 |
| GTCCTGGCCC | ACATGGAGGC | CACGGGGGTG | CGCCTGGACG | TGGCCTATCT | CAGGGCCTTG | 1380 |
| TCCCTGGAGG | TGGCCGGGGA | GATCGCCCGC | CTCGAGGCCG | AGGTCTTCCG | CCTGGCCGGC | 1440 |
| CACCCCTTCA | ACCTCAACTC | CCGGGACCAG | CTGGAAAGGG | TCCTCTTTGA | CGAGCTAGGG | 1500 |
| CTTCCCGCCA | TCGGCAAGAC | GGAGAAGACC | GGCAAGCGCT | CCACCAGCGC | CGCCGTCCTG | 1560 |
| GAGGCCCTCC | GCGAGGCCCA | CCCCATCGTG | GAGAAGATCC | TGCAGTACCG | GGAGCTCACC | 1620 |
| AAGCTGAAGA | GCACCTACAT | TGACCCCTTG | CCGGACCTCA | TCCACCCCAG | GACGGGCCGC | 1680 |
| CTCCACACCC | GCTTCAACCA | GACGGCCACG | GCCACGGGCA | GGCTAAGTAG | CTCCGATCCC | 1740 |
| AACCTCCAGA | ACATCCCCGT | CCGCACCCCG | CTTGGGCAGA | GGATCCGCCG | GGCCTTCATC | 1800 |
| GCCGAGGAGG | GGTGGCTATT | GGTGGCCCTG | GACTATAGCC | AGATAGAGCT | CAGGGTGCTG | 1860 |
| GCCCACCTCT | CCGGCGACGA | GAACCTGATC | CGGGTCTTCC | AGGAGGGGCG | GGACATCCAC | 1920 |
| ACGGAGACCG | CCAGCTGGAT | GTTCGGCGTC | CCCCGGGAGG | CCGTGGACCC | CCTGATGCGC | 1980 |
| CGGGCGGCCA | AGACCATCAA | CTTCGGGGTC | CTCTACGGCA | TGTCGGCCCA | CCGCCTCTCC | 2040 |
| CAGGAGCTAG | CTAGCCATCC | CTTACGAGGA | GGCCCAGGCC | TTCATTGA | | 2088 |

( 2 ) INFORMATION FOR SEQ ID NO:11:

( i ) SEQUENCE CHARACTERISTICS:
( A ) LENGTH: 962 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:11:

| | | | | | | |
|---|---|---|---|---|---|---|
| ATGAATTCGG | GGATGCTGCC | CCTCTTTGAG | CCCAAGGGCC | GGGTCCTCCT | GGTGGACGGC | 60 |
| CACCACCTGG | CCTACCGCAC | CTTCCACGCC | CTGAAGGGCC | TCACCACCAG | CCGGGGGGAG | 120 |
| CCGGTGCAGG | CGGTCTACGG | CTTCGCCAAG | AGCCTCCTCA | AGGCCCTCAA | GGAGGACGGG | 180 |
| GACGCGGTGA | TCGTGGTCTT | TGACGCCAAG | GCCCCCTCCT | TCCGCCACGA | GGCCTACGGG | 240 |
| GGGTACAAGG | CGGGCCGGGC | CCCCACGCCG | GAGGACTTTC | CCCGGCAACT | CGCCCTCATC | 300 |
| AAGGAGCTGG | TGGACCTCCT | GGGGCTGGCG | CGCCTCGAGG | TCCCGGGCTA | CGAGGCGGAC | 360 |
| GACGTCCTGG | CCAGCCTGGC | CAAGAAGGCG | GAAAAGGAGG | CTACGAGGT | CCGCATCCTC | 420 |
| ACCGCCGACA | AAGACCTTTA | CCAGCTTCTT | TCCGACCGCA | TCCACGTCCT | CCACCCCGAG | 480 |
| GGGTACCTCA | TCACCCCGGC | CTGGCTTTGG | GAAAAGTACG | GCCTGAGGCC | CGACCAGTGG | 540 |
| GCCGACTACC | GGGCCCTGAC | CGGGGACGAG | TCCGACAACC | TTCCCGGGGT | CAAGGGCATC | 600 |
| GGGGAGAAGA | CGGCGAGGAA | GCTTCTGGAG | GAGTGGGGGA | GCCTGGAAGC | CCTCCTCAAG | 660 |
| AACCTGGACC | GGCTGAAGCC | CGCCATCCGG | GAGAAGATCC | TGGCCCACAT | GGACGATCTG | 720 |
| AAGCTCTCCT | GGGACCTGGC | CAAGGTGCGC | ACCGACCTGC | CCCTGGAGGT | GGACTTCGCC | 780 |
| AAAAGGCGGG | AGCCCGACCG | GGAGAGGCTT | AGGGCCTTTC | TGGAGAGGCT | TGAGTTTGGC | 840 |
| AGCCTCCTCC | ACGAGTTCGG | CCTTCTGGAA | AGCCCCAAGT | CATGGAGGGG | GTGTATCCCC | 900 |
| TGGCCGTGCC | CCTGGAGGTG | GAGGTGGGGA | TAGGGAGGA | CTGGCTCTCC | GCCAAGGAGT | 960 |
| GA | | | | | | 962 |

( 2 ) INFORMATION FOR SEQ ID NO:12:

( i ) SEQUENCE CHARACTERISTICS:
        ( A ) LENGTH: 1600 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:12:

| | | | | | | |
|---|---|---|---|---|---|---|
| ATGGAATTCG | GGATGCTGC | CCCTCTTTGA | GCCCAAGGGC | CGGGTCCTCC | TGGTGGACGG | 60 |
| CCACCACCTG | GCCTACCGCA | CCTTCCACGC | CCTGAAGGGC | CTCACCACCA | GCCGGGGGA | 120 |
| GCCGGTGCAG | GCGGTCTACG | GCTTCGCCAA | GAGCCTCCTC | AAGGCCCTCA | AGGAGGACGG | 180 |
| GGACGCGGTG | ATCGTGGTCT | TTGACGCCAA | GGCCCCCTCC | TTCCGCCACG | AGGCCTACGG | 240 |
| GGGGTACAAG | GCGGGCCGGG | CCCCCACGCC | GGAGGACTTT | CCCCGGCAAC | TCGCCCTCAT | 300 |
| CAAGGAGCTG | GTGGACCTCC | TGGGGCTGGC | GCGCCTCGAG | GTCCCGGGCT | ACGAGGCGGA | 360 |
| CGACGTCCTG | GCCAGCCTGG | CCAAGAAGGC | GGAAAAGGAG | GCTACGAGG | TCCGCATCCT | 420 |
| CACCGCCGAC | AAAGACCTTT | ACCAGCTCCT | TTCCGACCGC | ATCCACGTCC | TCCACCCCGA | 480 |
| GGGGTACCTC | ATCACCCCGG | CCTGGCTTTG | GGAAAAGTAC | GGCCTGAGGC | CCGACCAGTG | 540 |
| GGCCGACTAC | CGGGCCCTGA | CCGGGGACGA | GTCCGACAAC | CTTCCCGGGG | TCAAGGGCAT | 600 |
| CGGGGAGAAG | ACGGCGAGGA | AGCTTCTGGA | GGAGTGGGGG | AGCCTGGAAG | CCCTCCTCAA | 660 |
| GAACCTGGAC | CGGCTGAAGC | CCGCCATCCG | GGAGAAGATC | CTGGCCCACA | TGGACGATCT | 720 |
| GAAGCTCTCC | TGGGACCTGG | CCAAGGTGCG | CACCGACCTG | CCCCTGGAGG | TGGACTTCGC | 780 |
| CAAAAGGCGG | GAGCCCGACC | GGGAGAGGCT | TAGGGCCTTT | CTGGAGAGGC | TTGAGTTTGG | 840 |
| CAGCCTCCTC | CACGAGTTCG | GCCTTCTGGA | AAGCCCCAAG | ATCCGCCGGG | CCTTCATCGC | 900 |
| CGAGGAGGGG | TGGCTATTGG | TGGCCCTGGA | CTATAGCCAG | ATAGAGCTCA | GGGTGCTGGC | 960 |

| | | | | | |
|---|---|---|---|---|---|
| CCACCTCTCC | GGCGACGAGA | ACCTGATCCG | GGTCTTCCAG | GAGGGGCGGG | ACATCCACAC | 1020
| GGAGACCGCC | AGCTGGATGT | TCGGCGTCCC | CCGGGAGGCC | GTGGACCCCC | TGATGCGCCG | 1080
| GGCGGCCAAG | ACCATCAACT | TCGGGGTCCT | CTACGGCATG | TCGGCCCACC | GCCTCTCCCA | 1140
| GGAGCTAGCC | ATCCCTTACG | AGGAGGCCCA | GGCCTTCATT | GAGCGCTACT | TTCAGAGCTT | 1200
| CCCCAAGGTG | CGGGCCTGGA | TTGAGAAGAC | CCTGGAGGAG | GGCAGGAGGC | GGGGTACGT | 1260
| GGAGACCCTC | TTCGGCCGCC | GCCGCTACGT | GCCAGACCTA | GAGGCCCGGG | TGAAGAGCGT | 1320
| GCGGGAGGCG | GCCGAGCGCA | TGGCCTTCAA | CATGCCCGTC | CGGGGCACCG | CCGCCGACCT | 1380
| CATGAAGCTG | GCTATGGTGA | AGCTCTTCCC | CAGGCTGGAG | GAAATGGGGG | CCAGGATGCT | 1440
| CCTTCAGGTC | CACGACGAGC | TGGTCCTCGA | GGCCCCAAAA | GAGAGGGCGG | AGGCCGTGGC | 1500
| CCGGCTGGCC | AAGGAGGTCA | TGGAGGGGGT | GTATCCCCTG | GCCGTGCCCC | TGGAGGTGGA | 1560
| GGTGGGGATA | GGGGAGGACT | GGCTCTCCGC | CAAGGAGTGA | | | 1600

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

| | | | |
|---|---|---|---|
| CACGAATTCG | GGGATGCTGC | CCCTCTTTGA | GCCCAA | 36

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| | | | |
|---|---|---|---|
| GTGAGATCTA | TCACTCCTTG | GCGGAGAGCC | AGTC | 34

( 2 ) INFORMATION FOR SEQ ID NO:15:

( i ) SEQUENCE CHARACTERISTICS:
        ( A ) LENGTH: 91 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

| | | | | | |
|---|---|---|---|---|---|
| TAATACGACT | CACTATAGGG | AGACCGGAAT | TCGAGCTCGC | CCGGGCGAGC | TCGAATTCCG | 60
| TGTATTCTAT | AGTGTCACCT | AAATCGAATT | C | | | 91

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:16:

TAATACGACT CACTATAGGG    20

(2) INFORMATION FOR SEQ ID NO:17:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

GAATTCGATT TAGGTGACAC TATAGAA    27

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

GTAATCATGG TCATAGCTGG TAGCTTGCTA C    31

(2) INFORMATION FOR SEQ ID NO:19:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

GGATCCTCTA GAGTCGACCT GCAGGCATGC CTACCTTGGT AG    42

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

GGATCCTCTA GAGTCGACCT GCAGGCATGC    30

(2) INFORMATION FOR SEQ ID NO:21:

(i) SEQUENCE CHARACTERISTICS:
        (A) LENGTH: 2502 base pairs
        (B) TYPE: nucleic acid
        (C) STRANDEDNESS: double
        (D) TOPOLOGY: linear (i i) MOLECULE TYPE: DNA (genomic)

(x i) SEQUENCE DESCRIPTION: SEQ ID NO:21:

ATGAATTCGG GGATGCTGCC CCTCTTTGAG CCCAAGGGCC GGGTCCTCCT GGTGGACGGC    60

```
CACCACCTGG CCTACCGCAC CTTCCACGCC CTGAAGGGCC TCACCACCAG CCGGGGGGAG    120
CCGGTGCAGG CGGTCTACGG CTTCGCCAAG AGCCTCCTCA AGGCCCTCAA GGAGGACGGG    180
GACGCGGTGA TCGTGGTCTT TGACGCCAAG GCCCCCTCCT TCCGCCACGA GGCCTACGGG    240
GGGTACAAGG CGGGCCGGGC CCCCACGCCG GAGGACTTTC CCCGGCAACT CGCCCTCATC    300
AAGGAGCTGG TGGACCTCCT GGGGCTGGCG CGCCTCGAGG TCCCGGGCTA CGAGGCGGAC    360
GACGTCCTGG CCAGCCTGGC CAAGAAGGCG GAAAAGGAGG CTACGAGGT CCGCATCCTC    420
ACCGCCGACA AAGACCTTTA CCAGCTCCTT TCCGACCGCA TCCACGTCCT CCACCCCGAG    480
GGGTACCTCA TCACCCCGGC CTGGCTTTGG GAAAAGTACG GCCTGAGGCC CGACCAGTGG    540
GCCGACTACC GGGCCCTGAC CGGGGACGAG TCCGACAACC TTCCCGGGGT CAAGGGCATC    600
GGGGAGAAGA CGGCGAGGAA GCTTCTGGAG GAGTGGGGGA GCCTGGAAGC CCTCCTCAAG    660
AACCTGGACC GGCTGAAGCC CGCCATCCGG GAGAAGATCC TGGCCCACAT GGACGATCTG    720
AAGCTCTCCT GGGACCTGGC CAAGGTGCGC ACCGACCTGC CCCTGGAGGT GGACTTCGCC    780
AAAAGGCGGG AGCCCGACCG GGAGAGGCTT AGGGCCTTTC TGGAGAGGCT TGAGTTTGGC    840
AGCCTCCTCC ACGAGTTCGG CCTTCTGGAA AGCCCCAAGG CCCTGGAGGA GGCCCCCTGG    900
CCCCCGCCGG AAGGGGCCTT CGTGGGCTTT GTGCTTTCCC GCAAGGAGCC CATGTGGGCC    960
GATCTTCTGG CCCTGGCCGC CGCCAGGGGG GGCCGGGTCC ACCGGGCCCC CGAGCCTTAT   1020
AAAGCCCTCA GGGACCTGAA GGAGGCGCGG GGGCTTCTCG CCAAAGACCT GAGCGTTCTG   1080
GCCCTGAGGG AAGGCCTTGG CCTCCCGCCC GGCGACGACC CCATGCTCCT CGCCTACCTC   1140
CTGGACCCTT CCAACACCAC CCCCGAGGGG GTGGCCCGGC GCTACGGCGG GGAGTGGACG   1200
GAGGAGGCGG GGGAGCGGGC CGCCCTTTCC GAGAGGCTCT TCGCCAACCT GTGGGGAGG    1260
CTTGAGGGGG AGGAGAGGCT CCTTTGGCTT TACCGGGAGG TGGAGAGGCC CCTTTCCGCT   1320
GTCCTGGCCC ACATGGAGGC CACGGGGGTG CGCCTGGACG TGGCCTATCT CAGGGCCTTG   1380
TCCCTGGAGG TGGCCGGGGA GATCGCCCGC CTCGAGGCCG AGGTCTTCCG CCTGGCCGGC   1440
CACCCCTTCA ACCTCAACTC CCGGGACCAG CTGGAAAGGG TCCTCTTTGA CGAGCTAGGG   1500
CTTCCCGCCA TCGGCAAGAC GGAGAAGACC GGCAAGCGCT CCACCAGCGC CGCCGTCCTG   1560
GAGGCCCTCC GCGAGGCCCA CCCCATCGTG GAGAAGATCC TGCAGTACCG GGAGCTCACC   1620
AAGCTGAAGA GCACCTACAT TGACCCCTTG CCGGACCTCA TCCACCCCAG GACGGGCCGC   1680
CTCCACACCC GCTTCAACCA GACGGCCACG GCCACGGGCA GGCTAAGTAG CTCCGATCCC   1740
AACCTCCAGA ACATCCCCGT CCGCACCCCG CTTGGGCAGA GGATCCGCCG GGCCTTCATC   1800
GCCGAGGAGG GGTGGCTATT GGTGGCCCTG GACTATAGCC AGATAGAGCT CAGGGTGCTG   1860
GCCCACCTCT CCGGCGACGA GAACCTGATC CGGGTCTTCC AGGAGGGGCG GGACATCCAC   1920
ACGGAGACCG CCAGCTGGAT GTTCGGCGTC CCCCGGGAGG CCGTGGACCC CCTGATGCGC   1980
CGGGCGGCCA AGACCATCAA CTTCGGGGTC CTCTACGGCA TGTCGGCCCA CCGCCTCTCC   2040
CAGGAGCTAG CCATCCCTTA CGAGGAGGCC CAGGCCTTCA TTGAGCGCTA CTTTCAGAGC   2100
TTCCCCAAGG TGCGGGCCTG GATTGAGAAG ACCCTGGAGG AGGGCAGGAG GCGGGGGTAC   2160
GTGGAGACCC TCTTCGGCCG CCGCCGCTAC GTGCCAGACC TAGAGGCCCG GGTGAAGAGC   2220
GTGCGGGAGG CGGCCGAGCG CATGGCCTTC AACATGCCCG TCCGGGGCAC CGCCGCCGAC   2280
CTCATGAAGC TGGCTATGGT GAAGCTCTTC CCCAGGCTGG AGGAAATGGG GGCCAGGATG   2340
CTCCTTCAGG TCCACGACGA GCTGGTCCTC GAGGCCCCAA AAGAGAGGGC GGAGGCCGTG   2400
GCCCGGCTGG CCAAGGAGGT CATGGAGGGG GTGTATCCCC TGGCCGTGCC CCTGGAGGTG   2460
```

GAGGTGGGGA TAGGGGAGGA CTGGCTCTCC GCCAAGGAGT GA    2502

( 2 ) INFORMATION FOR SEQ ID NO:22:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

GATTTAGGTG ACACTATAG    19

( 2 ) INFORMATION FOR SEQ ID NO:23:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

CGGACGAACA AGCGAGACAG CGACACAGGT ACCACATGGT ACAAGAGGCA AGAGAGACGA    60

CACAGCAGAA AC    72

( 2 ) INFORMATION FOR SEQ ID NO:24:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

GTTTCTGCTG TGTCGTCTCT CTTGCCTCTT GTACCATGTG GTACCTGTGT CGCTGTCTCG    60

CTTGTTCGTC    70

( 2 ) INFORMATION FOR SEQ ID NO:25:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

GACGAACAAG CGAGACAGCG    20

( 2 ) INFORMATION FOR SEQ ID NO:26:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

GTTTCTGCTG TGTCGTCTCT CTTG    24

( 2 ) INFORMATION FOR SEQ ID NO:27:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

```
CCTCTTGTAC   CATGTGGTAC   CTGTGTCGCT   GTCTCGCTTG   TTCGTC                        46
```

( 2 ) INFORMATION FOR SEQ ID NO:28:

( i ) SEQUENCE CHARACTERISTICS:
        ( A ) LENGTH: 50 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

```
ACACAGGTAC   CACATGGTAC   AAGAGGCAAG   AGAGACGACA   CAGCAGAAAC                    50
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: unknown ( i i ) MOLECULE TYPE: protein ( x i ) SEQUENCE DESCRIPTION: SEQ ID NO:29:

```
Met  Ala  Ser  Met  Thr  Gly  Gly  Gln  Gln  Met  Gly  Arg  Ile  Asn  Ser
 1              5                        10                        15
```

( 2 ) INFORMATION FOR SEQ ID NO:30:

( i ) SEQUENCE CHARACTERISTICS:
        ( A ) LENGTH: 969 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

```
ATGGCTAGCA   TGACTGGTGG   ACAGCAAATG   GGTCGGATCA   ATTCGGGGAT   GCTGCCCCTC       60
TTTGAGCCCA   AGGGCCGGGT   CCTCCTGGTG   GACGGCCACC   ACCTGGCCTA   CCGCACCTTC      120
CACGCCCTGA   AGGGCCTCAC   CACCAGCCGG   GGGGAGCCGG   TGCAGGCGGT   CTACGGCTTC      180
GCCAAGAGCC   TCCTCAAGGC   CCTCAAGGAG   GACGGGGACG   CGGTGATCGT   GGTCTTTGAC      240
GCCAAGGCCC   CCTCCTTCCG   CCACGAGGCC   TACGGGGGGT   ACAAGGCGGG   CCGGGCCCCC      300
ACGCCGGAGG   ACTTTCCCCG   GCAACTCGCC   CTCATCAAGG   AGCTGGTGGA   CCTCCTGGGG      360
CTGGCGCGCC   TCGAGGTCCC   GGGCTACGAG   GCGGACGACG   TCCTGGCCAG   CCTGGCCAAG      420
AAGGCGGAAA   AGGAGGGCTA   CGAGGTCCGC   ATCCTCACCG   CCGACAAAGA   CCTTTACCAG      480
CTTCTTTCCG   ACCGCATCCA   CGTCCTCCAC   CCCGAGGGGT   ACCTCATCAC   CCCGGCCTGG      540
CTTTGGGAAA   AGTACGGCCT   GAGGCCCGAC   CAGTGGGCCG   ACTACCGGGC   CCTGACCGGG      600
```

| | | | | | | |
|---|---|---|---|---|---|---|
| GACGAGTCCG | ACAACCTTCC | CGGGGTCAAG | GGCATCGGGG | AGAAGACGGC | GAGGAAGCTT | 660 |
| CTGGAGGAGT | GGGGGAGCCT | GGAAGCCCTC | CTCAAGAACC | TGGACCGGCT | GAAGCCCGCC | 720 |
| ATCCGGGAGA | AGATCCTGGC | CCACATGGAC | GATCTGAAGC | TCTCCTGGGA | CCTGGCCAAG | 780 |
| GTGCGCACCG | ACCTGCCCCT | GGAGGTGGAC | TTCGCCAAAA | GGCGGGAGCC | CGACCGGGAG | 840 |
| AGGCTTAGGG | CCTTTCTGGA | GAGGCTTGAG | TTTGGCAGCC | TCCTCCACGA | GTTCGGCCTT | 900 |
| CTGGAAAGCC | CCAAGTCATG | GAGGGGGTGT | ATCCCCTGGC | CGTGCCCCTG | GAGGTGGAGG | 960 |
| TGGGGATAG | | | | | | 969 |

( 2 ) INFORMATION FOR SEQ ID NO:31:

( i ) SEQUENCE CHARACTERISTICS:
        ( A ) LENGTH: 948 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:31:

| | | | | | | |
|---|---|---|---|---|---|---|
| ATGGCTAGCA | TGACTGGTGG | ACAGCAAATG | GGTCGGATCA | ATTCGGGGAT | GCTGCCCCTC | 60 |
| TTTGAGCCCA | AGGGCCGGGT | CCTCCTGGTG | GACGGCCACC | ACCTGGCCTA | CCGCACCTTC | 120 |
| CACGCCCTGA | AGGGCCTCAC | CACCAGCCGG | GGGGAGCCGG | TGCAGGCGGT | CTACGGCTTC | 180 |
| GCCAAGAGCC | TCCTCAAGGC | CCTCAAGGAG | GACGGGGACG | CGGTGATCGT | GGTCTTTGAC | 240 |
| GCCAAGGCCC | CCTCCTTCCG | CCACGAGGCC | TACGGGGGGT | ACAAGGCGGG | CCGGGCCCCC | 300 |
| ACGCCGGAGG | ACTTTCCCCG | GCAACTCGCC | CTCATCAAGG | AGCTGGTGGA | CCTCCTGGGG | 360 |
| CTGGCGCGCC | TCGAGGTCCC | GGGCTACGAG | GCGGACGACG | TCCTGGCCAG | CCTGGCCAAG | 420 |
| AAGGCGGAAA | AGGAGGGCTA | CGAGGTCCGC | ATCCTCACCG | CCGACAAAGA | CCTTTACCAG | 480 |
| CTTCTTTCCG | ACCGCATCCA | CGTCCTCCAC | CCCGAGGGGT | ACCTCATCAC | CCCGGCCTGG | 540 |
| CTTTGGGAAA | AGTACGGCCT | GAGGCCCGAC | CAGTGGGCCG | ACTACCGGGC | CCTGACCGGG | 600 |
| GACGAGTCCG | ACAACCTTCC | CGGGGTCAAG | GGCATCGGGG | AGAAGACGGC | GAGGAAGCTT | 660 |
| CTGGAGGAGT | GGGGGAGCCT | GGAAGCCCTC | CTCAAGAACC | TGGACCGGCT | GAAGCCCGCC | 720 |
| ATCCGGGAGA | AGATCCTGGC | CCACATGGAC | GATCTGAAGC | TCTCCTGGGA | CCTGGCCAAG | 780 |
| GTGCGCACCG | ACCTGCCCCT | GGAGGTGGAC | TTCGCCAAAA | GGCGGGAGCC | CGACCGGGAG | 840 |
| AGGCTTAGGG | CCTTTCTGGA | GAGGCTTGAG | TTTGGCAGCC | TCCTCCACGA | GTTCGGCCTT | 900 |
| CTGGAAAGCC | CCAAGGCCGC | ACTCGAGCAC | CACCACCACC | ACCACTGA | | 948 |

( 2 ) INFORMATION FOR SEQ ID NO:32:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:32:

| | | | | | | |
|---|---|---|---|---|---|---|
| CGCCAGGGTT | TTCCCAGTCA | CGACGTTGTA | AAACGACGGC | CAGTGAATTG | TAATACGACT | 60 |
| CACTATAGGG | CGAATTCGAG | CTCGGTACCC | GGGGATCCTC | TAGAGTCGAC | CTGCAGGCAT | 120 |
| GCAAGCTTGA | GTATTCTATA | GTGTCACCTA | AATAGCTTGG | CGTAATCATG | GTCATAGCTG | 180 |
| TTTCCTGTGT | GAAATTGTTA | TCCGCT | | | | 206 |

( 2 ) INFORMATION FOR SEQ ID NO:33:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:33:

TTCTGGGTTC TCTGCTCTCT GGTCGCTGTC TCGCTTGTTC GTC     43

( 2 ) INFORMATION FOR SEQ ID NO:34:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:34:

GCTGTCTCGC TTGTTCGTC     19

( 2 ) INFORMATION FOR SEQ ID NO:35:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:35:

GACGAACAAG CGAGACAGCG     20

( 2 ) INFORMATION FOR SEQ ID NO:36:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:36:

TTCTGGGTTC TCTGCTCTCT GGTC     24

( 2 ) INFORMATION FOR SEQ ID NO:37:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:37:

GACGAACAAG CGAGACAGCG ACCAGAGAGC AGAGAACCCA GAA     43

( 2 ) INFORMATION FOR SEQ ID NO:38:

( i ) SEQUENCE CHARACTERISTICS:
        ( A ) LENGTH: 23 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:38:

ACCAGAGAGC AGAGAACCCA GAA                                                  23

(2) INFORMATION FOR SEQ ID NO:39:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:39:

AACAGCTATG ACCATGATTA C                                                    21

(2) INFORMATION FOR SEQ ID NO:40:

(i) SEQUENCE CHARACTERISTICS:
    (A) LENGTH: 157 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:40:

CACCGTCCTC TTCAAGAAGT TTATCCAGAA GCCAATGCAC CCATTGGACA TAACCGGGAA           60
TCCTACATGG TTCCTTTTAT ACCACTGTAC AGAAATGGTG ATTTCTTTAT TTCATCCAAA          120
GATCTGGGCT ATGACTATAG CTATCTACAA GATTCAG                                   157

(2) INFORMATION FOR SEQ ID NO:41:

(i) SEQUENCE CHARACTERISTICS:
    (A) LENGTH: 157 base pairs
    (B) TYPE: nucleic acid
    (C) STRANDEDNESS: double
    (D) TOPOLOGY: linear (ii) MOLECULE TYPE: DNA (genomic)

(xi) SEQUENCE DESCRIPTION: SEQ ID NO:41:

CACCGTCCTC TTCAAGAAGT TTATCCAGAA GCCAATGCAC CCATTAGACA TAACCGGGAA           60
TCCTACATGG TTCCTTTTAT ACCACTGTAC AGAAATGGTG ATTTCTTTAT TTCATCCAAA          120
GATCTGGGCT ATGACTATAG CTATCTACAA GATTCAG                                   157

(2) INFORMATION FOR SEQ ID NO:42:

(i) SEQUENCE CHARACTERISTICS:
    (A) LENGTH: 19 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:42:

CACCGTCCTC TTCAAGAAG                                                       19

(2) INFORMATION FOR SEQ ID NO:43:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:43:

CTGAATCTTG TAGATAGCTA 20

( 2 ) INFORMATION FOR SEQ ID NO:44:

( i ) SEQUENCE CHARACTERISTICS:
  ( A ) LENGTH: 339 base pairs
  ( B ) TYPE: nucleic acid
  ( C ) STRANDEDNESS: double
  ( D ) TOPOLOGY: linear ( i i ) MOLECULE TYPE: DNA (genomic)

( x i ) SEQUENCE DESCRIPTION: SEQ ID NO:44:

GCCTTATTTT ACTTTAAAAA TTTTCAAATG TTTCTTTTAT ACACAATATG TTTCTTAGTC 60

TGAATAACCT TTTCCTCTGC AGTATTTTTG AGCAGTGGCT CCGAAGGCAC CGTCCTCTTC 120

AAGAAGTTTA TCCAGAAGCC AATGCACCCA TTAGACATAA CCGGGAATCC TACATGGTTC 180

CTTTTATACC ACTGTACAGA AATGGTGATT TCTTTATTTC ATCCAAAGAT CTGGGCTATG 240

ACTATAGCTA TCTACAAGAT TCAGGTAAAG TTTACTTTCT TTCAGAGGAA TTGCTGAATC 300

TAGTGTTACC AATTTATTTT GAGATAACAC AAAACTTTA 339

( 2 ) INFORMATION FOR SEQ ID NO:45:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:45:

GCCTTATTTT ACTTTAAAAA T 21

( 2 ) INFORMATION FOR SEQ ID NO:46:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:46:

TAAAGTTTTG TGTTATCTCA 20

( 2 ) INFORMATION FOR SEQ ID NO:47:

( i ) SEQUENCE CHARACTERISTICS:
  ( A ) LENGTH: 157 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:47:

```
CACCGTCCTC    TTCAAGAAGT    TTATCCAGAA    GCCAATGCAC    CCATTGGACA    TAACCGGGAA        60

TCCTACATGG    TTCCTTTTAT    ACCACTGTAC    AGAAATGGTG    ATTTCTTTAT    TTCATCCAAA       120

GATCTGGGCT    ATGACTATAG    CTATCTACAA    GATTCAG                                      157
```

( 2 ) INFORMATION FOR SEQ ID NO:48:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:48:

```
CTGAATCTTG    TAGATAGCTA    TAGTCATAGC    CCAGATCTTT    GGATGAAATA    AAGAAATCAC        60

CATTTCTGTA    CAGTGGTATA    AAAGGAACCA    TGTAGGATTC    CCGGTTATGT    CCAATGGGTG       120

CATTGGCTTC    TGGATAAACT    TCTTGAAGAG    GACGGTG                                      157
```

( 2 ) INFORMATION FOR SEQ ID NO:49:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:49:

```
AGCGGATAAC    AATTTCACAC    AGGAAACAGC    TATGACCATG    ATTACGCCAA    GCTATTTAGG        60

TGACACTATA    GAATACTCAA    GCTTGCATGC    CTGCAGGTCG    ACTCTAGAGG    ATCCCCGGGT       120

ACCGAGCTCG    AATTCGCCCT    ATAGTGAGTC    GTATTAGGAT    CCGTG                          165
```

( 2 ) INFORMATION FOR SEQ ID NO:50:

( i ) SEQUENCE CHARACTERISTICS:
        ( A ) LENGTH: 206 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:50:

```
CGCCAGGGTT    TTCCCAGTCA    CGACGTTGTA    AAACGACGGC    CAGTGAATTG    TAATACGACT        60

CACTATAGGG    CGAATTCGAG    CTCGGTACCC    GGGGATCCTC    TAGAGTCGAC    CTGCAGGCAT       120

GCAAGCTTGA    GTATTCTATA    GTGTCACCTA    AATAGCTTGG    CGTAATCATG    GTCATAGCTG       180

TTTCCTGTGT    GAAATTGTTA    TCCGCT                                                    206
```

( 2 ) INFORMATION FOR SEQ ID NO:51:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:51:

```
AGCGGATAAC    AATTTCACAC    AGGA                                                       24
```

( 2 ) INFORMATION FOR SEQ ID NO:52:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:52:

```
CACGGATCCT AATACGACTC ACTATAGGG                                              29
```

( 2 ) INFORMATION FOR SEQ ID NO:53:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:53:

```
CGCCAGGGTT TTCCCAGTCA CGAC                                                   24
```

( 2 ) INFORMATION FOR SEQ ID NO:54:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:54:

```
CACCGTCCTC TTCAAGAAGT TTATCCAGAA GCCAATGCAC CCATTAGACA TAACCGGGAA            60
TCCTACATGG TTCCTTTTAT ACCACTGTAC AGAAATGGTG ATTTCTTTAT TTCATCCAAA           120
GATCTGGGCT ATGACTATAG CTATCTACAA GATTCAG                                    157
```

( 2 ) INFORMATION FOR SEQ ID NO:55:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:55:

```
CACCGTCCTC TTCAAGAAGT TTATCCAGAA GCCAATGCAC CCATTGGACA TAACCAGGAA            60
TCCTACATGG TTCCTTTTAT ACCACTGTAC AGAAATGGTG ATTTCTTTAT TTCATCCAAA           120
GATCTGGGCT ATGACTATAG CTATCTACAA GATTCAG                                    157
```

( 2 ) INFORMATION FOR SEQ ID NO:56:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:56:

| | | | | | |
|---|---|---|---|---|---|
| CACCGTCCTC | TTCAAGAAGT | TTATCCAGAA | GCCAATGCAC | CCATTGGACA | TAACCGGGAA | 60
| TCCTACATGG | TTCCTTTTAT | ACCACTGTAC | AGAAATGGTG | ATTTCTTTAT | TTCATCCAAA | 120
| GATCTGGGCT | ATGACTATAG | CTATCTACAA | GATTCAGACC | CAGACTCTTT | TCAAGACTAC | 180
| ATTAAGTCCT | ATTTGGAACA | AGCGAGTCGG | ATCTGGTCAT | GGCTCCTTGG | GGCGGCGATG | 240
| GTAGGGGCCG | TCCTCACTGC | CCTGCTGGCA | GGGCTTGTGA | GCTTGCTGTG | TCGTCACAAG | 300
| AGAAAGCAGC | TTCCTGAAGA | AAAGCAGCCA | CTCCTCATGG | AGAAAGAGGA | TTACCACAGC | 360
| TTGTATCAGA | GCCATTTA | | | | | 378

( 2 ) INFORMATION FOR SEQ ID NO:57:

( i ) SEQUENCE CHARACTERISTICS:
        ( A ) LENGTH: 378 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:57:

| | | | | | |
|---|---|---|---|---|---|
| CACCGTCCTC | TTCAAGAAGT | TTATCCAGAA | GCCAATGCAC | CCATTGGACA | TAACCAGGAA | 60
| TCCTACATGG | TTCCTTTTAT | ACCACTGTAC | AGAAATGGTG | ATTTCTTTAT | TTCATCCAAA | 120
| GATCTGGGCT | ATGACTATAG | CTATCTACAA | GATTCAGACC | CAGACTCTTT | TCAAGACTAC | 180
| ATTAAGTCCT | ATTTGGAACA | AGCGAGTCGG | ATCTGGTCAT | GGCTCCTTGG | GGCGGCGATG | 240
| GTAGGGGCCG | TCCTCACTGC | CCTGCTGGCA | GGGCTTGTGA | GCTTGCTGTG | TCGTCACAAG | 300
| AGAAAGCAGC | TTCCTGAAGA | AAAGCAGCCA | CTCCTCATGG | AGAAAGAGGA | TTACCACAGC | 360
| TTGTATCAGA | GCCATTTA | | | | | 378

( 2 ) INFORMATION FOR SEQ ID NO:58:

( i ) SEQUENCE CHARACTERISTICS:
        ( A ) LENGTH: 1059 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

| | | | | | |
|---|---|---|---|---|---|
| GCAAGTTTGG | CTTTTGGGGA | CCAAACTGCA | CAGAGAGACG | ACTCTTGGTG | AGAAGAAACA | 60
| TCTTCGATTT | GAGTGCCCCA | GAGAAGGACA | AATTTTTTGC | CTACCTCACT | TTAGCAAAGC | 120
| ATACCATCAG | CTCAGACTAT | GTCATCCCCA | TAGGGACCTA | TGGCCAAATG | AAAAATGGAT | 180
| CAACACCCAT | GTTAACGAC | ATCAATATTT | ATGACCTCTT | TGTCTGGATG | CATTATTATG | 240
| TGTCAATGGA | TGCACTGCTT | GGGGGATATG | AAATCTGGAG | AGACATTGAT | TTTGCCCATG | 300
| AAGCACCAGC | TTTTCTGCCT | TGGCATAGAC | TCTTCTTGTT | GCGGTGGGAA | CAAGAAATCC | 360
| AGAAGCTGAC | AGGAGATGAA | AACTTCACTA | TTCCATATTG | GGACTGGCGG | GATGCAGAAA | 420
| AGTGTGACAT | TTGCACAGAT | GAGTACATGG | GAGGTCAGCA | CCCCACAAAT | CCTAACTTAC | 480
| TCAGCCCAGC | ATCATTCTTC | TCCTCTTGGC | AGATTGTCTG | TAGCCGATTG | GAGGAGTACA | 540
| ACAGCCATCA | GTCTTTATGC | AATGGAACGC | CCGAGGGACC | TTTACGGCGT | AATCCTGGAA | 600
| ACCATGACAA | ATCCAGAACC | CCAAGGCTCC | CCTCTTCAGC | TGATGTAGAA | TTTTGCCTGA | 660
| GTTTGACCCA | ATATGAATCT | GGTTCCATGG | ATAAAGCTGC | CAATTTCAGC | TTTAGAAATA | 720

| | | | | | |
|---|---|---|---|---|---|
| CACTGGAAGG | ATTTGCTAGT | CCACTTACTG | GGATAGCGGA | TGCCTCTCAA | AGCAGCATGC | 780 |
| ACAATGCCTT | GCACATCTAT | ATGAATGGAA | CAATGTCCCA | GGTACAGGGA | TCTGCCAACG | 840 |
| ATCCTATCTT | CCTTCTTCAC | CATGCATTTG | TTGACAGTAT | TTTTGAGCAG | TGGCTCCGAA | 900 |
| GGCACCGTCC | TCTTCAAGAA | GTTTATCCAG | AAGCCAATGC | ACCCATTGGA | CATAACCGGG | 960 |
| AATCCTACAT | GGTTCCTTTT | ATACCACTGT | ACAGAAATGG | TGATTTCTTT | ATTTCATCCA | 1020 |
| AAGATCTGGG | CTATGACTAT | AGCTATCTAC | AAGATTCAG | | | 1059 |

( 2 ) INFORMATION FOR SEQ ID NO:59:

( i ) SEQUENCE CHARACTERISTICS:
        ( A ) LENGTH: 1059 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

| | | | | | |
|---|---|---|---|---|---|
| GCAAGTTTGG | CTTTTGGGGA | CCAAACTGCA | CAGAGAGACG | ACTCTTGGTG | AGAAGAAACA | 60 |
| TCTTCGATTT | GAGTGCCCCA | GAGAAGGACA | AATTTTTTGC | CTACCTCACT | TTAGCAAAGC | 120 |
| ATACCATCAG | CTCAGACTAT | GTCATCCCCA | TAGGGACCTA | TGGCCAAATG | AAAAATGGAT | 180 |
| CAACACCCAT | GTTTAACGAC | ATCAATATTT | ATGACCTCTT | TGTCTGGATG | CATTATTATG | 240 |
| TGTCAATGGA | TGCACTGCTT | GGGGGATATG | AAATCTGGAG | AGACATTGAT | TTTGCCCATG | 300 |
| AAGCACCAGC | TTTTCTGCCT | TGGCATAGAC | TCTTCTTGTT | GCGGTGGGAA | CAAGAAATCC | 360 |
| AGAAGCTGAC | AGGAGATGAA | AACTTCACTA | TTCCATATTG | GGACTGGCGG | GATGCAGAAA | 420 |
| AGTGTGACAT | TTGCACAGAT | GAGTACATGG | GAGGTCAGCA | CCCCACAAAT | CCTAACTTAC | 480 |
| TCAGCCCAGC | ATCATTCTTC | TCCTCTTGGC | AGATTGTCTG | TAGCCGATTG | GAGGAGTACA | 540 |
| ACAGCCATCA | GTCTTTATGC | AATGGAACGC | CCGAGGGACC | TTTACGGCGT | AATCCTGGAA | 600 |
| ACCATGACAA | ATCCAGAACC | CCAAGGCTCC | CCTCTTCAGC | TGATGTAGAA | TTTTGCCTGA | 660 |
| GTTTGACCCA | ATATGAATCT | GGTTCCATGG | ATAAAGCTGC | CAATTTCAGC | TTTAGAAATA | 720 |
| CACTGGAAGG | ATTTGCTAGT | CCACTTACTG | GGATAGCGGA | TGCCTCTCAA | AGCAGCATGC | 780 |
| ACAATGCCTT | GCACATCTAT | ATGAATGGAA | CAATGTCCCA | GGTACAGGGA | TCTGCCAACG | 840 |
| ATCCTATCTT | CCTTCTTCAC | CATGCATTTG | TTGACAGTAT | TTTTGAGCAG | TGGCTCCGAA | 900 |
| GGCACCGTCC | TCTTCAAGAA | GTTTATCCAG | AAGCCAATGC | ACCCATTGGA | CATAACCAGG | 960 |
| AATCCTACAT | GGTTCCTTTT | ATACCACTGT | ACAGAAATGG | TGATTTCTTT | ATTTCATCCA | 1020 |
| AAGATCTGGG | CTATGACTAT | AGCTATCTAC | AAGATTCAG | | | 1059 |

( 2 ) INFORMATION FOR SEQ ID NO:60:

( i ) SEQUENCE CHARACTERISTICS:
        ( A ) LENGTH: 1587 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

| | | | | | |
|---|---|---|---|---|---|
| ATGCTCCTGG | CTGTTTTGTA | CTGCCTGCTG | TGGAGTTTCC | AGACCTCCGC | TGGCCATTTC | 60 |
| CCTAGAGCCT | GTGTCTCCTC | TAAGAACCTG | ATGGAGAAGG | AATGCTGTCC | ACCGTGGAGC | 120 |
| GGGGACAGGA | GTCCCTGTGG | CCAGCTTTCA | GGCAGAGGTT | CCTGTCAGAA | TATCCTTCTG | 180 |

| | | | | | |
|---|---|---|---|---|---|
| TCCAATGCAC | CACTTGGGCC | TCAATTTCCC | TTCACAGGGG | TGGATGACCG | GGAGTCGTGG | 240 |
| CCTTCCGTCT | TTTATAATAG | GACCTGCCAG | TGCTCTGGCA | ACTTCATGGG | ATTCAACTGT | 300 |
| GGAAACTGCA | AGTTTGGCTT | TTGGGGACCA | AACTGCACAG | AGAGACGACT | CTTGGTGAGA | 360 |
| AGAAACATCT | TCGATTTGAG | TGCCCCAGAG | AAGGACAAAT | TTTTTGCCTA | CCTCACTTTA | 420 |
| GCAAAGCATA | CCATCAGCTC | AGACTATGTC | ATCCCCATAG | GGACCTATGG | CCAAATGAAA | 480 |
| AATGGATCAA | CACCCATGTT | TAACGACATC | AATATTTATG | ACCTCTTTGT | CTGGATGCAT | 540 |
| TATTATGTGT | CAATGGATGC | ACTGCTTGGG | GGATATGAAA | TCTGGAGAGA | CATTGATTTT | 600 |
| GCCCATGAAG | CACCAGCTTT | TCTGCCTTGG | CATAGACTCT | TCTTGTTGCG | GTGGGAACAA | 660 |
| GAAATCCAGA | AGCTGACAGG | AGATGAAAAC | TTCACTATTC | CATATTGGGA | CTGGCGGGAT | 720 |
| GCAGAAAAGT | GTGACATTTG | CACAGATGAG | TACATGGGAG | GTCAGCACCC | CACAAATCCT | 780 |
| AACTTACTCA | GCCCAGCATC | ATTCTTCTCC | TCTTGGCAGA | TTGTCTGTAG | CCGATTGGAG | 840 |
| GAGTACAACA | GCCATCAGTC | TTTATGCAAT | GGAACGCCCG | AGGGACCTTT | ACGGCGTAAT | 900 |
| CCTGGAAACC | ATGACAAATC | CAGAACCCCA | AGGCTCCCCT | CTTCAGCTGA | TGTAGAATTT | 960 |
| TGCCTGAGTT | TGACCCAATA | TGAATCTGGT | TCCATGGATA | AAGCTGCCAA | TTTCAGCTTT | 1020 |
| AGAAATACAC | TGGAAGGATT | TGCTAGTCCA | CTTACTGGGA | TAGCGGATGC | CTCTCAAAGC | 1080 |
| AGCATGCACA | ATGCCTTGCA | CATCTATATG | AATGGAACAA | TGTCCCAGGT | ACAGGGATCT | 1140 |
| GCCAACGATC | CTATCTTCCT | TCTTCACCAT | GCATTTGTTG | ACAGTATTTT | TGAGCAGTGG | 1200 |
| CTCCGAAGGC | ACCGTCCTCT | TCAAGAAGTT | TATCCAGAAG | CCAATGCACC | CATTGGACAT | 1260 |
| AACCGGGAAT | CCTACATGGT | TCCTTTTATA | CCACTGTACA | GAAATGGTGA | TTTCTTTATT | 1320 |
| TCATCCAAAG | ATCTGGGCTA | TGACTATAGC | TATCTACAAG | ATTCAGACCC | AGACTCTTTT | 1380 |
| CAAGACTACA | TTAAGTCCTA | TTTGGAACAA | GCGAGTCGGA | TCTGGTCATG | GCTCCTTGGG | 1440 |
| GCGGCGATGG | TAGGGGCCGT | CCTCACTGCC | CTGCTGGCAG | GGCTTGTGAG | CTTGCTGTGT | 1500 |
| CGTCACAAGA | GAAAGCAGCT | TCCTGAAGAA | AAGCAGCCAC | TCCTCATGGA | GAAAGAGGAT | 1560 |
| TACCACAGCT | TGTATCAGAG | CCATTTA | | | | 1587 |

( 2 ) INFORMATION FOR SEQ ID NO:61:

( i ) SEQUENCE CHARACTERISTICS:
        ( A ) LENGTH: 1587 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

| | | | | | |
|---|---|---|---|---|---|
| ATGCTCCTGG | CTGTTTTGTA | CTGCCTGCTG | TGGAGTTTCC | AGACCTCCGC | TGGCCATTTC | 60 |
| CCTAGAGCCT | GTGTCTCCTC | TAAGAACCTG | ATGGAGAAGG | AATGCTGTCC | ACCGTGGAGC | 120 |
| GGGGACAGGA | GTCCCTGTGG | CCAGCTTTCA | GGCAGAGGTT | CCTGTCAGAA | TATCCTTCTG | 180 |
| TCCAATGCAC | CACTTGGGCC | TCAATTTCCC | TTCACAGGGG | TGGATGACCG | GGAGTCGTGG | 240 |
| CCTTCCGTCT | TTTATAATAG | GACCTGCCAG | TGCTCTGGCA | ACTTCATGGG | ATTCAACTGT | 300 |
| GGAAACTGCA | AGTTTGGCTT | TTGGGGACCA | AACTGCACAG | AGAGACGACT | CTTGGTGAGA | 360 |
| AGAAACATCT | TCGATTTGAG | TGCCCCAGAG | AAGGACAAAT | TTTTTGCCTA | CCTCACTTTA | 420 |
| GCAAAGCATA | CCATCAGCTC | AGACTATGTC | ATCCCCATAG | GGACCTATGG | CCAAATGAAA | 480 |
| AATGGATCAA | CACCCATGTT | TAACGACATC | AATATTTATG | ACCTCTTTGT | CTGGATGCAT | 540 |
| TATTATGTGT | CAATGGATGC | ACTGCTTGGG | GGATATGAAA | TCTGGAGAGA | CATTGATTTT | 600 |

| | | | | | |
|---|---|---|---|---|---|
| GCCCATGAAG | CACCAGCTTT | TCTGCCTTGG | CATAGACTCT | TCTTGTTGCG | GTGGGAACAA | 660 |
| GAAATCCAGA | AGCTGACAGG | AGATGAAAAC | TTCACTATTC | CATATTGGGA | CTGGCGGGAT | 720 |
| GCAGAAAAGT | GTGACATTTG | CACAGATGAG | TACATGGGAG | GTCAGCACCC | CACAAATCCT | 780 |
| AACTTACTCA | GCCCAGCATC | ATTCTTCTCC | TCTTGGCAGA | TTGTCTGTAG | CCGATTGGAG | 840 |
| GAGTACAACA | GCCATCAGTC | TTTATGCAAT | GGAACGCCCG | AGGGACCTTT | ACGGCGTAAT | 900 |
| CCTGGAAACC | ATGACAAATC | CAGAACCCCA | AGGCTCCCCT | CTTCAGCTGA | TGTAGAATTT | 960 |
| TGCCTGAGTT | TGACCCAATA | TGAATCTGGT | TCCATGGATA | AAGCTGCCAA | TTTCAGCTTT | 1020 |
| AGAAATACAC | TGGAAGGATT | TGCTAGTCCA | CTTACTGGGA | TAGCGGATGC | CTCTCAAAGC | 1080 |
| AGCATGCACA | ATGCCTTGCA | CATCTATATG | AATGGAACAA | TGTCCCAGGT | ACAGGGATCT | 1140 |
| GCCAACGATC | CTATCTTCCT | TCTTCACCAT | GCATTTGTTG | ACAGTATTTT | TGAGCAGTGG | 1200 |
| CTCCGAAGGC | ACCGTCCTCT | TCAAGAAGTT | TATCCAGAAG | CCAATGCACC | CATTGGACAT | 1260 |
| AACCAGGAAT | CCTACATGGT | TCCTTTTATA | CCACTGTACA | GAAATGGTGA | TTTCTTTATT | 1320 |
| TCATCCAAAG | ATCTGGGCTA | TGACTATAGC | TATCTACAAG | ATTCAGACCC | AGACTCTTTT | 1380 |
| CAAGACTACA | TTAAGTCCTA | TTTGGAACAA | GCGAGTCGGA | TCTGGTCATG | GCTCCTTGGG | 1440 |
| GCGGCGATGG | TAGGGGCCGT | CCTCACTGCC | CTGCTGGCAG | GGCTTGTGAG | CTTGCTGTGT | 1500 |
| CGTCACAAGA | GAAAGCAGCT | TCCTGAAGAA | AAGCAGCCAC | TCCTCATGGA | GAAAGAGGAT | 1560 |
| TACCACAGCT | TGTATCAGAG | CCATTTA | | | | 1587 |

( 2 ) INFORMATION FOR SEQ ID NO:62:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

TAAATGGCTC TGATACAAGC T                                                                                            21

( 2 ) INFORMATION FOR SEQ ID NO:63:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

GCAAGTTTGG CTTTTGGGGA                                                                                                20

( 2 ) INFORMATION FOR SEQ ID NO:64:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

ATGCTCCTGG CTGTTTTGTA CTG                                                                        23

( 2 ) INFORMATION FOR SEQ ID NO:65:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

```
CTGAATCTTG  TAGATAGCTA  TAGTCATAGC  CCAGATCTTT  GGATGAAATA  AAGAAATCAC    60
CATTTCTGTA  CAGTGGTATA  AAAGGAACCA  TGTAGGATTC  CCGGTTATGT  CTAATGGGTG   120
CATTGGCTTC  TGGATAAACT  TCTTGAAGAG  GACGGTG                              157
```

( 2 ) INFORMATION FOR SEQ ID NO:66:

( i ) SEQUENCE CHARACTERISTICS:
        ( A ) LENGTH: 157 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

```
CTGAATCTTG  TAGATAGCTA  TAGTCATAGC  CCAGATCTTT  GGATGAAATA  AAGAAATCAC    60
CATTTCTGTA  CAGTGGTATA  AAAGGAACCA  TGTAGGATTC  CTGGTTATGT  CCAATGGGTG   120
CATTGGCTTC  TGGATAAACT  TCTTGAAGAG  GACGGTG                              157
```

( 2 ) INFORMATION FOR SEQ ID NO:67:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

```
GGTTGGCCAA  TCTACTCCCA  GG                                                22
```

( 2 ) INFORMATION FOR SEQ ID NO:68:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:68:

```
GCTCACTCAG  TGTGGCAAAG                                                    20
```

( 2 ) INFORMATION FOR SEQ ID NO:69:

( i ) SEQUENCE CHARACTERISTICS:
        ( A ) LENGTH: 536 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:69:

| GGTTGGCCAA | TCTACTCCCA | GGAGCAGGGA | GGGCAGGAGC | CAGGGCTGGG | CATAAAAGTC | 60 |
|---|---|---|---|---|---|---|
| AGGGCAGAGC | CATCTATTGC | TTACATTTGC | TTCTGACACA | ACTGTGTTCA | CTAGCAACCT | 120 |
| CAAACAGACA | CCATGGTGCA | CCTGACTCCT | GAGGAGAAGT | CTGCCGTTAC | TGCCCTGTGG | 180 |
| GGCAAGGTGA | ACGTGGATGA | AGTTGGTGGT | GAGGCCCTGG | GCAGGTTGGT | ATCAAGGTTA | 240 |
| CAAGACAGGT | TTAAGGAGAC | CAATAGAAAC | TGGGCATGTG | GAGACAGAGA | AGACTCTTGG | 300 |
| GTTTCTGATA | GGCACTGACT | CTCTCTGCCT | ATTGGTCTAT | TTTCCCACCC | TTAGGCTGCT | 360 |
| GGTGGTCTAC | CCTTGGACCC | AGAGGTTCTT | TGAGTCCTTT | GGGGATCTGT | CCACTCCTGA | 420 |
| TGCTGTTATG | GGCAACCCTA | AGGTGAAGGC | TCATGGCAAG | AAAGTGCTCG | GTGCCTTTAG | 480 |
| TGATGGCCTG | GCTCACCTGG | ACAACCTCAA | GGGCACCTTT | GCCACACTGA | GTGAGC | 536 |

(2) INFORMATION FOR SEQ ID NO:70:

(i) SEQUENCE CHARACTERISTICS:
(A) LENGTH: 534 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:70:

| GGTTGGCCAA | TCTACTCCCA | GGAGCAGGGA | GGGCAGGAGC | CAGGGCTGGG | CATAAAAGTC | 60 |
|---|---|---|---|---|---|---|
| AGGGCAGAGC | CATCTATTGC | TTACATTTGC | TTCTGACACA | ACTGTGTTCA | CTAGCAACCT | 120 |
| CAAACAGACA | CCATGGTGCA | TCTGACTCCT | GAGGAGGTCT | GCCGTTACTG | CCCTGTGGGG | 180 |
| CAAGGTGAAC | GTGGATGAAG | TTGGTGGTGA | GGCCCTGGGC | AGGTTGGTAT | CAAGGTTACA | 240 |
| AGACAGGTTT | AAGGAGACCA | ATAGAAACTG | GCATGTGGA | GACAGAGAAG | ACTCTTGGGT | 300 |
| TTCTGATAGG | CACTGACTCT | CTCTGCCTAT | TGGTCTATTT | TCCCACCCTT | AGGCTGCTGG | 360 |
| TGGTCTACCC | TTGGACCCAG | AGGTTCTTTG | AGTCCTTTGG | GGATCTGTCC | ACTCCTGATG | 420 |
| CTGTTATGGG | CAACCCTAAG | GTGAAGGCTC | ATGGCAAGAA | AGTGCTCGGT | GCCTTTAGTG | 480 |
| ATGGCCTGGC | TCACCTGGAC | AACCTCAAGG | GCACCTTTGC | CACACTGAGT | GAGC | 534 |

(2) INFORMATION FOR SEQ ID NO:71:

(i) SEQUENCE CHARACTERISTICS:
(A) LENGTH: 536 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:71:

| GGTTGGCCAA | TCTACTCCCA | GGAGCAGGGA | GGGCAGGAGC | CAGGGCTGGG | CATAAAAGTC | 60 |
|---|---|---|---|---|---|---|
| AGGGCAGAGC | CATCTATTGC | TTACATTTGC | TTCTGACACA | ACTGTGTTCA | CTAGCAACCT | 120 |
| CAAACAGACA | CCATGGTGCA | CCTGACTCCT | GAGGAGAAGT | CTGCCGTTAC | TGCCCTGTGG | 180 |
| GGCAAGGTGA | ACGTGGATGA | AGTTGGTGGT | GAGGCCCTGG | GCAGGTTGGT | ATCAAGGTTA | 240 |
| CAAGACAGGT | TTAAGGAGAC | CAATAGAAAC | TGGGCATGTG | GAGACAGAGA | AGACTCTTGG | 300 |
| GTTTCTGATA | GGCACTGACT | CTCTCTGCCT | ATTGGTCTAT | TTTCCCACCC | TTAGGCTGCT | 360 |
| GGTGGTCTAC | CCTTGGACCT | AGAGGTTCTT | TGAGTCCTTT | GGGGATCTGT | CCACTCCTGA | 420 |
| TGCTGTTATG | GGCAACCCTA | AGGTGAAGGC | TCATGGCAAG | AAAGTGCTCG | GTGCCTTTAG | 480 |
| TGATGGCCTG | GCTCACCTGG | ACAACCTCAA | GGGCACCTTT | GCCACACTGA | GTGAGC | 536 |

( 2 ) INFORMATION FOR SEQ ID NO:72:

( i ) SEQUENCE CHARACTERISTICS:
        ( A ) LENGTH: 536 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:72:

```
GGTTGGCCAA  TCTACTCCCA  GGAGCAGGGA  GGGCAGGAGC  CAGGGCTGGG  CATAAAAGTC      60
AGGGCAGAGC  CATCTATTGC  TTACATTTGC  TTCTGACACA  ACTGTGTTCA  CTAGCAACCT     120
CAAACAGACA  CCATGGTGCA  CCTGACTCCT  GAGGAGAAGT  CTGCCGTTAC  TGCCCTGTGG     180
GGCAAGGTGA  ACGTGGATGA  AGTTGGAGGT  GAGGCCCTGG  GCAGGTTGGT  ATCAAGGTTA     240
CAAGACAGGT  TTAAGGAGAC  CAATAGAAAC  TGGGCATGTG  GAGACAGAGA  AGACTCTTGG     300
GTTTCTGATA  GGCACTGACT  CTCTCTGCCT  ATTGGTCTAT  TTTCCCACCC  TTAGGCTGCT     360
GGTGGTCTAC  CCTTGGACCC  AGAGGTTCTT  TGAGTCCTTT  GGGGATCTGT  CCACTCCTGA     420
TGCTGTTATG  GGCAACCCTA  AGGTGAAGGC  TCATGGCAAG  AAAGTGCTCG  GTGCCTTTAG     480
TGATGGCCTG  GCTCACCTGG  ACAACCTCAA  GGGCACCTTT  GCCACACTGA  GTGAGC         536
```

( 2 ) INFORMATION FOR SEQ ID NO:73:

( i ) SEQUENCE CHARACTERISTICS:
        ( A ) LENGTH: 64 base pairs
        ( B ) TYPE: nucleic acid
        ( C ) STRANDEDNESS: single
        ( D ) TOPOLOGY: linear ( i i ) MOLECULE TYPE: RNA (genomic)

( x i ) SEQUENCE DESCRIPTION: SEQ ID NO:73:

```
GAAUACUCAA  GCUUGCAUGC  CUGCAGGUCG  ACUCUAGAGG  AUCCCCGGGU  ACCGAGCUCG      60
AAUU                                                                        64
```

( 2 ) INFORMATION FOR SEQ ID NO:74:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:74:

```
GGCTGACAAG  AAGGAAACTC                                                      20
```

( 2 ) INFORMATION FOR SEQ ID NO:75:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:75:

```
CCAGGCGGCG  GCTAGGAGAG  ATGGG                                               25
```

( 2 ) INFORMATION FOR SEQ ID NO:76:

( i ) SEQUENCE CHARACTERISTICS:
        ( A ) LENGTH: 351 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:76:

```
GGCTGACAAG AAGGAAACTC GCTGAGACAG CAGGGACTTT CCACAAGGGG ATGTTACGGG      60
GAGGTACTGG GGAGGAGCCG GTCGGGAACG CCCACTCTCT TGATGTATAA ATATCACTGC     120
ATTTCGCTCT GTATTCAGTC GCTCTGCGGA GAGGCTGGCA GATTGAGCCC TGGGAGGTTC     180
TCTCCAGCAC TAGCAGGTAG AGCCTGGGTG TTCCCTGCTA GACTCTCACC AGCACTTGGC     240
CGGTGCTGGG CAGAGTGGCT CCACGCTTGC TTGCTTAAAG ACCTCTTCAA TAAAGCTGCC     300
ATTTTAGAAG TAGGCCAGTG TGTGTTCCCA TCTCTCCTAG CCGCCGCCTG G             351
```

( 2 ) INFORMATION FOR SEQ ID NO:77:

( i ) SEQUENCE CHARACTERISTICS:
        ( A ) LENGTH: 340 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:77:

```
GGCTGACAAG AAGGAAACTC GCTGAGATAG CAGGGACTTT CCACAAGGGG ATGTTATGGG      60
GAGGAGCCGG TCGGGAACAC CCACTTTCTT GATGTATAAA TATCACTGCA TTTCGCTCTG     120
TATTCAGTCG CTCTGCGGAG AGGCTGGCAG ATTGAGCCCT GGGAGGTTCT CTCCAGCACT     180
AGCAGGTAGA GCCTGGGTGT TCCCTGCTAG ACTCTCACCA GCACTTAGCC AGTGCTGGGC     240
AGAGTGGCTC CACGCTTGCT TGCTTAAAGA CCTCTTCAAT AAAGCTGCCA TTTTAGAAGT     300
AAGCCAGTGT GTGTTCCCAT CTCTCCTAGC CGCCGCCTGG                            340
```

( 2 ) INFORMATION FOR SEQ ID NO:78:

( i ) SEQUENCE CHARACTERISTICS:
        ( A ) LENGTH: 340 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:78:

```
GGCTGACAAG AAGGAAACTC GCTGAGATAG CAGGGACTTT CCACAAGGGG ATGTTATGGG      60
GAGGAGCCGG TCGGGAACAC CCACTTTCTT GGTGTATAAA TATCACTGCA TTTCGCTCTG     120
TATTCAGTCG CTCTGCGGAG AGGCTGGCAG ATTGAGCCCT GGGAGGTTCT CTCCAGCACT     180
AGCAGGTAGA GCCTGGGTGT TCCCTGCTAG ACTCTCACCA GCACTTGGCC AGTGCTGGGC     240
AGAGTGGCTC CACGCTTGCT TGCTTAAAGA CCTCTTCAAT AAAGCTGCCA TTTTAGAAGT     300
AAGCCAGTGT GTGTTCCCAT CTCTCCTAGC CGCCGCCTGG                            340
```

( 2 ) INFORMATION FOR SEQ ID NO:79:

( i ) SEQUENCE CHARACTERISTICS:
        ( A ) LENGTH: 351 base pairs
        ( B ) TYPE: nucleic acid (C) STRANDEDNESS: double
(D) TOPOLOGY: linear (i i) MOLECULE TYPE: DNA (genomic)

(x i) SEQUENCE DESCRIPTION: SEQ ID NO:79:

| | | | | | | |
|---|---|---|---|---|---|---|
| GGCTGACAAG | AAGGAAACTC | GCTGAGACAG | CAGGGACTTT | CCACAAGGGG | ATGTTACGGG | 60 |
| GAGGTACTGG | GGAGGAGCCG | GTCGGGAACG | CCCCCTCTCT | TGATGTATAA | ATATCACTGC | 120 |
| ATTTCGCTCT | GTATTCAGTC | GCTCTGCGGA | GAGGCTGGCA | GATTGAGCCC | TGGGAGGTTC | 180 |
| TCTCCAGCAC | TAGCAGGTAG | AGCCTGGGTG | TTCCCTGCTA | GACTCTCACC | AGCACTTGGC | 240 |
| CGGTGCTGGG | CAGAGTGGCT | CCACGCTTGC | TTGCTTAAAG | ACCTCTTCAA | TAAAGCTGCC | 300 |
| ATTTTAGAAG | TAGGCTAGTG | TGTGTTCCCA | TCTCTCCTAG | CCGCCGCCTG | G | 351 |

(2) INFORMATION FOR SEQ ID NO:80:

(i) SEQUENCE CHARACTERISTICS:
(A) LENGTH: 351 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:80:

| | | | | | | |
|---|---|---|---|---|---|---|
| GGCTGACAAG | AAGGAAACTC | GCTGAAACAG | CAGGGACTTT | CCACAAGGGG | ATGTTACGGG | 60 |
| GAGGTACTGG | GAAGGAGCCG | GTCGGGAACG | CCCACTTTCT | TGATGTATAA | ATATCACTGC | 120 |
| ATTTCGCTCT | GTATTCAGTC | GCTCTGCGGA | GAGGCTGGCA | GATTGAGCCC | TGGGAGGTTC | 180 |
| TCTCCAGCAC | TAGCAGGTAG | AGCCTGGGTG | TTCCCTGCTA | GACTCTCACC | AGCACTTGGC | 240 |
| CGGTGCTGGG | CAGAGTGACT | CCACGCTTGC | TTGCTTAAAG | CCCTCTTCAA | TAAAGCTGCC | 300 |
| ATTTTAGAAG | TAAGCTAGTG | TGTGTTCCCA | TCTCTCCTAG | CCGCCGCCTG | G | 351 |

(2) INFORMATION FOR SEQ ID NO:81:

(i) SEQUENCE CHARACTERISTICS:
(A) LENGTH: 351 base pairs
(B) TYPE: nucleic acid
(C) STRANDEDNESS: double
(D) TOPOLOGY: linear (i i) MOLECULE TYPE: DNA (genomic)

(x i) SEQUENCE DESCRIPTION: SEQ ID NO:81:

| | | | | | | |
|---|---|---|---|---|---|---|
| GGCTGACAAG | AAGGAAACTC | GCTGAGACAG | CAGGGACTTT | CCACAAGGGG | ATGTTACGGA | 60 |
| GAGGTACTGG | GGAGGAGCCG | GTCGGGAACG | CCCACTCTCT | TGATGTATAA | ATATCACTGC | 120 |
| ATTTCGCTCT | GTATTCAGTC | GCTCTGCGGA | GAGGCTGGCA | GATTGAGCCC | TAGGAGGTTC | 180 |
| TCTCCAGCAC | TAGCAGGTAG | AGCCTGAGTG | TTCCCTGCTA | AACTCTCACC | AGCACTTGGC | 240 |
| CGGTGCTGGG | CAGAGCGGCT | CCACGCTTGC | TTGCTTAAAG | ACCTCTTCAA | TAAAGCTGCC | 300 |
| ATTTTAGAAG | TAGGCTAGTG | TGTGTTCCCA | TCTCTCCTAG | CCGCCGCCTG | G | 351 |

(2) INFORMATION FOR SEQ ID NO:82:

(i) SEQUENCE CHARACTERISTICS:
(A) LENGTH: 536 base pairs
(B) TYPE: nucleic acid
(C) STRANDEDNESS: double
(D) TOPOLOGY: linear (i i) MOLECULE TYPE: DNA (genomic)

( x i ) SEQUENCE DESCRIPTION: SEQ ID NO:82:

```
GGTTGGCCAA  TCTACTCCCA  GGAGCAGGGA  GGGCAGGAGC  CAGGGCTGGG  CATAAAAGTC      60
AGGGCAGAGC  CATCTATTGC  TTACATTTGC  TTCTGACACA  ACTGTGTTCA  CTAGCAACCT     120
CAAACAGACA  CCATGGTGCA  TCTGACTCCT  GAGGAGAAGT  CTGCCGTTAC  TGCCCTGTGG     180
GGCAAGGTGA  ACGTGGATGA  AGTTGGTGGT  AAGGCCCTGG  GCAGGTTGGT  ATCAAGGTTA     240
CAAGACAGGT  TTAAGGAGAC  CAATAGAAAC  TGGGCATGTG  GAGACAGAGA  AGACTCTTGG     300
GTTTCTGATA  GGCACTGACT  CTCTCTGCCT  ATTGGTCTAT  TTTCCCACCC  TTAGGCTGCT     360
GGTGGTCTAC  CCTTGGACCC  AGAGGTTCTT  TGAGTCCTTT  GGGGATCTGT  CCACTCCTGA     420
TGCTGTTATG  GGCAACCCTA  AGGTGAAGGC  TCATGGCAAG  AAAGTGCTCG  GTGCCTTTAG     480
TGATGGCCTG  GCTCACCTGG  ACAACCTCAA  GGGCACCTTT  GCCACACTGA  GTGAGC         536
```

( 2 ) INFORMATION FOR SEQ ID NO:83:

( i ) SEQUENCE CHARACTERISTICS:
        ( A ) LENGTH: 536 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:83:

```
GGTTGGCCAA  TCTACTCCCA  GGAGCAGGGA  GGGCAGGAGC  CAGGGCTGGG  CATAAAAGTC      60
AGGGCAGAGC  CATCTATTGC  TTACATTTGC  TTCTGACACA  ACTGTGTTCA  CTAGCAACCT     120
CAAACAGACA  CCATGGTGCA  CCTGACTCCT  GAGGAGAAGT  CTGCCGTTAC  TGCCCTGTGG     180
GGCAAGGTGA  ACGTGGATGA  AGTTGGTGGT  GAGGCCCTGG  GCAGGTTGGT  ATCAAGGTTA     240
CAAGACAGGT  TTAAGGAGAC  CAATAGAAAC  TGGGCATGTG  GAGACAGAGA  AGACTCTTGG     300
GTTTCTGATA  GGCACTGACT  CTCTCTGCCT  ATTAGTCTAT  TTTCCCACCC  TTAGGCTGCT     360
GGTGGTCTAC  CCTTGGACCC  AGAGGTTCTT  TGAGTCCTTT  GGGGATCTGT  CCACTCCTGA     420
TGCTGTTATG  GGCAACCCTA  AGGTGAAGGC  TCATGGCAAG  AAAGTGCTCG  GTGCCTTTAG     480
TGATGGCCTG  GCTCACCTGG  ACAACCTCAA  GGGCACCTTT  GCCACACTGA  GTGAGC         536
```

( 2 ) INFORMATION FOR SEQ ID NO:84:

( i ) SEQUENCE CHARACTERISTICS:
        ( A ) LENGTH: 157 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:84:

```
CACCGTCCTC  TTCAAGAAGT  TTATCCAGAA  GCCAATGCAC  CCATTGGACA  TAACCAGGAA      60
TCCTACATGG  TTCCTTTTAT  ACCACTGTAC  AGAAATGGTG  ATTTCTTTAT  TTCATCCAAA     120
GATCTGGGCT  ATGACTATAG  CTATCTACAA  GATTCAG                                157
```

( 2 ) INFORMATION FOR SEQ ID NO:85:

( i ) SEQUENCE CHARACTERISTICS:
        ( A ) LENGTH: 833 amino acids
        ( B ) TYPE: amino acid
        ( C ) STRANDEDNESS: single
        ( D ) TOPOLOGY: linear ( i i ) MOLECULE TYPE: protein (xi) SEQUENCE DESCRIPTION: SEQ ID NO:85:

Met Asn Ser Gly Met Leu Pro Leu Phe Glu Pro Lys Gly Arg Val Leu
1               5                   10                  15

Leu Val Asp Gly His His Leu Ala Tyr Arg Thr Phe His Ala Leu Lys
        20                  25                  30

Gly Leu Thr Thr Ser Arg Gly Glu Pro Val Gln Ala Val Tyr Gly Phe
            35                  40                  45

Ala Lys Ser Leu Leu Lys Ala Leu Lys Glu Asp Gly Asp Ala Val Ile
    50                  55                  60

Val Val Phe Asp Ala Lys Ala Pro Ser Phe Arg His Glu Ala Tyr Gly
65                  70                  75                  80

Gly Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Leu Ala Arg Leu
                100                 105                 110

Glu Val Pro Gly Tyr Glu Ala Asp Asp Val Leu Ala Ser Leu Ala Lys
            115                 120                 125

Lys Ala Glu Lys Glu Gly Tyr Glu Val Arg Ile Leu Thr Ala Asp Lys
    130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
            195                 200                 205

Leu Glu Glu Trp Gly Ser Leu Glu Ala Leu Leu Lys Asn Leu Asp Arg
210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
            245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
            275                 280                 285

Leu Glu Ser Pro Lys Ala Leu Glu Glu Ala Pro Trp Pro Pro Pro Glu
        290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
        370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

-continued

```
Leu  Trp  Gly  Arg  Leu  Glu  Gly  Glu  Glu  Arg  Leu  Leu  Trp  Leu  Tyr  Arg
          420                     425                          430

Glu  Val  Glu  Arg  Pro  Leu  Ser  Ala  Val  Leu  Ala  His  Met  Glu  Ala  Thr
          435                     440                          445

Gly  Val  Arg  Leu  Asp  Val  Ala  Tyr  Leu  Arg  Ala  Leu  Ser  Leu  Glu  Val
     450                     455                     460

Ala  Gly  Glu  Ile  Ala  Arg  Leu  Glu  Ala  Glu  Val  Phe  Arg  Leu  Ala  Gly
465                      470                     475                          480

His  Pro  Phe  Asn  Leu  Asn  Ser  Arg  Asp  Gln  Leu  Glu  Arg  Val  Leu  Phe
                    485                     490                          495

Asp  Glu  Leu  Gly  Leu  Pro  Ala  Ile  Gly  Lys  Thr  Glu  Lys  Thr  Gly  Lys
               500                     505                     510

Arg  Ser  Thr  Ser  Ala  Ala  Val  Leu  Glu  Ala  Leu  Arg  Glu  Ala  His  Pro
          515                     520                     525

Ile  Val  Glu  Lys  Ile  Leu  Gln  Tyr  Arg  Glu  Leu  Thr  Lys  Leu  Lys  Ser
          530                     535                     540

Thr  Tyr  Ile  Asp  Pro  Leu  Pro  Asp  Leu  Ile  His  Pro  Arg  Thr  Gly  Arg
545                      550                     555                          560

Leu  His  Thr  Arg  Phe  Asn  Gln  Thr  Ala  Thr  Ala  Thr  Gly  Arg  Leu  Ser
                    565                     570                          575

Ser  Ser  Asp  Pro  Asn  Leu  Gln  Asn  Ile  Pro  Val  Arg  Thr  Pro  Leu  Gly
               580                     585                     590

Gln  Arg  Ile  Arg  Arg  Ala  Phe  Ile  Ala  Glu  Glu  Gly  Trp  Leu  Leu  Val
          595                     600                     605

Ala  Leu  Asp  Tyr  Ser  Gln  Ile  Glu  Leu  Arg  Val  Leu  Ala  His  Leu  Ser
          610                     615                     620

Gly  Asp  Glu  Asn  Leu  Ile  Arg  Val  Phe  Gln  Glu  Gly  Arg  Asp  Ile  His
625                      630                     635                          640

Thr  Glu  Thr  Ala  Ser  Trp  Met  Phe  Gly  Val  Pro  Arg  Glu  Ala  Val  Asp
                    645                     650                          655

Pro  Leu  Met  Arg  Arg  Ala  Ala  Lys  Thr  Ile  Asn  Phe  Gly  Val  Leu  Tyr
               660                     665                     670

Gly  Met  Ser  Ala  His  Arg  Leu  Ser  Gln  Glu  Leu  Ala  Ile  Pro  Tyr  Glu
          675                     680                     685

Glu  Ala  Gln  Ala  Phe  Ile  Glu  Arg  Tyr  Phe  Gln  Ser  Phe  Pro  Lys  Val
          690                     695                     700

Arg  Ala  Trp  Ile  Glu  Lys  Thr  Leu  Glu  Glu  Gly  Arg  Arg  Arg  Gly  Tyr
705                      710                     715                          720

Val  Glu  Thr  Leu  Phe  Gly  Arg  Arg  Arg  Tyr  Val  Pro  Asp  Leu  Glu  Ala
                    725                     730                          735

Arg  Val  Lys  Ser  Val  Arg  Glu  Ala  Ala  Glu  Arg  Met  Ala  Phe  Asn  Met
               740                     745                     750

Pro  Val  Arg  Gly  Thr  Ala  Ala  Asp  Leu  Met  Lys  Leu  Ala  Met  Val  Lys
          755                     760                     765

Leu  Phe  Pro  Arg  Leu  Glu  Glu  Met  Gly  Ala  Arg  Met  Leu  Leu  Gln  Val
          770                     775                     780

His  Asp  Glu  Leu  Val  Leu  Glu  Ala  Pro  Lys  Glu  Arg  Ala  Glu  Ala  Val
785                      790                     795                          800

Ala  Arg  Leu  Ala  Lys  Glu  Val  Met  Glu  Gly  Val  Tyr  Pro  Leu  Ala  Val
                    805                     810                          815

Pro  Leu  Glu  Val  Glu  Val  Gly  Ile  Gly  Glu  Asp  Trp  Leu  Ser  Ala  Lys
               820                     825                     830

Glu
```

( 2 ) INFORMATION FOR SEQ ID NO:86:

( i ) SEQUENCE CHARACTERISTICS:
        ( A ) LENGTH: 548 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:86:

```
Met Asn Ser Gly Met Leu Pro Leu Phe Glu Pro Lys Gly Arg Val Leu
  1               5                  10                  15

Leu Val Asp Gly His His Leu Ala Tyr Arg Thr Phe His Ala Leu Lys
             20                  25                  30

Gly Leu Thr Thr Ser Arg Gly Glu Pro Val Gln Ala Val Tyr Gly Phe
         35                  40                  45

Ala Lys Ser Leu Leu Lys Ala Leu Lys Glu Asp Gly Asp Ala Val Ile
     50                  55                  60

Val Val Phe Asp Ala Lys Ala Pro Ser Phe Arg His Glu Ala Tyr Gly
 65                  70                  75                  80

Gly Tyr Lys Ala Gly Arg Ala Pro Thr Pro Glu Asp Phe Pro Arg Gln
                 85                  90                  95

Leu Ala Leu Ile Lys Glu Leu Val Asp Leu Leu Gly Leu Ala Arg Leu
                100                 105                 110

Glu Val Pro Gly Tyr Glu Ala Asp Asp Val Leu Ala Ser Leu Ala Lys
            115                 120                 125

Lys Ala Glu Lys Glu Gly Tyr Glu Val Arg Ile Leu Thr Ala Asp Lys
        130                 135                 140

Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350
```

-continued

```
Leu  Ala  Lys  Asp  Leu  Ser  Val  Leu  Ala  Leu  Arg  Glu  Gly  Leu  Gly  Leu
          355                      360                      365

Pro  Pro  Gly  Asp  Asp  Pro  Met  Leu  Leu  Ala  Tyr  Leu  Leu  Asp  Pro  Ser
     370                      375                      380

Asn  Thr  Thr  Pro  Glu  Gly  Val  Ala  Arg  Arg  Tyr  Gly  Gly  Glu  Trp  Thr
385                      390                      395                      400

Glu  Glu  Ala  Gly  Glu  Arg  Ala  Ala  Leu  Ser  Glu  Arg  Leu  Phe  Ala  Asn
               405                      410                      415

Leu  Trp  Gly  Arg  Leu  Glu  Gly  Glu  Glu  Arg  Leu  Leu  Trp  Leu  Tyr  Arg
               420                      425                      430

Glu  Val  Glu  Arg  Pro  Leu  Ser  Ala  Val  Leu  Ala  His  Met  Glu  Ala  Thr
               435                      440                      445

Gly  Val  Arg  Leu  Asp  Val  Ala  Tyr  Leu  Arg  Ala  Leu  Ser  Leu  Glu  Val
          450                      455                      460

Ala  Gly  Glu  Ile  Ala  Arg  Leu  Glu  Ala  Glu  Val  Phe  Arg  Leu  Ala  Gly
465                      470                      475                      480

His  Pro  Phe  Asn  Leu  Asn  Ser  Arg  Asp  Gln  Leu  Glu  Arg  Val  Leu  Phe
                    485                      490                      495

Asp  Glu  Leu  Gly  Leu  Pro  Ala  Ile  Gly  Lys  Thr  Glu  Lys  Thr  Gly  Lys
               500                      505                      510

Arg  Ser  Thr  Ser  Ala  Ala  Val  Leu  Glu  Ala  Leu  Arg  Glu  Ala  His  Pro
          515                      520                      525

Ile  Val  Glu  Lys  Ile  Leu  Gln  Ala  Cys  Lys  Leu  Gly  Thr  Gly  Arg  Arg
     530                      535                      540

Phe  Thr  Thr  Ser
545
```

( 2 ) INFORMATION FOR SEQ ID NO:87:

( i ) SEQUENCE CHARACTERISTICS:
        ( A ) LENGTH: 695 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:87:

```
Met  Asn  Ser  Gly  Met  Leu  Pro  Leu  Phe  Glu  Pro  Lys  Gly  Arg  Val  Leu
1                   5                        10                       15

Leu  Val  Asp  Gly  His  His  Leu  Ala  Tyr  Arg  Thr  Phe  His  Ala  Leu  Lys
               20                       25                       30

Gly  Leu  Thr  Thr  Ser  Arg  Gly  Glu  Pro  Val  Gln  Ala  Val  Tyr  Gly  Phe
          35                       40                       45

Ala  Lys  Ser  Leu  Leu  Lys  Ala  Leu  Lys  Glu  Asp  Gly  Asp  Ala  Val  Ile
     50                       55                       60

Val  Val  Phe  Asp  Ala  Lys  Ala  Pro  Ser  Phe  Arg  His  Glu  Ala  Tyr  Gly
65                       70                       75                       80

Gly  Tyr  Lys  Ala  Gly  Arg  Ala  Pro  Thr  Pro  Glu  Asp  Phe  Pro  Arg  Gln
                    85                       90                       95

Leu  Ala  Leu  Ile  Lys  Glu  Leu  Val  Asp  Leu  Leu  Gly  Leu  Ala  Arg  Leu
               100                      105                      110

Glu  Val  Pro  Gly  Tyr  Glu  Ala  Asp  Asp  Val  Leu  Ala  Ser  Leu  Ala  Lys
          115                      120                      125

Lys  Ala  Glu  Lys  Glu  Gly  Tyr  Glu  Val  Arg  Ile  Leu  Thr  Ala  Asp  Lys
     130                      135                      140
```

```
Asp Leu Tyr Gln Leu Leu Ser Asp Arg Ile His Val Leu His Pro Glu
145                 150                 155                 160

Gly Tyr Leu Ile Thr Pro Ala Trp Leu Trp Glu Lys Tyr Gly Leu Arg
                165                 170                 175

Pro Asp Gln Trp Ala Asp Tyr Arg Ala Leu Thr Gly Asp Glu Ser Asp
            180                 185                 190

Asn Leu Pro Gly Val Lys Gly Ile Gly Glu Lys Thr Ala Arg Lys Leu
        195                 200                 205

Leu Glu Glu Trp Gly Ser Leu Glu Ala Leu Leu Lys Asn Leu Asp Arg
    210                 215                 220

Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
                245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ala Leu Glu Glu Ala Pro Trp Pro Pro Pro Glu
    290                 295                 300

Gly Ala Phe Val Gly Phe Val Leu Ser Arg Lys Glu Pro Met Trp Ala
305                 310                 315                 320

Asp Leu Leu Ala Leu Ala Ala Ala Arg Gly Gly Arg Val His Arg Ala
                325                 330                 335

Pro Glu Pro Tyr Lys Ala Leu Arg Asp Leu Lys Glu Ala Arg Gly Leu
            340                 345                 350

Leu Ala Lys Asp Leu Ser Val Leu Ala Leu Arg Glu Gly Leu Gly Leu
        355                 360                 365

Pro Pro Gly Asp Asp Pro Met Leu Leu Ala Tyr Leu Leu Asp Pro Ser
370                 375                 380

Asn Thr Thr Pro Glu Gly Val Ala Arg Arg Tyr Gly Gly Glu Trp Thr
385                 390                 395                 400

Glu Glu Ala Gly Glu Arg Ala Ala Leu Ser Glu Arg Leu Phe Ala Asn
                405                 410                 415

Leu Trp Gly Arg Leu Glu Gly Glu Glu Arg Leu Leu Trp Leu Tyr Arg
            420                 425                 430

Glu Val Glu Arg Pro Leu Ser Ala Val Leu Ala His Met Glu Ala Thr
        435                 440                 445

Gly Val Arg Leu Asp Val Ala Tyr Leu Arg Ala Leu Ser Leu Glu Val
    450                 455                 460

Ala Gly Glu Ile Ala Arg Leu Glu Ala Glu Val Phe Arg Leu Ala Gly
465                 470                 475                 480

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
        515                 520                 525

Ile Val Glu Lys Ile Leu Gln Tyr Arg Glu Leu Thr Lys Leu Lys Ser
    530                 535                 540

Thr Tyr Ile Asp Pro Leu Pro Asp Leu Ile His Pro Arg Thr Gly Arg
545                 550                 555                 560

Leu His Thr Arg Phe Asn Gln Thr Ala Thr Ala Thr Gly Arg Leu Ser
                565                 570                 575
```

Ser  Ser  Asp  Pro  Asn  Leu  Gln  Asn  Ile  Pro  Val  Arg  Thr  Pro  Leu  Gly
               580                585                          590

Gln  Arg  Ile  Arg  Arg  Ala  Phe  Ile  Ala  Glu  Glu  Gly  Trp  Leu  Leu  Val
          595                600                          605

Ala  Leu  Asp  Tyr  Ser  Gln  Ile  Glu  Leu  Arg  Val  Leu  Ala  His  Leu  Ser
          610                615                     620

Gly  Asp  Glu  Asn  Leu  Ile  Arg  Val  Phe  Gln  Gly  Arg  Asp  Ile  His
625                     630                635                          640

Thr  Glu  Thr  Ala  Ser  Trp  Met  Phe  Gly  Val  Pro  Arg  Glu  Ala  Val  Asp
                    645                     650                          655

Pro  Leu  Met  Arg  Arg  Ala  Ala  Lys  Thr  Ile  Asn  Phe  Gly  Val  Leu  Tyr
               660                665                          670

Gly  Met  Ser  Ala  His  Arg  Leu  Ser  Gln  Glu  Leu  Ala  Ser  His  Pro  Leu
          675                     680                     685

Arg  Gly  Gly  Pro  Gly  Leu  His
690                          695

(2) INFORMATION FOR SEQ ID NO:88:

(i) SEQUENCE CHARACTERISTICS:
    (A) LENGTH: 310 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:88:

Met  Asn  Ser  Gly  Met  Leu  Pro  Leu  Phe  Glu  Pro  Lys  Gly  Arg  Val  Leu
1                    5                          10                     15

Leu  Val  Asp  Gly  His  His  Leu  Ala  Tyr  Arg  Thr  Phe  His  Ala  Leu  Lys
                20                     25                          30

Gly  Leu  Thr  Thr  Ser  Arg  Gly  Glu  Pro  Val  Gln  Ala  Val  Tyr  Gly  Phe
                35                     40                     45

Ala  Lys  Ser  Leu  Leu  Lys  Ala  Leu  Lys  Glu  Asp  Gly  Asp  Ala  Val  Ile
          50                     55                     60

Val  Val  Phe  Asp  Ala  Lys  Ala  Pro  Ser  Phe  Arg  His  Glu  Ala  Tyr  Gly
65                          70                     75                          80

Gly  Tyr  Lys  Ala  Gly  Arg  Ala  Pro  Thr  Pro  Glu  Asp  Phe  Pro  Arg  Gln
                    85                     90                          95

Leu  Ala  Leu  Ile  Lys  Glu  Leu  Val  Asp  Leu  Leu  Gly  Leu  Ala  Arg  Leu
               100                     105                          110

Glu  Val  Pro  Gly  Tyr  Glu  Ala  Asp  Asp  Val  Leu  Ala  Ser  Leu  Ala  Lys
          115                     120                          125

Lys  Ala  Glu  Lys  Glu  Gly  Tyr  Glu  Val  Arg  Ile  Leu  Thr  Ala  Asp  Lys
     130                     135                          140

Asp  Leu  Tyr  Gln  Leu  Leu  Ser  Asp  Arg  Ile  His  Val  Leu  His  Pro  Glu
145                          150                     155                          160

Gly  Tyr  Leu  Ile  Thr  Pro  Ala  Trp  Leu  Trp  Glu  Lys  Tyr  Gly  Leu  Arg
                    165                     170                          175

Pro  Asp  Gln  Trp  Ala  Asp  Tyr  Arg  Ala  Leu  Thr  Gly  Asp  Glu  Ser  Asp
               180                     185                          190

Asn  Leu  Pro  Gly  Val  Lys  Gly  Ile  Gly  Glu  Lys  Thr  Ala  Arg  Lys  Leu
          195                     200                     205

Leu  Glu  Glu  Trp  Gly  Ser  Leu  Glu  Ala  Leu  Leu  Lys  Asn  Leu  Asp  Arg
     210                     215                     220

-continued

```
Leu Lys Pro Ala Ile Arg Glu Lys Ile Leu Ala His Met Asp Asp Leu
225                 230                 235                 240

Lys Leu Ser Trp Asp Leu Ala Lys Val Arg Thr Asp Leu Pro Leu Glu
            245                 250                 255

Val Asp Phe Ala Lys Arg Arg Glu Pro Asp Arg Glu Arg Leu Arg Ala
            260                 265                 270

Phe Leu Glu Arg Leu Glu Phe Gly Ser Leu Leu His Glu Phe Gly Leu
        275                 280                 285

Leu Glu Ser Pro Lys Ser Trp Arg Gly Cys Ile Pro Trp Pro Cys Pro
        290                 295                 300

Trp Arg Trp Arg Trp Gly
305                 310
```

( 2 ) INFORMATION FOR SEQ ID NO:89:

( i ) SEQUENCE CHARACTERISTICS:
        ( A ) LENGTH: 322 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:89:

```
Met Ala Ser Met Thr Gly Gly Gln Gln Met Gly Arg Ile Asn Ser Gly
1               5                   10                  15

Met Leu Pro Leu Phe Glu Pro Lys Gly Arg Val Leu Leu Val Asp Gly
            20                  25                  30

His His Leu Ala Tyr Arg Thr Phe His Ala Leu Lys Gly Leu Thr Thr
        35                  40                  45

Ser Arg Gly Glu Pro Val Gln Ala Val Tyr Gly Phe Ala Lys Ser Leu
    50                  55                  60

Leu Lys Ala Leu Lys Glu Asp Gly Asp Ala Val Ile Val Val Phe Asp
65                  70                  75                  80

Ala Lys Ala Pro Ser Phe Arg His Glu Ala Tyr Gly Gly Tyr Lys Ala
            85                  90                  95

Gly Arg Ala Pro Thr Pro Glu Asp Phe Pro Arg Gln Leu Ala Leu Ile
            100                 105                 110

Lys Glu Leu Val Asp Leu Leu Gly Leu Ala Arg Leu Glu Val Pro Gly
            115                 120                 125

Tyr Glu Ala Asp Asp Val Leu Ala Ser Leu Ala Lys Lys Ala Glu Lys
            130                 135                 140

Glu Gly Tyr Glu Val Arg Ile Leu Thr Ala Asp Lys Asp Leu Tyr Gln
145                 150                 155                 160

Leu Leu Ser Asp Arg Ile His Val Leu His Pro Glu Gly Tyr Leu Ile
                165                 170                 175

Thr Pro Ala Trp Leu Trp Glu Lys Tyr Gly Leu Arg Pro Asp Gln Trp
            180                 185                 190

Ala Asp Tyr Arg Ala Leu Thr Gly Asp Glu Ser Asp Asn Leu Pro Gly
            195                 200                 205

Val Lys Gly Ile Gly Glu Lys Thr Ala Arg Lys Leu Leu Glu Glu Trp
            210                 215                 220

Gly Ser Leu Glu Ala Leu Leu Lys Asn Leu Asp Arg Leu Lys Pro Ala
225                 230                 235                 240

Ile Arg Glu Lys Ile Leu Ala His Met Asp Asp Leu Lys Leu Ser Trp
                245                 250                 255
```

|     |     |     |     |     |     |     |     |     |     |     |     |     |     |     |
| --- | --- | --- | --- | --- | --- | --- | --- | --- | --- | --- | --- | --- | --- | --- |
| Asp | Leu | Ala | Lys | Val | Arg | Thr | Asp | Leu | Pro | Leu | Glu | Val | Asp | Phe | Ala |
|     |     |     | 260 |     |     |     | 265 |     |     |     |     | 270 |     |     |     |
| Lys | Arg | Arg | Glu | Pro | Asp | Arg | Glu | Arg | Leu | Arg | Ala | Phe | Leu | Glu | Arg |
|     | 275 |     |     |     |     | 280 |     |     |     |     | 285 |     |     |     |     |
| Leu | Glu | Phe | Gly | Ser | Leu | Leu | His | Glu | Phe | Gly | Leu | Leu | Glu | Ser | Pro |
|     | 290 |     |     |     |     | 295 |     |     |     |     | 300 |     |     |     |     |
| Lys | Ser | Trp | Arg | Gly | Cys | Ile | Pro | Trp | Pro | Cys | Pro | Trp | Arg | Trp | Arg |
| 305 |     |     |     |     | 310 |     |     |     |     | 315 |     |     |     |     | 320 |
| Trp | Gly |     |     |     |     |     |     |     |     |     |     |     |     |     |     |

( 2 ) INFORMATION FOR SEQ ID NO:90:

( i ) SEQUENCE CHARACTERISTICS:
        ( A ) LENGTH: 528 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:90:

|     |     |     |     |     |     |     |     |     |     |     |     |     |     |     |     |
| --- | --- | --- | --- | --- | --- | --- | --- | --- | --- | --- | --- | --- | --- | --- | --- |
| Met | Leu | Pro | Leu | Phe | Glu | Pro | Lys | Gly | Arg | Val | Leu | Leu | Val | Asp | Gly |
| 1   |     |     |     | 5   |     |     |     |     | 10  |     |     |     |     | 15  |     |
| His | His | Leu | Ala | Tyr | Arg | Thr | Phe | His | Ala | Leu | Lys | Gly | Leu | Thr | Thr |
|     |     |     | 20  |     |     |     |     | 25  |     |     |     |     | 30  |     |     |
| Ser | Arg | Gly | Glu | Pro | Val | Gln | Ala | Val | Tyr | Gly | Phe | Ala | Lys | Ser | Leu |
|     |     | 35  |     |     |     |     | 40  |     |     |     |     | 45  |     |     |     |
| Leu | Lys | Ala | Leu | Lys | Glu | Asp | Gly | Asp | Ala | Val | Ile | Val | Val | Phe | Asp |
|     | 50  |     |     |     |     | 55  |     |     |     |     | 60  |     |     |     |     |
| Ala | Lys | Ala | Pro | Ser | Phe | Arg | His | Glu | Ala | Tyr | Gly | Gly | Tyr | Lys | Ala |
| 65  |     |     |     |     | 70  |     |     |     |     | 75  |     |     |     |     | 80  |
| Gly | Arg | Ala | Pro | Thr | Pro | Glu | Asp | Phe | Pro | Arg | Gln | Leu | Ala | Leu | Ile |
|     |     |     |     | 85  |     |     |     |     | 90  |     |     |     |     | 95  |     |
| Lys | Glu | Leu | Val | Asp | Leu | Leu | Gly | Leu | Ala | Arg | Leu | Glu | Val | Pro | Gly |
|     |     |     |     | 100 |     |     |     |     | 105 |     |     |     |     | 110 |     |
| Tyr | Glu | Ala | Asp | Asp | Val | Leu | Ala | Ser | Leu | Ala | Lys | Lys | Ala | Glu | Lys |
|     |     |     | 115 |     |     |     |     | 120 |     |     |     |     | 125 |     |     |
| Glu | Gly | Tyr | Glu | Val | Arg | Ile | Leu | Thr | Ala | Asp | Lys | Asp | Leu | Tyr | Gln |
|     | 130 |     |     |     |     | 135 |     |     |     |     | 140 |     |     |     |     |
| Leu | Leu | Ser | Asp | Arg | Ile | His | Val | Leu | His | Pro | Glu | Gly | Tyr | Leu | Ile |
| 145 |     |     |     |     | 150 |     |     |     |     | 155 |     |     |     |     | 160 |
| Thr | Pro | Ala | Trp | Leu | Trp | Glu | Lys | Tyr | Gly | Leu | Arg | Pro | Asp | Gln | Trp |
|     |     |     |     | 165 |     |     |     |     | 170 |     |     |     |     | 175 |     |
| Ala | Asp | Tyr | Arg | Ala | Leu | Thr | Gly | Asp | Glu | Ser | Asp | Asn | Leu | Pro | Gly |
|     |     |     | 180 |     |     |     |     | 185 |     |     |     |     | 190 |     |     |
| Val | Lys | Gly | Ile | Gly | Glu | Lys | Thr | Ala | Arg | Lys | Leu | Leu | Glu | Glu | Trp |
|     |     | 195 |     |     |     |     | 200 |     |     |     |     | 205 |     |     |     |
| Gly | Ser | Leu | Glu | Ala | Leu | Leu | Lys | Asn | Leu | Asp | Arg | Leu | Lys | Pro | Ala |
|     | 210 |     |     |     |     | 215 |     |     |     |     | 220 |     |     |     |     |
| Ile | Arg | Glu | Lys | Ile | Leu | Ala | His | Met | Asp | Asp | Leu | Lys | Leu | Ser | Trp |
| 225 |     |     |     |     | 230 |     |     |     |     | 235 |     |     |     |     | 240 |
| Asp | Leu | Ala | Lys | Val | Arg | Thr | Asp | Leu | Pro | Leu | Glu | Val | Asp | Phe | Ala |
|     |     |     |     | 245 |     |     |     |     | 250 |     |     |     |     | 255 |     |
| Lys | Arg | Arg | Glu | Pro | Asp | Arg | Glu | Arg | Leu | Arg | Ala | Phe | Leu | Glu | Arg |
|     |     |     | 260 |     |     |     |     | 265 |     |     |     |     | 270 |     |     |
| Leu | Glu | Phe | Gly | Ser | Leu | Leu | His | Glu | Phe | Gly | Leu | Leu | Glu | Ser | Pro |
|     |     | 275 |     |     |     |     | 280 |     |     |     |     | 285 |     |     |     |

Lys Ile Arg Arg Ala Phe Ile Ala Glu Glu Gly Trp Leu Leu Val Ala
290             295             300

Leu Asp Tyr Ser Gln Ile Glu Leu Arg Val Leu Ala His Leu Ser Gly
305             310             315             320

Asp Glu Asn Leu Ile Arg Val Phe Gln Gly Arg Asp Ile His Thr
                325             330             335

Glu Thr Ala Ser Trp Met Phe Gly Val Pro Arg Glu Ala Val Asp Pro
                340             345             350

Leu Met Arg Arg Ala Ala Lys Thr Ile Asn Phe Gly Val Leu Tyr Gly
        355             360             365

Met Ser Ala His Arg Leu Ser Gln Glu Leu Ala Ile Pro Tyr Glu Glu
    370             375             380

Ala Gln Ala Phe Ile Glu Arg Tyr Phe Gln Ser Phe Pro Lys Val Arg
385             390             395             400

Ala Trp Ile Glu Lys Thr Leu Glu Glu Gly Arg Arg Arg Gly Tyr Val
                405             410             415

Glu Thr Leu Phe Gly Arg Arg Arg Tyr Val Pro Asp Leu Glu Ala Arg
            420             425             430

Val Lys Ser Val Arg Glu Ala Ala Glu Arg Met Ala Phe Asn Met Pro
        435             440             445

Val Arg Gly Thr Ala Ala Asp Leu Met Lys Leu Ala Met Val Lys Leu
    450             455             460

Phe Pro Arg Leu Glu Glu Met Gly Ala Arg Met Leu Leu Gln Val His
465             470             475             480

Asp Glu Leu Val Leu Glu Ala Pro Lys Glu Arg Ala Glu Ala Val Ala
                485             490             495

Arg Leu Ala Lys Glu Val Met Glu Gly Val Tyr Pro Leu Ala Val Pro
            500             505             510

Leu Glu Val Glu Val Gly Ile Gly Glu Asp Trp Leu Ser Ala Lys Glu
        515             520             525

(2) INFORMATION FOR SEQ ID NO:91:

(i) SEQUENCE CHARACTERISTICS:
        (A) LENGTH: 315 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:91:

Met Ala Ser Met Thr Gly Gly Gln Gln Met Gly Arg Ile Asn Ser Gly
1               5               10              15

Met Leu Pro Leu Phe Glu Pro Lys Gly Arg Val Leu Leu Val Asp Gly
                20              25              30

His His Leu Ala Tyr Arg Thr Phe His Ala Leu Lys Gly Leu Thr Thr
            35              40              45

Ser Arg Gly Glu Pro Val Gln Ala Val Tyr Gly Phe Ala Lys Ser Leu
        50              55              60

Leu Lys Ala Leu Lys Glu Asp Gly Asp Ala Val Ile Val Val Phe Asp
65              70              75              80

Ala Lys Ala Pro Ser Phe Arg His Glu Ala Tyr Gly Gly Tyr Lys Ala
                85              90              95

Gly Arg Ala Pro Thr Pro Glu Asp Phe Pro Arg Gln Leu Ala Leu Ile
                100             105             110

| | | | | | | | | | | | | | | |
|---|---|---|---|---|---|---|---|---|---|---|---|---|---|---|
| Lys | Glu | Leu 115 | Val | Asp | Leu | Leu | Gly 120 | Leu | Ala | Arg | Leu | Glu 125 | Val | Pro | Gly |
| Tyr | Glu 130 | Ala | Asp | Asp | Val | Leu 135 | Ala | Ser | Leu | Ala | Lys 140 | Lys | Ala | Glu | Lys |
| Glu 145 | Gly | Tyr | Glu | Val | Arg 150 | Ile | Leu | Thr | Ala | Asp 155 | Lys | Asp | Leu | Tyr | Gln 160 |
| Leu | Leu | Ser | Asp | Arg 165 | Ile | His | Val | Leu | His 170 | Pro | Glu | Gly | Tyr | Leu 175 | Ile |
| Thr | Pro | Ala | Trp 180 | Leu | Trp | Glu | Lys | Tyr 185 | Gly | Leu | Arg | Pro | Asp 190 | Gln | Trp |
| Ala | Asp | Tyr 195 | Arg | Ala | Leu | Thr | Gly 200 | Asp | Glu | Ser | Asp | Asn 205 | Leu | Pro | Gly |
| Val | Lys 210 | Gly | Ile | Gly | Glu | Lys 215 | Thr | Ala | Arg | Lys | Leu 220 | Leu | Glu | Glu | Trp |
| Gly 225 | Ser | Leu | Glu | Ala | Leu 230 | Leu | Lys | Asn | Leu | Asp 235 | Arg | Leu | Lys | Pro | Ala 240 |
| Ile | Arg | Glu | Lys | Ile 245 | Leu | Ala | His | Met | Asp 250 | Asp | Leu | Lys | Leu | Ser 255 | Trp |
| Asp | Leu | Ala | Lys 260 | Val | Arg | Thr | Asp | Leu 265 | Pro | Leu | Glu | Val | Asp 270 | Phe | Ala |
| Lys | Arg | Arg 275 | Glu | Pro | Asp | Arg | Glu 280 | Arg | Leu | Arg | Ala | Phe 285 | Leu | Glu | Arg |
| Leu | Glu 290 | Phe | Gly | Ser | Leu | Leu 295 | His | Glu | Phe | Gly | Leu 300 | Leu | Glu | Ser | Pro |
| Lys 305 | Ala | Ala | Leu | Glu | His 310 | His | His | His | His 315 | His | | | | | |

RAPID DETECTION AND IDENTIFICATION OF NUCLEIC ACID VARIANTS

This is a Continuation Application of application Ser. No. 08/402,601, filed Mar. 9, 1995, now abandoned which is a Continuation-In-Part Application of application Ser. No. 08/337,164, filed Nov. 9, 1994 now abandoned, which is a Continuation-In-Part Application of application Ser. No. 08/254,359, filed Jun. 6, 1994 now U.S. Pat. No. 5,614,802, which is a Continuation-In-Part Application of application Ser. No. 08/073,384, filed Jun. 4, 1993, now issued as U.S. Pat. No. 5,541,311 on Jul. 30, 1996, which is a Continuation-In-Part Application of application Ser. No. 07/986,330, filed Dec. 7, 1992, now issued as U.S. Pat. No. 5,422,253 on Jun. 6, 1995.

FIELD OF THE INVENTION

The present invention relates to methods and compositions for treating nucleic acid, and in particular, methods and compositions for detection and characterization of nucleic acid sequences and sequence changes.

BACKGROUND OF THE INVENTION

The detection and characterization of specific nucleic acid sequences and sequence changes have been utilized to detect the presence of viral or bacterial nucleic acid sequences indicative of an infection, the presence of variants or alleles of mammalian genes associated with disease and cancers, and the identification of the source of nucleic acids found in forensic samples, as well as in paternity determinations.

Various methods are known in the art which may be used to detect and characterize specific nucleic acid sequences and sequence changes. Nonetheless, as nucleic acid sequence data of the human genome, as well as the genomes of pathogenic organisms accumulates, the demand for fast, reliable, cost-effective and user-friendly tests for specific sequences continues to grow. Importantly, these tests must be able to create a detectable signal from a very low copy number of the sequence of interest. The following discussion examines three levels of nucleic acid detection currently in use: I. Signal Amplification Technology for detection of rare sequences; II. Direct Detection Technology for detection of higher copy number sequences; and III. Detection of Unknown Sequence Changes for rapid screening of sequence changes anywhere within a defined DNA fragment.

I. Signal Amplification Technology Methods For Amplification

The "Polymerase Chain Reaction" (PCR) comprises the first generation of methods for nucleic acid amplification. However, several other methods have been developed that employ the same basis of specificity, but create signal by different amplification mechanisms. These methods include the "Ligase Chain Reaction" (LCR), "Self-Sustained Synthetic Reaction" (3SR/NASBA), and "Qβ-Replicase" (Qβ).

Polymerase Chain Reaction (PCR)

The polymerase chain reaction (PCR), as described in U.S. Pat. Nos. 4,683,195 and 4,683,202 to Mullis and Mullis et al., describe a method for increasing the concentration of a segment of target sequence in a mixture of genomic DNA without cloning or purification. This technology provides one approach to the problems of low target sequence concentration. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated as often as needed, in order to obtain relatively high concentrations of a segment of the desired target sequence.

The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified."

Ligase Chain Reaction (LCR or LAR)

The ligase chain reaction (LCR; sometimes referred to as "Ligase Amplification Reaction" (LAR) described by Barany, Proc. Natl. Acad. Sci., 88:189 (1991); Barany, PCR Methods and Applic., 1:5 (1991); and Wu and Wallace, Genomics 4:560 (1989) has developed into a well-recognized alternative method for amplifying nucleic acids. In LCR, four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. LCR has also been used in combination with PCR to achieve enhanced detection of single-base changes. Segev, PCT Public. No. WO09001069 A1 (1990). However, because the four oligonucleotides used in this assay can pair to form two short ligatable fragments, there is the potential for the generation of target-independent background signal. The use of LCR for mutant screening is limited to the examination of specific nucleic acid positions.

Self-Sustained Synthetic Reaction (3SR/NASBA)

The self-sustained sequence replication reaction (3SR) (Guatelli et al., Proc. Natl. Acad. Sci., 87:1874–1878 [1990], with an erratum at Proc. Natl. Acad. Sci., 87:7797 [1990]) is a transcription-based in vitro amplification system (Kwok et al., Proc. Natl. Acad. Sci., 86:1173–1177 [1989]) that can exponentially amplify RNA sequences at a uniform temperature. The amplified RNA can then be utilized for mutation detection (Fahy et al., PCR Meth. Appl., 1:25–33 [1991]). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. The use of 3SR to detect mutations is kinetically limited to screening small segments of DNA (e.g., 200–300 base pairs).

Q-Beta (Qβ) Replicase

In this method, a probe which recognizes the sequence of interest is attached to the replicatable RNA template for Qβ replicase. A previously identified major problem with false positives resulting from the replication of unhybridized probes has been addressed through use of a sequence-specific ligation step. However, available thermostable DNA ligases are not effective on this RNA substrate, so the ligation must be performed by T4 DNA ligase at low temperatures (37° C.). This prevents the use of high temperature as a means of achieving specificity as in the LCR, the ligation event can be used to detect a mutation at the junction site, but not elsewhere.

Table 1 below, lists some of the features desirable for systems useful in sensitive nucleic acid diagnostics, and summarizes the abilities of each of the major amplification methods (See also, Landgren, Trends in Genetics 9:199 [1993]).

A successful diagnostic method must be very specific. A straight-forward method of controlling the specificity of nucleic acid hybridization is by controlling the temperature of the reaction. While the 3SR/NASBA, and Qβ systems are all able to generate a large quantity of signal, one or more of the enzymes involved in each cannot be used at high temperature (i.e., >55° C.). Therefore the reaction temperatures cannot be raised to prevent non-specific hybridization of the probes. If probes are shortened in order to make them melt more easily at low temperatures, the likelihood of having more than one perfect match in a complex genome increases. For these reasons, PCR and LCR currently dominate the research field in detection technologies.

TABLE 1

| FEATURE | METHOD: | | | | |
| --- | --- | --- | --- | --- | --- |
| | PCR | LCR | PCR & LCR | 3SR NASBA | Qβ |
| Amplifies Target | + | + | + | + | |
| Recognition of Independent Sequences Required | + | + | + | + | + |
| Performed at High Temp. | + | + | | | |
| Operates at Fixed Temp. | | | | + | + |
| Exponential Amplification | + | + | + | + | + |
| Generic Signal Generation | | | | | + |
| Easily Automatable | | | | | |

The basis of the amplification procedure in the PCR and LCR is the fact that the products of one cycle become usable templates in all subsequent cycles, consequently doubling the population with each cycle. The final yield of any such doubling system can be expressed as: $(1+X)^n = y$, where "X" is the mean efficiency (percent copied in each cycle), "n" is the number of cycles, and "y" is the overall efficiency, or yield of the reaction (Mullis, PCR Methods Applic., 1:1 [1991]). If every copy of a target DNA is utilized as a template in every cycle of a polymerase chain reaction, then the mean efficiency is 100%. If 20 cycles of PCR are performed, then the yield will be $2^{20}$, or 1,048,576 copies of the starting material. If the reaction conditions reduce the mean efficiency to 85%, then the yield in those 20 cycles will be only $1.85^{20}$, or 220,513 copies of the starting material. In other words, a PCR running at 85% efficiency will yield only 21% as much final product, compared to a reaction running at 100% efficiency. A reaction that is reduced to 50% mean efficiency will yield less than 1% of the possible product.

In practice, routine polymerase chain reactions rarely achieve the theoretical maximum yield, and PCRs are usually run for more than 20 cycles to compensate for the lower yield. At 50% mean efficiency, it would take 34 cycles to achieve the million-fold amplification theoretically possible in 20, and at lower efficiencies, the number of cycles required becomes prohibitive. In addition, any background products that amplify with a better mean efficiency than the intended target will become the dominant products.

Also, many variables can influence the mean efficiency of PCR, including target DNA length and secondary structure, primer length and design, primer and dNTP concentrations, and buffer composition, to name but a few. Contamination of the reaction with exogenous DNA (e.g., DNA spilled onto lab surfaces) or cross-contamination is also a major consideration. Reaction conditions must be carefully optimized for each different primer pair and target sequence, and the process can take days, even for an experienced investigator. The laboriousness of this process, including numerous technical considerations and other factors, presents a significant drawback to using PCR in the clinical setting. Indeed, PCR has yet to penetrate the clinical market in a significant way. The same concerns arise with LCR, as LCR must also be optimized to use different oligonucleotide sequences for each target sequence. In addition, both methods require expensive equipment, capable of precise temperature cycling.

Many applications of nucleic acid detection technologies, such as in studies of allelic variation, involve not only detection of a specific sequence in a complex background, but also the discrimination between sequences with few, or single, nucleotide differences. One method for the detection of allele-specific variants by PCR is based upon the fact that it is difficult for Taq polymerase to synthesize a DNA strand when there is a mismatch between the template strand and the 3' end of the primer. An allele-specific variant may be detected by the use of a primer that is perfectly matched with only one of the possible alleles; the mismatch to the other allele acts to prevent the extension of the primer, thereby preventing the amplification of that sequence. This method has a substantial limitation in that the base composition of the mismatch influences the ability to prevent extension across the mismatch, and certain mismatches do not prevent extension or have only a minimal effect (Kwok et al., Nucl. Acids Res., 18:999 [1990]).

A similar 3'-mismatch strategy is used with greater effect to prevent ligation in the LCR (Barany, PCR Meth. Applic., 1:5 [1991]). Any mismatch effectively blocks the action of the thermostable ligase, but LCR still has the drawback of target-independent background ligation products initiating the amplification. Moreover, the combination of PCR with subsequent LCR to identify the nucleotides at individual positions is also a clearly cumbersome proposition for the clinical laboratory.

II. Direct Detection Technology

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats. Two examples are the "Cycling Probe Reaction" (CPR), and "Branched DNA" (bDNA)

The cycling probe reaction (CPR) (Duck et al., BioTech., 9:142 [1990]), uses a long chimeric oligonucleotide in which a central portion is made of RNA while the two termini are made of DNA. Hybridization of the probe to a target DNA and exposure to a thermostable RNase H causes the RNA portion to be digested. This destabilizes the remaining DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Branched DNA (bDNA), described by Urdea et al., Gene 61:253–264 (1987), involves oligonucleotides with branched structures that allow each individual oligonucleotide to carry 35 to 40 labels (e.g., alkaline phosphatase enzymes). While this enhances the signal from a hybridization event, signal from non-specific binding is similarly increased.

III. Detection Of Unknown Sequence Changes

The demand for tests which allow the detection of specific nucleic acid sequences and sequence changes is growing rapidly in clinical diagnostics. As nucleic acid sequence data for genes from humans and pathogenic organisms accumulates, the demand for fast, cost-effective, and easy-to-use tests for as yet unknown mutations within specific sequences is rapidly increasing.

A handful of methods have been devised to scan nucleic acid segments for mutations. One option is to determine the entire gene sequence of each test sample (e.g., a bacterial isolate). For sequences under approximately 600 nucleotides, this may be accomplished using amplified material (e.g., PCR reaction products). This avoids the time and expense associated with cloning the segment of interest. However, specialized equipment and highly trained personnel are required, and the method is too labor-intense and expensive to be practical and effective in the clinical setting.

In view of the difficulties associated with sequencing, a given segment of nucleic acid may be characterized on several other levels. At the lowest resolution, the size of the molecule can be determined by electrophoresis by comparison to a known standard run on the same gel. A more detailed picture of the molecule may be achieved by cleavage with combinations of restriction enzymes prior to electrophoresis, to allow construction of an ordered map. The presence of specific sequences within the fragment can be detected by hybridization of a labeled probe, or the precise nucleotide sequence can be determined by partial chemical degradation or by primer extension in the presence of chain-terminating nucleotide analogs.

For detection of single-base differences between like sequences, the requirements of the analysis are often at the highest level of resolution. For cases in which the position of the nucleotide in question is known in advance, several methods have been developed for examining single base changes without direct sequencing. For example, if a mutation of interest happens to fall within a restriction recognition sequence, a change in the pattern of digestion can be used as a diagnostic tool (e.g., restriction fragment length polymorphism [RFLP] analysis).

Single point mutations have been also detected by the creation or destruction of RFLPs. Mutations are detected and localized by the presence and size of the RNA fragments generated by cleavage at the mismatches. Single nucleotide mismatches in DNA heteroduplexes are also recognized and cleaved by some chemicals, providing an alternative strategy to detect single base substitutions, generically named the "Mismatch Chemical Cleavage" (MCC) (Gogos et al., Nucl. Acids Res., 18:6807–6817 [1990]). However, this method requires the use of osmium tetroxide and piperidine, two highly noxious chemicals which are not suited for use in a clinical laboratory.

RFLP analysis suffers from low sensitivity and requires a large amount of sample. When RFLP analysis is used for the detection of point mutations, it is, by its nature, limited to the detection of only those single base changes which fall within a restriction sequence of a known restriction endonuclease. Moreover, the majority of the available enzymes have 4 to 6 base-pair recognition sequences, and cleave too frequently for many large-scale DNA manipulations (Eckstein and Lilley (eds.), *Nucleic Acids and Molecular Biology*, vol. 2, Springer-Verlag, Heidelberg [1988]). Thus, it is applicable only in a small fraction of cases, as most mutations do not fall within such sites.

A handful of rare-cutting restriction enzymes with 8 base-pair specificities have been isolated and these are widely used in genetic mapping, but these enzymes are few in number, are limited to the recognition of G+C-rich sequences, and cleave at sites that tend to be highly clustered (Barlow and Lehrach, Trends Genet., 3:167 [1987]). Recently, endonucleases encoded by group I introns have been discovered that might have greater than 12 base-pair specificity (Perlman and Butow, Science 246:1106 [1989]), but again, these are few in number.

If the change is not in a recognition sequence, then allele-specific oligonucleotides (ASOs), can be designed to hybridize in proximity to the unknown nucleotide, such that a primer extension or ligation event can be used as the indicator of a match or a mis-match. Hybridization with radioactively labeled allelic specific oligonucleotides (ASO) also has been applied to the detection of specific point mutations (Conner et al., Proc. Natl. Acad. Sci., 80:278–282 [1983]). The method is based on the differences in the melting temperature of short DNA fragments differing by a single nucleotide. Stringent hybridization and washing conditions can differentiate between mutant and wild-type alleles. The ASO approach applied to PCR products also has been extensively utilized by various researchers to detect and characterize point mutations in ras genes (Vogelstein et al., N. Eng. J. Med., 319:525–532 [1988]; and Farr et al., Proc. Natl. Acad. Sci., 85:1629–1633 [1988]), and gsp/gip oncogenes (Lyons et al., Science 249:655–659 [1990]). Because of the presence of various nucleotide changes in multiple positions, the ASO method requires the use of many oligonucleotides to cover all possible oncogenic mutations.

With either of the techniques described above (i.e., RFLP and ASO), the precise location of the suspected mutation must be known in advance of the test. That is to say, they are inapplicable when one needs to detect the presence of a mutation of an unknown character and position within a gene or sequence of interest.

Two other methods rely on detecting changes in electrophoretic mobility in response to minor sequence changes. One of these methods, termed "Denaturing Gradient Gel Electrophoresis" (DGGE) is based on the observation that slightly different sequences will display different patterns of local melting when electrophoretically resolved on a gradient gel. In this manner, variants can be distinguished, as differences in melting properties of homoduplexes versus heteroduplexes differing in a single nucleotide can detect the presence of mutations in the target sequences because of the corresponding changes in their electrophoretic mobilities. The fragments to be analyzed, usually PCR products, are "clamped" at one end by a long stretch of G–C base pairs (30–80) to allow complete denaturation of the sequence of interest without complete dissociation of the strands. The attachment of a GC "clamp" to the DNA fragments increases the fraction of mutations that can be recognized by DGGE (Abrams et al., Genomics 7:463–475 [1990]). Attaching a GC clamp to one primer is critical to ensure that the amplified sequence has a low dissociation temperature (Sheffield et al., Proc. Natl. Acad. Sci., 86:232–236 [1989]; and Lerman and Silverstein, Meth. Enzymol., 155:482–501 [1987]). Modifications of the technique have been developed, using temperature gradients (Wartell et al., Nucl. Acids Res., 18:2699–2701 [1990]), and the method can be also applied to RNA:RNA duplexes (Smith et al., Genomics 3:217–223 [1988]).

Limitations on the utility of DGGE include the requirement that the denaturing conditions must be optimized for each type of DNA to be tested. Furthermore, the method requires specialized equipment to prepare the gels and maintain the needed high temperatures during electrophoresis. The expense associated with the synthesis of the clamping tail on one oligonucleotide for each sequence to be tested is also a major consideration.

Another common method, called "Single-Strand Conformation Polymorphism" (SSCP) was developed by Hayashi, Sekya and colleagues (reviewed by Hayashi, PCR Meth. Appl., 1:34–38, [1991]) and is based on the observation that single strands of nucleic acid can take on characteristic conformations in non-denaturing conditions, and these conformations influence electrophoretic mobility. The complementary strands assume sufficiently different structures that one strand may be resolved from the other. Changes in sequences within the fragment will also change the conformation, consequently altering the mobility and allowing this to be used as an assay for sequence variations (Orita, et al., Genomics 5:874–879, [1989]).

The SSCP process involves denaturing a DNA segment (e.g., a PCR product) that is labelled on both strands, followed by slow electrophoretic separation on a non-denaturing polyacrylamide gel, so that intra-molecular interactions can form and not be disturbed during the run. This technique is extremely sensitive to variations in gel composition and temperature. A serious limitation of this method is the relative difficulty encountered in comparing data generated in different laboratories, under apparently similar conditions.

In addition to the above limitations, all of these methods are limited as to the size of the nucleic acid fragment that can be analyzed. For the direct sequencing approach, sequences of greater than 600 base pairs require cloning, with the consequent delays and expense of either deletion subcloning or primer walking, in order to cover the entire fragment. SSCP and DGGE have even more severe size limitations. Because of reduced sensitivity to sequence changes, these methods are not considered suitable for larger fragments. Although SSCP is reportedly able to detect 90% of single-base substitutions within a 200 base-pair fragment, the detection drops to less than 50% for 400 base pair fragments. Similarly, the sensitivity of DGGE decreases as the length of the fragment reaches 500 base-pairs.

Clearly, there remains a need for a method that is less sensitive to size so that entire genes, rather than gene fragments, may be analyzed. Such a tool must also be robust, so that data from different labs, generated by researchers of diverse backgrounds and skills will be comparable. Ideally, such a method would be compatible with "multiplexing," (i.e., the simultaneous analysis of several molecules or genes in a single reaction or gel lane, usually resolved from each other by differential labelling or probing). Such an analytical procedure would facilitate the use of internal standards for subsequent analysis and data comparison, and increase the productivity of personnel and equipment. The ideal method would also be easily automatable.

SUMMARY OF THE INVENTION

The present invention relates to methods and compositions for treating nucleic acid, and in particular, methods and compositions for detection and characterization of nucleic acid sequences and sequence changes. The present invention provides means for cleaving a nucleic acid cleavage structure in a site-specific manner. In one embodiment, the means for cleaving is an enzyme capable of cleaving cleavage structures on a nucleic acid substrate, forming the basis of a novel method of detection of specific nucleic acid sequences. The present invention contemplates use of the novel detection method for, among other uses, clinical diagnostic purposes.

In one embodiment, the present invention contemplates a DNA sequence encoding a DNA polymerase altered in sequence (i.e., a "mutant" DNA polymerase) relative to the native sequence such that it exhibits altered DNA synthetic activity from that of the native (ie., "wild type") DNA polymerase. It is preferred that the encoded DNA polymerase is altered such that it exhibits reduced synthetic activity from that of the native DNA polymerase. In this manner, the enzymes of the invention are nucleases and are capable of cleaving nucleic acids in a structure-specific manner.

Importantly, the nucleases of the present invention are capable of cleaving cleavage structures to create discrete cleavage products.

The present invention contemplates nucleases from a variety of sources, including nucleases that are thermostable. Thermostable nucleases are contemplated as particularly useful in that they operate at temperatures where nucleic acid hybridization is extremely specific, allowing for allele-specific detection (including single-base mismatches). In one embodiment, the thermostable 5' nucleases are selected from the group consisting of altered polymerases derived from the native polymerases of *Thermus aquaticus, Thermus flavus* and *Thermus thermophilus*.

The present invention utilizes such enzymes in methods for detection and characterization of nucleic acid sequences and sequence changes. The present invention relates to means for cleaving a nucleic acid cleavage structure in a site-specific manner. Nuclease activity is used to screen for known and unknown mutations, including single base changes, in nucleic acids.

In one embodiment, the present invention contemplates a method for detecting secondary structure (or characteristic folded structure) in nucleic acid substrates comprising: a) providing: i) a cleavage means; and ii) a nucleic acid target substrate; b) mixing said cleavage means and said substrate under conditions such that said substrate forms one or more secondary structures and said cleavage means cleaves said secondary structures resulting in the generation of multiple cleavage products; and c) separating said multiple cleavage products so as to generate a pattern of cleavage products. By detecting secondary structure, the method of the present invention indirectly detects sequences. In one embodiment, the method further comprises step d) comparing said pattern of cleavage products from said target substrate with the pattern of cleavage products generated by cleaving a different (a second) target substrate. In such a case the sequence of the second target substrate may be related but different (e.g., a wild type control for a mutant sequence).

The present invention contemplates further a method for detecting sequence variation in nucleic acid target substrates comprising: a) providing: i) a cleavage means; and ii) a nucleic acid target substrate suspected of containing sequence variation relative to a wild type control; b) mixing said cleavage means and said substrate under conditions such that said substrate forms one or more secondary structures and said cleavage means cleaves said secondary structures resulting in the generation of multiple cleavage products; and c) separating said multiple cleavage products so as to detect said sequence variation. In one embodiment, the method further comprises step d) comparing said separated cleavage products from said target nucleic acid with a wild type control. In a preferred embodiment, said cleavage means comprises a nuclease.

The present invention further contemplates a method for detecting sequence variation in nucleic acid target substrates comprising: a) providing: i) a cleavage means; and ii) a nucleic acid target substrate suspected of containing sequence variation relative to a wild type control; b) mixing said cleavage means and said substrate at an elevated temperature and under conditions such that said substrate forms one or more secondary structures and said cleavage means cleaves said secondary structures resulting in the generation of multiple cleavage products; and c) separating said multiple cleavage products so as to detect said sequence variation. The method may further comprise step d) comparing said separated cleavage products from said target nucleic acid with a wild type control. Again, the cleavage means may comprise a thermostable 5' nuclease. As noted above, such an enzyme may have a portion of its amino acid sequence that is homologous to a portion of the amino acid sequence of a thermostable DNA polymerase derived from a eubacterial thermophile, the latter being selected from the group consisting of *Thermus aquaticus, Thermus favus* and *Thermus thermophilus*. Useful nucleases include those encoded by DNA sequences selected from the group consisting of SEQ ID NOS:9, 11, 12, 30 and 31.

The present invention further contemplates a method for detecting sequence variation in nucleic acid target substrates comprising: a) providing: i) a thermostable DNA polymerase altered in amino acid sequence such that it exhibits reduced DNA synthetic activity from that of the wild-type DNA polymerase but retains substantially the same 5' nuclease activity of the wild-type DNA polymerase; and ii) a nucleic acid target substrate suspected of containing sequence variation relative to a wild type control; b) mixing said polymerase and said substrate under conditions such that said substrate forms one or more secondary structures and said polymerase cleaves said secondary structures resulting in the generation of multiple cleavage products; and c) separating said multiple cleavage products so as to detect said sequence variation. With regard to the polymerase, a complete absence of synthesis is not required; it is desired that cleavage reactions occur in the absence of polymerase activity at a level where it interferes with the method. In one embodiment, the method further comprises step d) comparing said separated cleavage products from said target nucleic acid with a wild type control. In one embodiment, the nucleic acid target contains a fluorescent label and the detection of step c) comprises detection of said fluorescently labelled fragments.

The present invention also contemplates generally a method for treating nucleic acid, comprising: a) providing i) a cleavage means, and ii) nucleic acid substrate; b) treating said nucleic acid substrate under conditions such that said substrate forms one or more cleavage structures; and c) reacting said cleavage means with said cleavage structures so that one or more cleavage products are produced.

In one embodiment, the method contemplates that the nucleic acid of step (a) is double stranded. The treating of step (b) may comprise i) rendering said double-stranded nucleic acid substantially single-stranded, and ii) exposing said single-stranded nucleic acid to conditions such that said single-stranded nucleic acid has secondary structure. In one case, the double stranded nucleic acid is rendered substantially single-stranded by increased temperature.

The present invention also contemplates a method for treating nucleic acid, comprising:a) providing i) a cleavage means in a solution containing manganese, ii) nucleic acid substrate; b) treating said nucleic acid substrate with increased temperature such that said substrate is substantially single-stranded; c) reducing said temperature under conditions such that said single-stranded substrate forms one or more cleavage structures; d) reacting said cleavage means with said cleavage structures so that one or more cleavage products are produced; and e) detecting said one or more cleavage products.

The preferred cleavage means is an enzyme, such as a nuclease. Examples of enzymes that can be used with success with the method of the present invention include (but are not limited to) the Cleavase™ BN enzyme, *Thermus aquaticus* DNA polymerase, *Thermus thermophilus* DNA polymerase, *Escherichia coli* Exo III, and the *Saccharomyces cerevisiae* Rad1/Rad10 complex.

The present invention is not limited by the nature of the nucleic acid target substrates. In the above-described embodiments, the nucleic acid target may be single-stranded DNA, double-stranded DNA, or RNA.

The present invention also contemplates a nucleic acid treatment kit, comprising: a) an enzyme capable of reacting with cleavage structures so as to generate cleavage products, and b) a solution containing manganese. The present invention contemplates other reagents useful for the treatment of nucleic acid. For example, the kit may include reagents for detecting said cleavage products. Furthermore, the kit may include reagents for the cleavage reaction including salt solutions (e.g., KCl and NaCl solutions), manganese chloride solutions, buffer solutions and solutions which terminate the cleavage reaction.

The present invention also contemplates a process for detection and identifying strains of microorganisms comprising: a) extracting nucleic acid from a sample suspected of containing a microorganism; b) contacting said extracted nucleic acid with a cleavage means under conditions such that said extracted nucleic acid forms one or more secondary structures and said cleavage means cleaves said secondary structures resulting in the generation of multiple cleavage products; c) separating said multiple cleavage products d) comparing said separated cleavage products generated from cleavage of nucleic acid isolated from said sample with separated cleavage products generated by cleavage of nucleic acids derived from known microorganisms. In a preferred embodiment, the additional step of isolating a polymorphic locus (e.g, ribosomal genes) from the extracted nucleic acid by restriction enzyme digestion and/or amplification using suitable primers and the PCR is employed after the extraction of step a) to generate a nucleic acid substrate for use in the cleavage reaction.

It is not intended that the present invention be limited by the nature of the microorganism. The detection and identification is application to all organisms, including viruses and bacteria.

The present invention also contemplates a process for creating a record reference (e.g., library) of genetic fingerprints characteristic (i.e., diagnostic) of pathogenic microorganisms comprising: a) providing: i) a cleavage means; and ii) a nucleic acid substrate characteristic of (e.g., derived from a polymorphic locus) isolated from a known pathogenic microorganism; b) contacting said nucleic acid substrate with a cleavage means under conditions such that said extracted nucleic acid forms one or more secondary structures and said cleavage means cleaves said secondary structures resulting in the generation of multiple cleavage products; c) separating said multiple cleavage products; and d) maintaining a record reference of said separated cleavage products.

By the term "genetic fingerprint" it is meant that changes in the sequence of the nucleic acid (e.g., a deletion, insertion or a single point substitution) alter the structures formed, thus changing the banding pattern (i.e., the "fingerprint") to reflect the difference in the sequence, allowing rapid detection and identification of variants.

The present invention also contemplates a process for creating a record reference library of genetic fingerprints characteristic (ie., diagnostic) of one or more alleles of one or more genes from a eukaryotic organism (mammal) comprising: a) providing: i) a cleavage means; and ii) nucleic acid substrate derived from one or more alleles of a gene derived from a eukaryotic organism; b) contacting said nucleic acid substrate with a cleavage means under conditions such that said extracted nucleic acid forms one or more secondary structures and said cleavage means cleaves said secondary structures resulting in the generation of multiple cleavage products; c) separating said multiple cleavage products; and d) maintaining a testable record reference of said separated cleavage products.

The methods of the present invention allow for simultaneous analysis of both strands (e.g., the sense and antisense strands) and are ideal for high-level multiplexing. The products produced are amenable to qualitative, quantitative and positional analysis. The methods may be automated and may be practiced in solution or in the solid phase (e.g., on a solid support). The methods are powerful in that they allow for analysis of longer fragments of nucleic acid than current methodologies.

DESCRIPTION OF THE DRAWINGS

FIGS. 1B and 1C provide a schematic of a second embodiment of the detection method of the present invention.

Figure 2C:
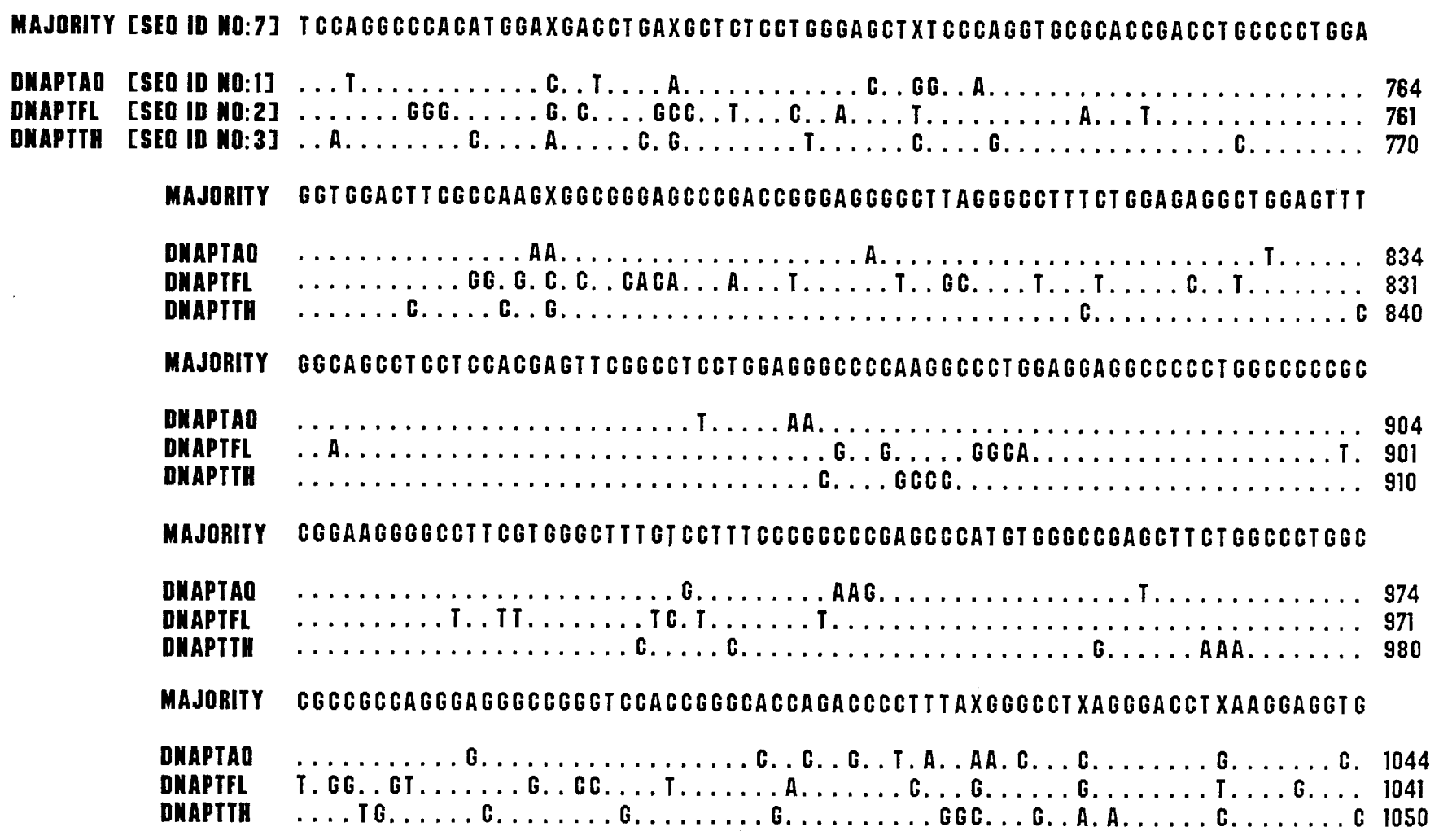
Figure 2D:
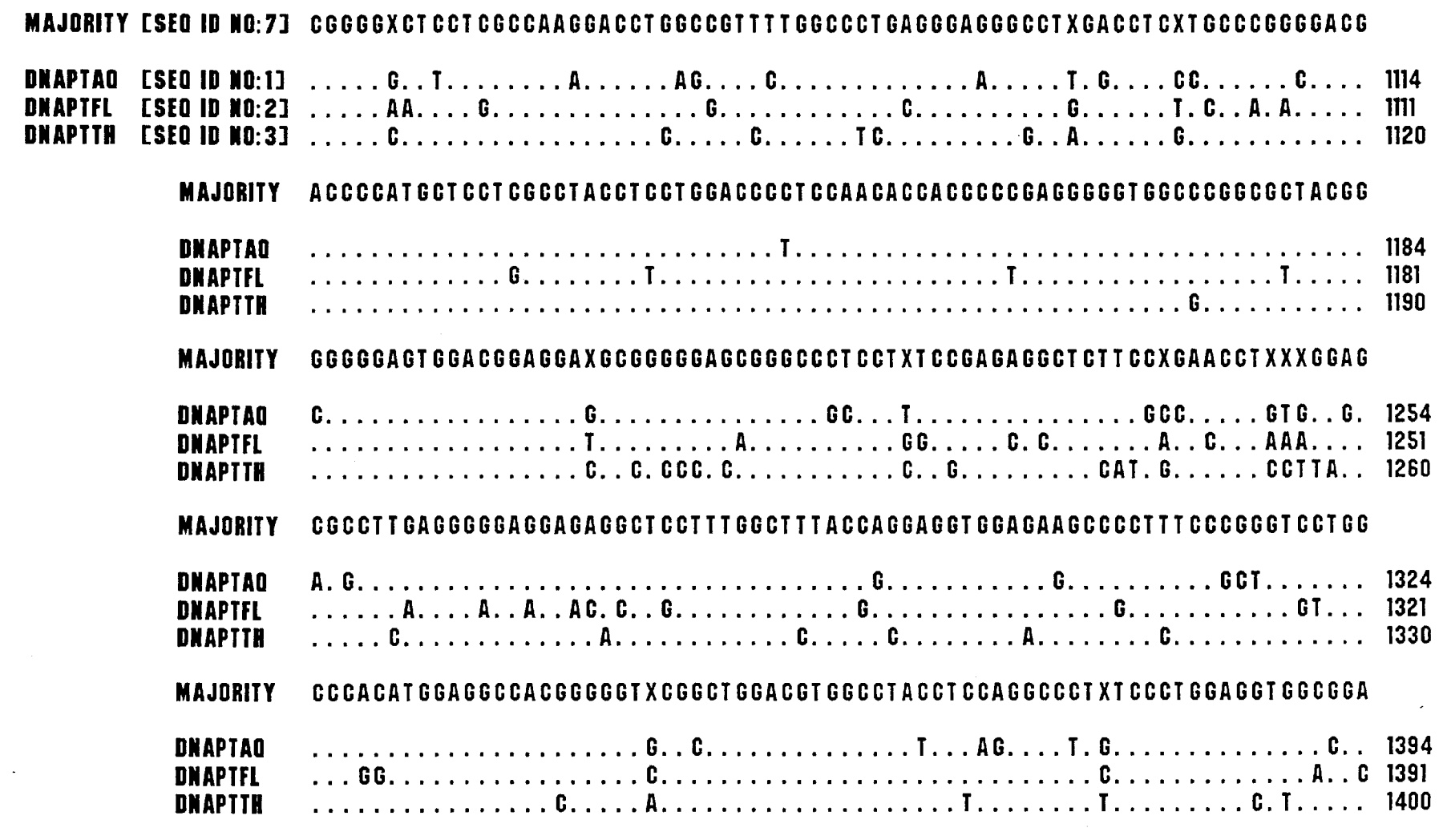
Figure 2F:
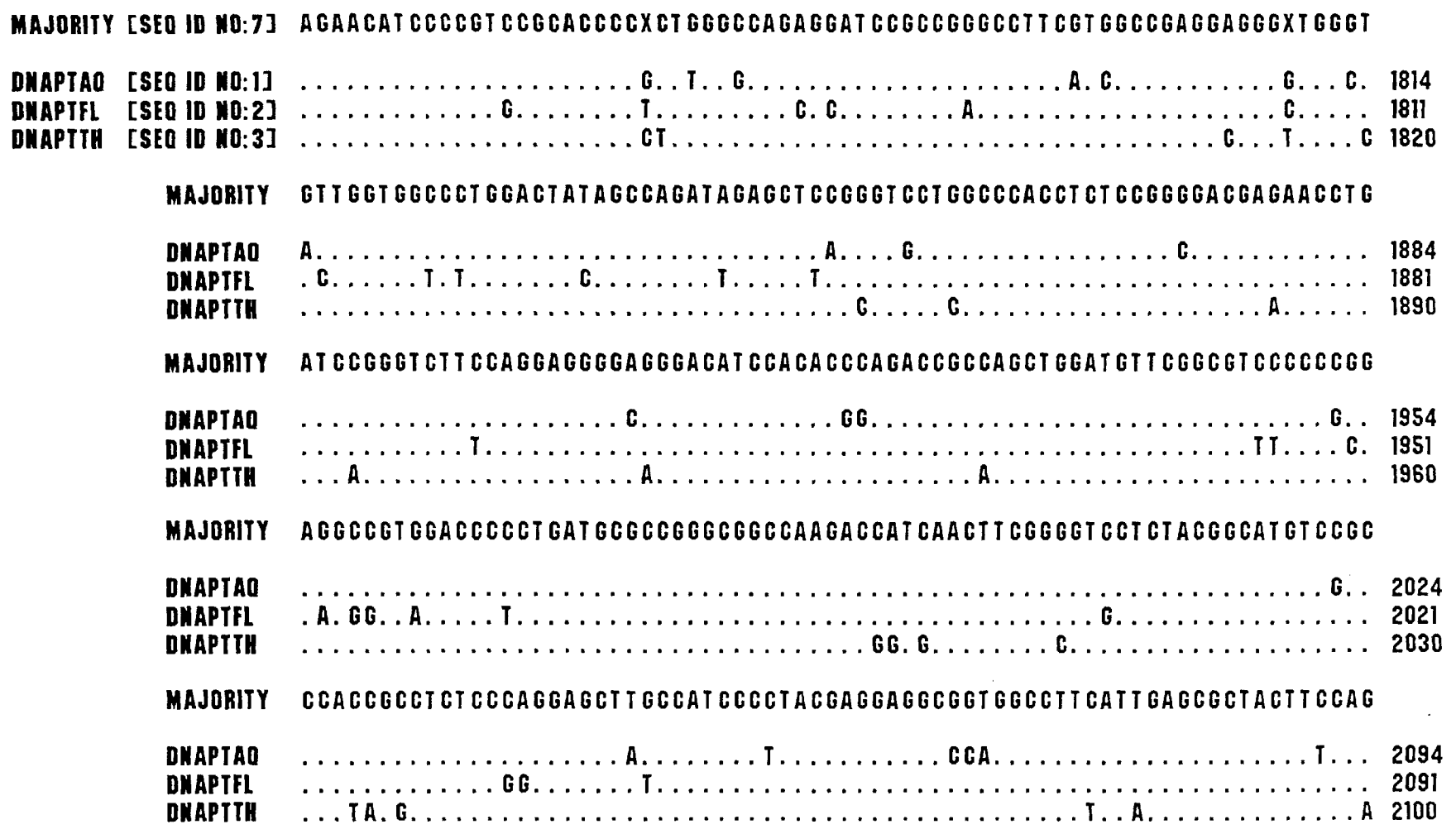

FIGS. 2A–H depict a comparison of the nucleotide structure of the DNAP genes isolated from *Thermus aquaticus* (SEQ ID NO:1), *Thermus favus* (SEQ ID NO:2) and *Thermus thermophilus* (SEQ ID NO:3); the consensus sequence (SEQ ID NO:7) is shown at the top of each row.

FIGS. 3A–C depict a comparison of the amino acid sequence of the DNAP isolated from *Thermus aquaticus* (SEQ ID NO:4), *Thermus flavus* (SEQ ID NO:5), and *Thermus thermophilus* (SEQ ID NO:6); the consensus sequence (SEQ ID NO:8) is shown at the top of each row.

FIGS. 4A–G are a set of diagrams of wild-type and synthesis-deficient DNAPTaq genes.

FIG. 5A depicts the wild-type *Thermus flavus* polymerase gene.

FIG. 5B depicts a synthesis-deficient *Thermus flavus* polymerase gene.

FIGS. 14A–C provide a diagram of vector pTTQ 18.

FIG. 19B shows an autoradiogram of a gel resolving the products of a cleavage reaction run using the substrate shown in FIG. 19A.

FIG. 20A shows the A- and T-hairpin molecules used in the trigger/detection assay.

FIG. 20B shows the sequence of the alpha primer used in the trigger/detection assay.

FIG. 20C shows the structure of the cleaved A- and T-hairpin molecules.

FIG. 20D depicts the complementarity between the A- and T-hairpin molecules.

FIG. 36 shows an autoradiograph of a gel resolving the products of cleavage reactions run for different lengths of time.

FIG. 49 depicts the nucleotide sequence of six SIV LTR clones corresponding to SEQ ID NOS:76–81.

FIG. 69 shows an autoradiograph of a gel resolving the products of single-stranded cleavage reactions run using the *E. coli* Exo III enzyme in two different concentrations of KCl.

FIG. 70 shows an autoradiograph of a gel resolving the products of single-stranded cleavage reactions run on three different tyrosinase gene substrates (SEQ ID NOS:47, 54 and 55) using either the Tth DNA polymerase, the *E. coli* Exo III enzyme or Cleavase™ BN.

FIG. 71 is a schematic drawing depicting the location of the 5' and 3' cleavage sites on a cleavage structure.

DESCRIPTION OF THE INVENTION

Figure 1A:
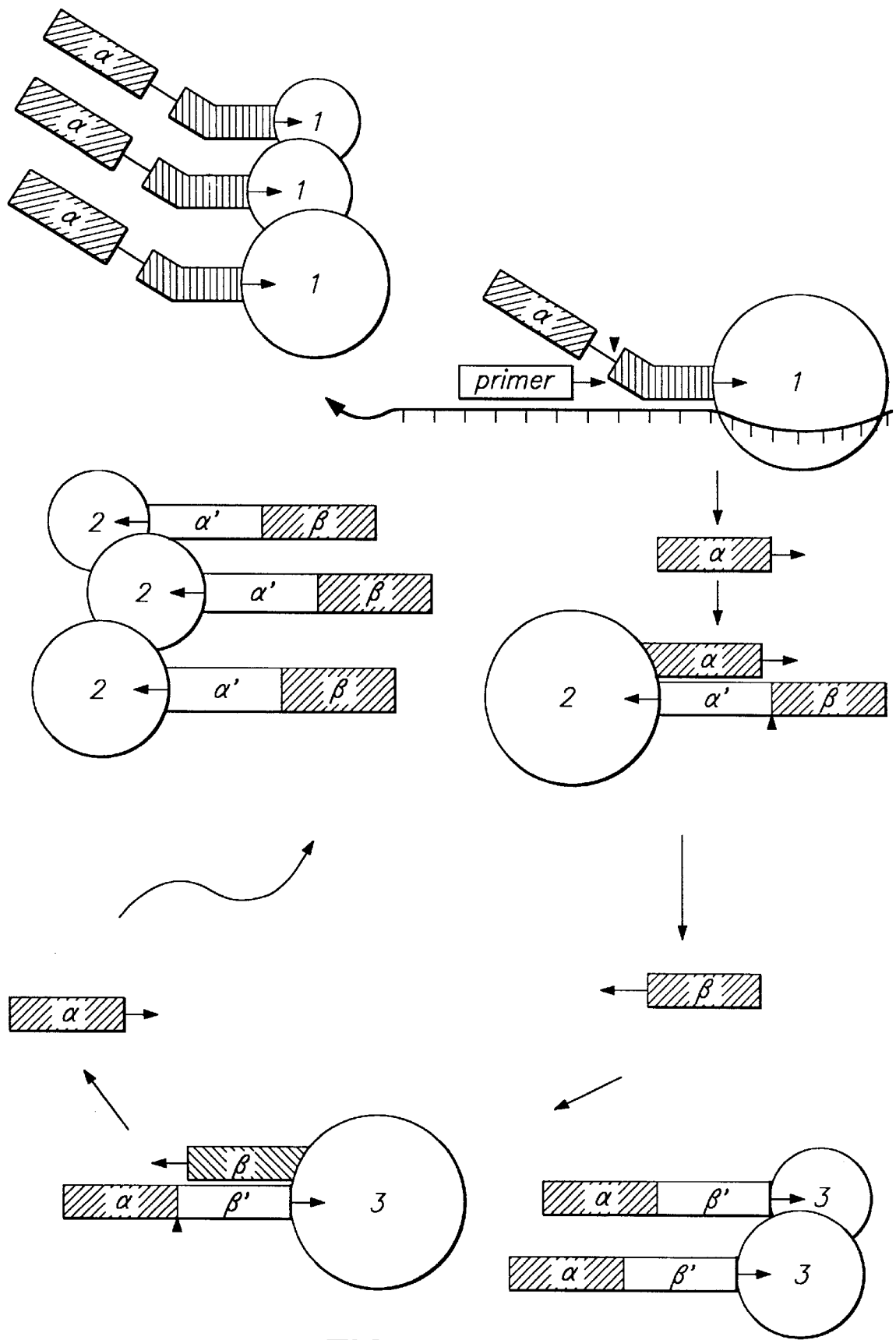
FIG. 1A provides a schematic of one embodiment of the detection method of the present invention.

The present invention relates to methods and compositions for treating nucleic acid, and in particular, methods and compositions for detection and characterization of nucleic acid sequences and sequence changes.

The present invention relates to means for cleaving a nucleic acid cleavage structure in a site-specific manner. In particular, the present invention relates to a cleaving enzyme having 5' nuclease activity without interfering nucleic acid synthetic ability.

This invention provides 5' nucleases derived from thermostable DNA polymerases which exhibit altered DNA synthetic activity from that of native thermostable DNA polymerases. The 5' nuclease activity of the polymerase is retained while the synthetic activity is reduced or absent. Such 5' nucleases are capable of catalyzing the structure-specific cleavage of nucleic acids in the absence of interfering synthetic activity. The lack of synthetic activity during a cleavage reaction results in nucleic acid cleavage products of uniform size.

The novel properties of the polymerases of the invention form the basis of a method of detecting specific nucleic acid sequences. This method relies upon the amplification of the detection molecule rather than upon the amplification of the target sequence itself as do existing methods of detecting specific target sequences.

DNA polymerases (DNAPs), such as those isolated from *E. coli* or from thermophilic bacteria of the genus Thermus, are enzymes that synthesize new DNA strands. Several of the known DNAPs contain associated nuclease activities in addition to the synthetic activity of the enzyme.

Some DNAPs are known to remove nucleotides from the 5' and 3' ends of DNA chains [Kornberg, *DNA Replication*, W. H. Freeman and Co., San Francisco, pp. 127–139 (1980)]. These nuclease activities are usually referred to as 5' exonuclease and 3' exonuclease activities, respectively. For example, the 5' exonuclease activity located in the N-terminal domain of several DNAPs participates in the removal of RNA primers during lagging strand synthesis during DNA replication and the removal of damaged nucleotides during repair. Some DNAPs, such as the *E. coli* DNA polymerase (DNAPEc1), also have a 3' exonuclease activity responsible for proof-reading during DNA synthesis (Kornberg, supra).

A DNAP isolated from *Thermus aquaticus*, termed Taq DNA polymerase (DNAPTaq), has a 5' exonuclease activity, but lacks a functional 3' exonucleolytic domain [Tindall and Kunkell, *Biochem.* 27:6008 (1988)]. Derivatives of DNAPEc1 and DNAPTaq, respectively called the Klenow and Stoffel fragments, lack 5' exonuclease domains as a result of enzymatic or genetic manipulations [Brutlag et al., *Biochem. Biophys. Res. Commun.* 37:982 (1969); Erlich et al., *Science* 252:1643 (1991); Setlow and Komberg, *J. Biol. Chem.* 247:232 (1972)].

The 5' exonuclease activity of DNAPTaq was reported to require concurrent synthesis [Gelfand, *PCR Technology— Principles and Applications for DNA Amplification* (H. A. Erlich, Ed.), Stockton Press, New York, p. 19 (1989)]. Although mononucleotides predominate among the digestion products of the 5' exonucleases of DNAPTaq and DNAPEc1, short oligonucleotides ($\leq 12$ nucleotides) can also be observed implying that these so-called 5' exonucleases can function endonucleolytically [Setlow, supra; Holland et al., *Proc. Natl. Acad. Sci. USA* 88:7276 (1991)].

In WO 92/06200, Gelfand et al. show that the preferred substrate of the 5' exonuclease activity of the thermostable DNA polymerases is displaced single-stranded DNA. Hydrolysis of the phosphodiester bond occurs between the displaced single-stranded DNA and the double-helical DNA with the preferred exonuclease cleavage site being a phosphodiester bond in the double helical region. Thus, the 5' exonuclease activity usually associated with DNAPs is a structure-dependent single-stranded endonuclease and is more properly referred to as a 5' nuclease. Exonucleases are enzymes which cleave nucleotide molecules from the ends of the nucleic acid molecule. Endonucleases, on the other hand, are enzymes which cleave the nucleic acid molecule at internal rather than terminal sites. The nuclease activity associated with some thermostable DNA polymerases cleaves endonucleolytically but this cleavage requires contact with the 5' end of the molecule being cleaved. Therefore, these nucleases are referred to as 5' nucleases.

When a 5' nuclease activity is associated with a eubacterial Type A DNA polymerase, it is found in the one-third N-terminal region of the protein as an independent functional domain. The C-terminal two-thirds of the molecule constitute the polymerization domain which is responsible for the synthesis of DNA. Some Type A DNA polymerases also have a 3' exonuclease activity associated with the two-third C-terminal region of the molecule.

The 5' exonuclease activity and the polymerization activity of DNAPs have been separated by proteolytic cleavage or genetic manipulation of the polymerase molecule. To date thermostable DNAPs have been modified to remove or reduce the amount of 5' nuclease activity while leaving the polymerase activity intact.

The Klenow or large proteolytic cleavage fragment of DNAPEc1 contains the polymerase and 3' exonuclease activity but lacks the 5' nuclease activity. The Stoffel fragment of DNAPTaq (DNAPStf) lacks the 5' nuclease activity due to a genetic manipulation which deleted the N-terminal 289 amino acids of the polymerase molecule [Erlich et al., *Science* 252:1643 (1991)]. WO 92/06200 describes a thermostable DNAP with an altered level of 5' to 3' exonuclease. U.S. Pat. No. 5,108,892 describes a *Thermus aquaticus* DNAP without a 5' to 3' exonuclease. However, the art of molecular biology lacks a thermostable DNA polymerase with a lessened amount of synthetic activity.

The present invention provides 5' nucleases derived from thermostable Type A DNA polymerases that retain 5' nuclease activity but have reduced or absent synthetic activity. The ability to uncouple the synthetic activity of the enzyme from the 5' nuclease activity proves that the 5' nuclease activity does not require concurrent DNA synthesis as was previously reported (Gelfand, *PCR Technology*, supra).

The description of the invention is divided into: I. Detection of Specific Nucleic Acid Sequences Using 5' Nucleases; II. Generation of 5' Nucleases Derived From Thermostable DNA Polymerases; III. Therapeutic Uses of 5' Nucleases; IV. Detection of Antigenic or Nucleic Acid Targets by a Dual Capture Assay; and V. Cleavase™ Fragment Length Polymorphism for the Detection of Secondary Structure. To facilitate understanding of the invention, a number of terms are defined below.

The term "gene" refers to a DNA sequence that comprises control and coding sequences necessary for the production of a polypeptide or precursor. The polypeptide can be encoded by a full length coding sequence or by any portion of the coding sequence so long as the desired enzymatic activity is retained.

The term "wild-type" refers to a gene or gene product which has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product which displays modifications in sequence and or finctional properties (ie., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired coding sequence and appropriate DNA sequences necessary for the expression of the operably linked coding sequence in a particular host organism. DNA sequences necessary for expression in procaryotes include a promoter, optionally an operator sequence, a ribosome binding site and possibly other sequences. Eukaryotic cells are known to utilize promoters, polyadenlyation signals and enhancers.

The term "LTR" as used herein refers to the long terminal repeat found at each end of a provirus (i.e., the integrated form of a retrovirus). The LTR contains numerous regulatory signals including transcriptional control elements, polyadenylation signals and sequences needed for replication and integration of the viral genome. The viral LTR is divided into three regions called U3, R and U5.

The U3 region contains the enhancer and promoter elements. The U5 region contains the polyadenylation signals. The R (repeat) region separates the U3 and U5 regions and transcribed sequences of the R region appear at both the 5' and 3' ends of the viral RNA.

The term "oligonucleotide" as used herein is defmed as a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

Because mononucleotides are reacted to make oligonucleotides in a manner such that the 5' phosphate of one mononucleotide pentose ring is attached to the 3' oxygen of its neighbor in one direction via a phoshodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *Proc. Natl. Acad Sci. USA* 46:453 (1960) and Doty et al., *Proc. Natl. Acad. Sci. USA* 46:461 (1960) have been followed by the refinement of this process into an essential tool of modem biology. Nonetheless, a number of problems have prevented the wide scale use of hybridization as a tool in human diagnostics. Among the more formidable problems are: 1) the inefficiency of hybridization; 2) the low concentration of specific target sequences in a mixture of genomic DNA; and 3) the hybridization of only partially complementary probes and targets.

With regard to efficiency, it is experimentally observed that only a fraction of the possible number of probe-target complexes are formed in a hybridization reaction. This is particularly true with short oligonucleotide probes (less than 100 bases in length). There are three fundamental causes: a) hybridization cannot occur because of secondary and tertiary structure interactions; b) strands of DNA containing the target sequence have rehybridized (reannealed) to their complementary strand; and c) some target molecules are prevented from hybridization when they are used in hybridization formats that immobilize the target nucleic acids to a solid surface.

Even where the sequence of a probe is completely complementary to the sequence of the target, i.e., the target's primary structure, the target sequence must be made accessible to the probe via rearrangements of higher-order structure. These higher-order structural rearrangements may concern either the secondary structure or tertiary structure of the molecule. Secondary structure is determined by intramolecular bonding. In the case of DNA or RNA targets this consists of hybridization within a single, continuous strand of bases (as opposed to hybridization between two different strands). Depending on the extent and position of intramolecular bonding, the probe can be displaced from the target sequence preventing hybridization.

Solution hybridization of oligonucleotide probes to denatured double-stranded DNA is further complicated by the fact that the longer complementary target strands can renature or reanneal. Again, hybridized probe is displaced by this process. This results in a low yield of hybridization (low "coverage") relative to the starting concentrations of probe and target.

With regard to low target sequence concentration, the DNA fragment containing the target sequence is usually in relatively low abundance in genomic DNA. This presents great technical difficulties; most conventional methods that use oligonucleotide probes lack the sensitivity necessary to detect hybridization at such low levels.

One attempt at a solution to the target sequence concentration problem is the amplification of the detection signal. Most often this entails placing one or more labels on an oligonucleotide probe. In the case of non-radioactive labels, even the highest affinity reagents have been found to be unsuitable for the detection of single copy genes in genomic DNA with oligonucleotide probes. See Wallace et al., *Biochimie* 67:755 (1985). In the case of radioactive oligonucleotide probes, only extremely high specific activities are found to show satisfactory results. See Studencki and Wallace, *DNA* 3:1 (1984) and Studencki et al., *Human Genetics* 37:42 (1985).

With regard to complementarity, it is important for some diagnostic applications to determine whether the hybridization represents complete or partial complementarity. For example, where it is desired to detect simply the presence or absence of pathogen DNA (such as from a virus, bacterium, fungi, mycoplasma, protozoan) it is only important that the hybridization method ensures hybridization when the relevant sequence is present; conditions can be selected where both partially complementary probes and completely complementary probes will hybridize. Other diagnostic applications, however, may require that the hybridization method distinguish between partial and complete complementarity. It may be of interest to detect genetic polymorphisms. For example, human hemoglobin is composed, in part, of four polypeptide chains. Two of these chains are identical chains of 141 amino acids (alpha chains) and two of these chains are identical chains of 146 amino acids (beta chains). The gene encoding the beta chain is known to exhibit polymorphism. The normal allele encodes a beta chain having glutamic acid at the sixth position. The mutant allele encodes a beta chain having valine at the sixth position. This difference in amino acids has a profound (most profound when the individual is homozygous for the mutant allele) physiological impact known clinically as sickle cell anemia. It is well known that the genetic basis of the amino acid change involves a single base difference between the normal allele DNA sequence and the mutant allele DNA sequence.

Unless combined with other techniques (such as restriction enzyme analysis), methods that allow for the same level of hybridization in the case of both partial as well as complete complementarity are typically unsuited for such applications; the probe will hybridize to both the normal and variant target sequence. Hybridization, regardless of the method used, requires some degree of complementarity between the sequence being assayed (the target sequence) and the fragment of DNA used to perform the test (the probe). (Of course, one can obtain binding without any complementarity but this binding is nonspecific and to be avoided.)

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "$T_m$." The $T_m$ of a particular nucleic acid duplex under specified conditions is the temperature at which on average half of the base pairs have disassociated.

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The term "cleavage structure" as used herein, refers to a region of a single-stranded nucleic acid substrate containing secondary structure, said region being cleavable by a cleavage means, including but not limited to an enzyme. The cleavage structure is a substrate for specific cleavage by said cleavage means in contrast to a nucleic acid molecule which is a substrate for non-specific cleavage by agents such as phosphodiesterases which cleave nucleic acid molecules without regard to secondary structure (i.e., no folding of the substrate is required).

The term "cleavage means" as used herein refers to any means which is capable of cleaving a cleavage structure, including but not limited to enzymes. The cleavage means may include native DNAPs having 5' nuclease activity (e.g., Taq DNA polymerase, *E. coli* DNA polymerase I) and, more specifically, modified DNAPs having 5' nuclease but lacking synthetic activity. The ability of 5' nucleases to cleave naturally occurring structures in nucleic acid templates (structure-specific cleavage) is useful to detect internal sequence differences in nucleic acids without prior knowledge of the specific sequence of the nucleic acid. In this manner, they are structure-specific enzymes. Structure-specific enzymes are enzymes which recognize specific secondary structures in a nucleic molecule and cleave these structures. The site of cleavage may be on either the 5' or 3' side of the cleavage structure; alternatively the site of cleavage may be between the 5' and 3' side (i e., within or internal to) of the cleavage structure. The cleavage means of the invention cleave a nucleic acid molecule in response to the formation of cleavage structures; it is not necessary that the cleavage means cleave the cleavage structure at any particular location within the cleavage structure.

The cleavage means is not restricted to enzymes having 5' nuclease activity. The cleavage means may include nuclease activity provided from a variety of sources including the enzyme Cleavase™, Taq DNA polymerase, *E. coli* DNA polymerase I and eukaryotic structure-specific endonucleases, murine FEN-1 endonucleases [Harrington and Liener, (1994) Genes and Develop. 8:1344] and calf thymus 5' to 3' exonuclease [Murante, R. S., et al. (1994) J. Biol. Chem. 269:1191]). In addition, enzymes having 3' nuclease activity such as members of the family of DNA repair endonucleases (e.g., the RrpI enzyme from *Drosophila melanogaster*, the yeast RAD1/RAD10 complex and *E. coli* Exo III), are also suitable cleavage means for the practice of the methods of the invention.

The term "cleavage products" as used herein, refers to products generated by the reaction of a cleavage means with a cleavage structure (i.e., the treatment of a cleavage structure with a cleavage means).

The terms "nucleic acid substrate" and nucleic acid template" are used herein interchangeably and refer to a nucleic acid molecule which when denatured and allowed to renature (i.e., to fold upon itself by the formation of intra-strand hydrogen bonds), forms at least one cleavage structure. The nucleic acid substrate may comprise single- or double-stranded DNA or RNA.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

Nucleic acids form secondary structures which depend on base-pairing for stability. When single strands of nucleic acids (single-stranded DNA, denatured double-stranded DNA or RNA) with different sequences, even closely related ones, are allowed to fold on themselves, they assume characteristic secondary structures. At "elevated temperatures" the duplex regions of the structures are brought to the brink of instability, so that the effects of small changes in sequence are maximized, and revealed as alterations in the cleavage pattern. In other words, "an elevated temperature" is a temperature at which a given duplex region of the folded substrate molecule is near the temperature at which that duplex melts. An alteration in the sequence of the substrate will then be likely to cause the destruction of a duplex region(s) thereby generating a different cleavage pattern when a cleavage agent which is dependent upon the recognition of structure is utilized in the reaction. While not being limited to any particular theory, it is thought that individual molecules in the target (i.e., the substrate) population may each assume only one or a few of the potential cleavage structures (i.e., duplexed regions), but when the sample is analyzed as a whole, a composite pattern representing all cleavage sites is detected. Many of the structures recognized as active cleavage sites are likely to be only a few base-pairs long and would appear to be unstable when elevated temperatures used in the cleavage reaction. Nevertheless, transient formation of these structures allows recognition and cleavage of these structures by said cleavage means. The formation or disruption of these structures in response to small sequence changes results in changes in the patterns of cleavage. Temperatures in the range of 40°–85° C., with the range of 55°–85° C. being particularly preferred, are suitable elevated temperatures for the practice of the method of the invention.

The term "sequence variation" as used herein refers to differences in nucleic acid sequence between two nucleic acid templates. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exits. This second mutant form is said to vary in sequence from both the wild-type gene and the first mutant form of the gene. It is noted, however, that the invention does not require that a comparison be made between one or more forms of a gene to detect sequence variations. Because the method of the invention generates a characteristic and reproducible pattern of cleavage products for a given nucleic acid substrate, a characteristic "fingerprint" may be obtained from any nucleic substrate without reference to a wild-type or other control. The invention contemplates the use of the method for both "fingerprinting" nucleic acids without reference to a control and identification of mutant forms of a substrate nucleic acid by comparison of the mutant form of the substrate with a wild-type or known mutant control.

The term "liberating" as used herein refers to the release of a nucleic acid fragment from a larger nucleic acid fragment, such as an oligonucleotide, by the action of a 5' nuclease such that the released fragment is no longer covalently attached to the remainder of the oligonucleotide.

The term "substrate strand" as used herein, means that strand of nucleic acid in a cleavage structure in which the cleavage mediated by the 5' nuclease activity occurs.

The term "template strand" as used herein, means that strand of nucleic acid in a cleavage structure which is at least partially complementary to the substrate strand and which anneals to the substrate strand to form the cleavage structure.

The term "$K_m$" as used herein refers to the Michaelis-Menten constant for an enzyme and is defined as the concentration of the specific substrate at which a given enzyme yields one-half its maximum velocity in an enzyme catalyzed reaction.

V. Detection Of Specific Nucleic Acid Sequences Using 5' Nucleases

The 5' nucleases of the invention form the basis of a novel detection assay for the identification of specific nucleic acid sequences. This detection system identifies the presence of specific nucleic acid sequences by requiring the annealing of two oligonucleotide probes to two portions of the target sequence. As used herein, the term "target sequence" or "target nucleic acid sequence" refers to a specific nucleic acid sequence within a polynucleotide sequence, such as genomic DNA or RNA, which is to be either detected or cleaved or both.

FIG. 1A provides a schematic of one embodiment of the detection method of the present invention. The target sequence is recognized by two distinct oligonucleotides in the triggering or trigger reaction. It is preferred that one of these oligonucleotides is provided on a solid support. The other can be provided free. In FIG. 1A the free oligo is indicated as a "primer" and the other oligo is shown attached to a bead designated as type 1. The target nucleic acid aligns the two oligonucleotides for specific cleavage of the 5' arm (of the oligo on bead 1) by the DNAPs of the present invention (not shown in FIG. 1A).

The site of cleavage (indicated by a large solid arrowhead) is controlled by the distance between the 3' end of the "primer" and the downstream fork of the oligo on bead 1. The latter is designed with an uncleavable region (indicated by the striping). In this manner neither oligonucleotide is subject to cleavage when misaligned or when unattached to target nucleic acid.

Successful cleavage releases a single copy of what is referred to as the alpha signal oligo. This oligo may contain a detectable moiety (e.g., fluorescein). On the other hand, it may be unlabelled.

In one embodiment of the detection method, two more oligonucleotides are provided on solid supports. The oligonucleotide shown in FIG. 1A on bead 2 has a region that is complementary to the alpha signal oligo (indicated as alpha prime) allowing for hybridization. This structure can be cleaved by the DNAPs of the present invention to release the beta signal oligo. The beta signal oligo can then hybridize to type 3 beads having an oligo with a complementary region (indicated as beta prime). Again, this structure can be cleaved by the DNAPs of the present invention to release a new alpha oligo.

At this point, the amplification has been linear. To increase the power of the method, it is desired that the alpha signal oligo hybridized to bead type 2 be liberated after release of the beta oligo so that it may go on to hybridize with other oligos on type 2 beads. Similarly, after release of an alpha oligo from type 3 beads, it is desired that the beta oligo be liberated.

The liberation of "captured" signal oligos can be achieved in a number of ways. First, it has been found that the DNAPs of the present invention have a true 5' exonuclease capable of "nibbling" the 5' end of the alpha (and beta) prime oligo (discussed below in more detail). Thus, under appropriate conditions, the hybridization is destabilized by nibbling of the DNAP. Second, the alpha—alpha prime (as well as the beta—beta prime) complex can be destabilized by heat (e.g., thermal cycling).

With the liberation of signal oligos by such techniques, each cleavage results in a doubling of the number of signal oligos. In this manner, detectable signal can quickly be achieved.

FIG. 1B provides a schematic of a second embodiment of the detection method of the present invention. Again, the target sequence is recognized by two distinct oligonucleotides in the triggering or trigger reaction and the target nucleic acid aligns the two oligonucleotides for specific cleavage of the 5' arm by the DNAPs of the present invention (not shown in FIG. 1B). The first oligo is completely complementary to a portion of the target sequence. The second oligonucleotide is partially complementary to the target sequence; the 3' end of the second oligonucleotide is fully complementary to the target sequence while the 5' end is non-complementary and forms a single-stranded arm. The non-complementary end of the second oligonucleotide may be a generic sequence which can be used with a set of standard hairpin structures (described below). The detection of different target sequences would require unique portions of two oligonucleotides: the entire first oligonucleotide and the 3' end of the second oligonucleotide. The 5' arm of the second oligonucleotide can be invariant or generic in sequence.

The annealing of the first and second oligonucleotides near one another along the target sequence forms a forked cleavage structure which is a substrate for the 5' nuclease of DNA polymerases. The approximate location of the cleavage site is again indicated by the large solid arrowhead in FIG. 1B.

The 5' nucleases of the invention are capable of cleaving this structure but are not capable of polymerizing the extension of the 3' end of the first oligonucleotide. The lack of polymerization activity is advantageous as extension of the first oligonucleotide results in displacement of the annealed region of the second oligonucleotide and results in moving the site of cleavage along the second oligonucleotide. If polymerization is allowed to occur to any significant amount, multiple lengths of cleavage product will be generated. A single cleavage product of uniform length is desirable as this cleavage product initiates the detection reaction.

The trigger reaction may be run under conditions that allow for thermocycling. Thermocycling of the reaction allows for a logarithmic increase in the amount of the trigger oligonucleotide released in the reaction.

The second part of the detection method allows the annealing of the fragment of the second oligonucleotide liberated by the cleavage of the first cleavage structure formed in the triggering reaction (called the third or trigger oligonucleotide) to a first hairpin structure. This first hairpin structure has a single-stranded 5' arm and a single-stranded 3' arm. The third oligonucleotide triggers the cleavage of this first hairpin structure by annealing to the 3' arm of the hairpin thereby forming a substrate for cleavage by the 5' nuclease of the present invention. The cleavage of this first hairpin structure generates two reaction products: 1) the cleaved 5' arm of the hairpin called the fourth oligonucleotide, and 2) the cleaved hairpin structure which now lacks the 5' arm and is smaller in size than the uncleaved hairpin. This cleaved first hairpin may be used as a detection molecule to indicate that cleavage directed by the trigger or third oligonucleotide occurred. Thus, this indicates that the first two oligonucleotides found and annealed to the target sequence thereby indicating the presence of the target sequence in the sample.

The detection products are amplified by having the fourth oligonucleotide anneal to a second hairpin structure. This hairpin structure has a 5' single-stranded arm and a 3' single-stranded arm. The fourth oligonucleotide generated by cleavage of the first hairpin structure anneals to the 3' arm of the second hairpin structure thereby creating a third cleavage structure recognized by the 5' nuclease. The cleavage of this second hairpin structure also generates two reaction products: 1) the cleaved 5' arm of the hairpin called the fifth oligonucleotide which is similar or identical in sequence to the third nucleotide, and 2) the cleaved second hairpin structure which now lacks the 5' arm and is smaller in size than the uncleaved hairpin. This cleaved second hairpin may be as a detection molecule and amplifies the signal generated by the cleavage of the first hairpin structure. Simultaneously with the annealing of the forth oligonucleotide, the third oligonucleotide is dissociated from the cleaved first hairpin molecule so that it is free to anneal to a new copy of the first hairpin structure. The disassociation of the oligonucleotides from the hairpin structures may be accomplished by heating or other means suitable to disrupt base-pairing interactions.

Further amplification of the detection signal is achieved by annealing the fifth oligonucleotide (similar or identical in sequence to the third oligonucleotide) to another molecule of the first hairpin structure. Cleavage is then performed and the oligonucleotide that is liberated then is annealed to another molecule of the second hairpin structure. Successive rounds of annealing and cleavage of the first and second hairpin structures, provided in excess, are performed to generate a sufficient amount of cleaved hairpin products to be detected. The temperature of the detection reaction is cycled just below and just above the annealing temperature for the oligonucleotides used to direct cleavage of the hairpin structures, generally about 55° C. to 70° C. The number of cleavages will double in each cycle until the amount of hairpin structures remaining is below the $K_m$ for the hairpin structures. This point is reached when the hairpin structures are substantially used up. When the detection reaction is to be used in a quantitative manner, the cycling reactions are stopped before the accumulation of the cleaved hairpin detection products reach a plateau.

Detection of the cleaved hairpin structures may be achieved in several ways. In one embodiment detection is achieved by separation on agarose or polyacrylamide gels followed by staining with ethidium bromide. In another embodiment, detection is achieved by separation of the cleaved and uncleaved hairpin structures on a gel followed by autoradiography when the hairpin structures are first labelled with a radioactive probe and separation on chromatography columns using HPLC or FPLC followed by detection of the differently sized fragments by absorption at $OD_{260}$. Other means of detection include detection of changes in fluorescence polarization when the single-stranded 5' arm is released by cleavage, the increase in fluorescence of an intercalating fluorescent indicator as the amount of primers annealed to 3' arms of the hairpin structures increases. The formation of increasing amounts of duplex DNA (between the primer and the 3' arm of the hairpin) occurs if successive rounds of cleavage occur.

The hairpin structures may be attached to a solid support, such as an agarose, styrene or magnetic bead, via the 3' end of the hairpin. A spacer molecule may be placed between the 3' end of the hairpin and the bead, if so desired. The advantage of attaching the hairpin structures to a solid support is that this prevents the hybridization of the two hairpin structures to one another over regions which are complementary. If the hairpin structures anneal to one another, this would reduce the amount of hairpins available for hybridization to the primers released during the cleavage reactions. If the hairpin structures are attached to a solid support, then additional methods of detection of the products of the cleavage reaction may be employed. These methods include, but are not limited to, the measurement of the released single-stranded 5' arm when the 5' arm contains a label at the 5' terminus. This label may be radioactive, fluorescent, biotinylated, etc. If the hairpin structure is not cleaved, the 5' label will remain attached to the solid support. If cleavage occurs, the 5' label will be released from the solid support.

The 3' end of the hairpin molecule may be blocked through the use of dideoxynucleotides. A 3' terminus containing a dideoxynucleotide is unavailable to participate in reactions with certain DNA modifying enzymes, such as terminal transferase. Cleavage of the hairpin having a 3' terminal dideoxynucleotide generates a new, unblocked 3' terminus at the site of cleavage. This new 3' end has a free hydroxyl group which can interact with terminal transferase thus providing another means of detecting the cleavage products.

The hairpin structures are designed so that their self-complementary regions are very short (generally in the range of 3–8 base pairs). Thus, the hairpin structures are not stable at the high temperatures at which this reaction is performed (generally in the range of 50°–75° C.) unless the hairpin is stabilized by the presence of the annealed oligonucleotide on the 3' arm of the hairpin. This instability prevents the polymerase from cleaving the hairpin structure in the absence of an associated primer thereby preventing false positive results due to non-oligonucleotide directed cleavage.

As discussed above, the use of the 5' nucleases of the invention which have reduced polymerization activity is advantageous in this method of detecting specific nucleic acid sequences. Significant amounts of polymerization during the cleavage reaction would cause shifting of the site of cleavage in unpredictable ways resulting in the production of a series of cleaved hairpin structures of various sizes rather than a single easily quantifiable product. Additionally, the primers used in one round of cleavage could, if elongated, become unusable for the next cycle, by either forming an incorrect structure or by being too long to melt off under moderate temperature cycling conditions. In a pristine system (i.e., lacking the presence of dNTPs), one could use the unmodified polymerase, but the presence of nucleotides (dNTPs) can decrease the per cycle efficiency enough to give a false negative result. When a crude extract (genomic DNA preparations, crude cell lysates, etc.) is employed or where a sample of DNA from a PCR reaction, or any other sample that might be contaminated with dNTPs, the 5' nucleases of the present invention that were derived from thermostable polymerases are particularly useful.

II. Generation Of 5' Nucleases From Thermostable DNA Polymerases

The genes encoding Type A DNA polymerases share about 85% homology to each other on the DNA sequence level. Preferred examples of thermostable polymerases include those isolated from *Thermus aquaticus, Thermus flavus,* and *Thermus thermophilus.* However, other thermostable Type A polymerases which have 5' nuclease activity are also suitable. FIGS. 2 and 3 compare the nucleotide and amino acid sequences of the three above mentioned polymerases. In FIGS. 2 and 3, the consensus or majority sequence derived from a comparison of the nucleotide (FIG. 2) or amino acid (FIG. 3) sequence of the three thermostable DNA polymerases is shown on the top line. A dot appears in the sequences of each of these three polymerases whenever an amino acid residue in a given sequence is identical to that contained in the consensus amino acid sequence. Dashes are used to introduce gaps in order to maximize alignment between the displayed sequences. When no consensus nucleotide or amino acid is present at a given position, an "X" is placed in the consensus sequence. SEQ ID NOS:1–3 display the nucleotide sequences and SEQ ID NOS:4–6 display the amino acid sequences of the three wild-type polymerases. SEQ ID NO:1 corresponds to the nucleic acid sequence of the wild type *Thermus aquaticus* DNA polymerase gene isolated from the YT-1 strain [Lawyer et al., *J. Biol. Chem.* 264:6427 (1989)]. SEQ ID NO:2 corresponds to the nucleic acid sequence of the wild type *Thermus flavus* DNA polymerase gene [Akhmetzjanov and Vakhitov, *Nucl. Acids Res.* 20:5839 (1992)]. SEQ ID NO:3 corresponds to the nucleic acid sequence of the wild type *Thermus thermophilus* DNA polymerase gene [Gelfand et al., WO 91/09950 (1991)]. SEQ ID NOS:7–8 depict the consensus nucleotide and amino acid sequences, respectively for the above three DNAPs (also shown on the top row in FIGS. 2 and 3).

The 5' nucleases of the invention derived from thermostable polymerases have reduced synthetic ability, but retain substantially the same 5' exonuclease activity as the native DNA polymerase. The term "substantially the same 5' nuclease activity" as used herein means that the 5' nuclease activity of the modified enzyme retains the ability to function as a structure-dependent single-stranded endonuclease but not necessarily at the same rate of cleavage as compared to the unmodified enzyme. Type A DNA polymerases may also be modified so as to produce an enzyme which has increases 5' nuclease activity while having a reduced level of synthetic activity. Modified enzymes having reduced synthetic activity and increased 5' nuclease activity are also envisioned by the present invention.

By the term "reduced synthetic activity" as used herein it is meant that the modified enzyme has less than the level of synthetic activity found in the unmodified or "native" enzyme. The modified enzyme may have no synthetic activity remaining or may have that level of synthetic activity that will not interfere with the use of the modified enzyme in the detection assay described below. The 5' nucleases of the present invention are advantageous in situations where the cleavage activity of the polymerase is desired, but the synthetic ability is not (such as in the detection assay of the invention).

As noted above, it is not intended that the invention be limited by the nature of the alteration necessary to render the polymerase synthesis deficient. The present invention contemplates a variety of methods, including but not limited to: 1) proteolysis; 2) recombinant constructs (including mutants); and 3) physical and/or chemical modification and/or inhibition.

1. Proteolysis

Thermostable DNA polymerases having a reduced level of synthetic activity are produced by physically cleaving the unmodified enzyme with proteolytic enzymes to produce fragments of the enzyme that are deficient in synthetic activity but retain 5' nuclease activity. Following proteolytic digestion, the resulting fragments are separated by standard chromatographic techniques and assayed for the ability to synthesize DNA and to act as a 5' nuclease. The assays to determine synthetic activity and 5' nuclease activity are described below.

2. Recombinant Constructs

The examples below describe a preferred method for creating a construct encoding a 5' nuclease derived from a thermostable DNA polymerase. As the Type A DNA polymerases are similar in DNA sequence, the cloning strategies employed for the *Thermus aquaticus* and *flavus* polymerases are applicable to other thermostable Type A polymerases. In general, a thermostable DNA polymerase is cloned by isolating genomic DNA using molecular biological methods from a bacteria containing a thermostable Type A DNA polymerase. This genomic DNA is exposed to primers which are capable of amplifying the polymerase gene by PCR.

This amplified polymerase sequence is then subjected to standard deletion processes to delete the polymerase portion of the gene. Suitable deletion processes are described below in the examples.

The example below discusses the strategy used to detennine which portions of the DNAPTaq polymerase domain could be removed without eliminating the 5' nuclease activity. Deletion of amino acids from the protein can be done either by deletion of the encoding genetic material, or by introduction of a translational stop codon by mutation or frame shift. In addition, proteolytic treatment of the protein molecule can be performed to remove segments of the protein.

In the examples below, specific alterations of the Taq gene were: a deletion between nucleotides 1601 and 2502 (the end of the coding region), a 4 nucleotide insertion at position 2043, and deletions between nucleotides 1614 and 1848 and between nucleotides 875 and 1778 (numbering is as in SEQ ID NO:1). These modified sequences are described below in the examples and at SEQ ID NOS:9–12.

Those skilled in the art understand that single base pair changes can be innocuous in terms of enzyme structure and function. Similarly, small additions and deletions can be present without substantially changing the exonuclease or polymerase function of these enzymes.

Other deletions are also suitable to create the 5' nucleases of the present invention. It is preferable that the deletion decrease the polymerase activity of the 5' nucleases to a level at which synthetic activity will not interfere with the use of the 5' nuclease in the detection assay of the invention. Most preferably, the synthetic ability is absent. Modified polymerases are tested for the presence of synthetic and 5' nuclease activity as in assays described below. Thoughtful consideration of these assays allows for the screening of candidate enzymes whose structure is heretofore as yet unknown. In other words, construct "X" can be evaluated according to the protocol described below to determine whether it is a member of the genus of 5' nucleases of the present invention as defined functionally, rather than structurally.

In the example below, the PCR product of the amplified *Thermus aquaticus* genomic DNA did not have the identical nucleotide structure of the native genomic DNA and did not have the same synthetic ability of the original clone. Base pair changes which result due to the infidelity of DNAPTaq during PCR amplification of a polymerase gene are also a method by which the synthetic ability of a polymerase gene may be inactivated. The examples below and FIGS. 4A and 5A indicate regions in the native *Thermus aquaticus* and *flavus* DNA polymerases likely to be important for synthetic ability. There are other base pair changes and substitutions that will likely also inactivate the polymerase.

It is not necessary, however, that one start out the process of producing a 5' nuclease from a DNA polymerase with such a mutated amplified product. This is the method by which the examples below were performed to generate the synthesis-deficient DNAPTaq mutants, but it is understood by those skilled in the art that a wild-type DNA polymerase sequence may be used as the starting material for the introduction of deletions, insertion and substitutions to produce a 5' nuclease. For example, to generate the synthesis-deficient DNAPTf1 mutant, the primers listed in SEQ ID NOS:13–14 were used to amplify the wild type DNA polymerase gene from *Thermus flavus* strain AT-62. The amplified polymerase gene was then subjected to restriction enzyme digestion to delete a large portion of the domain encoding the synthetic activity.

The present invention contemplates that the nucleic acid construct of the present invention be capable of expression in a suitable host. Those in the art know methods for attaching various promoters and 3' sequences to a gene structure to achieve efficient expression. The examples below disclose two suitable vectors and six suitable vector constructs. Of course, there are other promoter/vector combinations that would be suitable. It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega Corporation, Madison, Wis.).

Once a suitable nucleic acid construct has been made, the 5' nuclease may be produced from the construct. The examples below and standard molecular biological teachings enable one to manipulate the construct by different suitable methods.

Once the 5' nuclease has been expressed, the polymerase is tested for both synthetic and nuclease activity as described below.

3. Physical And/Or Chemical Modification And/Or Inhibition

The synthetic activity of a thermostable DNA polymerase may be reduced by chemical and/or physical means. In one embodiment, the cleavage reaction catalyzed by the 5' nuclease activity of the polymerase is run under conditions which preferentially inhibit the synthetic activity of the polymerase. The level of synthetic activity need only be reduced to that level of activity which does not interfere with cleavage reactions requiring no significant synthetic activity.

As shown in the examples below, concentrations of $Mg^{++}$ greater than 5 mM inhibit the polymerization activity of the native DNAPTaq. The ability of the 5' nuclease to function under conditions where synthetic activity is inhibited is tested by running the assays for synthetic and 5' nuclease activity, described below, in the presence of a range of $Mg^{++}$ concentrations (5 to 10 mM). The effect of a given concentration of $Mg^{++}$ is determined by quantitation of the amount of synthesis and cleavage in the test reaction as compared to the standard reaction for each assay.

The inhibitory effect of other ions, polyamines, denaturants, such as urea, formamide, dimethylsulfoxide, glycerol and non-ionic detergents (Triton X-100 and Tween-20), nucleic acid binding chemicals such as, actinomycin D, ethidium bromide and psoralens, are tested by their addition to the standard reaction buffers for the synthesis and 5' nuclease assays. Those compounds having a preferential inhibitory effect on the synthetic activity of a thermostable polymerase are then used to create reaction conditions under which 5' nuclease activity (cleavage) is retained while synthetic activity is reduced or eliminated.

Physical means may be used to preferentially inhibit the synthetic activity of a polymerase. For example, the synthetic activity of thermostable polymerases is destroyed by exposure of the polymerase to extreme heat (typically 96° to 100° C.) for extended periods of time (greater than or equal to 20 minutes). While these are minor differences with respect to the specific heat tolerance for each of the enzymes, these are readily determined. Polymerases are treated with heat for various periods of time and the effect of the heat treatment upon the synthetic and 5' nuclease activities is determined.

III. Therapeutic Utility Of 5' Nucleases

The 5' nucleases of the invention have not only the diagnostic utility discussed above, but additionally have therapeutic utility for the cleavage and inactivation of specific mRNAs inside infected cells. The mRNAs of pathogenic agents, such as viruses, bacteria, are targeted for cleavage by a synthesis-deficient DNA polymerase by the introduction of a oligonucleotide complementary to a given mRNA produced by the pathogenic agent into the infected cell along with the synthesis-deficient polymerase. Any pathogenic agent may be targeted by this method provided the nucleotide sequence information is available so that an appropriate oligonucleotide may be synthesized. The synthetic oligonucleotide anneals to the complementary mRNA thereby forming a cleavage structure recognized by the modified enzyme. The ability of the 5' nuclease activity of thermostable DNA polymerases to cleave RNA-DNA hybrids is shown herein in Example 1D.

Liposomes provide a convenient delivery system. The synthetic oligonucleotide may be conjugated or bound to the nuclease to allow for co-delivery of these molecules. Additional delivery systems may be employed.

Inactivation of pathogenic mRNAs has been described using antisense gene regulation and using ribozymes (Rossi, U.S. Pat. No. 5,144,019, hereby incorporated by reference). Both of these methodologies have limitations.

The use of antisense RNA to impair gene expression requires stoichiometric and therefore, large molar excesses of anti-sense RNA relative to the pathogenic RNA to be effective. Ribozyme therapy, on the other hand, is catalytic and therefore lacks the problem of the need for a large molar excess of the therapeutic compound found with antisense methods. However, ribozyme cleavage of a given RNA requires the presence of highly conserved sequences to form the catalytically active cleavage structure. This requires that the target pathogenic mRNA contain the conserved sequences (GAAAC $(X)_n$ GU) thereby limiting the number of pathogenic mRNAs that can be cleaved by this method. In contrast, the catalytic cleavage of RNA by the use of a DNA oligonucleotide and a 5' nuclease is dependent upon structure only; thus, virtually any pathogenic RNA sequence can be used to design an appropriate cleavage structure.

IV. Detection Of Antigenic Or Nucleic Acid Targets By A Dual Capture Assay

The ability to generate 5' nucleases from thermostable DNA polymerases provides the basis for a novel means of detecting the presence of antigenic or nucleic acid targets. In this dual capture assay, the polymerase domains encoding the synthetic activity and the nuclease activity are covalently attached to two separate and distinct antibodies or oligonucleotides. When both the synthetic and the nuclease domains are present in the same reaction and dATP, dTTP and a small amount of poly d(A-T) are provided, an enormous amount of poly d(A-T) is produced. The large amounts of poly d(A-T) are produced as a result of the ability of the 5' nuclease to cleave newly made poly d(A-T) to generate primers that are, in turn, used by the synthetic domain to catalyze the production of even more poly d(A-T). The 5' nuclease is able to cleave poly d(A-T) because poly d(A-T) is self-complementary and easily forms alternate structures at elevated temperatures. These structures are recognized by the 5' nuclease and are then cleaved to generate more primer for the synthesis reaction.

The following is an example of the dual capture assay to detect an antigen(s): A sample to be analyzed for a given antigen(s) is provided. This sample may comprise a mixture of cells; for example, cells infected with viruses display virally-encoded antigens on their surface. If the antigen(s) to be detected are present in solution, they are first attached to a solid support such as the wall of a microtiter dish or to a bead using conventional methodologies. The sample is then mixed with 1) the synthetic domain of a thermostable DNA polymerase conjugated to an antibody which recognizes either a first antigen or a first epitope on an antigen, and 2) the 5' nuclease domain of a thermostable DNA polymerase conjugated to a second antibody which recognizes either a second, distinct antigen or a second epitope on the same antigen as recognized by the antibody conjugated to the synthetic domain. Following an appropriate period to allow the interaction of the antibodies with their cognate antigens (conditions will vary depending upon the antibodies used; appropriate conditions are well known in the art), the sample is then washed to remove unbound antibody-enzyme domain complexes. dATP, dTTP and a small amount of poly d(A-T) is then added to the washed sample and the sample is incubated at elevated temperatures (generally in the range of 60°–80° C. and more preferably, 70°–75° C.) to permit the thermostable synthetic and 5' nuclease domains to function. If the sample contains the antigen(s) recognized by both separately conjugated domains of the polymerase, then an exponential increase in poly d(A-T) production occurs. If only the antibody conjugated to the synthetic domain of the polymerase is present in the sample such that no 5' nuclease domain is present in the washed sample, then only an arithmetic increase in poly d(A-T) is possible. The reaction conditions may be controlled in such a way so that an arithmetic increase in poly d(A-T) is below the threshold of detection. This may be accomplished by controlling the length of time the reaction is allowed to proceed or by adding so little poly d(A-T) to act as template that in the absence of nuclease activity to generate new poly d(A-T) primers very little poly d(A-T) is synthesized.

It is not necessary for both domains of the enzyme to be conjugated to an antibody. One can provide the synthetic domain conjugated to an antibody and provide the 5' nuclease domain in solution or vice versa. In such a case the conjugated antibody-enzyme domain is added to the sample, incubated, then washed. DATP, dTTP, poly d(A-T) and the remaining enzyme domain in solution is then added.

Additionally, the two enzyme domains may be conjugated to oligonucleotides such that target nucleic acid sequences can be detected. The oligonucleotides conjugated to the two different enzyme domains may recognize different regions on the same target nucleic acid strand or may recognize two unrelated target nucleic acids.

The production of poly d(A-T) may be detected in many ways including: 1) use of a radioactive label on either the dATP or dTTP supplied for the synthesis of the poly d(A-T), followed by size separation of the reaction products and autoradiography; 2) use of a fluorescent probe on the dATP and a biotinylated probe on the dTTP supplied for the synthesis of the poly d(A-T), followed by passage of the reaction products over an avidin bead, such as magnetic beads conjugated to avidin; the presence of the florescent probe on the avidin-containing bead indicates that poly d(A-T) has been formed as the fluorescent probe will stick to the avidin bead only if the fluorescenated dATP is incorporated into a covalent linkage with the biotinylated dTTP; and 3) changes fluorescence polarization indicating an increase in size. Other means of detecting the presence of poly d(A-T) include the use of intercalating fluorescence indicators to monitor the increase in duplex DNA formation.

The advantages of the above dual capture assay for detecting antigenic or nucleic acid targets include:

1) No thermocycling of the sample is required. The polymerase domains and the dATP and dTTP are incubated at a fixed temperature (generally about 70° C.). After 30 minutes of incubation up to 75% of the added dNTPs are incorporated into poly d(A-T). The lack of thermocycling makes this assay well suited to clinical laboratory settings; there is no need to purchase a thermocycling apparatus and there is no need to maintain very precise temperature control.

2) The reaction conditions are simple. The incubation of the bound enzymatic domains is done in a buffer containing 0.5 mM $MgCl_2$ (higher concentrations may be used), 2–10 mM Tris-Cl, pH 8.5, approximately 50 $\mu$M dATP and dTTP. The reaction volume is 10–20 $\mu$l and reaction products are detectable within 10–20 minutes.

3) No reaction is detected unless both the synthetic and nuclease activities are present. Thus, a positive result indicates that both probes (antibody or oligonucleotide) have recognized their targets thereby increasing the specificity of recognition by having two different probes bind to the target.

The ability to separate the two enzymatic activities of the DNAP allows for exponential increases in poly d(A-T) production. If a DNAP is used which lacks 5' nuclease activity, such as the Klenow fragment of DNAPEc1, only a linear or arithmetic increase in poly d(A-T) production is possible [Setlow et al., J. Biol. Chem. 247:224 (1972)]. The ability to provide an enzyme having 5' nuclease activity but lacking synthetic activity is made possible by the disclosure of this invention.

V. Cleavase™ Fragment Length Polymorphism For The Detection Of Secondary Structure Nucleic acids assume secondary structures which depend on base-pairing for stability. When single strands of nucleic acids (single-stranded DNA, denatured DNA or RNA) with different sequences, even closely related ones, are allowed to fold on themselves, they assume characteristic secondary structures. These differences in structures account for the ability of single strand conformation polymorphism (SSCP) analysis to distinguish between DNA fragments having closely related sequences.

The 5' nuclease domains of certain DNA polymerases are specific endonucleases that recognize and cleave nucleic acids at specific structures rather than in a sequence-specific manner (as do restriction endonucleases). The isolated nuclease domain of DNAPTaq described herein (termed the enzyme Cleavase™) recognizes the end of a duplex that has non-base paired strands at the ends. The strand with the 5' end is cleaved at the junction between the single strand and the duplex.

Figure 29:
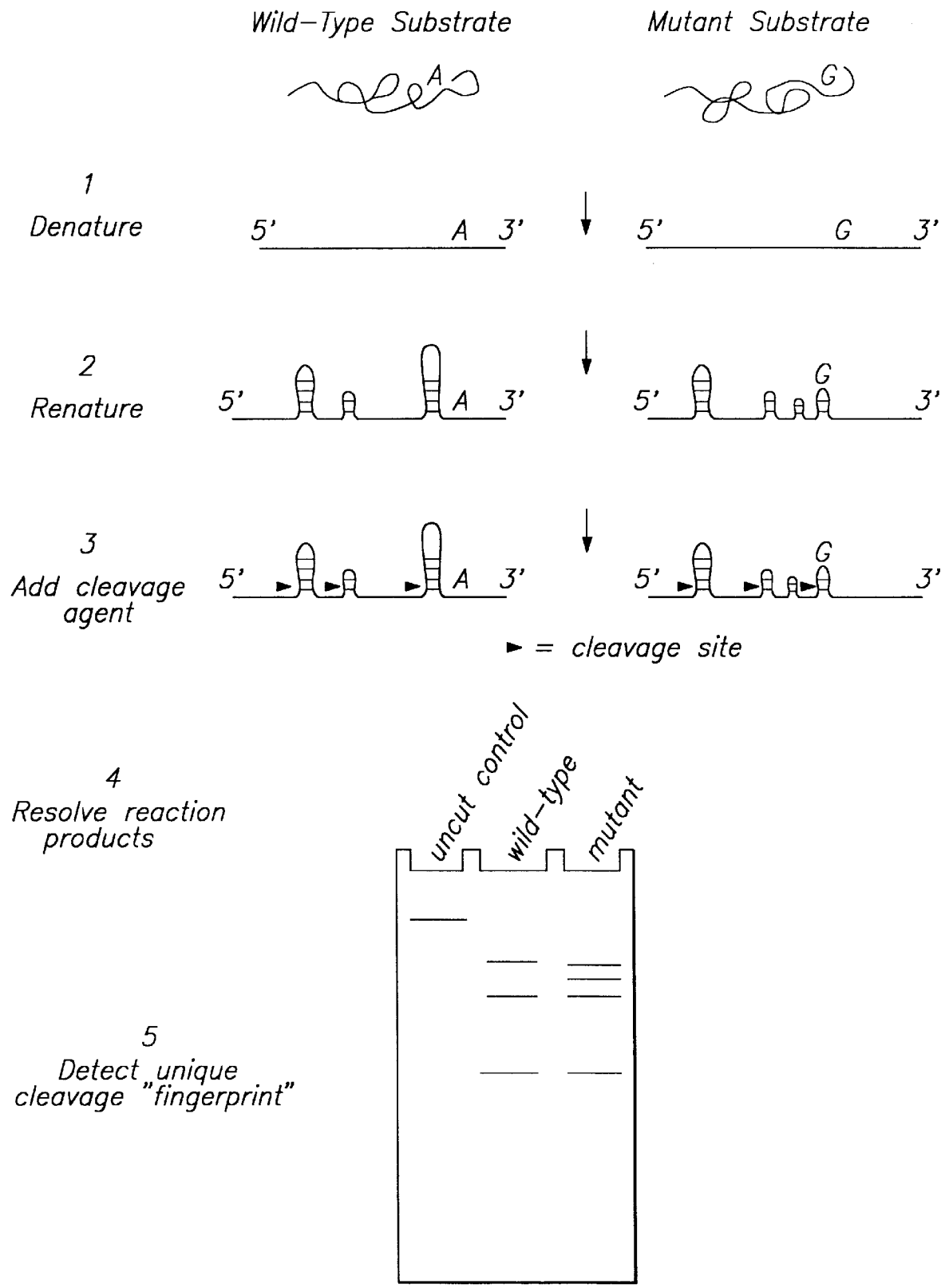
FIG. 29 is a schematic showing the CFLP™ method of generating a characteristic fingerprint from a nucleic acid substrate.

FIG. 29 depicts a wild-type substrate and a mutant substrate wherein the mutant substrate differs from the wild-type by a single base change (A to G as indicated). According to the method of the present invention, substrate structures form when nucleic acids are denatured and allowed to fold on themselves (See FIG. 29, steps 1 and 2). The step of denaturation may be achieved by treating the nucleic acid with heat, low (<3) or high pH (>10), the use of low salt concentrations, the absence of cations, chemicals (e.g., urea, formamide) or proteins (e.g., helicases). Folding or renaturation of the nucleic acid is achieved by lowering of the temperature, addition of salt, neutralization of the pH, withdrawal of the chemicals or proteins.

The manner in which the substrate folds is dependent upon the sequence of the substrate. The 5' nucleases of the invention cleave the structures (See FIG. 29, step 3). The end points of the resulting fragments reflect the locations of the cleavage sites. The cleavage itself is dependent upon the formation of a particular structure, not upon a particular sequence at the cleavage site.

When the 5' nucleases of the invention cleave a nucleic acid substrate, a collection of cleavage products or fragments is generated. These fragments constitute a characteristic fingerprint of the nucleic acid which can be detected [e.g., by electrophoresis on a gel (see step 4)]. Changes in the sequence of a nucleic acid (e.g., single point mutation between a wild-type and mutant gene) alter the pattern of cleavage structures formed. When the 5' nucleases of the invention cleave the structures formed by a wild-type and an altered or mutant form of the substrate, the distribution of the cleavage fragments generated will differ between the two substrates reflecting the difference in the sequence of the two substrates (See FIG. 29, Step 5).

The Cleavase™ enzyme generates a unique pattern of cleavage products for a substrate nucleic acid. Digestion with the Cleavase™ enzyme can be used to detect single base changes in DNA molecules of great length (e.g., 1.6 kb in length) to produce a characteristic pattern of cleavage products. The method of the invention is termed "Cleavase™ Fragment Length Polymorphism" (CFLP™). However, it is noted that the invention is not limited to the use of the enzyme Cleavase™; suitable enzymatic cleavage activity may be provided from a variety of sources including the Cleavase™ enzyme, Taq DNA polymerase, E. coli DNA polymerase I and eukaryotic structure-specific endonucleases (e.g., the yeast RAD2 protein and RAD1/RAD10 complex [Harrington, J. J. and Liener (1994) Genes and Develop. 8:1344], murine FEN-1 endonucleases (Harrington and Liener, supra) and calf thymus 5' to 3' exonuclease [Murante, R. S., et al. (1994) J. Biol. Chem. 269:1191]). Indeed actual experimental data is provided herein which demonstrates that numerous enzymes may be used to generate a unique pattern of cleavage products for a substrate nucleic acid. Enzymes which are shown herein to be suitable for use in the CFLP™ method include the Cleavase™ BN enzyme, Taq DNA polymerase, Tth DNA polymerase, Tfl DNA polymerase, E. coli Exo III, and the yeast Rad1/Rad10 complex.

The invention demonstrates that numerous enzymes may be suitable for use in the CFLP™ method including enzymes which have been characterized in the literature a being 3' exonucleases. In order to test whether an enzyme is suitable for use as a cleavage means in the CFLP™ method (i.e., capable of generating a unique pattern of cleavage products for a substrate nucleic acid), the following steps are taken. Careful consideration of the steps described below allows the evaluation of any enzyme ("enzyme X") for use in the CFLP™ method.

An initial CFLP™ reaction is prepared using a previously characterized substrate nucleic acid [for example the 157 nucleotide fragment of exon 4 of the human tyrosinase gene (SEQ ID NO:47)]. The substrate nucleic acid (approximately 100 fmoles; the nucleic acid template may contain a 5' end or other label to permit easy detection of the cleavage products) is placed into a thin wall microcentrifuge tube in a solution which comprises reaction conditions reported to be optimal for the characterized activity of the enzyme (i.e., enzyme X). For example, if the enzyme X is a DNA polymerase, the initial reaction conditions would utilize a buffer which has been reported to be optimal for the polymerization activity of the polymerase. If enzyme X is not a polymerase, or if no specific components are reported to be needed for activity, the initial reaction may be assembled by placing the substrate nucleic acid in a solution comprising 1× CFLP™ buffer (10 mM MOPS, 0.05% Tween-20, 0.05% Nonidet P-40), pH 7.2 to 8.2, 1 mM $MnCl_2$.

The substrate nucleic acid is denatured by heating the sample tube to 95° C. for 5 seconds and then the reaction is cooled to a temperature suitable for the enzyme being tested (e.g., if a thermostable polymerase is being tested the cleavage reaction may proceed at elevated temperatures such as 72° C.; if a mesophilic enzyme is being tested the tube is cooled to 37° C. for the cleavage reaction). Following denaturation and cooling to the target temperature, the cleavage reaction is initiated by the addition of a solution comprising 1 to 200 units of the enzyme to be tested (i.e., enzyme X; the enzyme may be diluted into 1× CFLP™ buffer, pH 8.2 if desired).

Following the addition of the enzyme X solution, the cleavage reaction is allowed to proceed at the target temperature for 2 to 5 minutes. The cleavage reaction is then terminated [this may be accomplished by the addition of a stop solution (95% formamide, 10 mM EDTA, 0.05% bromophenol blue, 0.05% xylene cyanol)] and the cleavage products are resolved and detected using any suitable method (e.g., electrophoresis on a denaturing polyacrylamide gel followed by transfer to a solid support and nonisotopic detection). The cleavage pattern generated is examined by the criteria described below for the CFLP™ optimization test.

An enzyme is suitable for use in the CFLP™ method if it is capable of generating a unique (i.e., characteristic) pattern of cleavage products from a substrate nucleic acid; this cleavage must be shown to be dependent upon the presence of the enzyme. Additionally, an enzyme must be able to reproducibly generate the same cleavage pattern when a given substrate is cleaved under the same reaction conditions. To test for reproducibility, the enzyme to be evaluated is used in at least two separate cleavage reactions run on different occasions using the same reaction conditions. If the same cleavage pattern is obtained on both occasions, the enzyme is capable of reproducibly generating a cleavage pattern and is therefore suitable for use in the CFLP™ method.

When enzymes derived from mesophilic organisms are to be tested in the CFLP™ reaction they may be initially tested at 37° C. However it may be desirable to use theses enzymes at higher temperatures in the cleavage reaction. The ability to cleave nucleic acid substrates over a range of temperatures is desirable when the cleavage reaction is being used to detect sequence variation (i.e., mutation) between different substrates. Strong secondary structures that may dominate the cleavage pattern are less likely to be destabilized by single-base changes and may therefore interfere with mutation detection. Elevated temperatures can then be used to bring these persistent structures to the brink of instability, so that the effects of small changes in sequence are maximized and revealed as alterations in the cleavage pattern. Mesophilic enzymes may be used at temperatures greater than 37° C. under certain conditions known to the art. These conditions include the use of high (i.e., 10–30%) concentrations of glycerol in the reaction conditions. Furthermore, it is noted that while an enzyme may be isolated from a mesophilic organism this fact alone does not mean that the enzyme may not demonstrate thermostability; therefore when testing the suitability of a mesophilic enzyme in the CFLP™ reaction, the reaction should be run at 37° C. and at higher temperatures. Alternatively, mild denaturants can be used to destablize the nucleic acid substrate at a lower temperature (e.g., 1–10% formamide, 1–10% DMSO and 1–10% glycerol have been used in enzymatic reactions to mimic thermal destablization).

Nucleic acid substrates that may be analyzed using a cleavage means, such as a 5' nuclease, include many types of both RNA and DNA. Such nucleic acid substrates may all be obtained using standard molecular biological techniques. For example, substrates may be isolated from a tissue sample, tissue culture cells, bacteria or viruses, may be transcribed in vitro from a DNA template, or may be chemically synthesized. Furthermore, substrates may be isolated from an organism, either as genomic material or as a plasmid or similar extrachromosomal DNA, or it may be a fragment of such material generated by treatment with a restriction endonuclease or other cleavage agents or it may be synthetic.

Substrates may also be produced by amplification using the PCR. When the substrate is to be a single-stranded substrate molecule, the substrate may be produced using the PCR with preferential amplification of one strand (asymmetric PCR). Single-stranded substrates may also be conveniently generated in other ways. For example, a double-stranded molecule containing a biotin label at the end of one of the two strands may be bound to a solid support (e.g., a magnetic bead) linked to a streptavidin moiety. The biotin-labeled strand is selectively captured by binding to the streptavidin-bead complex. It is noted that the subsequent cleavage reaction may be performed using substrate attached to the solid support, as the enzyme Cleavase™ can cleave the substrate while it is bound to the bead. A single-stranded substrate may also be produced from a double-stranded molecule by digestion of one strand with exonuclease.

The nucleic acids of interest may contain a label to aid in their detection following the cleavage reaction. The label may be a radioisotope (e.g., a $^{32}$P or $^{35}$S-labeled nucleotide) placed at either the 5' or 3' end of the nucleic acid or alternatively the label may be distributed throughout the nucleic acid (i.e., an internally labeled substrate). The label may be a nonisotopic detectable moiety, such as a fluorophore which can be detected directly, or a reactive group which permits specific recognition by a secondary agent. For example, biotinylated nucleic acids may be detected by probing with a streptavidin molecule which is coupled to an indicator (e.g., alkaline phosphatase or a fluorophore), or a hapten such as digoxigenin may be detected using a specific antibody coupled to a similar indicator. Alternatively, unlabeled nucleic acid may be cleaved and visualized by staining (e.g., ethidium bromide staining) or by hybridization using a labeled probe. In a preferred embodiment, the substrate nucleic acid is labeled at the 5' end with a biotin molecule and is detected using avidin or streptavidin coupled to alkaline phosphatase. In another preferred embodiment the substrate nucleic acid is labeled at the 5' end with a fluorescein molecule and is detected using an anti-fluorescein antibody-alkaline phosphatase conjugate.

The cleavage patterns are essentially partial digests of the substrate in the reaction. When the substrate is labelled at one end (e.g., with biotin), all detectable fragments share a common end. The extension of the time of incubation of the enzyme Cleavase™ reaction does not significantly increase the proportion of short fragments, indicating that each potential cleavage site assumes either an active or inactive conformation and that there is little inter-conversion between the states of any potential site, once they have formed. Nevertheless, many of the structures recognized as active cleavage sites are likely to be only a few base-pairs long and would appear to be unstable at the elevated temperatures used in the Cleavase™ reaction. The formation or disruption of these structures in response to small sequence changes results in changes in the patterns of cleavage.

The products of the cleavage reaction are a collection of fragments generated by structure specific cleavage of the input nucleic acid. Nucleic acids which differ in size may be analyzed and resolved by a number of methods including electrophoresis, chromatography, fluorescence polarization, mass spectrometry and chip hybridization. The invention is illustrated using electrophoretic separation. However, it is noted that the resolution of the cleavage products is not limited to electrophoresis. Electrophoresis is chosen to illustrate the method of the invention because electrophoresis is widely practiced in the art and is easily accessible to the average practitioner.

If abundant quantities of DNA are available for the analysis, it may be advantageous to use direct fluorescence to detect the cleavage fragments, raising the possibility of analyzing several samples in the same tube and on the same gel. This "multiplexing" would permit automated comparisons of closely related substrates such as wild-type and mutant forms of a gene.

The CFLP™ reaction is useful to rapidly screen for differences between similar nucleic acid molecules. To optimize the CFLP™ reaction for any desired nucleic acid system (e.g., a wild-type nucleic acid and one or more mutant forms of the wild-type nucleic acid), it is most convenient to use a single substrate from the test system (for example, the wild-type substrate) to determine the best CFLP™ reaction conditions. A single suitable condition is chosen for doing the comparison CFLP™ reactions on the other molecules of interest. For example, a cleavage reaction may be optimized for a wild-type sequence and mutant sequences may subsequently be cleaved under the same conditions for comparison with the wild-type pattern. The objective of the CFLP™ optimization test is the identification of a set of conditions which allow the test molecule to form an assortment (i.e., a population) of intra-strand structures that are sufficiently stable such that treatment with a structure-specific cleavage agent such as the Cleavase™ enzyme or DNAPTaq will yield a signature array of cleavage products, yet are sufficiently unstable that minor or single-base changes within the test molecule are likely to result in a noticeable change in the array of cleavage products.

The following discussion illustrates the optimization of the CFLP™ method for use with a single-stranded substrate.

A panel of reaction conditions with varying salt concentration and temperature is first performed to identify an optimal set of conditions for the single-stranded CFLP™. "Optimal CFLP™" is defined for this test case as the set of conditions that yields the most widely spaced set of bands after electrophoretic separation, with the most even signal intensity between the bands.

Two elements of the cleavage reaction that significantly affect the stability of the nucleic acid structures are the temperature at which the cleavage reaction is performed and the concentration of salt in the reaction solution. Likewise, other factors affecting nucleic acid structures, such as, formamide, urea or extremes in pH may be used. The initial test typically will comprise reactions performed at four temperatures (60° C., 65° C., 70° C. and 75° C.) in three different salt concentrations (0 mM, 25 mM and 50 mM) for a total of twelve individual reactions. It is not intended that the present invention be limited by the salt utilized. The salt utilized may be chosen from potassium chloride, sodium chloride, etc. with potassium chloride being a preferred salt.

For each salt concentration to be tested, 30 µl of a master mix containing a DNA substrate, buffer and salt is prepared. When the substrate is DNA, suitable buffers include 3-[N-Morpholino]propanesulfonic acid (MOPS), pH 6.5 to 9.0, with pH 7.5 to 8.4 being particularly preferred and other "Good" biological buffers such as tris[Hydroxymethyl] aminomethane (Tris) or N,N-bis[2-Hydroxyethyl]glycine (Bicine), pH 6.5 to 9.0, with pH 7.5 to 8.4 being particularly preferred. When the nucleic acid substrate is RNA, the pH of the buffer is reduced to the range of 6.0 to 8.5, with pH 6.0 to 7.0 being particularly preferred. When manganese is to used as the divalent cation in the reaction, the use of Tris buffers is not preferred. Manganese tends to precipitate as manganous oxide in Tris if the divalent cation is exposed to the buffer for prolonged periods (such as in incubations of greater than 5 minutes or in the storage of a stock buffer). When manganese is to be used as the divalent cation, a preferred buffer is the MOPS buffer.

For reactions containing no salt (the "0 mM KCl" mix), the mix includes enough detectable DNA for 5 digests (e.g., approximately 500 fmoles of 5' biotinylated DNA or approximately 100 fmoles of $^{32}$P-5' end labeled DNA) in 30 µl of 1× CFLP™ buffer (10 mM MOPS, pH 8.2) with 1.7 mM MnCl$_2$ or MgCl$_2$ (the final concentration of the divalent cation will be 1 mM). Other concentrations of the divalent cation may be used if appropriate for the cleavage agent chosen (e.g., *E. coli* DNA polymerase I is commonly used in a buffer containing 5 mM MgCl$_2$). The "25 mM KCl" mix includes 41.5 mM KCl in addition to the above components; the "50 mM KCl" mix includes 83.3 mM KCl in addition to the above components.

The mixes are distributed into labeled reaction tubes (0.2 ml, 0.5 ml or 1.5 ml "Eppendorf" style microcentrifuge tubes) in 6 µl aliquots, overlaid with light mineral oil or a similar barrier, and stored on ice until use. Sixty microliters of an enzyme dilution cocktail is assembled, comprising a 5' nuclease at a suitable concentration in 1× CFLP™ buffer without MnCl$_2$. Preferred 5' nucleases and concentrations are 750 ng of the enzyme Cleavase™BN or 15 units of Taq DNA polymerase (or another eubacterial Pol A-type DNA polymerase). Suitable amounts of a similar structure-specific cleavage agent in 1× CFLP™ buffer without MnCl$_2$ may also be utilized.

If a strong (i.e., stable) secondary structure is formed by the substrates, a single nucleotide change is unlikely to significantly alter that structure, or the cleavage pattern it produces. Elevated temperatures can be used to bring structures to the brink of instability, so that the effects of small changes in sequence are maximized, and revealed as alterations in the cleavage pattern within the target substrate, thus allowing the cleavage reaction to occur at that point. Consequently, it is often desirable to run the reaction at an elevated temperature (i.e., above 55° C.).

Preferably, reactions are performed at 60° C., 65° C., 70° C. and 75° C. For each temperature to be tested, a trio of tubes at each of the three KCl concentrations are brought to 95° C. for 5 seconds, then cooled to the selected temperature. The reactions are then started immediately by the addition of 4 µl of the enzyme cocktail. A duplicate trio of tubes may be included (these tubes receiving 4 µl of 1× CFLP™ buffer without enzyme or MnCl$_2$), to assess the nucleic acid stability in these reaction conditions. All reactions proceed for 5 minutes, and are stopped by the addition of 8 µl of 95% formamide with 20 mM EDTA and 0.05% xylene cyanol and 0.05% bromophenol blue. Reactions may be assembled and stored on ice if necessary. Completed reactions are stored on ice until all reactions in the series have been performed.

Samples are heated to 72° C. for 2 minutes and 5 µl of each reaction is resolved by electrophoresis through a suitable gel, such as 6 to 10% polyacrylamide (19:1 cross-link), with 7M urea, in a buffer of 45 mM Tris-Borate, pH 8.3, 1.4 mM EDTA for nucleic acids up to approximately 1.5 kb, or native or denaturing agarose gels for larger molecules. The nucleic acids may be visualized as described above, by staining, autoradiography (for radioisotopes) or by transfer to a nylon or other membrane support with subsequent hybridization and/or nonisotopic detection. The patterns generated are examined by the criteria described above and a reaction condition is chosen for the performance of the variant comparison CFLP™s.

A "no enzyme" control allows the assessment of the stability of the nucleic acid substrate under particular reaction conditions. In this instance, the substrate is placed in a tube containing all reaction components except the enzyme and treated the same as the enzyme-containing reactions. Other control reactions may be run. A wild-type substrate may be cleaved each time a new mutant substrate is tested. Alternatively, a previously characterized mutant may be run in parallel with a substrate suspected of containing a different mutation. Previously characterized substrates allow for the comparison of the cleavage pattern produced by the new test substrate with a known cleavage pattern. In this manner, alterations in the new test substrate may be identified.

When the CFLP™ pattern generated by cleavage of a single-stranded substrate contains an overly strong (i.e., intense) band, this indicates the presence of a very stable structure. The preferred method for redistributing the signal is to alter the reaction conditions to increase structure stability (e.g., lower the temperature of the cleavage reaction, raise the monovalent salt concentration); this allows other less stable structures to compete more effectively for cleavage.

When the single-stranded substrate is labelled at one end (e.g., with biotin or 32P) all detectable fragments share a common end. For short DNA substrates (less than 250 nucleotides) the concentration of the enzyme (e.g., Cleavase™ BN) and the length of the incubation have minimal influence on the distribution of signal intensity, indicating that the cleavage patterns are not partial digests of a single structure assumed by the nucleic acid substrate, but rather are relatively complete digests of a collection of stable structures formed by the substrate. With longer DNA substrates (greater than 250 nucleotides) there is a greater chance of having multiple cleavage sites on each structure, giving apparent overdigestion as indicated by the absence of any residual full-length materials. For these DNA substrates, the enzyme concentration may be lowered in the cleavage reaction (for example, if 50 ng of the Cleavase™ BN enzyme were used initially and overdigestion was apparent, the concentration of enzyme may be reduced to 25, 10 or 1 ng per reaction).

When the CFLP™ reaction is to optimized for the cleavage a double-stranded substrate the following steps are taken. The cleavage of double-stranded DNA substrates up to 2,000 base pairs may be optimized in this manner.

The double-stranded substrate is prepared such that it contains a single end-label using any of the methods known to the art. The molar amount of DNA used in the optimization reactions is the same as that use for the optimization of reactions utilizing single-stranded substrates. The most notable differences between the optimization of the CFLP™ reaction for single- versus double-stranded substrates is that the double-stranded substrate is denatured in distilled water without buffer, the concentration of $MnCl_2$ in the reaction is reduced to 0.2 mM, the KCl (or other monovalent salt) is omitted, and the enzyme concentration is reduced to 10 to 25 ng per reaction. In contrast to the optimization of the single-stranded CFLP™ reaction (described above) where the variation of the monovalent salt (e.g., KCl) concentration is a critical controlling factor, in the optimization of the double-stranded CFLP™ reaction the range of temperature is the more critical controlling factor for optimization of the reaction. When optimizing the double-stranded CFLP™ reaction a reaction tube containing the substrate and other components described below is set up to allow performance of the reaction at each of the following temperatures: 40° C., 45° C., 50° C., 55° C., 60° C., 65° C., 70° C., and 75° C.

For each temperature to be tested, a mixture comprising the single end labelled double-stranded DNA substrate and distilled water in a volume of 15 µl is prepared and placed into a thin walled microcentrifuge tube. This mixture may be overlaid with light mineral oil or liquid wax (this overlay is not generally required but may provide more consistent results with some double-stranded DNA substrates).

A 2 mM solution of $MnCl_2$ is prepared. For each CFLP™ reaction, 5 µl of a diluted enzyme solution is prepared comprising 2 µl of 10× CFLP™ buffer (100 mM MOPS, pH 7.2 to 8.2, 0.5% Tween-20, 0.5% Nonidet P-40), 2 µl of 2 mM $MnCl_2$ and 25 ng of Cleavase™ BN enzyme and distilled water to yield a final volume of 5 µl.

The DNA mixture is heated to 95° C. for 10 to 30 seconds and then individual tubes are cooled to the reaction temperatures to be tested (e.g., 40° C., 45° C., 50° C., 55° C., 60° C., 65° C., 70° C., and 75° C.). The cleavage reaction is started by adding 5 µl of the dilute enzyme solution to each tube at the target reaction temperature. The reaction is incubated at the target temperature for 5 minutes and the reaction is terminated (e.g., by the addition of 16 µl of stop solution comprising 95% formamide with 10 mM EDTA and 0.05% xylene cyanol and 0.05% bromophenol blue).

Samples are heated to 72° C. for 1 to 2 minutes and 3 to 7 µl of each reaction is resolved by electrophoresis through a suitable gel, such as 6 to 10% polyacrylamide (19:1 cross-link), with 7M urea, in a buffer of 45 mM Tris-Borate, pH 8.3, 1.4 mM EDTA for nucleic acids up to approximately 1.5 kb, or native or denaturing agarose gels for larger molecules. The nucleic acids may be visualized as described above, by staining, autoradiography (for radioisotopes) or by transfer to a nylon or other membrane support with subsequent hybridization and/or nonisotopic detection. The patterns generated are examined by the criteria described above and a reaction condition is chosen for the performance of the double-stranded CFLP™.

A "no enzyme" control allows the assessment of the stability of the nucleic acid substrate under particular reaction conditions. In this instance, the substrate is placed in a tube containing all reaction components except the enzyme and treated the same as the enzyme-containing reactions. Other control reactions may be run. A wild-type substrate may be cleaved each time a new mutant substrate is tested. Alternatively, a previously characterized mutant may be run in parallel with a substrate suspected of containing a different mutation. Previously characterized substrates allow for the comparison of the cleavage pattern produced by the new test substrate with a known cleavage pattern. In this manner, alterations in the new test substrate may be identified.

When performing double-stranded CFLP™ reactions the $MnCl_2$ concentration preferably will not exceed 0.25 mM. If the end label on the double-stranded DNA substrate disappears (i.e., loses its 5' end label as judged by a loss of signal upon detection of the cleavage products), the concentration of $MnCl_2$ may be reduced to 0.1 mM. Any EDTA present in the DNA storage buffer will reduce the amount of free $Mn^{2+}$ in the reaction, so double-stranded DNA should be dissolved in water or Tris-HCl with a EDTA concentration of 0.1 mM or less.

Cleavage products produced by cleavage of either single- or double-stranded substrates which contain a biotin label may be detected using the following nonisotopic detection method. After electrophoresis of the reaction products, the gel plates are separated allowing the gel to remain flat on one plate. A positively charged nylon membrane (preferred membranes include Nytran®Plus, 0.2 or 0.45 mm-pore size, Schleicher and Schuell, Keene, N.H.), cut to size and pre-wetted in 0.5× TBE (45 mM tris-Borate, pH 8.3, 1.4 mM EDTA), is laid on top of the exposed gel. All air bubbles trapped between the gel and the membrane are removed (e.g., by rolling a 10 ml pipet firmly across the membrane). Two pieces of 3MM filter paper (Whatrnan) are then placed on top of the membrane, the other glass plate is replaced, and the sandwich is clamped with binder clips or pressed with books or weights. The transfer is allowed to proceed 2 hours to overnight (the signal increases with longer transfer).

After transfer, the membrane is carefully peeled from the gel and allowed to air dry. Distilled water from a squeeze bottle can be used to loosen any gel that sticks to the membrane. After complete drying, the membrane is agitated for 30 minutes in 1.2× Sequenase Images Blocking Buffer (United States Biochemical, Cleveland, Ohio; avoid any precipitates in the blocking buffer by decanting or filtering); 0.3 ml of the buffer is used per $cm^2$ of membrane (e.g., 30 mls for a 10 cm×10 cm blot). A streptavidin-alkaline phosphatase conjugate (SAAP, United Stated Biochemical) is added at a 1:4000 dilution directly to the blocking solution (avoid spotting directly on membrane), and agitated for 15 minutes. The membrane is rinsed briefly with $dH_2O$ and then washed 3 times (5 minutes of shaking per/wash) in 1× SAAP buffer (100 mM Tris-HCl, pH 10; 50 mM NaCl) with 0.1% sodium dodecyl sulfate (SDS), using 0.5 ml buffer/$cm^2$ of membrane, with brief water rinses between each wash. The membrane is then washed twice in 1× SAAP buffer (no SDS) with 1 mM $MgCl_2$, drained thoroughly, and placed in a plastic heat-sealable bag. Using a sterile pipet tip, 0.05 ml/$cm^2$ of CDP-Star™ (Tropix, Bedford, Mass.) is added to the bag and distributed over the entire membrane for 5 minutes. The bag is drained of all excess liquid and air bubbles, sealed, and the membrane is exposed to X-ray film (e.g, Kodak XRP) for 30 minutes. Exposure times are adjusted as necessary for resolution and clarity.

To date, every nucleic acid substrate tested in the CFLP™ system has produced a reproducible pattern of fragments. The sensitivity and specificity of the cleavage reaction make this method of analysis very suitable for the rapid screening of mutations in cancer diagnostics, tissue typing, genetic identity, bacterial and viral typing, polymorphism analysis, structure analysis, mutant screening in genetic crosses, etc. It could also be applied to enhanced RNA analysis, high level multiplexing and extension to longer fragments. One distinct benefit of using the CleavaseTm reaction to characterize nucleic acids is that the pattern of cleavage products constitutes a characteristic fingerprint, so a potential mutant can be compared to previously characterized mutants without sequencing. Also, the place in the fragment pattern where a change is observed gives a good indication of the position of the mutation. But it is noted that the mutation need not be at the precise site of cleavage, but only in an area that affects the stability of the structure.

EXPERIMENTAL

The following examples serve to illustrate certain preferred embodiments and aspects of the present invention and are not to be construed as limiting the scope thereof.

In the disclosure which follows, the following abbreviations apply:°C. (degrees Centigrade); g (gravitational field); vol (volume); w/v (weight to volume); v/v (volume to volume); BSA (bovine serum albumin); CTAB (cetyltrimethylammonium bromide); HPLC (high pressure liquid chromatography); DNA (deoxyribonucleic acid); IVS (intervening sequence); p (plasmid); μl (microliters); ml (milliliters); μg (micrograms); pmoles (picomoles); mg (milligrams); MOPS (3-[N-Morpholino]propanesulfonic acid); M (molar); mM (milliMolar); μM (microMolar); nm (nanometers); kdal (kilodaltons); OD (optical density); EDTA (ethylene diamine tetra-acetic acid); FITC (fluorescein isothiocyanate); SDS (sodium dodecyl sulfate); $NaPO_4$ (sodium phosphate); Tris (tris(hydroxymethyl)-aminomethane); PMSF (phenylmethylsulfonylfluoride); TBE (Tris-Borate-EDTA, i.e., Tris buffer titrated with boric acid rather than HCl and containing EDTA) ; PBS (phosphate buffered saline); PPBS (phosphate buffered saline containing 1 mM PMSF); PAGE (polyacrylamide gel electrophoresis); Tween (polyoxyethylene-sorbitan); Boehringer Mannheim (Boehringer Mannheim, Indianapolis, Ind.); Dynal (Dynal A.S., Oslo, Norway); Epicentre (Epicentre Technologies, Madison, Wis.); National Biosciences (National Biosciences, Plymouth, Minn.); New England Biolabs (New England Biolabs, Beverly, Mass.); Novagen (Novagen, Inc., Madison, Wis.); Perkin Elmer (Perkin Elmer, Norwalk, Conn.); Promega Corp. (Promega Corp., Madison, Wis.); RJ Research (RJ Research, Inc., Watertown, Mass.); Stratagene (Stratagene Cloning Systems, La Jolla, Calif.); USB (U.S. Biochemical, Cleveland, Ohio).

EXAMPLE 1

Characteristics Of Native Thermostable DNA Polymerases

A. 5' Nuclease Activity Of DNAPTaq

Figure 6:
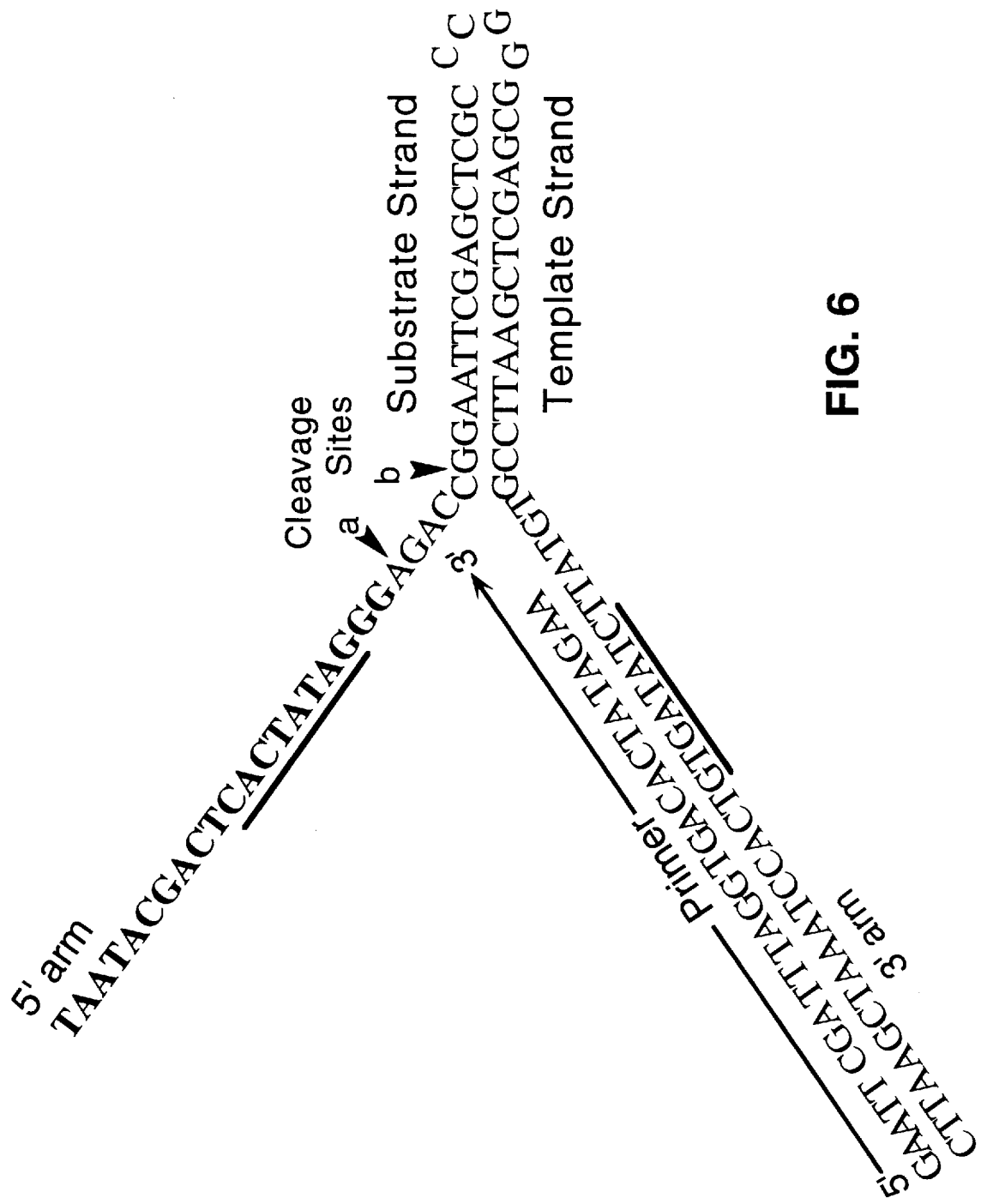
FIG. 6 depicts a structure which cannot be amplified using DNAPTaq.

During the polymerase chain reaction (PCR) [Saiki et al., *Science* 239:487 (1988); Mullis and Faloona, *Methods in Enzymology* 155:335 (1987)], DNAPTaq is able to amplify many, but not all, DNA sequences. One sequence that cannot be amplified using DNAPTaq is shown in FIG. 6 (Hairpin structure is SEQ ID NO:15, PRIMERS are SEQ ID NOS:16–17.) This DNA sequence has the distinguishing characteristic of being able to fold on itself to form a hairpin with two single-stranded arms, which correspond to the primers used in PCR.

To test whether this failure to amplify is due to the 5' nuclease activity of the enzyme, we compared the abilities of DNAPTaq and DNAPStf to amplify this DNA sequence during 30 cycles of PCR. Synthetic oligonucleotides were obtained from The Biotechnology Center at the University of Wisconsin-Madison. The DNAPTaq and DNAPStf were from Perkin Elmer (i.e., AmpliTaq™ DNA polymerase and the Stoffel fragment of Amplitaq™ DNA polymerase). The substrate DNA comprised the hairpin structure shown in FIG. 6 cloned in a double-stranded form into pUC19. The primers used in the amplification are listed as SEQ ID NOS:16–17. Primer SEQ ID NO:17 is shown annealed to the 3' arm of the hairpin structure in FIG. 6. Primer SEQ ID NO:16 is shown as the first 20 nucleotides in bold on the 5' arm of the hairpin in FIG. 6.

Polymerase chain reactions comprised 1 ng of supercoiled plasmid target DNA, 5 pmoles of each primer, 40 μM each dNTP, and 2.5 units of DNAPTaq or DNAPStf, in a 50 μl solution of 10 mM Tris.Cl pH 8.3. The DNAPTaq reactions included 50 mM KCl and 1.5 mM $MgCl_2$. The temperature profile was 95° C. for 30 sec., 55° C. for 1 min. and 72° C. for 1 min., through 30 cycles. Ten percent of each reaction was analyzed by gel electrophoresis through 6% polyacrylamide (cross-linked 29:1) in a buffer of 45 mM Tris.Borate, pH 8.3, 1.4 mM EDTA.

Figure 7:
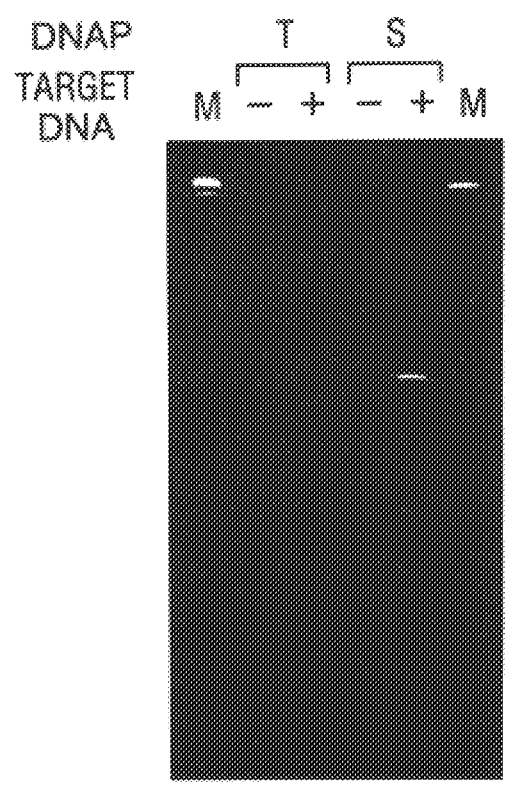
FIG. 7 is a ethidium bromide-stained gel demonstrating attempts to amplify a bifurcated duplex using either DNAPTaq or DNAPStf (Stoffel).

The results are shown in FIG. 7. The expected product was made by DNAPStf (indicated simply as "S") but not by DNAPTaq (indicated as "T"). We conclude that the 5' nuclease activity of DNAPTaq is responsible for the lack of amplification of this DNA sequence.

Figure 8:
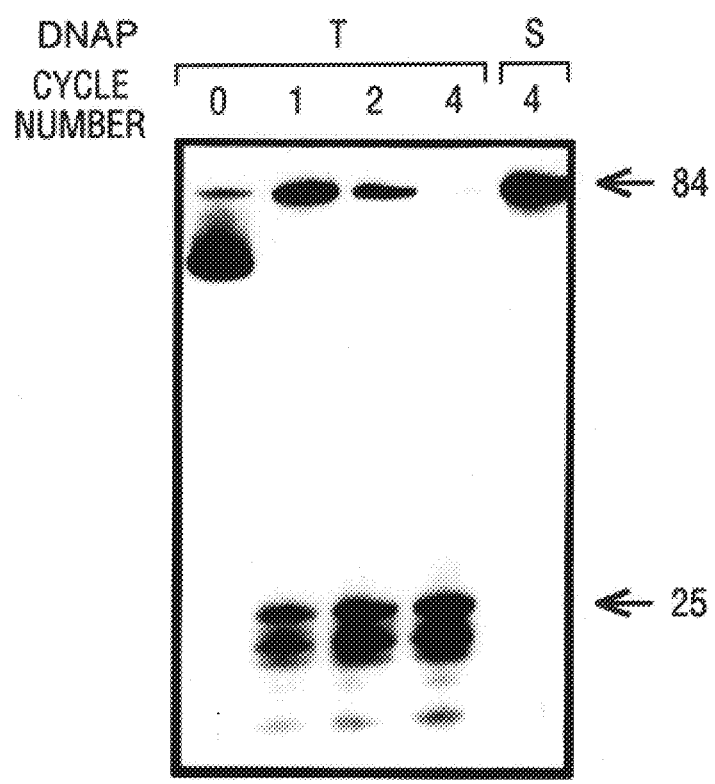
FIG. 8 is an autoradiogram of a gel analyzing the cleavage of a bifurcated duplex by DNAPTaq and lack of cleavage by DNAPStf.

To test whether the 5' unpaired nucleotides in the substrate region of this structured DNA are removed by DNAPTaq, the fate of the end-labeled 5' arm during four cycles of PCR was compared using the same two polymerases (FIG. 8). The hairpin templates, such as the one described in FIG. 6, were made using DNAPStf and a $^{32}$P-5'-end-labeled primer. The 5'-end of the DNA was released as a few large fragments by DNAPTaq but not by DNAPStf. The sizes of these fragments (based on their mobilities) show that they contain most or all of the unpaired 5' arm of the DNA. Thus, cleavage occurs at or near the base of the bifurcated duplex. These released fragments terminate with 3' OH groups, as evidenced by direct sequence analysis, and the abilities of the fragments to be extended by terminal deoxynucleotidyl transferase.

FIGS. 9–11 show the results of experiments designed to characterize the cleavage reaction catalyzed by DNAPTaq. Unless otherwise specified, the cleavage reactions comprised 0.01 pmoles of heat-denatured, end-labeled hairpin DNA (with the unlabeled complementary strand also present), 1 pmole primer (complementary to the 3' arm) and 0.5 units of DNAPTaq (estimated to be 0.026 pmoles) in a total volume of 10 μl of 10 mM Tris-Cl, ph 8.5, 50 mM KCl and 1.5 mM $MgCl_2$. As indicated, some reactions had different concentrations of KCl, and the precise times and temperatures used in each experiment are indicated in the individual figures. The reactions that included a primer used the one shown in FIG. 6 (SEQ ID NO:17). In some instances, the primer was extended to the junction site by providing polymerase and selected nucleotides.

Reactions were initiated at the final reaction temperature by the addition of either the $MgCl_2$ or enzyme. Reactions were stopped at their incubation temperatures by the addition of 8 μl of 95% formamide with 20 mM EDTA and 0.05% marker dyes. The $T_m$ calculations listed were made using the Oligo™ primer analysis software from National Biosciences, Inc. These were determined using 0.25 μM as the DNA concentration, at either 15 or 65 mM total salt (the 1.5 mM $MgCl_2$ in all reactions was given the value of 15 mM salt for these calculations).

Figure 9A:
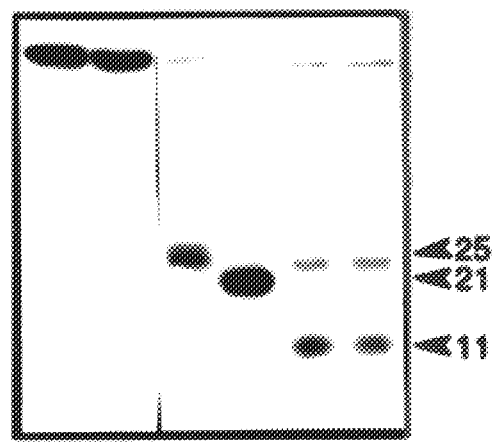
FIGS. 9A–B are a set of autoradiograms of gels analyzing cleavage or lack of cleavage upon addition of different reaction components and change of incubation temperature during attempts to cleave a bifurcated duplex with DNAPTaq.
Figure 9B:
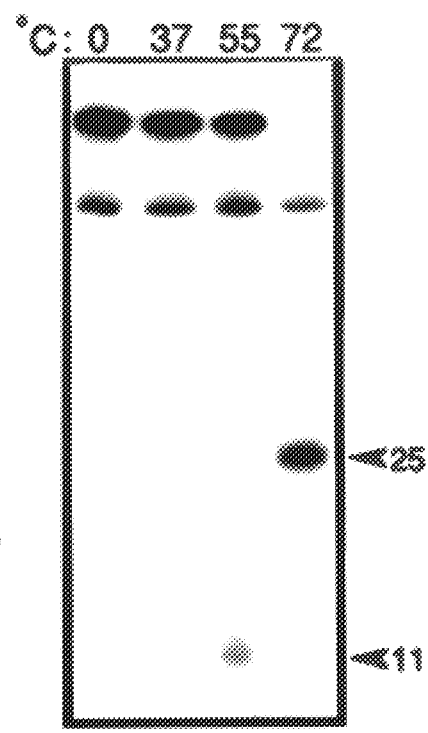

FIG. 9 is an autoradiogram containing the results of a set of experiments and conditions on the cleavage site. FIG. 9A is a determination of reaction components that enable cleavage. Incubation of 5'-end-labeled hairpin DNA was for 30 minutes at 55° C., with the indicated components. The products were resolved by denaturing polyacrylamide gel electrophoresis and the lengths of the products, in nucleotides, are indicated. FIG. 9B describes the effect of temperature on the site of cleavage in the absence of added primer. Reactions were incubated in the absence of KCl for 10 minutes at the indicated temperatures. The lengths of the products, in nucleotides, are indicated.

Surprisingly, cleavage by DNAPTaq requires neither a primer nor dNTPs (see FIG. 9A). Thus, the 5' nuclease activity can be uncoupled from polymerization. Nuclease activity requires magnesium ions, though manganese ions can be substituted, albeit with potential changes in specificity and activity. Neither zinc nor calcium ions support the cleavage reaction. The reaction occurs over a broad temperature range, from 25° C. to 85° C., with the rate of cleavage increasing at higher temperatures.

Still referring to FIG. 9, the primer is not elongated in the absence of added dNTPs. However, the primer influences both the site and the rate of cleavage of the hairpin. The change in the site of cleavage (FIG. 9A) apparently results from disruption of a short duplex formed between the arms of the DNA substrate. In the absence of primer, the sequences indicated by underlining in FIG. 6 could pair, forming an extended duplex. Cleavage at the end of the extended duplex would release the 11 nucleotide fragment seen on the FIG. 9A lanes with no added primer. Addition of excess primer (FIG. 9A, lanes 3 and 4) or incubation at an elevated temperature (FIG. 9B) disrupts the short extension of the duplex and results in a longer 5' arm and, hence, longer cleavage products.

The location of the 3' end of the primer can influence the precise site of cleavage. Electrophoretic analysis revealed that in the absence of primer (FIG. 9B), cleavage occurs at the end of the substrate duplex (either the extended or shortened form, depending on the temperature) between the first and second base pairs. When the primer extends up to the base of the duplex, cleavage also occurs one nucleotide into the duplex. However, when a gap of four or six nucleotides exists between the 3' end of the primer and the substrate duplex, the cleavage site is shifted four to six nucleotides in the 5' direction.

Figures 10A, 10B:
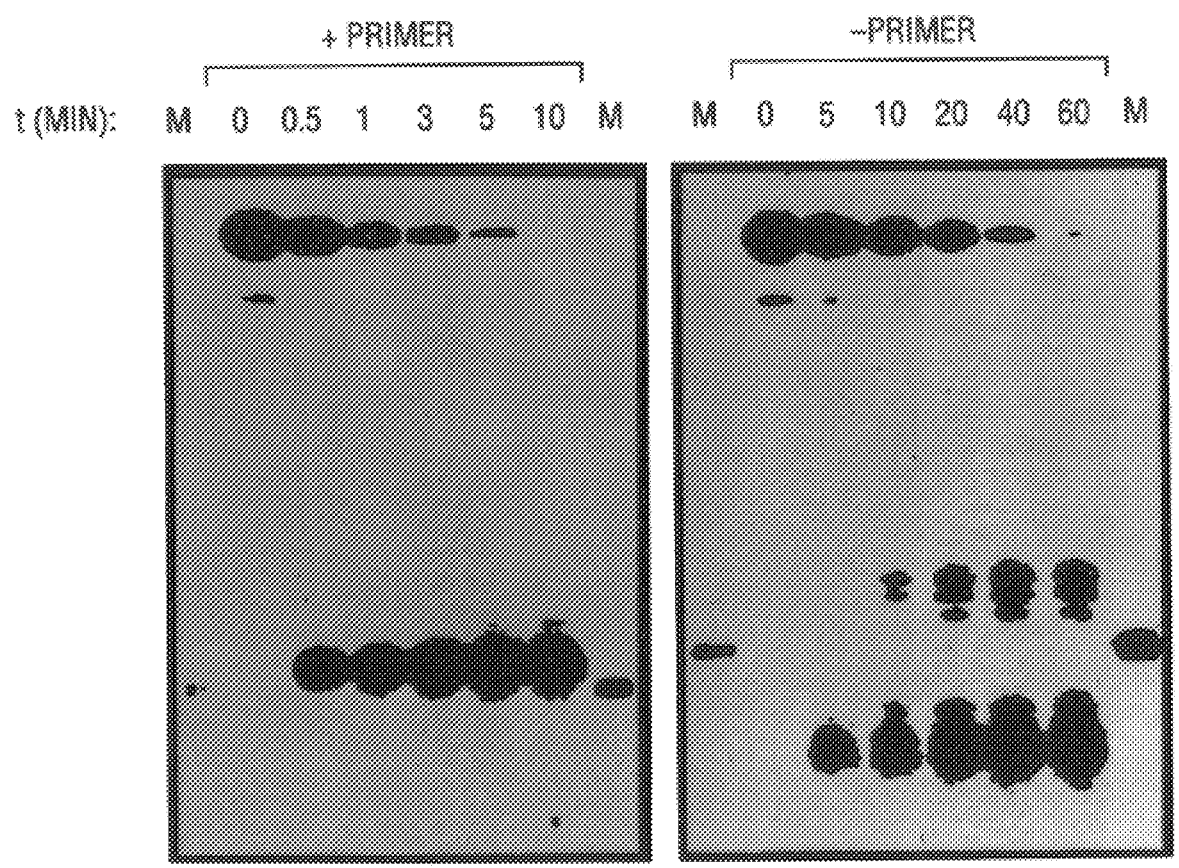
FIGS. 10A–B are an autoradiogram displaying timed cleavage reactions, with and without primer.

FIG. 10 describes the kinetics of cleavage in the presence (FIG. 10A) or absence (FIG. 10B) of a primer oligonucleotide. The reactions were run at 55° C. with either 50 mM KCl (FIG. 10A) or 20 mM KCl (FIG. 10B). The reaction products were resolved by denaturing polyacrylamide gel electrophoresis and the lengths of the products, in nucleotides, are indicated. "M", indicating a marker, is a 5' end-labeled 19-nt oligonucleotide. Under these salt conditions, FIGS. 10A and 10B indicate that the reaction appears to be about twenty times faster in the presence of primer than in the absence of primer. This effect on the efficiency may be attributable to proper alignment and stabilization of the enzyme on the substrate.

The relative influence of primer on cleavage rates becomes much greater when both reactions are run in 50 mM KCl. In the presence of primer, the rate of cleavage increases with KCl concentration, up to about 50 mM. However, inhibition of this reaction in the presence of primer is apparent at 100 mM and is complete at 150 mM KCl. In contrast, in the absence of primer the rate is enhanced by concentration of KCl up to 20 mM, but it is reduced at concentrations above 30 mM. At 50 mM KCl, the reaction is almost completely inhibited. The inhibition of cleavage by KCl in the absence of primer is affected by temperature, being more pronounced at lower temperatures.

Recognition of the 5' end of the arm to be cut appears to be an important feature of substrate recognition. Substrates that lack a free 5' end, such as circular M13 DNA, cannot be cleaved under any conditions tested. Even with substrates having defined 5' arms, the rate of cleavage by DNAPTaq is influenced by the length of the arm. In the presence of primer and 50 mM KCl, cleavage of a 5' extension that is 27 nucleotides long is essentially complete within 2 minutes at 55° C. In contrast, cleavages of molecules with 5' arms of 84 and 188 nucleotides are only about 90% and 40% complete after 20 minutes. Incubation at higher temperatures reduces the inhibitory effects of long extensions indicating that secondary structure in the 5' arm or a heat-labile structure in the enzyme may inhibit the reaction. A mixing experiment, run under conditions of substrate excess, shows that the molecules with long arms do not preferentially tie up the available enzyme in non-productive complexes. These results may indicate that the 5' nuclease domain gains access to the cleavage site at the end of the bifurcated duplex by moving down the 5' arm from one end to the other. Longer 5' arms would be expected to have more adventitious secondary structures (particularly when KCl concentrations are high), which would be likely to impede this movement.

Cleavage does not appear to be inhibited by long 3' arms of either the substrate strand target molecule or pilot nucleic acid, at least up to 2 kilobases. At the other extreme, 3' arms of the pilot nucleic acid as short as one nucleotide can support cleavage in a primer-independent reaction, albeit inefficiently. Fully paired oligonucleotides do not elicit cleavage of DNA templates during primer extension.

The ability of DNAPTaq to cleave molecules even when the complementary strand contains only one unpaired 3' nucleotide may be useful in optimizing allele-specific PCR. PCR primers that have unpaired 3' ends could act as pilot oligonucleotides to direct selective cleavage of unwanted templates during preincubation of potential template-primer complexes with DNAPTaq in the absence of nucleoside triphosphates.

B. 5' Nuclease Activities Of Other DNAPs

To determine whether other 5' nucleases in other DNAPs would be suitable for the present invention, an array of enzymes, several of which were reported in the literature to be free of apparent 5' nuclease activity, were examined. The ability of these other enzymes to cleave nucleic acids in a structure-specific manner was tested using the hairpin substrate shown in FIG. 6 under conditions reported to be optimal for synthesis by each enzyme.

DNAPEc1 and DNAP Klenow were obtained from Promega Corporation; the DNAP of *Pyrococcus furious* ["Pfu", Bargseid et al, Strategies 4:34 (1991)] was from Stratagene; the DNAP of *Thermococcus litoralis* ["Tli", Vent™(exo-), Perler et al., Proc. Natl. Acad. Sci. USA 89:5577 (1992)] was from New England Biolabs; the DNAP of *Thermus flavus* ["Tfl", Kaledin et al., *Biokhimiya* 46:1576 (1981)] was from Epicentre Technologies; and the DNAP of *Thermus thermophilus* ["Tth", Carballeira et al., Biotechniques 9:276 (1990); Myers et al., *Biochem.* 30:7661 (1991)] was from U.S. Biochemicals.

0.5 units of each DNA polymerase was assayed in a 20 μl reaction, using either the buffers supplied by the manufacturers for the primer-dependent reactions, or 10 mM Tris.Cl, pH 8.5, 1.5 mM MgCl$_2$, and 20 mM KCl. Reaction mixtures were at held 72° C. before the addition of enzyme.

Figures 11A, 11B:
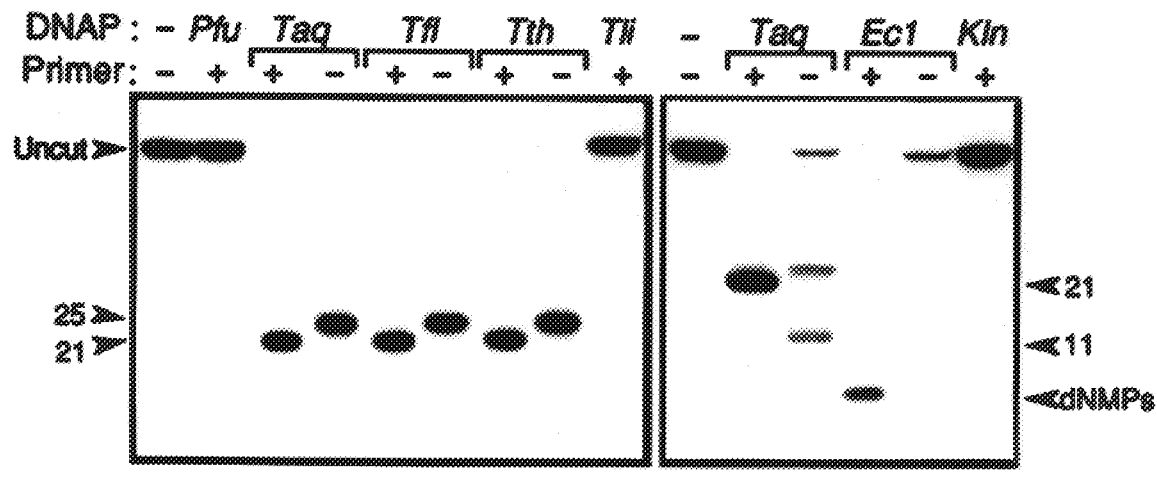
FIGS. 11A–B are a set of autoradiograms of gels demonstrating attempts to cleave a bifurcated duplex (with and without primer) with various DNAPs.

FIG. 11 is an autoradiogram recording the results of these tests. FIG. 11A demonstrates reactions of endonucleases of DNAPs of several thermophilic bacteria. The reactions were incubated at 55° C. for 10 minutes in the presence of primer or at 72° C. for 30 minutes in the absence of primer, and the products were resolved by denaturing polyacrylamide gel electrophoresis. The lengths of the products, in nucleotides, are indicated. FIG. 11B demonstrates endonucleolytic cleavage by the 5' nuclease of DNAPEc1. The DNAPEc1 and DNAP Klenow reactions were incubated for 5 minutes at 37° C. Note the light band of cleavage products of 25 and 11 nucleotides in the DNAPEc1 lanes (made in the presence and absence of primer, respectively). FIG. 7B also demonstrates DNAPTaq reactions in the presence (+) or absence (−) of primer. These reactions were run in 50 mM and 20 mM KCl, respectively, and were incubated at 55° C. for 10 minutes.

Referring to FIG. 11A, DNAPs from the eubacteria *Thermus thermophilus* and *Thermus flavus* cleave the substrate at the same place as DNAPTaq, both in the presence and absence of primer. In contrast, DNAPs from the archaebacteria *Pyrococcus furiosus* and *Thermococcus litoralis* are unable to cleave the substrates endonucleolytically. The DNAPs from *Pyrococcus furious* and *Thermococcus litoralis* share little sequence homology with eubacterial enzymes (Ito et al., *Nucl. Acids Res.* 19:4045 (1991); Mathur et al., *Nucl. Acids. Res.* 19:6952 (1991); see also Perler et al.). Referring to FIG. 11B, DNAPEc1 also cleaves the substrate, but the resulting cleavage products are difficult to detect unless the 3' exonuclease is inhibited. The amino acid sequences of the 5' nuclease domains of DNAPEc1 and DNAPTaq are about 38% homologous (Gelfand, supra).

The 5' nuclease domain of DNAPTaq also shares about 19% homology with the 5' exonuclease encoded by gene 6 of bacteriophage T7 [Dunn et al., *J. Mol. Biol.* 166:477 (1983)]. This nuclease, which is not covalently attached to a DNAP polymerization domain, is also able to cleave DNA endonucleolytically, at a site similar or identical to the site that is cut by the 5' nucleases described above, in the absence of added primers.

C. Transcleavage

Figure 12A:
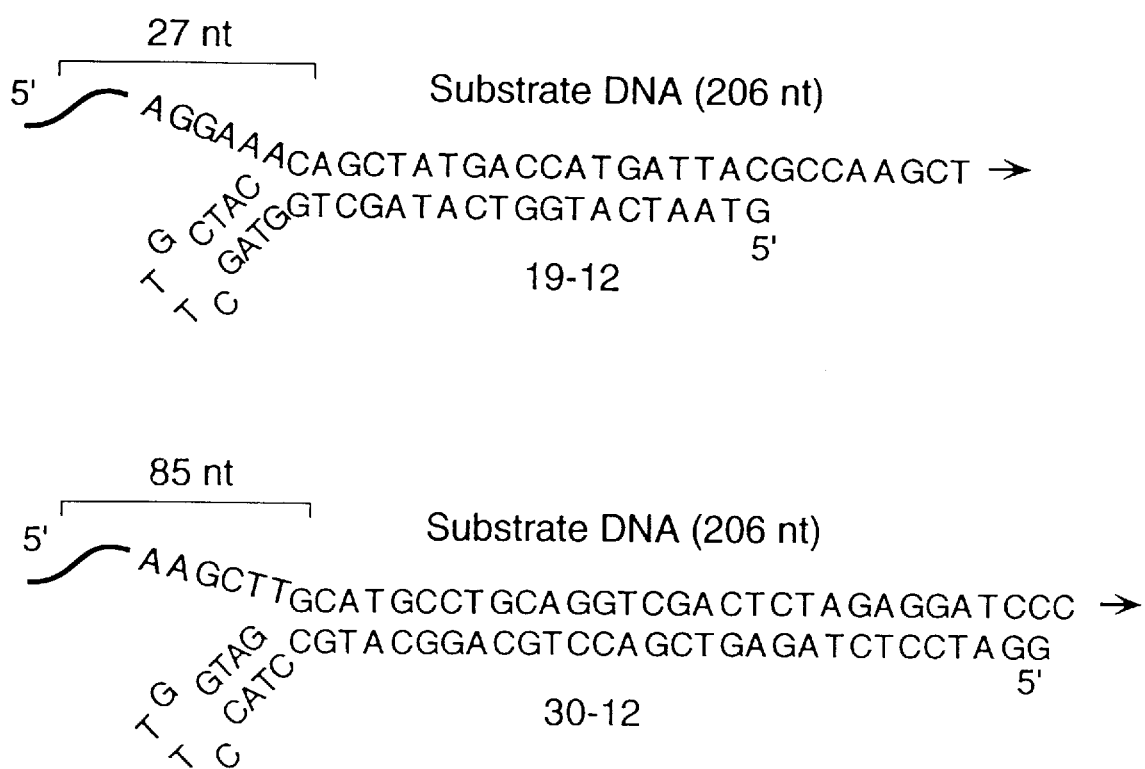
FIGS. 12A shows the substrates and oligonucleotides used to test the specific cleavage of substrate DNAs targeted by pilot oligonucleotides.

The ability of a 5' nuclease to be directed to cleave efficiently at any specific sequence was demonstrated in the following experiment. A partially complementary oligonucleotide termed a "pilot oligonucleotide" was hybridized to sequences at the desired point of cleavage. The non-complementary part of the pilot oligonucleotide provided a structure analogous to the 3' arm of the template (see FIG. 6), whereas the 5' region of the substrate strand became the 5' arm. A primer was provided by designing the 3' region of the pilot so that it would fold on itself creating a short hairpin with a stabilizing tetra-loop [Antao et al., *Nucl. Acids Res.* 19:5901 (1991)]. Two pilot oligonucleotides are shown in FIG. 12A. Oligonucleotides 19-12 (SEQ ID NO:18) and 30-12 (SEQ ID NO:19) are 31 or 42 nucleotides long, respectively. However, oligonucleotides 19-12 (SEQ ID NO:18) and 34-19 (SEQ ID NO:19) have only 19 and 30 nucleotides, respectively, that are complementary to different sequences in the substrate strand. The pilot oligonucleotides are calculated to melt off their complements at about 50° C. (19-12) and about 75° C. (30-12). Both pilots have 12 nucleotides at their 3' ends, which act as 3' arms with base-paired primers attached.

To demonstrate that cleavage could be directed by a pilot oligonucleotide, we incubated a single-stranded target DNA with DNAPTaq in the presence of two potential pilot oligonucleotides. The transcleavage reactions, where the target and pilot nucleic acids are not covalently linked, includes 0.01 pmoles of single end-labeled substrate DNA, 1 unit of DNAPTaq and 5 pmoles of pilot oligonucleotide in a volume of 20 µl of the same buffers. These components were combined during a one minute incubation at 95° C., to denature the PCR-generated double-stranded substrate DNA, and the temperatures of the reactions were then reduced to their final incubation temperatures. Oligonucleotides 30-12 and 19-12 can hybridize to regions of the substrate DNAs that are 85 and 27 nucleotides from the 5' end of the targeted strand.

Figure 21:
FIG. 21 provides the complete 206-mer duplex sequence employed as a substrate for the 5' nucleases of the present invention FIGS. 22A and B show the cleavage of linear nucleic acid substrates (based on the 206-mer of FIG. 21) by wild type DNAPs and 5' nucleases isolated from *Thermus aquaticus* and *Thermus flavus*.

FIG. 21 shows the complete 206-mer sequence (SEQ ID NO:32). The 206-mer was generated by PCR. The M13/pUC 24-mer reverse sequencing (−48) primer and the M13/pUC sequencing (−47) primer from New England Biolabs (catalogue nos. 1233 and 1224 respectively) were used (50 pmoles each) with the pGEM3z(f+) plasmid vector (Promega Corp.) as template (10 ng) containing the target sequences. The conditions for PCR were as follows: 50 µM of each dNTP and 2.5 units of Taq DNA polymerase in 100 µl of 20 mM Tris-Cl, pH 8.3, 1.5 mM MgCl$_2$, 50 mM KCl with 0.05% Tween-20 and 0.05% NP-40. Reactions were cycled 35 times through 95° C. for 45 seconds, 63° C. for 45 seconds, then 72° C. for 75 seconds. After cycling, reactions were finished off with an incubation at 72° C. for 5 minutes. The resulting fragment was purified by electrophoresis through a 6% polyacrylamide gel (29:1 cross link) in a buffer of 45 mM Tris-Borate, pH 8.3, 1.4 MM EDTA, visualized by ethidium bromide staining or autoradiography, excised from the gel, eluted by passive diffusion, and concentrated by ethanol precipitation.

Figure 12B:
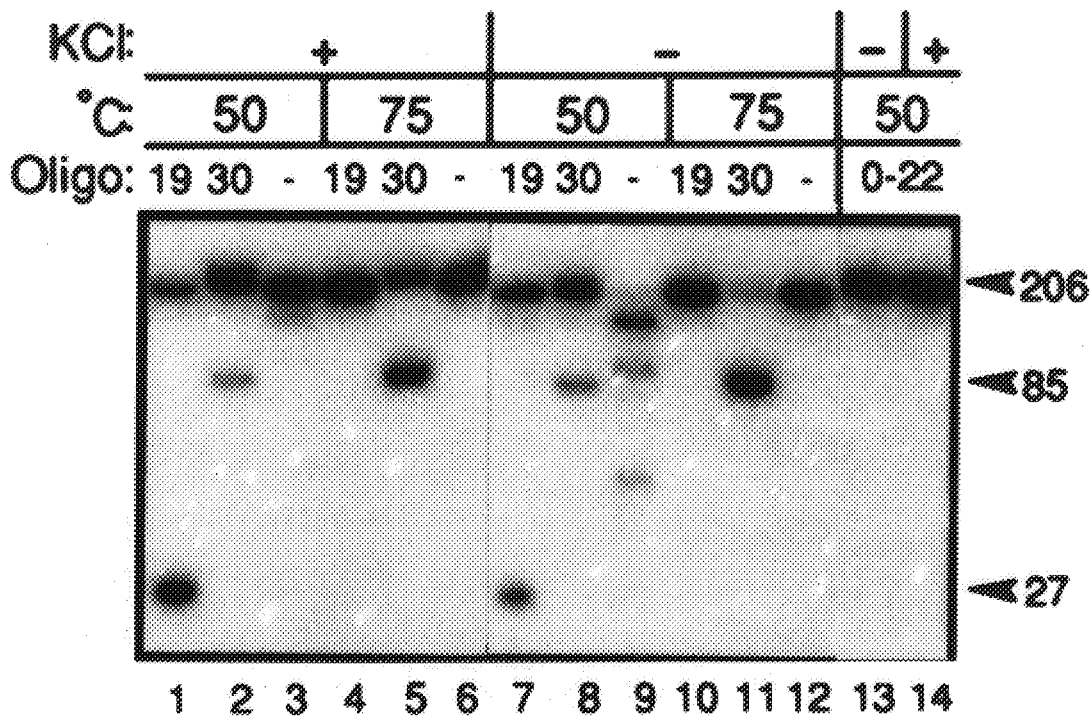
FIG. 12B shows an autoradiogram of a gel showing the results of cleavage reactions using the substrates and oligonucleotides shown FIG. 12A.

Cleavage of the substrate DNA occurred in the presence of the pilot oligonucleotide 19-12 at 50° C. (FIG. 12B, lanes 1 and 7) but not at 75° C. (lanes 4 and 10). In the presence of oligonucleotide 30-12 cleavage was observed at both temperatures. Cleavage did not occur in the absence of added oligonucleotides (lanes 3, 6 and 12) or at about 80° C. even though at 50° C. adventitious structures in the substrate allowed primer-independent cleavage in the absence of KCl (FIG. 12B, lane 9). A non-specific oligonucleotide with no complementarity to the substrate DNA did not direct cleavage at 50° C., either in the absence or presence of 50 mM KCl (lanes 13 and 14). Thus, the specificity of the cleavage reactions can be controlled by the extent of complementarity to the substrate and by the conditions of incubation.

D. Cleavage Of RNA

Figure 13A:
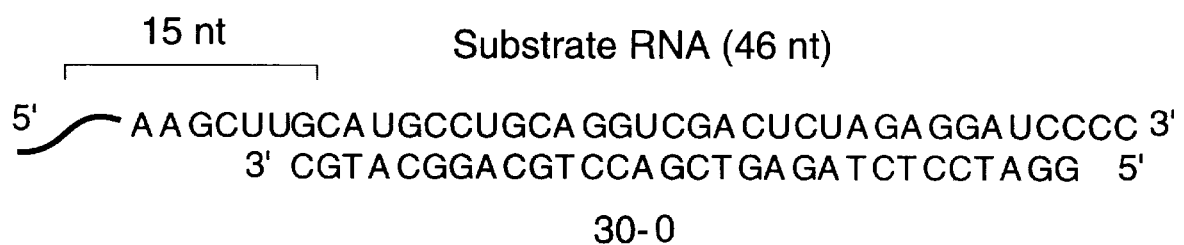
FIG. 13A shows the substrate and oligonucleotide used to test the specific cleavage of a substrate RNA targeted by a pilot oligonucleotide.

An shortened RNA version of the sequence used in the transcleavage experiments discussed above was tested for its ability to serve as a substrate in the reaction. The RNA is cleaved at the expected place, in a reaction that is dependent upon the presence of the pilot oligonucleotide. The RNA substrate, made by T7 RNA polymerase in the presence of [α-$^{32}$P]UTP, corresponds to a truncated version of the DNA substrate used in FIG. 12B. Reaction conditions were similar to those in used for the DNA substrates described above, with 50 mM KCl; incubation was for 40 minutes at 55° C. The pilot oligonucleotide used is termed 30-0 (SEQ ID NO:20) and is shown in FIG. 13A.

Figure 13B:
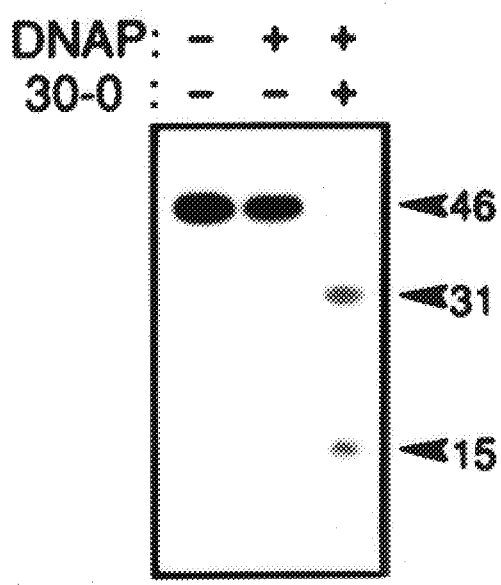
FIG. 13B shows an autoradiogram of a gel showing the results of a cleavage reaction using the substrate and oligonucleotide shown in FIG. 13A.

The results of the cleavage reaction is shown in FIG. 13B. The reaction was run either in the presence or absence of DNAPTaq or pilot oligonucleotide as indicated in FIG. 13B.

Strikingly, in the case of RNA cleavage, a 3' arm is not required for the pilot oligonucleotide. It is very unlikely that this cleavage is due to previously described RNaseH, which would be expected to cut the RNA in several places along the 30 base-pair long RNA-DNA duplex. The 5' nuclease of DNAPTaq is a structure-specific RNaseH that cleaves the RNA at a single site near the 5' end of the heteroduplexed region.

It is surprising that an oligonucleotide lacking a 3' arm is able to act as a pilot in directing efficient cleavage of an RNA target because such oligonucleotides are unable to direct efficient cleavage of DNA targets using native DNAPs. However, some 5' nucleases of the present invention (for example, clones E, F and G of FIG. 4) can cleave DNA in the absence of a 3' arm. In other words, a non-extendable cleavage structure is not required for specific cleavage with some 5' nucleases of the present invention derived from thermostable DNA polymerases.

We tested whether cleavage of an RNA template by DNAPTaq in the presence of a fully complementary primer could help explain why DNAPTaq is unable to extend a DNA oligonucleotide on an RNA template, in a reaction resembling that of reverse transcriptase. Another thermophilic DNAP, DNAPTth, is able to use RNA as a template, but only in the presence of Mn++, so we predicted that this enzyme would not cleave RNA in the presence of this cation. Accordingly, we incubated an RNA molecule with an appropriate pilot oligonucleotide in the presence of DNAPTaq or DNAPTth, in buffer containing either Mg++ or Mn++. As expected, both enzymes cleaved the RNA in the presence of Mg++. However, DNAPTaq, but not DNAPTth, degraded the RNA in the presence of Mn++. We conclude that the 5' nuclease activities of many DNAPs may contribute to their inability to use RNA as templates.

EXAMPLE 2

Generation Of 5' Nucleases From Thermostable DNA Polymerases

Thermostable DNA polymerases were generated which have reduced synthetic activity, an activity that is an undesirable side-reaction during DNA cleavage in the detection assay of the invention, yet have maintained thermostable nuclease activity. The result is a thermostable polymerase which cleaves nucleic acids DNA with extreme specificity.

Type A DNA polymerases from eubacteria of the genus Thermus share extensive protein sequence identity (90% in the polymerization domain, using the Lipman-Pearson method in the DNA analysis software from DNAStar, Wis.) and behave similarly in both polymerization and nuclease assays. Therefore, we have used the genes for the DNA polymerase of *Thermus aquaticus* (DNAPTaq) and *Thermus flavus* (DNAPTfl) as representatives of this class. Polymerase genes from other eubacterial organisms, such as *Thermus thermophilus, Thermus sp., Thermotoga maritima, Thermosipho africanus* and *Bacillus stearothermophilus* are equally suitable. The DNA polymerases from these thermophilic organisms are capable of surviving and performing at elevated temperatures, and can thus be used in reactions in which temperature is used as a selection against non-specific hybridization of nucleic acid strands.

The restriction sites used for deletion mutagenesis, described below, were chosen for convenience. Different sites situated with similar convenience are available in the *Thermus thermophilus* gene and can be used to make similar constructs with other Type A polymerase genes from related organisms.

A. Creation Of 5' Nuclease Constructs

1. Modified DNAPTaq Genes

The first step was to place a modified gene for the Taq DNA polymerase on a plasmid under control of an inducible promoter. The modified Taq polymerase gene was isolated as follows: The Taq DNA polymerase gene was amplified by polymerase chain reaction from genomic DNA from Thermus aquaticus, strain YT-1 (Lawyer et al., supra), using as primers the oligonucleotides described in SEQ ID NOS:13–14. The resulting fragment of DNA has a recognition sequence for the restriction endonuclease EcoRI at the 5' end of the coding sequence and a BglII sequence at the 3' end. Cleavage with BglII leaves a 5' overhang or "sticky end" that is compatible with the end generated by BamHI. The PCR-amplified DNA was digested with EcoRI and BamHI. The 2512 bp fragment containing the coding region for the polymerase gene was gel purified and then ligated into a plasmid which contains an inducible promoter.

In one embodiment of the invention, the pTTQ18 vector, which contains the hybrid trp-lac (tac) promoter, was used [M. J. R. Stark, *Gene* 5:255 (1987)] and shown in FIG. 14. The tac promoter is under the control of the *E. coli* lac repressor. Repression allows the synthesis of the gene product to be suppressed until the desired level of bacterial growth has been achieved, at which point repression is removed by addition of a specific inducer, isopropyl-β-D-thiogalactopyranoside (IPTG). Such a system allows the expression of foreign proteins that may slow or prevent growth of transformants.

Figures 15A, 15B, 15C:
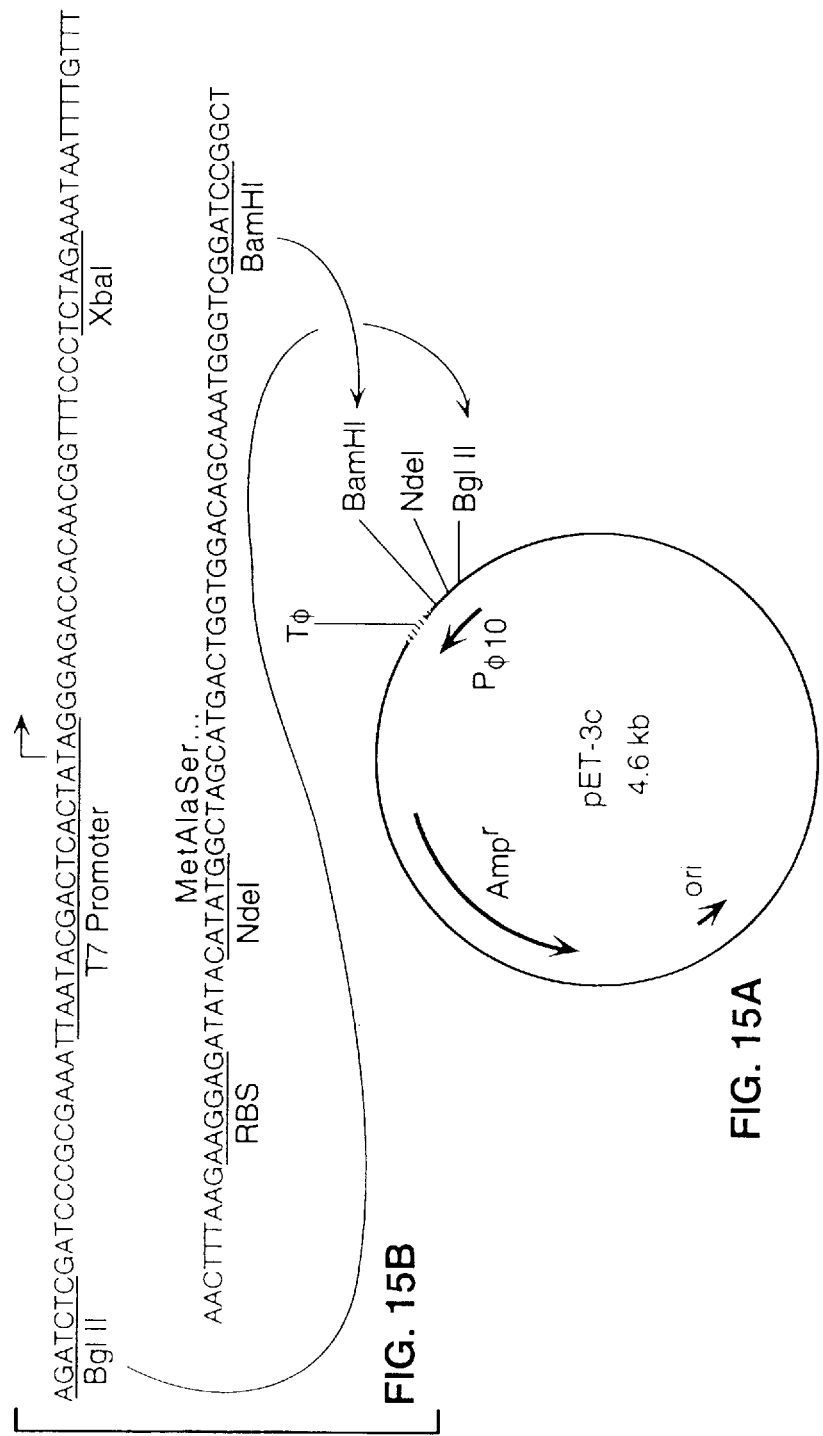
FIGS. 15A–C provide a diagram of vector pET-3c.

Bacterial promoters, such as tac, may not be adequately suppressed when they are present on a multiple copy plasmid. If a highly toxic protein is placed under control of such a promoter, the small amount of expression leaking through can be harmful to the bacteria. In another embodiment of the invention, another option for repressing synthesis of a cloned gene product was used. The non-bacterial promoter, from bacteriophage T7, found in the plasmid vector series pET-3 was used to express the cloned mutant Taq polymerase genes [FIG. 15; Studier and Moffatt, *J. Mol. Biol.* 189:113 (1986)]. This promoter initiates transcription only by T7 RNA polymerase. In a suitable strain, such as BL21 (DE3)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy.

For ligation into the pTTQ 18 vector (FIG. 14), the PCR product DNA containing the Taq polymerase coding region (mutTaq, clone 4B, SEQ ID NO:21) was digested with EcoRI and BglII and this fragment was ligated under standard "sticky end" conditions [Sambrook et al. *Molecular Cloning*, Cold Spring Harbor Laboratory Press, Cold Spring Harbor, pp. 1.63–1.69 (1989)] into the EcoRI and BamHI sites of the plasmid vector pTTQ18. Expression of this construct yields a translational fusion product in which the first two residues of the native protein (Met-Arg) are replaced by three from the vector (Met-Asn-Ser), but the remainder of the natural protein would not change. The construct was transformed into the JM109 strain of *E. coli* and the transformants were plated under incompletely repressing conditions that do not permit growth of bacteria expressing the native protein. These plating conditions allow the isolation of genes containing pre-existing mutations, such as those that result from the infidelity of Taq polymerase during the amplification process.

Using this amplification/selection protocol, we isolated a clone (depicted in FIG. 4B) containing a mutated Taq polymerase gene (mutTaq, clone 4B). The mutant was first detected by its phenotype, in which temperature-stable 5' nuclease activity in a crude cell extract was normal, but polymerization activity was almost absent (approximately less than 1% of wild type Taq polymerase activity).

DNA sequence analysis of the recombinant gene showed that it had changes in the polymerase domain resulting in two amino acid substitutions: an A to G change at nucleotide position 1394 causes a Glu to Gly change at amino acid position 465 (numbered according to the natural nucleic and amino acid sequences, SEQ ID NOS:1 and 4) and another A to G change at nucleotide position 2260 causes a Gln to Arg change at amino acid position 754. Because the Gln to Gly mutation is at a nonconserved position and because the Glu to Arg mutation alters an amino acid that is conserved in virtually all of the known Type A polymerases, this latter mutation is most likely the one responsible for curtailing the synthesis activity of this protein. The nucleotide sequence for the FIG. 4B construct is given in SEQ ID NO:21. The corresponding amino acid sequence encoded by the nucleotide sequence of SEQ ID NO:21 is listed in SEQ ID NO:85.

Subsequent derivatives of DNAPTaq constructs were made from the mutTaq gene, thus, they all bear these amino acid substitutions in addition to their other alterations, unless these particular regions were deleted. These mutated sites are indicated by black boxes at these locations in the diagrams in FIG. 4. In FIG. 4, the designation "3' Exo" is used to indicate the location of the 3' exonuclease activity associated with Type A polymerases which is not present in DNAPTaq. All constructs except the genes shown in FIGS. 4E, F and G were made in the pTTQ18 vector.

The cloning vector used for the genes in FIGS. 4E and F was from the commercially available pET-3 series, described above. Though this vector series has only a BamHI site for cloning downstream of the T7 promoter, the series contains variants that allow cloning into any of the three reading frames. For cloning of the PCR product described above, the variant called pET-3c was used (FIG. 15). The vector was digested with BamHI, dephosphorylated with calf intestinal phosphatase, and the sticky ends were filled in using the Klenow fragment of DNAPEc1 and dNTPs. The gene for the mutant Taq DNAP shown in FIG. 4B (mutTaq, clone 4B) was released from pTTQ18 by digestion with EcoRI and SalI, and the "sticky ends" were filled in as was done with the vector. The fragment was ligated to the vector under standard blunt-end conditions (Sambrook et al., *Molecular Cloning*, supra), the construct was transformed into the BL21(DE3)pLYS strain of *E. coli*, and isolates were screened to identify those that were ligated with the gene in the proper orientation relative to the promoter. This construction yields another translational fusion product, in which the first two amino acids of DNAPTaq (Met-Arg) are replaced by 13 from the vector plus two from the PCR primer (Met-Ala-Ser-Met-Thr-Gly-Gly-Gln-Gln-Met-Gly-Arg-Ile-Asn-Ser) (SEQ ID NO:29).

Our goal was to generate enzymes that lacked the ability to synthesize DNA, but retained the ability to cleave nucleic acids with a 5' nuclease activity. The act of primed, templated synthesis of DNA is actually a coordinated series of events, so it is possible to disable DNA synthesis by disrupting one event while not affecting the others. These steps include, but are not limited to, primer recognition and binding, dNTP binding and catalysis of the inter-nucleotide phosphodiester bond. Some of the amino acids in the polymerization domain of DNAPEcI have been linked to these functions, but the precise mechanisms are as yet poorly defined.

One way of destroying the polymerizing ability of a DNA polymerase is to delete all or part of the gene segment that encodes that domain for the protein, or to otherwise render the gene incapable of making a complete polymerization domain. Individual mutant enzymes may differ from each other in stability and solubility both inside and outside cells. For instance, in contrast to the 5' nuclease domain of DNAPEcI, which can be released in an active form from the polymerization domain by gentle proteolysis [Setlow and Kornberg, *J. Biol. Chem.* 247:232 (1972)], the Thermus nuclease domain, when treated similarly, becomes less soluble and the cleavage activity is often lost.

Using the mutant gene shown in FIG. 4B as starting material, several deletion constructs were created. All cloning technologies were standard (Sambrook et al., supra) and are summarized briefly, as follows:

FIG. 4C: The mutTaq construct was digested with PstI, which cuts once within the polymerase coding region, as indicated, and cuts immediately downstream of the gene in the multiple cloning site of the vector. After release of the fragment between these two sites, the vector was re-ligated, creating an 894-nucleotide deletion, and bringing into frame a stop codon 40 nucleotides downstream of the junction. The nucleotide sequence of this 5' nuclease (clone 4C) is given in SEQ ID NO:9. The corresponding amino acid sequence encoded by the nucleotide sequence of SEQ ID NO:9 is listed in SEQ ID NO:86.

FIG. 4D: The mutTaq construct was digested with NheI, which cuts once in the gene at position 2047. The resulting four-nucleotide 5' overhanging ends were filled in, as described above, and the blunt ends were re-ligated. The resulting four-nucleotide insertion changes the reading frame and causes termination of translation ten amino acids downstream of the mutation. The nucleotide sequence of this 5' nuclease (clone 4D) is given in SEQ ID NO:10. The corresponding amino acid sequence encoded by the nucleotide sequence of SEQ ID NO:10 is listed in SEQ ID NO:87.

FIG. 4E: The entire mutTaq gene was cut from pTTQ18 using EcoRI and SalI and cloned into pET-3c, as described above. This clone was digested with BstXI and XcmI, at unique sites that are situated as shown in FIG. 4E. The DNA was treated with the Klenow fragment of DNAPEc1 and dNTPs, which resulted in the 3' overhangs of both sites being trimmed to blunt ends. These blunt ends were ligated together, resulting in an out-of-frame deletion of 1540 nucleotides. An in-frame termination codon occurs 18 triplets past the junction site. The nucleotide sequence of this 5' nuclease (clone 4E) is given in SEQ ID NO:11 [The corresponding amino acid sequence encoded by the nucleotide sequence of SEQ ID NO:11 is listed in SEQ ID NO:88]., with the appropriate leader sequence given in SEQ ID NO:30 [The corresponding amino acid sequence encoded by the nucleotide sequence of SEQ ID NO:30 is listed in SEQ ID NO:89. It is also referred to as the enzyme Cleavase™ BX.

FIG. 4F: The entire mutTaq gene was cut from pTTQ18 using EcoRI and SalI and cloned into pET-3c, as described above. This clone was digested with BstXI and BamHI, at unique sites that are situated as shown in the diagram. The DNA was treated with the Klenow fragment of DNAPEc1 and dNTPs, which resulted in the 3' overhang of the BstX I site being trimmed to a blunt end, while the 5' overhang of the Bam HI site was filled in to make a blunt end. These ends were ligated together, resulting in an in-frame deletion of 903 nucleotides. The nucleotide sequence of the 5' nuclease (clone 4F) is given in SEQ ID NO:12. It is also referred to as the enzyme Cleavase™ BB. The corresponding amino acid sequence encoded by the nucleotide sequence of SEQ ID NO:12 is listed in SEQ ID NO:90.

FIG. 4G: This polymerase is a variant of that shown in FIG. 4E. It was cloned in the plasmid vector pET-21 (Novagen). The non-bacterial promoter from bacteriophage T7, found in this vector, initiates transcription only by T7 RNA polymerase. See Studier and Moffatt, supra. In a suitable strain, such as (DES)pLYS, the gene for this RNA polymerase is carried on the bacterial genome under control of the lac operator. This arrangement has the advantage that expression of the multiple copy gene (on the plasmid) is completely dependent on the expression of T7 RNA polymerase, which is easily suppressed because it is present in a single copy. Because the expression of these mutant genes is under this tightly controlled promoter, potential problems of toxicity of the expressed proteins to the host cells are less of a concern.

The pET-21 vector also features a "His-Tag", a stretch of six consecutive histidine residues that are added on the carboxy terminus of the expressed proteins. The resulting proteins can then be purified in a single step by metal chelation chromatography, using a commercially available (Novagen) column resin with immobilized $Ni^{++}$ ions. The 2.5 ml columns are reusable, and can bind up to 20 mg of the target protein under native or denaturing (guanidine-HCl or urea) conditions.

E. coli (DES)pLYS cells are transformed with the constructs described above using standard transformation techniques, and used to inoculate a standard growth medium (e.g., Luria-Bertani broth). Production of T7 RNA polymerase is induced during log phase growth by addition of IPTG and incubated for a further 12 to 17 hours. Aliquots of culture are removed both before and after induction and the proteins are examined by SDS-PAGE. Staining with Coomassie Blue allows visualization of the foreign proteins if they account for about 3–5% of the cellular protein and do not co-migrate with any of the major host protein bands. Proteins that co-migrate with major host proteins must be expressed as more than 10% of the total protein to be seen at this stage of analysis.

Some mutant proteins are sequestered by the cells into inclusion bodies. These are granules that form in the cytoplasm when bacteria are made to express high levels of a foreign protein, and they can be purified from a crude lysate, and analyzed by SDS-PAGE to determine their protein content. If the cloned protein is found in the inclusion bodies, it must be released to assay the cleavage and polymerase activities. Different methods of solubilization may be appropriate for different proteins, and a variety of methods are known. See e.g., Builder & Ogez, U.S. Pat. No. 4,511,502 (1985); Olson, U.S. Pat. No. 4,518,526 (1985); Olson & Pai, U.S. Pat. No. 4,511,503 (1985); Jones et al., U.S. Pat. No. 4,512,922 (1985), all of which are hereby incorporated by reference.

The solubilized protein is then purified on the $Ni^{++}$ column as described above, following the manufacturers instructions (Novagen). The washed proteins are eluted from the column by a combination of imidazole competitor (1M) and high salt (0.5M NaCl), and dialyzed to exchange the buffer and to allow denatured proteins to refold. Typical recoveries result in approximately 20 µg of specific protein per ml of starting culture. The DNAP mutant is referred to as the enzyme Cleavase™ BN and the sequence is given in SEQ ID NO:31. The corresponding amino acid sequence encoded by the nucleotide sequence of SEQ ID NO:31 is listed in SEQ ID NO:91.

2. Modified DNAPTfl Gene

The DNA polymerase gene of *Thermus flavus* was isolated from the "*T. flavus*" AT-62 strain obtained from the American Type Tissue Collection (ATCC 33923). This strain has a different restriction map then does the *T. flavus* strain used to generate the sequence published by Akhmetzjanov and Vakhitov, supra. The published sequence is listed as SEQ ID NO:2. No sequence data has been published for the DNA polymerase gene from the AT-62 strain of *T. flavus*.

Genomic DNA from *T. flavus* was amplified using the same primers used to amplify the *T. aquaticus* DNA polymerase gene (SEQ ID NOS:13–14). The approximately 2500 base pair PCR fragment was digested with EcoRI and BamHI. The over-hanging ends were made blunt with the Klenow fragment of DNAPEc1 and dNTPs. The resulting approximately 1800 base pair fragment containing the coding region for the N-terminus was ligated into pET-3c, as described above. This construct, clone 5B, is depicted in FIG. 5B. The wild type T. favus DNA polymerase gene is depicted in FIG. 5A. In FIG. 5, the designation "3' Exo" is used to indicate the location of the 3' exonuclease activity associated with Type A polymerases which is not present in DNAPTfl. The 5B clone has the same leader amino acids as do the DNAPTaq clones 4E and F which were cloned into pET-3c; it is not known precisely where translation termination occurs, but the vector has a strong transcription termination signal immediately downstream of the cloning site.

B. Growth And Induction Of Transformed Cells

Bacterial cells were transformed with the constructs described above using standard transformation techniques and used to inoculate 2 mls of a standard growth medium (e.g., Luria-Bertani broth). The resulting cultures were incubated as appropriate for the particular strain used, and induced if required for a particular expression system. For all of the constructs depicted in FIGS. 4 and 5, the cultures were grown to an optical density (at 600 nm wavelength) of 0.5 OD.

To induce expression of the cloned genes, the cultures were brought to a final concentration of 0.4 mM IPTG and the incubations were continued for 12 to 17 hours. 50 µl aliquots of each culture were removed both before and after induction and were combined with 20 µl of a standard gel loading buffer for sodium dodecyl sulfate-polyacrylamide gel electrophoresis (SDS-PAGE). Subsequent staining with Coomassie Blue (Sambrook et al., supra) allows visualization of the foreign proteins if they account for about 3–5% of the cellular protein and do not co-migrate with any of the major *E. coli* protein bands. Proteins that do co-migrate with a major host protein must be expressed as more than 10% of the total protein to be seen at this stage of analysis.

C. Heat Lysis And Fractionation

Expressed thermostable proteins, ie., the 5' nucleases, were isolated by heating crude bacterial cell extracts to cause denaturation and precipitation of the less stable *E. coli* proteins. The precipitated *E. coli* proteins were then, along with other cell debris, removed by centrifugation. 1.7 mls of the culture were pelleted by microcentrifugation at 12,000 to 14,000 rpm for 30 to 60 seconds. After removal of the supernatant, the cells were resuspended in 400 µl of buffer A (50 mM Tris-HCl, pH 7.9, 50 mM dextrose, 1 mM EDTA), re-centrifuged, then resuspended in 80 µl of buffer A with 4 mg/ml lysozyme. The cells were incubated at room temperature for 15 minutes, then combined with 80 µl of buffer B (10 mM Tris-HCl, pH 7.9, 50 mM KCl, 1 mM EDTA, 1 mM PMSF, 0.5% Tween-20, 0.5% Nonidet-P40).

This mixture was incubated at 75° C. for 1 hour to denature and precipitate the host proteins. This cell extract was centrifuged at 14,000 rpm for 15 minutes at 4° C., and the supernatant was transferred to a fresh tube. An aliquot of 0.5 to 1 μl of this supernatant was used directly in each test reaction, and the protein content of the extract was determined by subjecting 7 μl to electrophoretic analysis, as above. The native recombinant Taq DNA polymerase [Englke, Anal. Biochem 191:396 (1990)], and the double point mutation protein shown in FIG. 4B are both soluble and active at this point.

The foreign protein may not be detected after the heat treatments due to sequestration of the foreign protein by the cells into inclusion bodies. These are granules that form in the cytoplasm when bacteria are made to express high levels of a foreign protein, and they can be purified from a crude lysate, and analyzed SDS PAGE to determine their protein content. Many methods have been described in the literature, and one approach is described below.

D. Isolation And Solubilization Of Inclusion Bodies

A small culture was grown and induced as described above. A 1.7 ml aliquot was pelleted by brief centrifugation, and the bacterial cells were resuspended in 100 μl of Lysis buffer (50 mM Tris-HCl, pH 8.0, 1 mM EDTA, 100 mM NaCl). 2.5 μl of 20 mM PMSF were added for a final concentration of 0.5 mM, and lysozyme was added to a concentration of 1.0 mg/ml. The cells were incubated at room temperature for 20 minutes, deoxycholic acid was added to 1 mg/ml (1 μl of 100 mg/ml solution), and the mixture was further incubated at 37° C. for about 15 minutes or until viscous. DNAse I was added to 10 μg/ml and the mixture was incubated at room temperature for about 30 minutes or until it was no longer viscous.

From this mixture the inclusion bodies were collected by centrifugation at 14,000 rpm for 15 minutes at 4° C., and the supernatant was discarded. The pellet was resuspended in 100 μl of lysis buffer with 10 mM EDTA (pH 8.0) and 0.5% Triton X-100. After 5 minutes at room temperature, the inclusion bodies were pelleted as before, and the supernatant was saved for later analysis. The inclusion bodies were resuspended in 50 μl of distilled water, and 5 μl was combined with SDS gel loading buffer (which dissolves the inclusion bodies) and analyzed electrophoretically, along with an aliquot of the supernatant.

If the cloned protein is found in the inclusion bodies, it may be released to assay the cleavage and polymerase activities and the method of solubilization must be compatible with the particular activity. Different methods of solubilization may be appropriate for different proteins, and a variety of methods are discussed in *Molecular Cloning* (Sambrook et al., supra). The following is an adaptation we have used for several of our isolates.

20 μl of the inclusion body-water suspension were pelleted by centrifugation at 14,000 rpm for 4 minutes at room temperature, and the supernatant was discarded. To further wash the inclusion bodies, the pellet was resuspended in 20 μl of lysis buffer with 2M urea, and incubated at room temperature for one hour. The washed inclusion bodies were then resuspended in 2 μl of lysis buffer with 8M urea; the solution clarified visibly as the inclusion bodies dissolved. Undissolved debris was removed by centrifugation at 14,000 rpm for 4 minutes at room temperature, and the extract supernatant was transferred to a fresh tube.

To reduce the urea concentration, the extract was diluted into $KH_2PO_4$. A fresh tube was prepared containing 180 μl of 50 mM $KH_2PO_4$, pH 9.5, 1 mM EDTA and 50 mM NaCl. A 2 μl aliquot of the extract was added and vortexed briefly to mix. This step was repeated until all of the extract had been added for a total of 10 additions. The mixture was allowed to sit at room temperature for 15 minutes, during which time some precipitate often forms. Precipitates were removed by centrifugation at 14,000 rpm, for 15 minutes at room temperature, and the supernatant was transferred to a fresh tube. To the 200 μl of protein in the $KH_2PO_4$ solution, 140–200 μl of saturated $(NH_4)_2SO_4$ were added, so that the resulting mixture was about 41% to 50% saturated $(NH_4)_2SO_4$. The mixture was chilled on ice for 30 minutes to allow the protein to precipitate, and the protein was then collected by centrifugation at 14,000 rpm, for 4 minutes at room temperature. The supernatant was discarded, and the pellet was dissolved in 20 μl Buffer C (20 mM HEPES, pH 7.9, 1 mM EDTA, 0.5% PMSF, 25 mM KCl and 0.5% each of Tween-20 and Nonidet P 40). The protein solution was centrifuged again for 4 minutes to pellet insoluble materials, and the supernatant was removed to a fresh tube. The protein contents of extracts prepared in this manner were visualized by resolving 1–4 μl by SDS-PAGE; 0.5 to 1 μl of extract was tested in the cleavage and polymerization assays as described.

E. Protein Analysis For Presence Of Nuclease And Synthetic Activity

The 5' nucleases described above and shown in FIGS. 4 and 5 were analyzed by the following methods.

1. Structure Specific Nuclease Assay

A candidate modified polymerase is tested for 5' nuclease activity by examining its ability to catalyze structure-specific cleavages. By the term "cleavage structure" as used herein, is meant a nucleic acid structure which is a substrate for cleavage by the 5' nuclease activity of a DNAP.

The polymerase is exposed to test complexes that have the structures shown in FIG. 16. Testing for 5' nuclease activity involves three reactions: 1) a primer-directed cleavage (FIG. 16B) is performed because it is relatively insensitive to variations in the salt concentration of the reaction and can, therefore, be performed in whatever solute conditions the modified enzyme requires for activity; this is generally the same conditions preferred by unmodified polymerases; 2) a similar primer-directed cleavage is performed in a buffer which permits primer-independent cleavage, i.e., a low salt buffer, to demonstrate that the enzyme is viable under these conditions; and 3) a primer-independent cleavage (FIG. 16A) is performed in the same low salt buffer.

The bifurcated duplex is formed between a substrate strand and a template strand as shown in FIG. 16. By the term "substrate strand" as used herein, is meant that strand of nucleic acid in which the cleavage mediated by the 5' nuclease activity occurs. The substrate strand is always depicted as the top strand in the bifurcated complex which serves as a substrate for 5' nuclease cleavage (FIG. 16). By the term "template strand" as used herein, is meant the strand of nucleic acid which is at least partially complementary to the substrate strand and which anneals to the substrate strand to form the cleavage structure. The template strand is always depicted as the bottom strand of the bifurcated cleavage structure (FIG. 16). If a primer (a short oligonucleotide of 19 to 30 nucleotides in length) is added to the complex, as when primer-dependent cleavage is to be tested, it is designed to anneal to the 3' arm of the template strand (FIG. 16B). Such a primer would be extended along the template strand if the polymerase used in the reaction has synthetic activity.

Figure 16B:
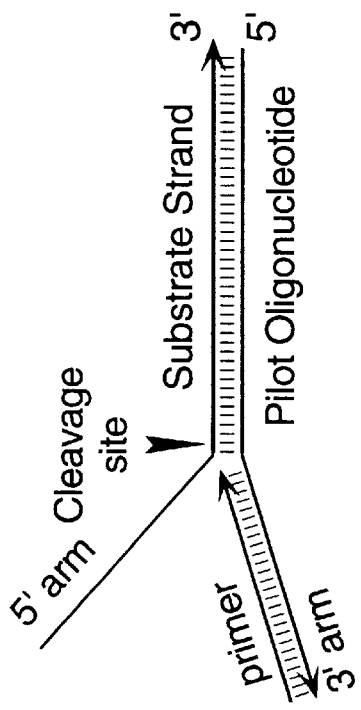
FIG. 16A–E depicts a set of molecules which are suitable substrates for cleavage by the 5' nuclease activity of DNAPs.
Figure 16D:
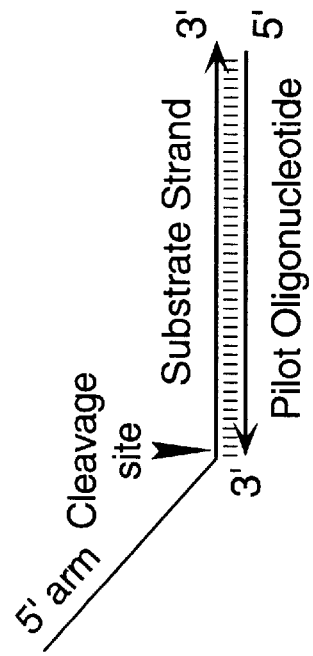
Figure 16A:
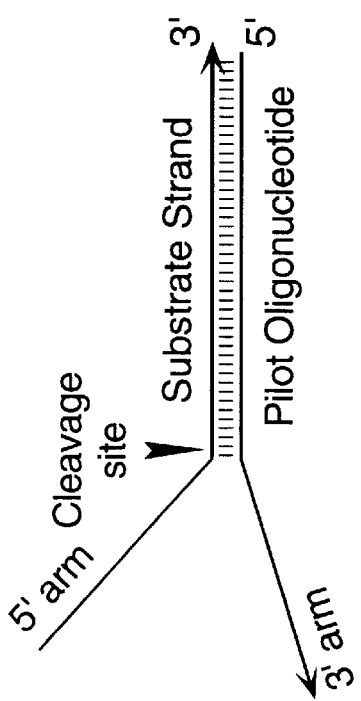
Figure 16C:
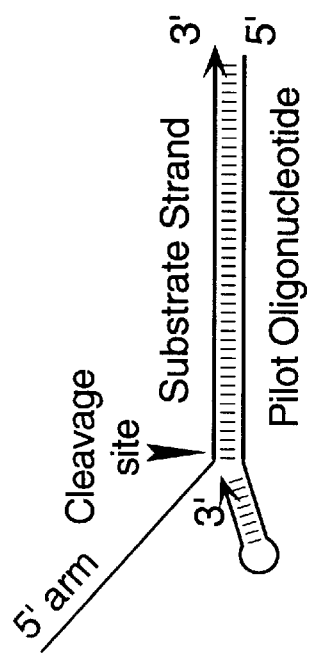
Figure 16E:
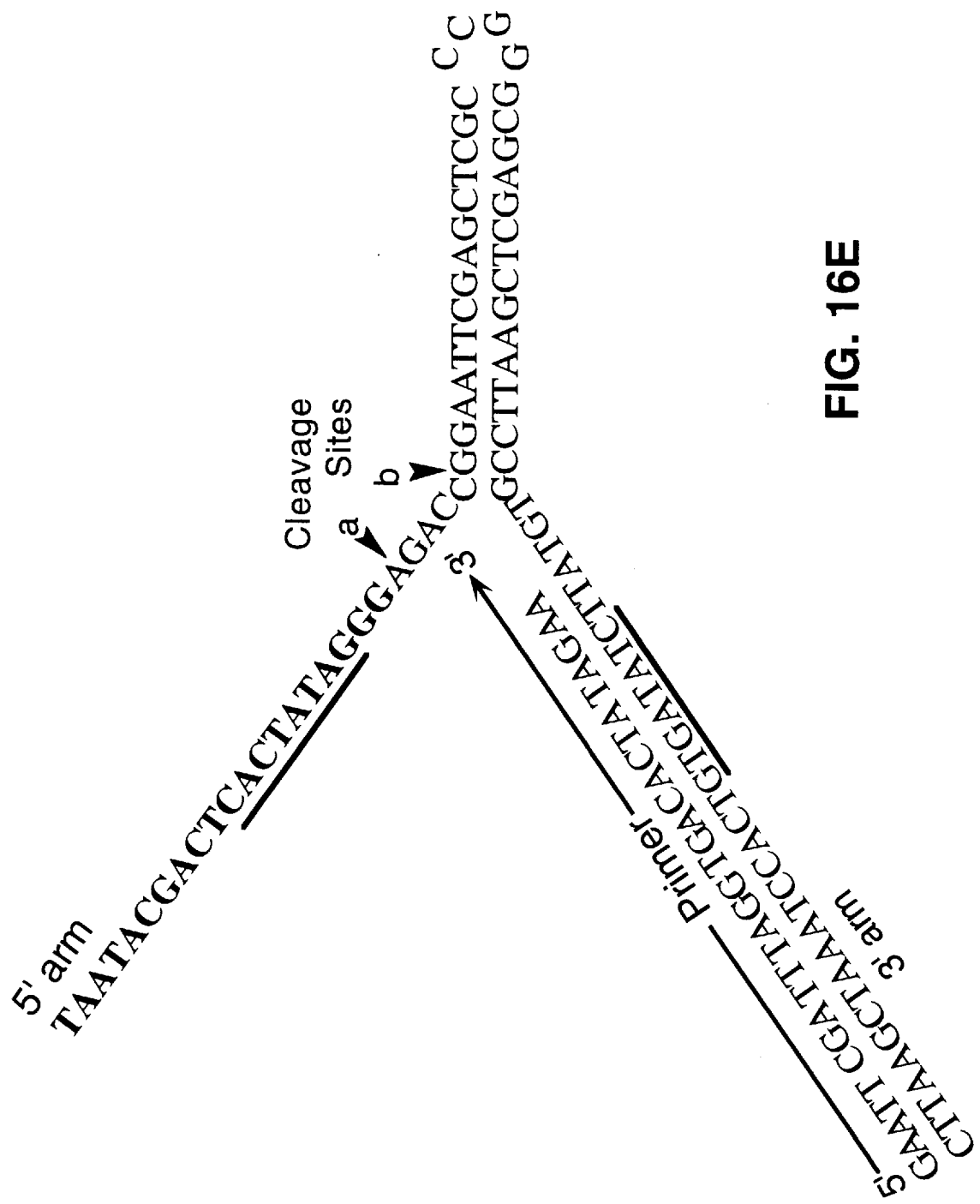

The cleavage structure may be made as a single hairpin molecule, with the 3' end of the target and the 5' end of the pilot joined as a loop as shown in FIG. 16E. A primer oligonucleotide complementary to the 3' arm is also required for these tests so that the enzyme's sensitivity to the presence of a primer may be tested.

Nucleic acids to be used to form test cleavage structures can be chemically synthesized, or can be generated by standard recombinant DNA techniques. By the latter method, the hairpin portion of the molecule can be created by inserting into a cloning vector duplicate copies of a short DNA segment, adjacent to each other but in opposing orientation. The double-stranded fragment encompassing this inverted repeat, and including enough flanking sequence to give short (about 20 nucleotides) unpaired 5' and 3' arms, can then be released from the vector by restriction enzyme digestion, or by PCR performed with an enzyme lacking a 5' exonuclease (e.g., the Stoffel fragment of Amplitaq™ DNA polymerase, Vent™ DNA polymerase).

The test DNA can be labeled on either end, or internally, with either a radioisotope, or with a non-isotopic tag. Whether the hairpin DNA is a synthetic single strand or a cloned double strand, the DNA is heated prior to use to melt all duplexes. When cooled on ice, the structure depicted in FIG. 16E is formed, and is stable for sufficient time to perform these assays.

To test for primer-directed cleavage (Reaction 1), a detectable quantity of the test molecule (typically 1–100 fmol of $^{32}$P-labeled hairpin molecule) and a 10 to 100-fold molar excess of primer are placed in a buffer known to be compatible with the test enzyme. For Reaction 2, where primer-directed cleavage is performed under condition which allow primer-independent cleavage, the same quantities of molecules are placed in a solution that is the same as the buffer used in Reaction 1 regarding pH, enzyme stabilizers (e.g., bovine serum albumin, nonionic detergents, gelatin) and reducing agents (e.g., dithiothreitol, 2-mercaptoethanol) but that replaces any monovalent cation salt with 20 mM KCl; 20 mM KCl is the demonstrated optimum for primer-independent cleavage. Buffers for enzymes, such as DNAPEc1, that usually operate in the absence of salt are not supplemented to achieve this concentration. To test for primer-independent cleavage (Reaction 3) the same quantity of the test molecule, but no primer, are combined under the same buffer conditions used for Reaction 2.

All three test reactions are then exposed to enough of the enzyme that the molar ratio of enzyme to test complex is approximately 1:1. The reactions are incubated at a range of temperatures up to, but not exceeding, the temperature allowed by either the enzyme stability or the complex stability, whichever is lower, up to 80° C. for enzymes from thermophiles, for a time sufficient to allow cleavage (10 to 60 minutes). The products of Reactions 1, 2 and 3 are resolved by denaturing polyacrylamide gel electrophoresis, and visualized by autoradiography or by a comparable method appropriate to the labeling system used. Additional labeling systems include chemiluminescence detection, silver or other stains, blotting and probing and the like. The presence of cleavage products is indicated by the presence of molecules which migrate at a lower molecular weight than does the uncleaved test structure. These cleavage products indicate that the candidate polymerase has structure-specific 5' nuclease activity.

To determine whether a modified DNA polymerase has substantially the same 5' nuclease activity as that of the native DNA polymerase, the results of the above-described tests are compared with the results obtained from these tests performed with the native DNA polymerase. By "substantially the same 5' nuclease activity" we mean that the modified polymerase and the native polymerase will both cleave test molecules in the same manner. It is not necessary that the modified polymerase cleave at the same rate as the native DNA polymerase.

Some enzymes or enzyme preparations may have other associated or contaminating activities that may be functional under the cleavage conditions described above and that may interfere with 5' nuclease detection. Reaction conditions can be modified in consideration of these other activities, to avoid destruction of the substrate, or other masking of the 5' nuclease cleavage and its products. For example, the DNA polymerase I of *E. coli* (Pol I), in addition to its polymerase and 5' nuclease activities, has a 3' exonuclease that can degrade DNA in a 3' to 5' direction. Consequently, when the molecule in FIG. 16E is exposed to this polymerase under the conditions described above, the 3' exonuclease quickly removes the unpaired 3' arm, destroying the bifurcated structure required of a substrate for the 5' exonuclease cleavage and no cleavage is detected. The true ability of Pol I to cleave the structure can be revealed if the 3' exonuclease is inhibited by a change of conditions (e.g., pH), mutation, or by addition of a competitor for the activity. Addition of 500 pmoles of a single-stranded competitor oligonucleotide, unrelated to the FIG. 16E structure, to the cleavage reaction with Pol I effectively inhibits the digestion of the 3' arm of the FIG. 16E structure without interfering with the 5' exonuclease release of the 5' arm. The concentration of the competitor is not critical, but should be high enough to occupy the 3' exonuclease for the duration of the reaction.

Similar destruction of the test molecule may be caused by contaminants in the candidate polymerase preparation. Several sets of the structure specific nuclease reactions may be performed to determine the purity of the candidate nuclease and to find the window between under and over exposure of the test molecule to the polymerase preparation being investigated.

The above described modified polymerases were tested for 5' nuclease activity as follows: Reaction 1 was performed in a buffer of 10 mM Tris-Cl, pH 8.5 at 20° C., 1.5 mM MgCl$_2$ and 50 mM KCl and in Reaction 2 the KCl concentration was reduced to 20 mM. In Reactions 1 and 2, 10 fmoles of the test substrate molecule shown in FIG. 16E were combined with 1 pmole of the indicated primer and 0.5 to 1.0 μl of extract containing the modified polymerase (prepared as described above). This mixture was then incubated for 10 minutes at 55° C. For all of the mutant polymerases tested these conditions were sufficient to give complete cleavage. When the molecule shown in FIG. 16E was labeled at the 5' end, the released 5' fragment, 25 nucleotides long, was conveniently resolved on a 20% polyacrylamide gel (19:1 cross-linked) with 7M urea in a buffer containing 45 mM Tris-borate pH 8.3, 1.4 mM EDTA. Clones 4C–F and 5B exhibited structure-specific cleavage comparable to that of the unmodified DNA polymerase. Additionally, clones 4E, 4F and 4G have the added ability to cleave DNA in the absence of a 3' arm as discussed above.

Figure 17:
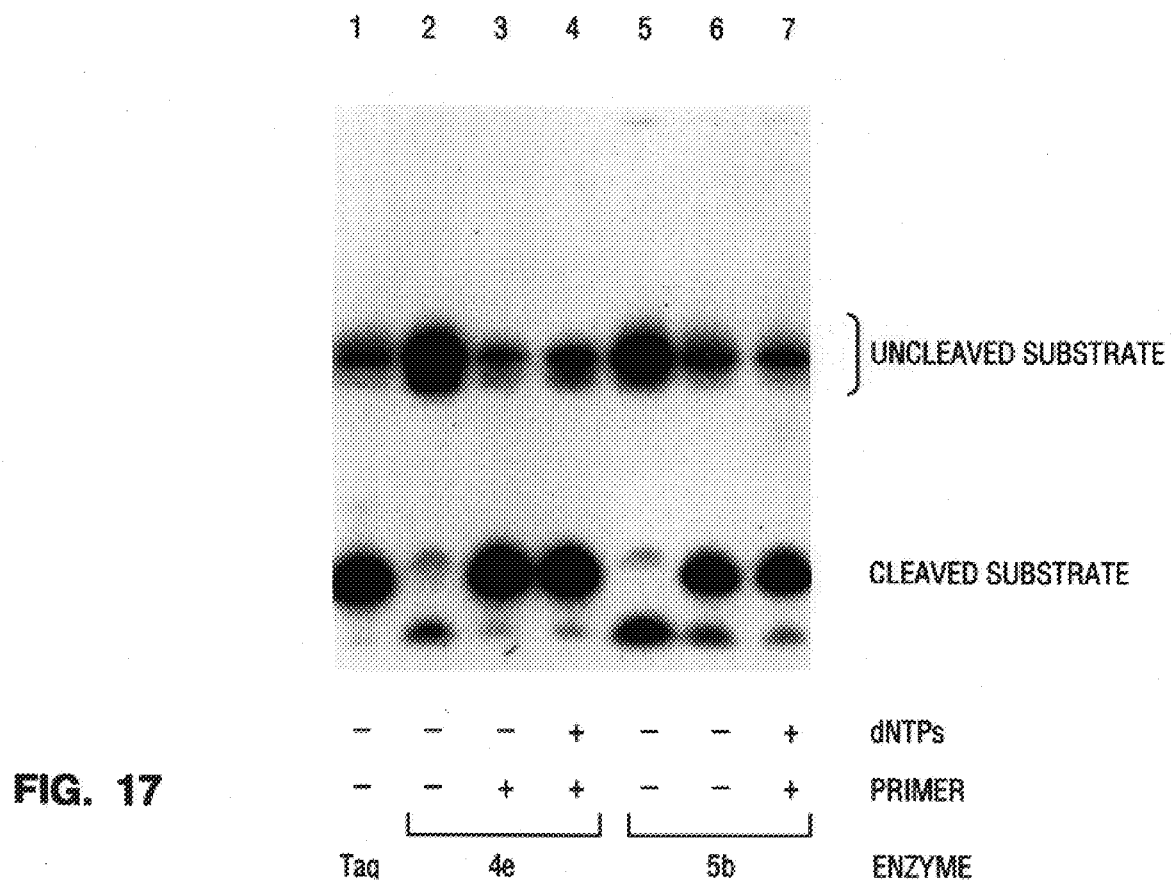
FIG. 17 is an autoradiogram of a gel showing the results of a cleavage reaction run with synthesis-deficient DNAPs.

Representative cleavage reactions are shown in FIG. 17.

For the reactions shown in FIG. 17, the mutant polymerase clones 4E (Taq mutant) and 5B (Tfl mutant) were examined for their ability to cleave the hairpin substrate molecule shown in FIG. 16E. The substrate molecule was labeled at the 5' terminus with $^{32}$P. Ten fmoles of heat-denatured, end-labeled substrate DNA and 0.5 units of DNAPTaq (lane 1) or 0.5 μl of 4e or 5b extract (FIG. 17, lanes 2–7, extract was prepared as described above) were mixed together in a buffer containing 10 mM Tris-Cl, pH 8.5, 50 mM KCl and 1.5 mM MgCl$_2$. The final reaction volume was 10 μl. Reactions shown in lanes 4 and 7 contain in addition 50 μM of each dNTP. Reactions shown in lanes 3, 4, 6 and 7 contain 0.2 μM of the primer oligonucleotide (complementary to the 3' arm of the substrate and shown in FIG. 16E). Reactions were incubated at 55° C. for 4 minutes. Reactions were stopped by the addition of 8 μl of 95% formamide containing 20 mM EDTA and 0.05% marker dyes per 10 μl reaction volume. Samples were then applied to 12% denaturing acrylamide gels. Following electrophoresis, the gels were autoradiographed. FIG. 17 shows that clones 4E and 5B exhibit cleavage activity similar to that of the native DNAPTaq. Note that some cleavage occurs in these reactions in the absence of the primer. When long hairpin structure, such as the one used here (FIG. 16E), are used in cleavage reactions performed in buffers containing 50 mM KCl a low level of primer-independent cleavage is seen. Higher concentrations of KCl suppress, but do not eliminate, this primer-independent cleavage under these conditions.

2. Assay For Synthetic Activity

The ability of the modified enzyme or proteolytic fragments is assayed by adding the modified enzyme to an assay system in which a primer is annealed to a template and DNA synthesis is catalyzed by the added enzyme. Many standard laboratory techniques employ such an assay. For example, nick translation and enzymatic sequencing involve extension of a primer along a DNA template by a polymerase molecule.

In a preferred assay for determining the synthetic activity of a modified enzyme an oligonucleotide primer is annealed to a single-stranded DNA template, e.g., bacteriophage M13 DNA, and the primer/template duplex is incubated in the presence of the modified polymerase in question, deoxynucleoside triphosphates (dNTPs) and the buffer and salts known to be appropriate for the unmodified or native enzyme.

Detection of either primer extension (by denaturing gel electrophoresis) or dNTP incorporation (by acid precipitation or chromatography) is indicative of an active polymerase. A label, either isotopic or non-isotopic, is preferably included on either the primer or as a dNTP to facilitate detection of polymerization products. Synthetic activity is quantified as the amount of free nucleotide incorporated into the growing DNA chain and is expressed as amount incorporated per unit of time under specific reaction conditions.

Figure 18:
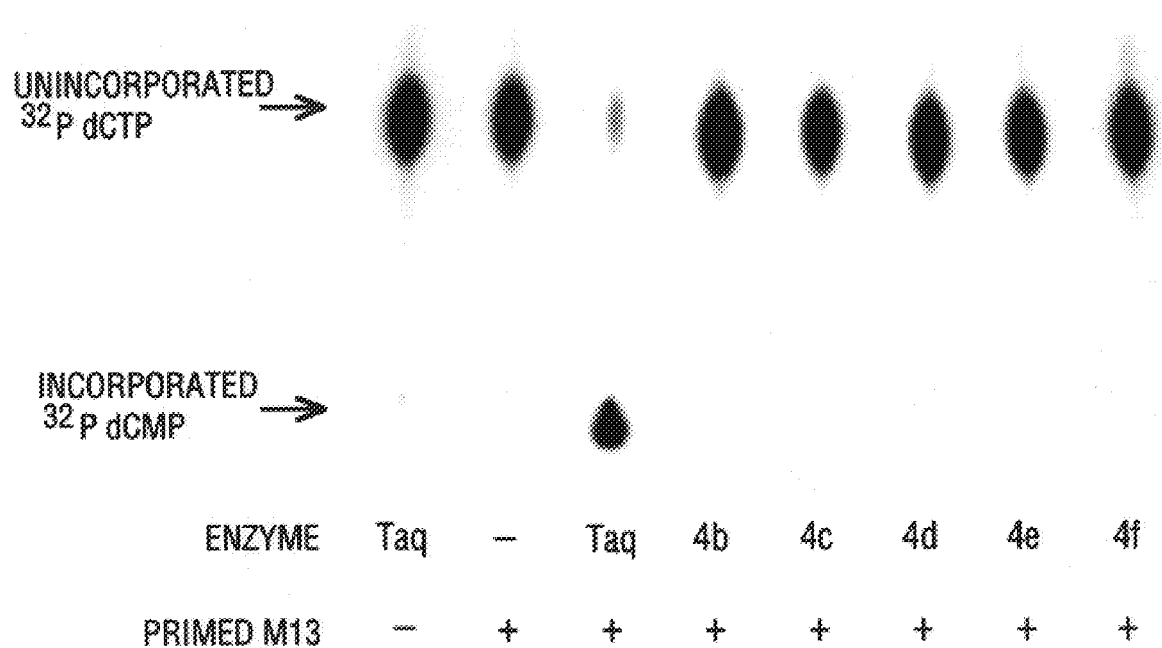
FIG. 18 is an autoradiogram of a PEI chromatogram resolving the products of an assay for synthetic activity in synthesis-deficient DNAPTaq clones.

Representative results of an assay for synthetic activity is shown in FIG. 18. The synthetic activity of the mutant DNAPTaq clones 4B–F was tested as follows: A master mixture of the following buffer was made: 1.2× PCR buffer (1× PCR buffer contains 50 mM KCl, 1.5 mM MgCl$_2$, 10 mM Tris-Cl, ph 8.5 and 0.05% each Tween 20 and Nonidet P40), 50 μM each of dGTP, dATP and dTTP, 5 μM dCTP and 0.125 μM α-$^{32}$P-dCTP at 600 Ci/mmol. Before adjusting this mixture to its final volume, it was divided into two equal aliquots. One received distilled water up to a volume of 50 μl to give the concentrations above. The other received 5 μg of single-stranded M13mp18 DNA (approximately 2.5 pmol or 0.05 μM final concentration) and 250 pmol of M13 sequencing primer (5 μM final concentration) and distilled water to a final volume of 50 μl. Each cocktail was warmed to 75° C. for 5 minutes and then cooled to room temperature. This allowed the primers to anneal to the DNA in the DNA-containing mixtures.

For each assay, 4 μl of the cocktail with the DNA was combined with 1 μl of the mutant polymerase, prepared as described, or I unit of DNAPTaq (Perkin Elmer) in 1 μl of dH$_2$O. A "no DNA" control was done in the presence of the DNAPTaq (FIG. 18, lane 1), and a "no enzyme" control was done using water in place of the enzyme (lane 2). Each reaction was mixed, then incubated at room temperature (approx. 22° C.) for 5 minutes, then at 55° C. for 2 minutes, then at 72° C. for 2 minutes. This step incubation was done to detect polymerization in any mutants that might have optimal temperatures lower than 72° C. After the final incubation, the tubes were spun briefly to collect any condensation and were placed on ice. One μl of each reaction was spotted at an origin 1.5 cm from the bottom edge of a polyethyleneimine (PEI) cellulose thin layer chromatography plate and allowed to dry. The chromatography plate was run in 0.75M NaH$_2$PO$_4$, pH 3.5, until the buffer front had run approximately 9 cm from the origin. The plate was dried, wrapped in plastic wrap, marked with luminescent ink, and exposed to X-ray film. Incorporation was detected as counts that stuck where originally spotted, while the unincorporated nucleotides were carried by the salt solution from the origin.

Comparison of the locations of the counts with the two control lanes confirmed the lack of polymerization activity in the mutant preparations. Among the modified DNAPTaq clones, only clone 4B retains any residual synthetic activity as shown in FIG. 18.

EXAMPLE 3

Figure 19A:
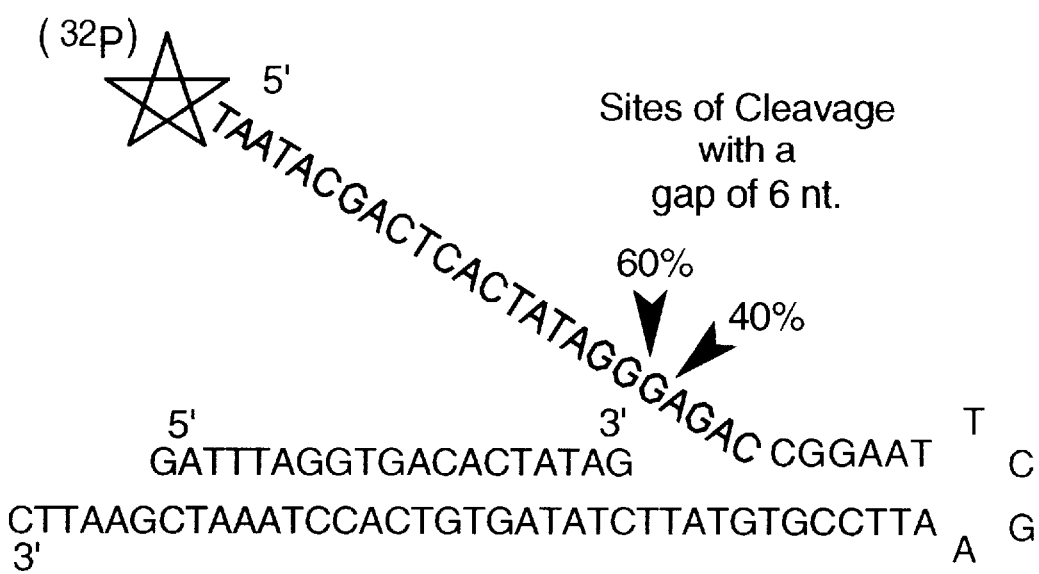
FIG. 19A depicts the substrate molecule used to test the ability of synthesis-deficient DNAPs to cleave short hairpin structures.

5' Nucleases Derived From Thermostable DNA Polymerases Can Cleave Short Hairpin Structures With Specificity The ability of the 5' nucleases to cleave hairpin structures to generate a cleaved hairpin structure suitable as a detection molecule was examined. The structure and sequence of the hairpin test molecule is shown in FIG. 19A (SEQ ID NO:15). The oligonucleotide (labeled "primer" in FIG. 19A, SEQ ID NO:22) is shown annealed to its complementary sequence on the 3' arm of the hairpin test molecule. The hairpin test molecule was single-end labeled with $^{32}$P using a labeled T7 promoter primer in a polymerase chain reaction. The label is present on the 5' arm of the hairpin test molecule and is represented by the star in FIG. 19A.

The cleavage reaction was performed by adding 10 fmoles of heat-denatured, end-labeled hairpin test molecule, 0.2 uM of the primer oligonucleotide (complementary to the 3' arm of the hairpin), 50 μM of each dNTP and 0.5 units of DNAPTaq (Perkin Elmer) or 0.5 μl of extract containing a 5' nuclease (prepared as described above) in a total volume of 10 μl in a buffer containing 10 mM Tris-Cl, pH 8.5, 50 mM KCl and 1.5 mM MgCl$_2$. Reactions shown in lanes 3, 5 and 7 were run in the absence of dNTPs.

Reactions were incubated at 55° C. for 4 minutes. Reactions were stopped at 55° C. by the addition of 8 μl of 95% formamide with 20 mM EDTA and 0.05% marker dyes per 10 μl reaction volume. Samples were not heated before loading onto denaturing polyacrylamide gels (10% polyacrylamide, 19:1 crosslinking, 7M urea, 89 mM Tris-borate, pH 8.3, 2.8 mM EDTA). The samples were not heated to allow for the resolution of single-stranded and re-duplexed uncleaved hairpin molecules.

FIG. 19B shows that altered polymerases lacking any detectable synthetic activity cleave a hairpin structure when an oligonucleotide is annealed to the single-stranded 3' arm of the hairpin to yield a single species of cleaved product (FIG. 19B, lanes 3 and 4). 5' nucleases, such as clone 4D, shown in lanes 3 and 4, produce a single cleaved product even in the presence of dNTPs. 5' nucleases which retain a residual amount of synthetic activity (less than 1% of wild type activity) produce multiple cleavage products as the polymerase can extend the oligonucleotide annealed to the 3' arm of the hairpin thereby moving the site of cleavage (clone 4B, lanes 5 and 6). Native DNATaq produces even more species of cleavage products than do mutant polymerases retaining residual synthetic activity and additionally converts the hairpin structure to a double-stranded form in the presence of dNTPs due to the high level of synthetic activity in the native polymerase (FIG. 19B, lane 8).

EXAMPLE 4

Test Of The Trigger/Detection Assay

To test the ability of an oligonucleotide of the type released in the trigger reaction of the trigger/detection assay to be detected in the detection reaction of the assay, the two hairpin structures shown in FIG. 20A were synthesized using standard techniques. The two hairpins are termed the A-hairpin (SEQ ID NO:23) and the T-hairpin (SEQ ID NO:24). The predicted sites of cleavage in the presence of the appropriate annealed primers are indicated by the arrows. The A- and T-hairpins were designed to prevent intra-strand mis-folding by omitting most of the T residues in the A-hairpin and omitting most of the A residues in the T-hairpin. To avoid mis-priming and slippage, the hairpins were designed with local variations in the sequence motifs (e.g., spacing T residues one or two nucleotides apart or in pairs). The A- and T-hairpins can be annealed together to form a duplex which has appropriate ends for directional cloning in pUC-type vectors; restriction sites are located in the loop regions of the duplex and can be used to elongate the stem regions if desired.

The sequence of the test trigger oligonucleotide is shown in FIG. 20B; this oligonucleotide is termed the alpha primer (SEQ ID NO:25). The alpha primer is complementary to the 3' arm of the T-hairpin as shown in FIG. 20A. When the alpha primer is annealed to the T-hairpin, a cleavage structure is formed that is recognized by thermostable DNA polymerases. Cleavage of the T-hairpin liberates the 5' single-stranded arm of the T-hairpin, generating the tau primer (SEQ ID NO:26) and a cleaved T-hairpin (FIG. 20B; SEQ ID NO:27). The tau primer is complementary to the 3' arm of the A-hairpin as shown in FIG. 20A. Annealing of the tau primer to the A-hairpin generates another cleavage structure; cleavage of this second cleavage structure liberates the 5' single-stranded arm of the A-hairpin, generating another molecule of the alpha primer which then is annealed to another molecule of the T-hairpin. Thermocycling releases the primers so they can function in additional cleavage reactions. Multiple cycles of annealing and cleavage are carried out. The products of the cleavage reactions are primers and the shortened hairpin structures shown in FIG. 20C. The shortened or cleaved hairpin structures may be resolved from the uncleaved hairpins by electrophoresis on denaturing acrylamide gels.

The annealing and cleavage reactions are carried as follows: In a 50 µl reaction volume containing 10 mM Tris-Cl, pH 8.5, 1.0 MgCl$_2$, 75 mM KCl, 1 pmole of A-hairpin, 1 pmole T-hairpin, the alpha primer is added at equimolar amount relative to the hairpin structures (1 pmole) or at dilutions ranging from 10- to $10^6$-fold and 0.5 µl of extract containing a 5' nuclease (prepared as described above) are added. The predicted melting temperature for the alpha or trigger primer is 60° C. in the above buffer. Annealing is performed just below this predicted melting temperature at 55° C. Using a Perkin Elmer DNA Thermal Cycler, the reactions are annealed at 55° C. for 30 seconds. The temperature is then increased slowly over a five minute period to 72° C. to allow for cleavage. After cleavage, the reactions are rapidly brought to 55° C. (1° C. per second) to allow another cycle of annealing to occur. A range of cycles are performed (20, 40 and 60 cycles) and the reaction products are analyzed at each of these number of cycles. The number of cycles which indicates that the accumulation of cleaved hairpin products has not reached a plateau is then used for subsequent determinations when it is desirable to obtain a quantitative result.

Following the desired number of cycles, the reactions are stopped at 55° C. by the addition of 8 µl of 95% formamide with 20 mM EDTA and 0.05% marker dyes per 10 µl reaction volume. Samples are not heated before loading onto denaturing polyacrylamide gels (10% polyacrylamide, 19:1 crosslinking, 7M urea, 89 mM tris-borate, pH 8.3, 2.8 mM EDTA). The samples were not heated to allow for the resolution of single-stranded and re-duplexed uncleaved hairpin molecules.

The hairpin molecules may be attached to separate solid support molecules, such as agarose, styrene or magnetic beads, via the 3' end of each hairpin. A spacer molecule may be placed between the 3' end of the hairpin and the bead if so desired. The advantage of attaching the hairpins to a solid support is that this prevents the hybridization of the A- and T-hairpins to one another during the cycles of melting and annealing. The A- and T-hairpins are complementary to one another (as shown in FIG. 20D) and if allowed to anneal to one another over their entire lengths this would reduce the amount of hairpins available for hybridization to the alpha and tau primers during the detection reaction.

The 5' nucleases of the present invention are used in this assay because they lack significant synthetic activity. The lack of synthetic activity results in the production of a single cleaved hairpin product (as shown in FIG. 19B, lane 4). Multiple cleavage products may be generated by 1) the presence of interfering synthetic activity (see FIG. 19B, lanes 6 and 8) or 2) the presence of primer-independent cleavage in the reaction. The presence of primer-independent cleavage is detected in the trigger/detection assay by the presence of different sized products at the fork of the cleavage structure. Primer-independent cleavage can be dampened or repressed, when present, by the use of uncleavable nucleotides in the fork region of the hairpin molecule. For example, thiolated nucleotides can be used to replace several nucleotides at the fork region to prevent primer-independent cleavage.

EXAMPLE 5

Cleavage Of Linear Nucleic Acid Substrates

Figure 22A:
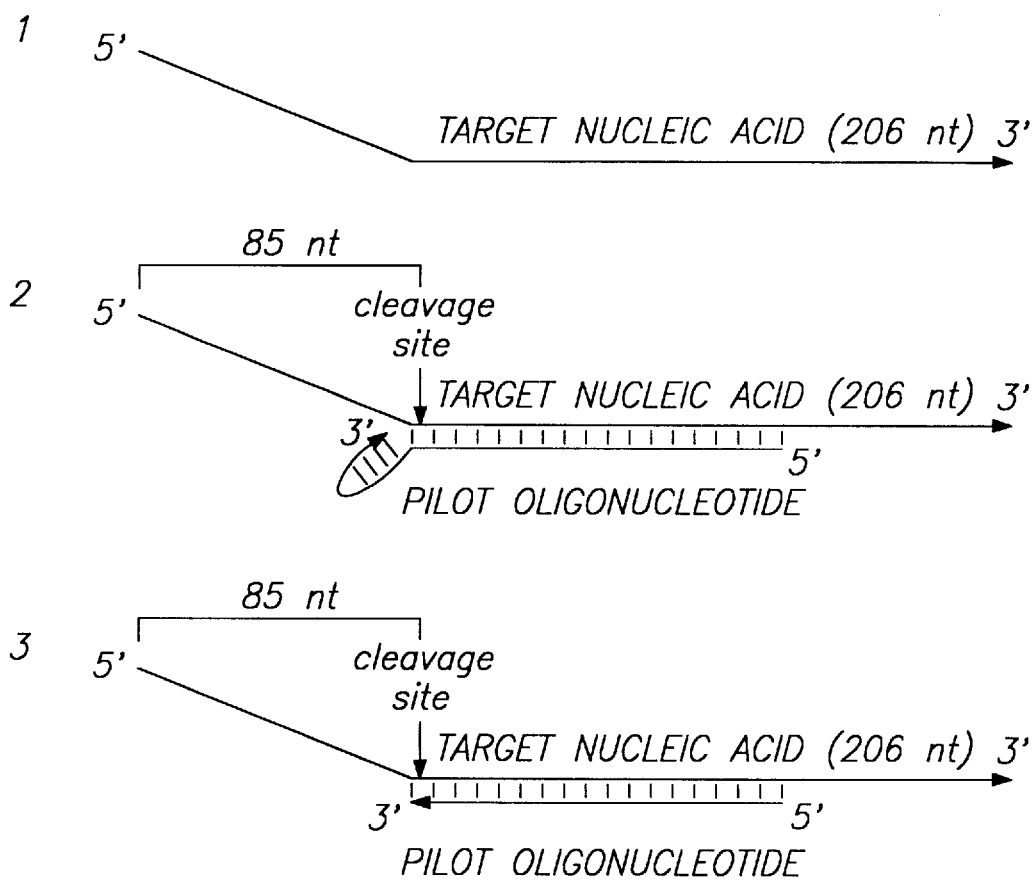

From the above, it should be clear that native (i.e., "wild type") thermostable DNA polymerases are capable of cleaving hairpin structures in a specific manner and that this discovery can be applied with success to a detection assay. In this example, the mutant DNAPs of the present invention are tested against three different cleavage structures shown in FIG. 22A. Structure 1 in FIG. 22A is simply single stranded 206-mer (the preparation and sequence information for which was discussed above). Structures 2 and 3 are duplexes; structure 2 is the same hairpin structure as shown in FIG. 12A (bottom), while structure 3 has the hairpin portion of structure 2 removed.

The cleavage reactions comprised 0.01 pmoles of the resulting substrate DNA, and 1 pmole of pilot oligonucleotide in a total volume of 10 μl of 10 mM Tris-Cl, pH 8.3, 100 mM KCl, 1 mM MgCl$_2$. Reactions were incubated for 30 minutes at 55° C., and stopped by the addition of 8 μl of 95% formamide with 20 mM EDTA and 0.05% marker dyes. Samples were heated to 75° C. for 2 minutes immediately before electrophoresis through a 10% polyacrylamide gel (19:1 cross link), with 7M urea, in a buffer of 45 mM Tris-Borate, pH 8.3, 1.4 mM EDTA.

Figure 22B:
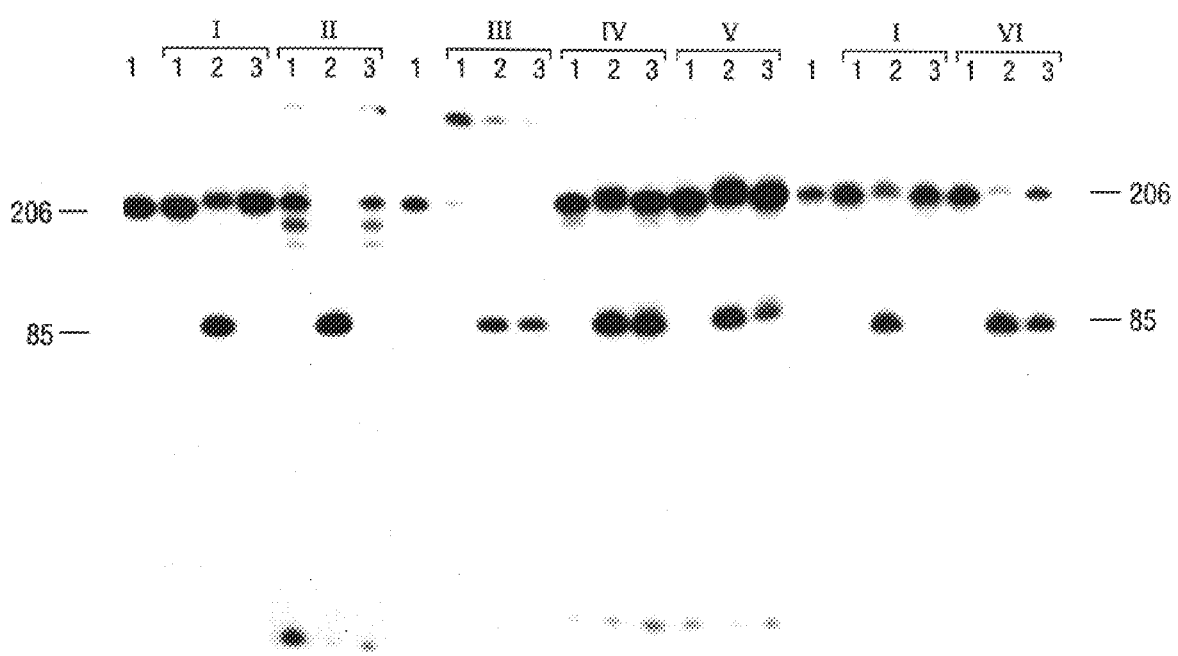

The results were visualized by autoradiography and are shown in FIG. 22B with the enzymes indicated as follows: I is native Taq DNAP; II is native Tfl DNAP; III is the enzyme Cleavase™ BX shown in FIG. 4E; IV is the enzyme Cleavase™ BB shown in FIG. 4F; V is the mutant shown in FIG. 5B; and VI is the enzyme Cleavase™ BN shown in FIG. 4G. Structure 2 was used to "normalize" the comparison. For example, it was found that it took 50 ng of Taq DNAP and 300 ng of the enzyme Cleavase™ BN to give similar amounts of cleavage of Structure 2 in thirty (30) minutes. Under these conditions native Taq DNAP is unable to cleave Structure 3 to any significant degree. Native Tfl DNAP cleaves Structure 3 in a manner that creates multiple products.

By contrast, all of the mutants tested cleave the linear duplex of Structure 3. This finding indicates that this characteristic of the mutant DNA polymerases is consistent of thermostable polymerases across thermophilic species.

Figure 23:
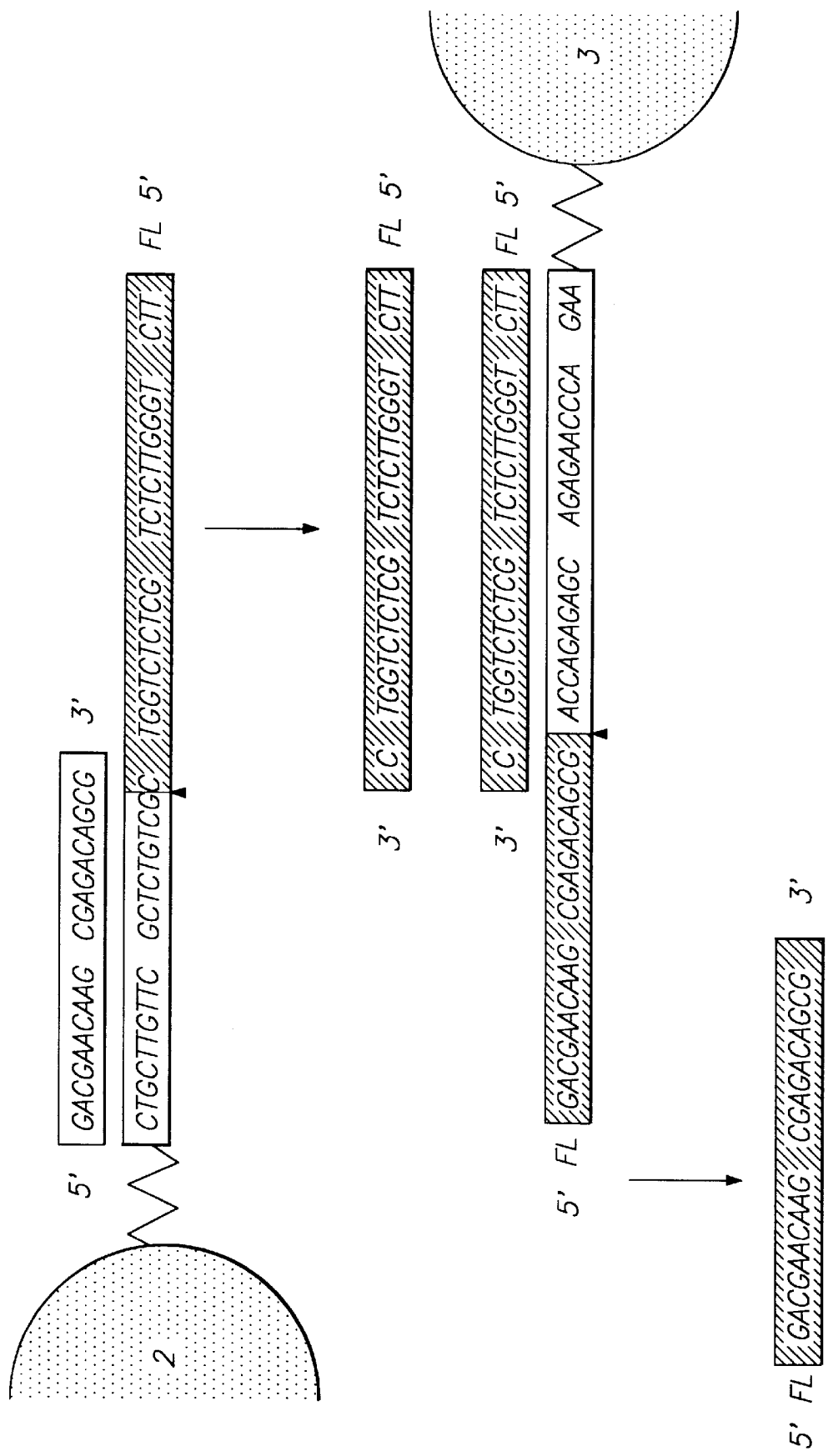
FIG. 23 provides a detailed schematic corresponding to the of one embodiment of the detection method of the present invention.

The finding described herein that the mutant DNA polymerases of the present invention are capable of cleaving linear duplex structures allows for application to a more straightforward assay design (FIG. 1A). FIG. 23 provides a more detailed schematic corresponding to the assay design of FIG. 1A.

The two 43-mers depicted in FIG. 23 were synthesized by standard methods. Each included a fluorescein on the 5'end for detection purposes and a biotin on the 3'end to allow attachment to streptavidin coated paramagnetic particles (the biotin-avidin attachment is indicated by "~").

Before the trityl groups were removed, the oligos were purified by HPLC to remove truncated by-products of the synthesis reaction. Aliquots of each 43-mer were bound to M-280 Dynabeads (Dynal) at a density of 100 pmoles per mg of beads. Two (2) mgs of beads (200 μl) were washed twice in 1× wash/bind buffer (1M NaCl, 5 mM Tris-Cl, pH 7.5, 0.5 mM EDTA) with 0.1% BSA, 200 μl per wash. The beads were magnetically sedimented between washes to allow supernatant removal. After the second wash, the beads were resuspended in 200 μl of 2× washibind buffer (2M Na Cl, 10 mM Tris-Cl, pH 7.5 with 1 mM EDTA), and divided into two 100 μl aliquots. Each aliquot received 1 μl of a 100 μM solution of one of the two oligonucleotides. After mixing, the beads were incubated at room temperature for 60 minutes with occasional gentle mixing. The beads were then sedimented and analysis of the supernatants showed only trace amounts of unbound oligonucleotide, indicating successful binding. Each aliquot of beads was washed three times, 100 μl per wash, with 1× wash/bind buffer, then twice in a buffer of 10 mM Tris-Cl, pH 8.3 and 75 mM KCl. The beads were resuspended in a final volume of 100 μl of the Tris/KCl, for a concentration of 1 pmole of oligo bound to 10 μg of beads per μl of suspension. The beads were stored at 4° C. between uses.

The types of beads correspond to FIG. 1A. That is to say, type 2 beads contain the oligo (SEQ ID NO:33) comprising the complementary sequence (SEQ ID NO:34) for the alpha signal oligo (SEQ ID NO:35) as well as the beta signal oligo (SEQ ID NO:36) which when liberated is a 24-mer. This oligo has no "As" and is "T" rich. Type 3 beads contain the oligo (SEQ ID NO:37) comprising the complementary sequence (SEQ ID NO:38) for the beta signal oligo (SEQ ID NO:39) as well as the alpha signal oligo (SEQ ID NO:35) which when liberated is a 20-mer. This oligo has no "Ts" and is "A" rich.

Cleavage reactions comprised 1 μl of the indicated beads, 10 pmoles of unlabelled alpha signal oligo as "pilot" (if indicated) and 500 ng of the enzyme Cleavase™ BN in 20 μl of 75 mM KCl, 10 mM Tris-Cl, pH 8.3, 1.5 mM MgCl$_2$ and 10 μM CTAB. All components except the enzyme were assembled, overlaid with light mineral oil and warmed to 53° C. The reactions were initiated by the addition of prewarmed enzyme and incubated at that temperature for 30 minutes. Reactions were stopped at temperature by the addition of 16 μl of 95% formamide with 20 mM EDTA and 0.05% each of bromophenol blue and xylene cyanol. This addition stops the enzyme activity and, upon heating, disrupts the biotin-avidin link, releasing the majority (greater than 95%) of the oligos from the beads. Samples were heated to 75° C. for 2 minutes immediately before electrophoresis through a 10% polyacrylamide gel (19:1 cross link), with 7M urea, in a buffer of 45 mM Tris-Borate, pH 8.3, 1.4 mM EDTA. Results were visualized by contact transfer of the resolved DNA to positively charged nylon membrane and probing of the blocked membrane with an anti-fluorescein antibody conjugated to alkaline phosphatase. After washing, the signal was developed by incubating the membrane in Western Blue (Promega) which deposits a purple precipitate where the antibody is bound.

Figure 24:
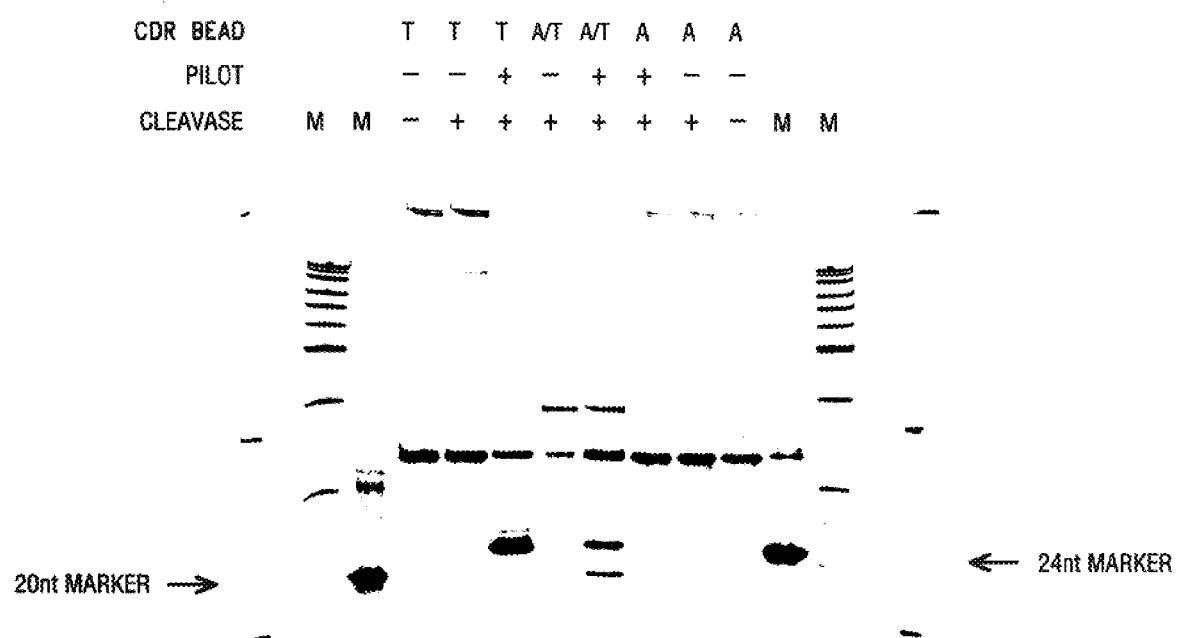
FIG. 24 shows the propagation of cleavage of the linear duplex nucleic acid structures of FIG. 23 by the 5' nucleases of the present invention.

FIG. 24 shows the propagation of cleavage of the linear duplex nucleic acid structures of FIG. 23 by the DNAP mutants of the present invention. The two center lanes contain both types of beads. As noted above, the beta signal oligo (SEQ ID NO:36) when liberated is a 24-mer and the alpha signal oligo (SEQ ID NO:35) when liberated is a 20-mer. The formation of the two lower bands corresponding to the 24-mer and 20-mer is clearly dependent on "pilot".

EXAMPLE 6

5' Exonucleolytic Cleavage ("Nibbling") By Thermostable DNAPs

It has been found that thermostable DNAPs, including those of the present invention, have a true 5' exonuclease capable of nibbling the 5' end of a linear duplex nucleic acid structures. In this example, the 206 base pair DNA duplex substrate is again employed (see above). In this case, it was produced by the use of one $^{32}$P-labeled primer and one unlabeled primer in a polymerase chain reaction. The cleavage reactions comprised 0.01 pmoles of heat-denatured, end-labeled substrate DNA (with the unlabeled strand also present), 5 pmoles of pilot oligonucleotide (see pilot oligos in FIG. 12A) and 0.5 units of DNAPTaq or 0.5 μ of the enzyme Cleavase™ BB in the E. coli extract (see above), in a total volume of 10 μl of 10 mM Tris.Cl, pH 8.5, 50 mM KCl, 1.5 mM MgCl$_2$.

Figures 25A, 25B:
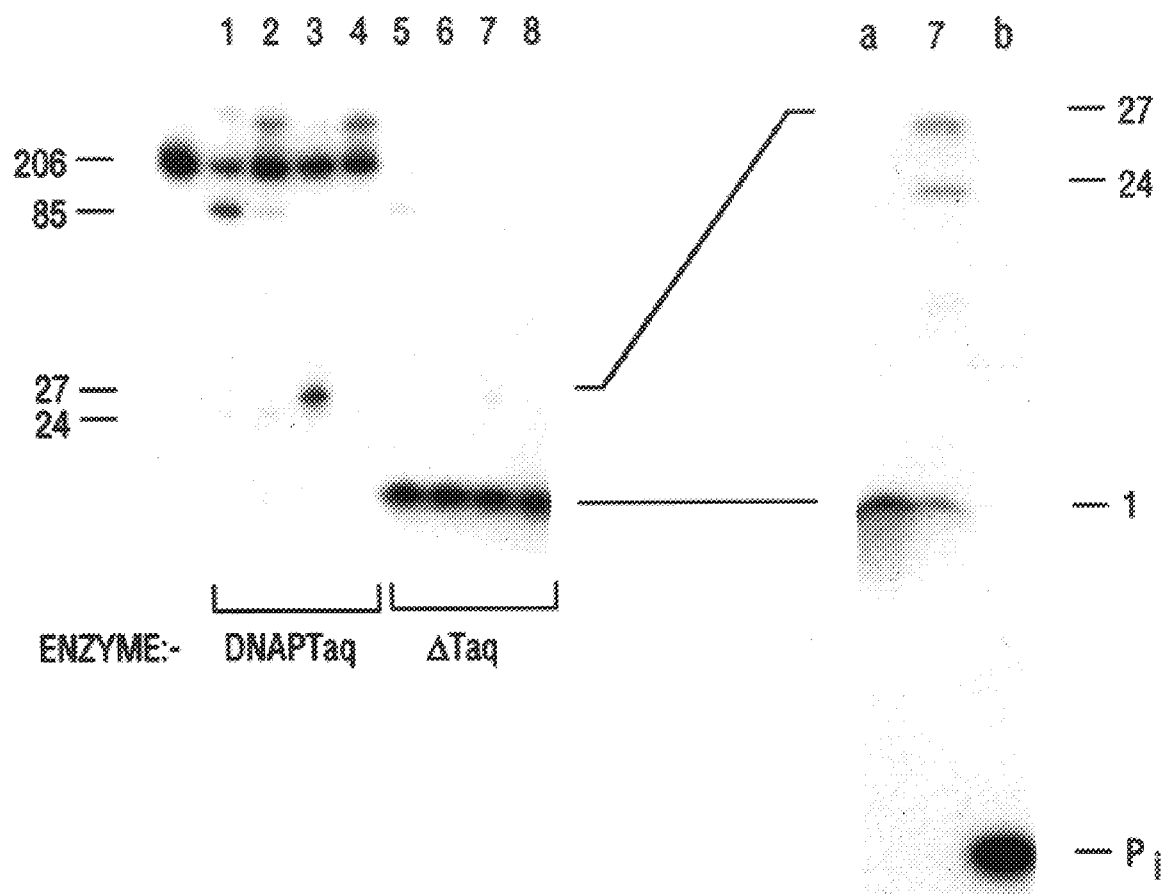
FIG. 25A shows the "nibbling" phenomenon detected with the DNAPs of the present invention.
FIG. 25B shows that the "nibbling" of FIG. 25A is 5' nucleolytic cleavage and not phosphatase cleavage.

Reactions were initiated at 65° C. by the addition of pre-warmed enzyme, then shifted to the final incubation temperature for 30 minutes. The results are shown in FIG. 25A. Samples in lanes 1–4 are the results with native Taq DNAP, while lanes 5–8 shown the results with the enzyme Cleavase™ BB. The reactions for lanes 1, 2, 5, and 6 were performed at 65° C. and reactions for lanes 3, 4, 7, and 8 were performed at 50° C. and all were stopped at temperature by the addition of 8 μl of 95% formamide with 20 mM EDTA and 0.05% marker dyes. Samples were heated to 75° C. for 2 minutes immediately before electrophoresis through a 10% acrylamide gel (19:1 cross-linked), with 7M urea, in a buffer of 45 mM Tris.Borate, pH 8.3, 1.4 mM EDTA. The expected product in reactions 1, 2, 5, and 6 is 85 nucleotides long; in reactions 3 and 7, the expected product is 27 nucleotides long. Reactions 4 and 8 were performed without pilot, and should remain at 206 nucleotides. The faint band seen at 24 nucleotides is residual end-labeled primer from the PCR.

The surprising result is that the enzyme Cleavase™ BB under these conditions causes all of the label to appear in a very small species, suggesting the possibility that the enzyme completely hydrolyzed the substrate. To determine the composition of the fastest-migrating band seen in lanes 5–8 (reactions performed with the deletion mutant), samples of the 206 base pair duplex were treated with either T7 gene 6 exonuclease (USB) or with calf intestine alkaline phosphatase (Promega), according to manufacturers' instructions, to produce either labeled mononucleotide (lane a of FIG. 25B) or free $^{32}$P-labeled inorganic phosphate (lane b of FIG. 25B), respectively. These products, along with the products seen in lane 7 of panel A were resolved by brief electrophoresis through a 20% acrylamide gel (19:1 cross-link), with 7M urea, in a buffer of 45 mM Tris.Borate, pH 8.3, 1.4 mM EDTA. The enzyme CleavaseTm BB is thus capable of converting the substrate to mononucleotides.

EXAMPLE 7

Nibbling Is Duplex Dependent

The nibbling by the enzyme Cleavase™ BB is duplex dependent. In this example, internally labeled, single strands of the 206-mer were produced by 15 cycles of primer extension incorporating α-$^{32}$P labeled dCTP combined with all four unlabeled dNTPs, using an unlabeled 206-bp fragment as a template. Single and double stranded products were resolved by electrophoresis through a non-denaturing 6% polyacrylamide gel (29:1 cross-link) in a buffer of 45 mM Tris.Borate, pH 8.3, 1.4 mM EDTA, visualized by autoradiography, excised from the gel, eluted by passive diffusion, and concentrated by ethanol precipitation.

Figure 26A:
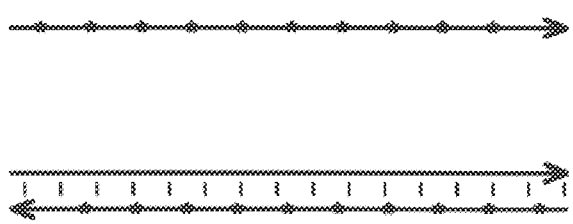
FIGS. 26A–B demonstrate that the "nibbling" phenomenon is duplex dependent.
Figure 26B:
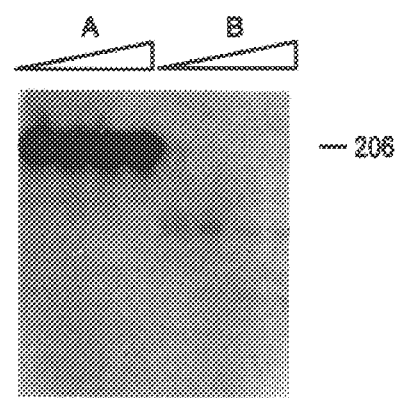

The cleavage reactions comprised 0.04 pmoles of substrate DNA, and 2 μl of the enzyme Cleavase™ BB (in an E. coli extract as described above) in a total volume of 40 μl of 10 mM Tris.Cl, pH 8.5, 50 mM KCl, 1.5 mM MgCl$_2$. Reactions were initiated by the addition of pre-warmed enzyme; 10 μl aliquots were removed at 5, 10, 20, and 30 minutes, and transferred to prepared tubes containing 8 μl of 95% formamide with 30 mM EDTA and 0.05% marker dyes. Samples were heated to 75° C. for 2 minutes immediately before electrophoresis through a 10% acrylamide gel (19:1 cross-linked), with 7M urea, in a buffer of 45 mM Tris.Borate, pH 8.3, 1.4 mM EDTA. Results were visualized by autoradiography as shown in FIG. 26. Clearly, the cleavage by the enzyme Cleavase™ BB depends on a duplex structure; no cleavage of the single strand structure is detected whereas cleavage of the 206-mer duplex is complete.

EXAMPLE 8

Nibbling Can Be Target Directed

Figure 27:
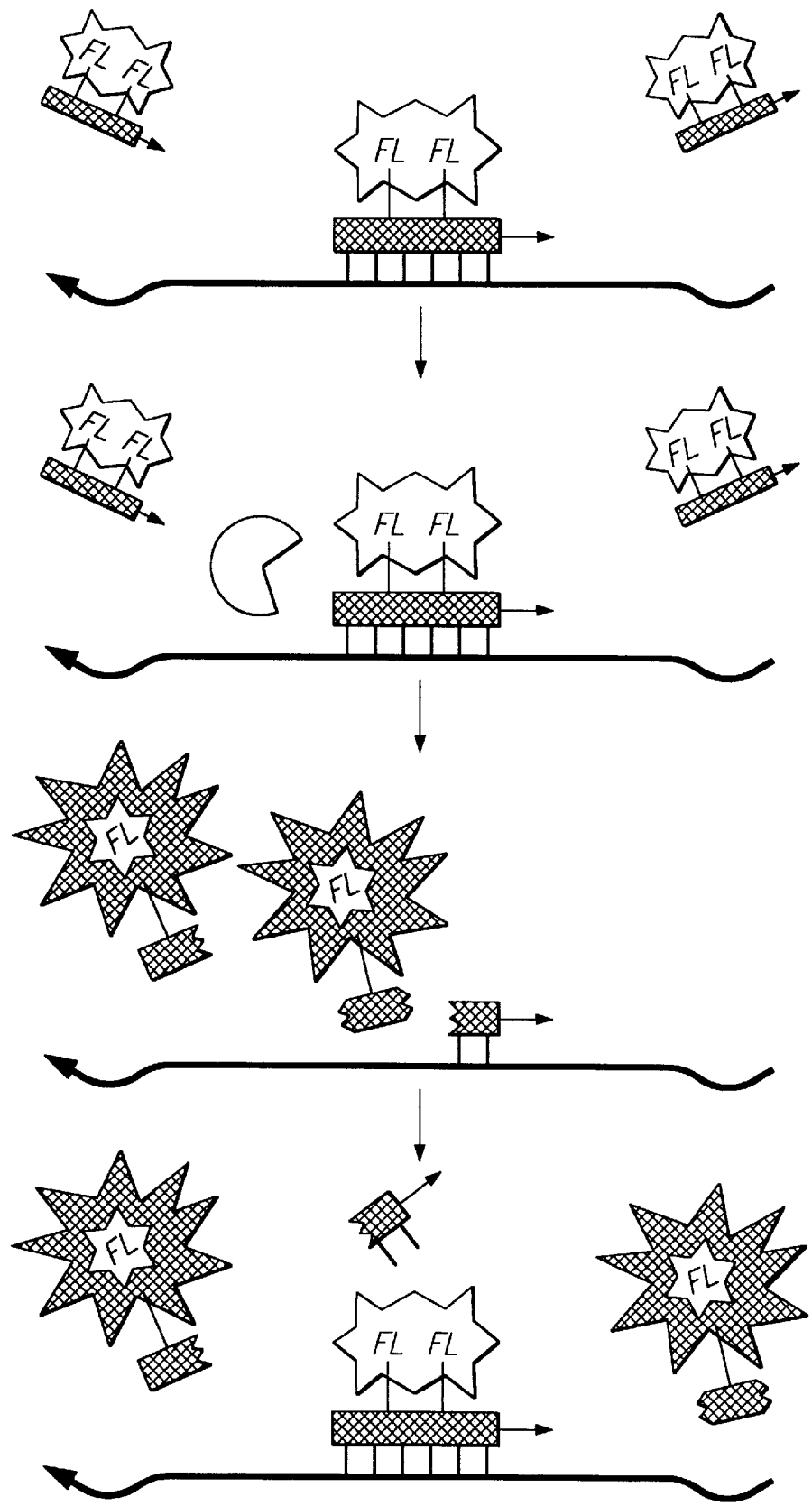
FIG. 27 is a schematic showing how "nibbling" can be employed in a detection assay.

The nibbling activity of the DNAPs of the present invention can be employed with success in a detection assay. One embodiment of such an assay is shown in FIG. 27. In this assay, a labelled oligo is employed that is specific for a target sequence. The oligo is in excess of the target so that hybridization is rapid. In this embodiment, the oligo contains two fluorescein labels whose proximity on the oligo causes their emission to be quenched. When the DNAP is permitted to nibble the oligo the labels separate and are detectable. The shortened duplex is destabilized and disassociates. Importantly, the target is now free to react with an intact labelled oligo. The reaction can continue until the desired level of detection is achieved. An analogous, although different, type of cycling assay has been described employing lambda exonuclease. See C. G. Copley and C. Boot, *BioTechniques* 13:888 (1992).

Figure 28A:
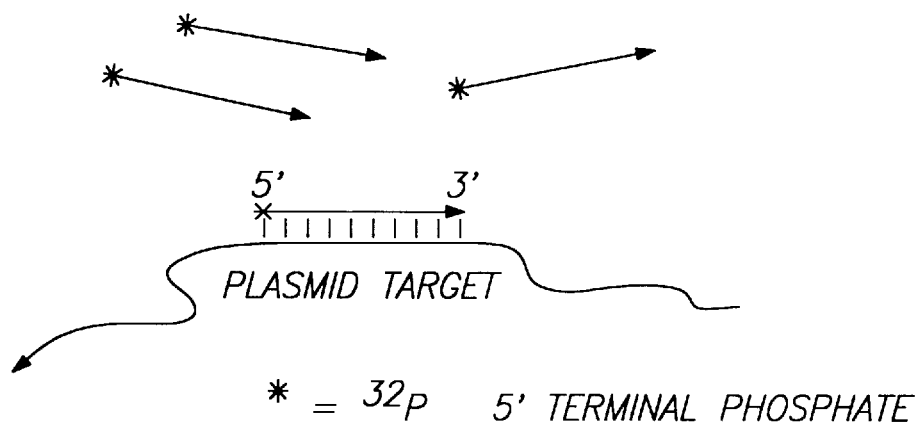
FIGS. 28A–B demonstrate that "nibbling" can be target directed.

The success of such an assay depends on specificity. In other words, the oligo must hybridize to the specific target. It is also preferred that the assay be sensitive; the oligo ideally should be able to detect small amounts of target. FIG. 28A shows a 5'-end $^{32}$P-labelled primer bound to a plasmid target sequence. In this case, the plasmid was pUC19 (commercially available) which was heat denatured by boiling two (2) minutes and then quick chilling. The primer is a 21-mer (SEQ ID NO:39). The enzyme Cleavase™ BX (a dilution equivalent to 5×10$^{-3}$ μl extract) was employed in 100 mM KCl, 10 mM Tris-Cl, pH 8.3, 2 mM MnCl$_2$. The reaction was performed at 55° C. for sixteen (16) hours with or without genomic background DNA (from chicken blood). The reaction was stopped by the addition of 8 μl of 95% formamide with 20 mM EDTA and marker dyes.

Figure 28B:
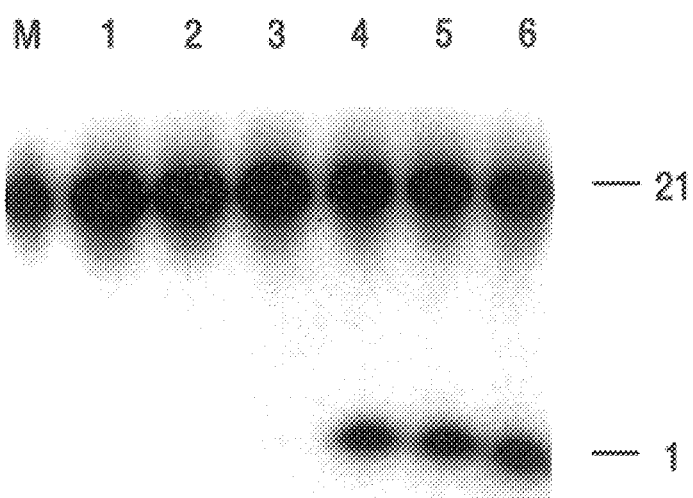

The products of the reaction were resolved by PAGE (10% polyacrylamide, 19:1 cross link, 1×TBE) as seen in FIG. 28B. Lane "M" contains the labelled 21-mer. Lanes 1–3 contain no specific target, although Lanes 2 and 3 contain 100 ng and 200 ng of genomic DNA, respectively. Lanes 4, 5 and 6 all contain specific target with either 0 ng, 100 ng or 200 ng of genomic DNA, respectively. It is clear that conversion to mononucleotides occurs in Lanes 4, 5 and 6 regardless of the presence or amount of background DNA. Thus, the nibbling can be target directed and specific.

EXAMPLE 9

Purification Of The Enzyme Cleavase™

As noted above, expressed thermostable proteins, ie., the 5' nucleases, were isolated by crude bacterial cell extracts. The precipitated E. coli proteins were then, along with other cell debris, removed by centrifugation. In this example, cells expressing the BN clone were cultured and collected (500 grams). For each gram (wet weight) of E. coli, 3 ml of lysis buffer (50 mM Tris-HCl, pH 8.0, 1 mM EDTA, 100 μM NaCl) was added. The cells were lysed with 200 μg/ml lysozyme at room temperature for 20 minutes. Thereafter deoxycholic acid was added to make a 0.2% final concentration and the mixture was incubated 15 minutes at room temperature.

The lysate was sonicated for approximately 6–8 minutes at 0° C. The precipitate was removed by centrifugation (39,000 g for 20 minutes). Polyethyleneimine was added (0.5%) to the supernatant and the mixture was incubated on ice for 15 minutes. The mixture was centrifuged (5,000g for 15 minutes) and the supernatant was retained. This was heated for 30 minutes at 60° C. and then centrifuged again (5,000g for 15 minutes) and the supernatant was again retained.

The supernatant was precipitated with 35% ammonium sulfate at 4° C. for 15 minutes. The mixture was then centrifuged (5,000g for 15 minutes) and the supernatant was removed. The precipitate was then dissolved in 0.25M KCl, 20 mM Tris, pH 7.6, 0.2% Tween and 0.1 EDTA) and then dialyzed against Binding Buffer (8× Binding Buffer comprises: 40 mM imidazole, 4M NaCl, 160 mM Tris-HCl, pH 7.9).

The solubilized protein is then purified on the $Ni^{++}$ column (Novagen). The Binding Buffer is allows to drain to the top of the column bed and load the column with the prepared extract. A flow rate of about 10 column volumes per hour is optimal for efficient purification. If the flow rate is too fast, more impurities will contaminate the eluted fraction.

The column is washed with 25 ml (10 volumes) of 1× Binding Buffer and then washed with 15 ml (6 volumes) of 1× Wash Buffer (8× Wash Buffer comprises: 480 mM imidazole, 4M NaCl, 160 mM Tris-HCl, pH 7.9). The bound protein was eluted with 15 ml (6 volumes) of 1× Elute Buffer (4× Elute Buffer comprises: 4 mM imidazole, 2M NaCl, 80 mM Tris-HCl, pH 7.9). Protein is then reprecipitated with 35% Ammonium Sulfate as above. The precipitate was then dissolved and dialyzed against: 20 mM Tris, 100 mM KCl, 1 mM EDTA). The solution was brought up to 0.1% each of Tween 20 and NP-40 and stored at 4° C.

EXAMPLE 10

5' Nucleases Cut Nucleic Acid Substrates At Naturally Occurring Areas Of Secondary Structure The ability of a 5' nuclease to recognize and cleave nucleic acid substrates at naturally occurring areas of secondary structure in the absence of a pilot oligonucleotide (i.e., primer independent cleavage) was shown in Example 1C (FIG. 12, lane 9). When DNAPTaq was incubated at 50° C. in the presence of a 206 bp DNA substrate (single end labeled, double stranded template) in a buffer containing 10 mM Tris-HCl, pH 8.5 and 1.5 mM $MgCl_2$, adventitious (Le., naturally occurring) structures in the DNA substrate were cleaved by the 5' nuclease activity of the enzyme. This cleavage generated three prominent fragments (FIG. 12, lane 9); this cleavage pattern provides a "fingerprint" of the DNA template.

The ability of 5' nucleases to cleave naturally occurring structures in nucleic acid templates (structure-specific cleavage) is useful to detect internal sequence differences in nucleic acids without prior knowledge of the specific sequence of the nucleic acid. To develop a general method to scan nucleic acids for mutations [e.g., single base changes (point mutations), small insertions or deletions, etc.] using 5' nucleases, the following series of experiments were performed.

A. The Substitution Of $MnCl_2$ For $MgCl_2$ In The Cleavage Reaction Produces Enhanced Cleavage Patterns The effect of substituting of $Mn^{2+}$ in place of $Mg^{2+}$ upon the cleavage pattern created by 5' nuclease activity on a double-stranded DNA substrate was examined. A 157 bp fragment derived from exon 4 of either the wild-type (SEQ ID NO:40) or the mutant G419R (SEQ ID NO:41) tyrosinase gene was prepared by PCR as follows.

The primer pair 5' biotin-CACCGTCCTCTTCAAGAAG 3' (SEQ ID NO:42) and 5' fluorescein-CTGAATCTTGTAGATAGCTA 3' (SEQ ID NO:43) was used to prime the PCRS. The synthetic primers were obtained from Promega; the primers were labeled on the 5' end with biotin or fluorescein during synthesis.

The target DNA for the generation of the 157 bp fragment of mutant G419R (King, R.A., et al., (1991) Mol. Biol. Med. 8:19; here after referred to as the 419 mutant) was a 339 bp PCR product (SEQ ID NO:44) generated using genomic DNA homozygous for the 419 mutation. Genomic DNA was isolated using standard techniques from peripheral blood leukocytes isolated from patients. This 339 bp PCR product was prepared as follows.

The symmetric PCR reaction comprised 10 ng of genomic DNA from the 419 mutant, 100 pmoles of the primer 5' biotin-GCCTTATTTTACTTTAAAAAT-3' (SEQ ID NO:45), 100 pmoles of the primer 5' fluorescein-TAAAGTTTTGTGTTATCTCA-3' (SEQ ID NO:46), 50 μM of each dNTP, 20 mM Tris-Cl, pH 8.3, 1.5 mM $MgCl_2$, 50 mM KCl, with 0.05% Tween 20 and 0.05% Nonidet P-40 (NP40). The primers of SEQ ID NOS:45 and 46 were obtained from Integrated DNA Technologies, Coralville, Iowa. A tube containing 45 μl of the above mixture was overlaid with two drops of light mineral oil and the tube was heated to 95° C. for 1 min. Taq polymerase was then added as 1.25 units of enzyme in 5 μl of 20 mM Tris-Cl, pH 8.3, 1.5 mM $MgCl_2$, 50 mM KCl, with 0.05% Tween 20 and 0.05% Nonidet P-40. The tube was heated to 94° C. for 40 sec, cooled to 55° C. for 50 sec, heated to 72° C. for 70 sec for 29 repetitions with a 5 min incubation at 72° C. after the last repetition.

The PCR products were gel purified as follows. The products were resolved by electrophoresis through a 6% polyacrylamide gel (29:1 cross-link) in a buffer containing 45 mM Tris-Borate, pH 8.3, 1.4 mM EDTA. The DNA was visualized by ethidium bromide staining and the 339 bp fragment was excised from the gel. The DNA was eluted from the gel slice by passive diffusion overnight into a solution containing 0.5M $NH_4OAc$, 0.1% SDS and 0.1M EDTA. The DNA was then precipitated with ethanol in the presence of 4 μg of glycogen carrier. The DNA was pelleted and resuspended in 40 μl of TE (10 mM Tris-Cl, pH 8.0, 0.1 mM EDTA).

To generate the 157 bp fragment from the 419 mutant, the purified 339 bp 419 PCR fragment was used as the target in an asymmetric PCR. The asymmetric PCR comprised 100 pmoles of the biotinylated primer of SEQ ID NO:45, 1 pmole of the fluoresceinated primer of SEQ ID NO:46, 50 μM of each dNTP, 20 mM Tris-Cl, pH 8.3, 1.5 mM $MgCl_2$, 50 mM KCl, with 0.05% Tween 20 and 0.05% Nonidet P-40. A tube containing 45 μl of the above mixture was overlaid with two drops of light mineral oil and the tube was heated to 95° C. for 5 sec and then cooled to 70° C. Taq polymerase was then added as 1.25 units of enzyme in 5 μl of 20 mM Tris-Cl, pH 8.3, 1.5 mM $MgCl_2$, 50 mM KCl, with 0.05% Tween 20 and 0.05% Nonidet P-40. The tube was heated to 95° C. for 45 sec, cooled to 50° C. for 45 sec, heated to 72° C. for 1 min 15 sec for 30 repetitions with a 5 min incubation at 72° C. after the last repetition.

The asymmetric PCR products were gel purified as follows. The products were resolved by electrophoresis through a 6% polyacrylamide gel (29:1 cross-link) in a buffer containing 45 mM Tris-Borate, pH 8.3, 1.4 mM EDTA. The DNA was visualized by ethidium bromide staining; the double-stranded DNA was differentiated from the single-stranded DNA due to the mobility shift commonly seen with single-stranded DNA produced from asymmetric PCR (In an asymmetric PCR both single-stranded and double-stranded products are produced; typically the single-stranded product will have a slower speed of migration through the gel and will appear closer to the origin than will the double-stranded product). The double-stranded 157 bp substrate corresponding to the 419 mutant (SEQ ID NO:41) was excised from the gel.

The 157 bp wild-type fragment was generated by asymmetric PCR as described above for the 419 mutant with the exception that the target DNA was 10 ng of supercoiled pcTYR-N1Tyr plasmid DNA. The pcTYR-N1Tyr plasmid contains the entire wild-type tyrosinase cDNA [Geibel, L. B., et al. (1991) Genomics 9:435].

Following the asymmetric PCRS, the reaction products were resolved on an acrylamide gel and the double-stranded fragments of interest were excised, eluted and precipitated as described above. The precipitated 157 bp wild-type (SEQ ID NO:40) and 419 mutant (SEQ ID NO:41) fragments were resuspended in 40 µl of TE.

Cleavage reactions comprised 100 fmoles of the resulting double-stranded substrate DNAs (the substrates contain a biotin moiety at the 5' end of the sense strand) in a total volume of 10 µl of 10 mM MOPS, pH 8.2, 1 mM divalent cation (either $MgCl_2$ or $MnCl_2$) and 1 unit of DNAPTaq. The reactions were overlaid with a drop of light mineral oil. Reactions were heated to 95° C. for 5 seconds to denature the substrate and then the tubes were quickly cooled to 65° C. (this step allows the DNA assume its unique secondary structure by allowing the formation of intra-strand hydrogen bonds between complimentary bases). The reaction can be performed in either a thermocycler (MJ Research, Watertown, Mass.) programmed to heat to 95° C. for 5 seconds then drop the temperature immediately to 65° C. or alternatively the tubes can be placed manually in a heat block set at 95° C. and then transferred to a second heat block set at 65° C.

The reaction was incubated at 65° C. for 10 minutes and was stopped by the addition of 8 µl of stop buffer (95% formamide containing 20 mM EDTA and 0.05% each xylene cyanol and bromophenol blue). Samples were heated to 72° C. for 2 minutes and 5 µl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated allowing the gel to remain flat on one plate. A 0.2 µm-pore positively-charged nylon membrane (Schleicher and Schuell, Keene, N.H.), pre-wetted in 0.5× TBE (45 mM Tris-Borate, pH 8.3, 1.4 mM EDTA), was laid on top of the exposed acrylamide gel. All air bubbles trapped between the gel and the membrane were removed. Two pieces of 3 MM filter paper (Whatman) were then placed on top of the membrane, the other glass plate was replaced, and the sandwich was clamped with binder clips. Transfer was allowed to proceed overnight. After transfer, the membrane was carefully peeled from the gel and allowed to air dry. After complete drying, the membrane was washed in 1.2× Sequenase Images Blocking Buffer (United States Biochemical) for 30 minutes. Three tenths of a ml of the buffer was used per $cm^2$ of membrane. A streptavidin-alkaline phosphatase conjugate (SAAP, United States Biochemical) was added to a 1:4000 dilution directly to the blocking solution, and agitated for 15 minutes. The membrane was rinsed briefly with $H_2O$ and then washed 3 times (5 minutes/wash) in 1× SAAP buffer (100 mM Tris-HCL, pH 10; 50 mM NaCl) with 0.1% sodium dodecyl sulfate (SDS) using 0.5 ml buffer/$cm^2$ of the buffer, with brief $H_2O$ rinses between each wash. Similarly, for fluorescein-labeled DNA, anti-fluorescein fragment (Boehringer Mannheim Biochemicals, Indianapolis, IN) at a 1:20,000 final dilution may be added followed by three washes (5 min/wash) in 1× SAAP buffer containing 0.1% SDS and 0.025% Tween 20. The membrane was then washed once in 1× SAAP buffer without SDS, drained thoroughly and placed in a plastic heat-sealable bag. Using a sterile pipet tip, 0.05 ml/$cm^2$ of CDP-Star™ (Tropix, Bedford, Mass.) was added to the bag and distributed over the entire membrane for 5 minutes. The bag was drained of all excess liquid and air bubbles. The membrane was then exposed to X-ray film (Kodax XRP) for an initial 30 minutes. Exposure times were adjusted as necessary for resolution and clarity. The results are shown in FIG. 30.

Figure 30:
FIG. 30 shows an autoradiograph of a gel resolving the products of cleavage reactions run in the presence of either $MgCl_2$ or $MnCl_2$.

In FIG. 30, the lane marked "M" contains molecular weight markers. The marker fragments were generated by digestion of pUC19 with HaeIII followed by the addition of biotinylated dideoxynucleotides (Boehringer Mannheim, Indianapolis, Ind.) to the cut ends using terminal transferase (Promega). Lanes 1, 3 and 5 contain the reaction products from the incubation of the wild type 157 nucleotide substrate in the absence of the DNAPTaq enzyme (lane 1), in the presence of $MgCl_2$ and enzyme (lane 3) or in the presence of $MnCl_2$ and enzyme (lane 5). Lanes 2, 4 and 6 contains the reaction products from the incubation of the 157 nucleotide substrate derived from the 419 mutant in the absence of enzyme (lane 2), in the presence of $MgCl_2$ and enzyme (lane 4) or in the presence of $MnCl_2$ and enzyme (lane 6).

FIG. 30 demonstrates that the use of $MnCl_2$ rather than $MgCl_2$ in the cleavage reaction results in the production of an enhanced cleavage pattern. It is desirable that the cleavage products are of different sizes so that the products do not all cluster at one end of the gel. The ability to spread the cleavage products out over the entire length of the gel makes it more likely that alterations in cleavage products between the wild type and mutant substrates will be identified. FIG. 30 shows that when $Mg^{2+}$ is used as the divalent cation, the majority of the cleavage products cluster together in the upper portion of the gel. In contrast when $Mn^{2+}$ is used as the divalent cation, the substrate assumes structures which, when cleaved, generate products of widely differing mobilities. These results show that $Mn^{2+}$ is the preferred divalent cation for the cleavage reaction.

B. 5' Nuclease Cleavage Of Different But Similarly Sized DNAs Generates Unique Cleavage Fragments The ability of 5' nuclease to generate a cleavage pattern or "fingerprint" which is unique to a given piece of DNA was shown by incubating four similarly sized DNA substrates with the enzyme Cleavase™ BN. The four DNA substrates used were a 157 nucleotide fragment from the sense (or coding) strand of exon 4 of the wild-type tyrosinase gene (SEQ ID NO:47); a 157 nucleotide fragment from the anti-sense (or non-coding) strand of exon 4 of the wild-type tyrosinase gene (SEQ ID NO:48); a 165 nucleotide DNA fragment derived from pGEM3Zf(+) (SEQ ID NO:49) and a 206 nucleotide DNA fragment derived from the bottom strand of pGEM3Zf(+) (SEQ ID NO:50). The DNA substrates contained either a biotin or fluorescein label at their 5' or 3' ends. The substrates were made as follows.

To produce the sense and anti-sense single-stranded substrates corresponding to exon 4 of the wild-type tyrosinase gene, a double-stranded DNA fragment, 157 nucleotides in length (SEQ ID NO:40), was generated using symmetric PCR. The target for the symmetric PCR was genomic DNA containing the wild-type tyrosinase gene. The symmetric PCR comprised 50–100 ng of genomic wild-type DNA, 25 pmoles each of primers SEQ ID NOS:42 and 43, 50 µM each DNTP and 1.25 units of Taq polymerase in 50 µl of 20 mM Tris-Cl, pH 8.3, 1.5 mM $MgCl_2$, 50 mM KCl, with 0.05% Tween 20 and 0.05% Nonidet P-40. The reaction mixture was overlaid with two drops of light mineral oil and the tube was heated to 94° C. for 30 sec, cooled to 50° C. for 1 min, heated to 72° C. for 2 min for 30 repetitions. The double-stranded PCR product was gel purified, precipitated and resuspended in 40 µl of TE buffer as described above in a).

The single-stranded sense and anti-sense 157 nucleotide DNA fragments were generated using the above 157 bp wild-type DNA fragment (SEQ ID NO:40) in two asymmetric PCR reactions. The sense strand fragment was generated using 5 µl of the above purified 157 bp fragment (SEQ ID NO:40) as the target in an asymmetric PCR. The reaction mixtures for the asymmetric PCR were as above for the symmetric PCR with the exception that 100 pmoles of the biotin-labeled sense primer (SEQ ID NO:42) and 1 pmole of the fluorescein-labeled anti-sense primer (SEQ ID NO:43) was used to prime the reaction. The anti-sense fragment was generated using 5 µl of the above purified 157 bp fragment as the target in an asymmetric PCR. The reaction conditions for the asymmetric PCR were as above for the symmetric PCR with the exception that 1 pmole of the sense primer (SEQ ID NO:42) and 100 pmoles of the anti-sense primer (SEQ ID NO:43) was used to prime the reaction.

The reaction conditions for the asymmetric PCR were 95° C. for 45 sec, 50° C. for 45 sec, 72° C. for 1 min and 15 sec for 30 repetitions with a 5 min incubation at 72° C. after the last repetition. The reaction products were visualized, extracted and collected as described above with the single stranded DNA being identified by a shift in mobility when compared to a double stranded DNA control.

The single-stranded 165 nucleotide fragment from pGEM3Zf(+) (SEQ ID NO:49) was generated by asymmetric PCR. The PCR comprised 50 pmoles of 5' biotin-AGCGGATAACAATTTCACACAGGA-3' (SEQ ID NO:51; Promega) and 1 pmole of 5'-CACGGATCCTAATACGACTCACTATAGGG-3' (SEQ ID NO:52; Integrated DNA Technologies, Coralville, Iowa), 50 µM each dNTP, 20 mM Tris-Cl, pH 8.3, 1.5 mM MgCl$_2$, 50 mM KCl, with 0.05% Tween 20 and 0.05% Nonidet P-40. Forty-five microliters of this reaction mixture was overlaid with two drops of light mineral oil and the tube was heated to 95° C. for 5 sec and then cooled to 70° C. Taq polymerase was then added at 1.25 units in 5 µl of 20 mM Tris-Cl, pH 8.3, 1.5 mM MgCl$_2$, 50 mM KCl, with 0.05% Tween 20 and 0.05% Nonidet P-40. The tubes were heated to 95° C. for 45 sec, cooled to 50° C. for 45 sec, heated to 72° C. for 1 min 15 sec for 30 repetitions with a 5 min incubation at 72° C. after the last repetition. The reaction products were visualized, extracted and collected as described above with the 164 nucleotide DNA fragment being identified by a shift in mobility when compared to a double stranded DNA control.

The 206 nucleotide DNA fragment (SEQ ID NO:50) was prepared by asymmetric as follows. The asymmetric PCR comprised 1 pmole of a double-stranded 206 bp PCR product (generated as described in Example IC), 50 pmoles of the primer 5'-CGCCAGGGTTTTCCCAGTCACGAC-3' (SEQ ID NO:53), 50 µM each dNTP, 20 mM Tris-Cl, pH 8.3, 1.5 mM MgCl$_2$, 50 mM KCl, with 0.05% Tween 20 and 0.05% Nonidet P-40. Ninety-five microliters of this reaction mixture was overlaid with three drops of light mineral oil and the tube was heated to 95° C. for 5 sec and then cooled to 70° C. Taq polymerase was then added at 2.5 units in 5 µl of 20 mM Tris-Cl, pH 8.3, 1.5 mM MgCl$_2$, 50 mM KCl, with 0.05% Tween 20 and 0.05% Nonidet P-40. The tubes were heated to 95° C. for 45 sec, cooled to 63° C. for 45 sec, heated to 72° C. for 1 min 15 sec for 15 repetitions with a 5 min incubation at 72° C. after the last repetition. The reaction products were visualized, extracted and collected as described above with the 206 nucleotide DNA fragment being identified by a shift in mobility when compared to a double stranded DNA control. The precipitated DNA was resuspended in 70 µl of TE buffer.

Twenty-five microliters of the above product was biotinylated on the 3' end using 10–20 units of terminal deoxynucleotidyl transferase (Promega) in a 50 µl reaction. The reaction comprised 0.5 nmoles of biotin-16-ddUTP (Boehringer Mannheim) and 1× buffer (500 mM cacoodylate buffer, pH 6.8, 5 mM CoCl$_2$, 0.5 mM DTT and 500 µg/ml BSA). The tubes were incubated at 37° C. for 15 min followed by ethanol precipitation in the presence of 4 µg of glyc7ogen. The DNA was ethanol precipitated a second time and then resuspended in 25 µl of 10 Mm Tris-HCl, pH 8.0, 0.1 mM EDTA.

The cleavage reactions were carried out in a final volume of 10 µl containing 1× CFLP™ buffer (10 mM MOPS, pH 8.2) with 1 mM MnCl$_2$ using approximately 100 fmoles of substrate DNA and 250 ng of the enzyme Cleavase™ BN. Parallel reactions lacking the enzyme Cleavase™ BN (no enzyme control) were set up as above with the exception that one third as much DNA template was used (approximately 33 fmoles of each template) to balance the signal on the autoradiograph.

Each substrate DNA was placed in a 200 µl thin wall microcentrifuge tube (BioRad, Hercules, Calif.) in 5 µl of 1× CFLP™ buffer with 2 mM MnCl$_2$. The solution was overlaid with one drop of light mineral oil. Tubes were brought to 95° C. for 5 seconds to denature the substrates and then the tubes were quickly cooled to 65° C.

Cleavage reactions were started immediately by the addition of a diluted enzyme mixture comprising 1 µl of the enzyme Cleavase™ BN [250 ng/µl in 1× dilution buffer (0.5% NP40, 0.5% Tween20, 20 mM Tris-HCl, pH 8.0, 50 mM KCl, 10 µg/ml BSA)] in 5 µl of 1× CFLP™ buffer without MnCl$_2$. The enzyme solution was at room temperature before addition to the cleavage reaction. After 5 minutes at 65° C., the reactions were stopped by the addition of 8 µl of stop buffer. Samples were heated to 72° C. for 2 minutes and 5 µl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a 0.45 µm-pore positively charged nylon membrane (United States Biochemical). The DNA was transferred to the membrane and the membrane was dried, washed in 1.2× Sequenase Images Blocking Buffer, treated with 1× SAAP buffer as described above. The signal was developed using Lumiphos-530 (United States Biochemical) or Quantum Yield Chemiluminescent Substrate (Promega) in place of the CDP-Star™; the membrane was then exposed to X-ray film as described above. The resulting autoradiograph is shown in FIG. 31.

Figure 31:
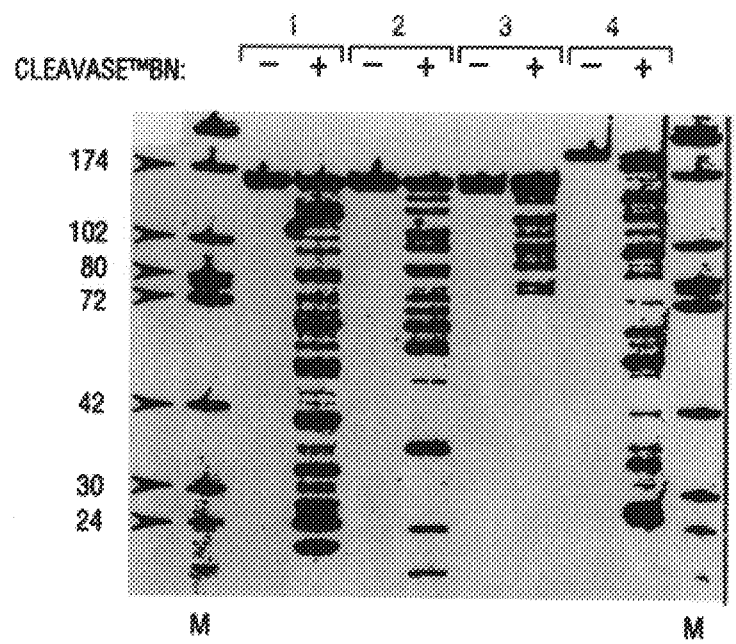
FIG. 31 shows an autoradiograph of a gel resolving the products of cleavage reactions run on four similarly sized DNA substrates.

FIG. 31 shows the results of incubation of the four substrates described above in the presence or absence of the enzyme Cleavase™ BN. Four sets of reactions are shown. Set one contains the reaction products from the incubation of the 157 nucleotide sense strand fragment of the tyrosinase gene (SEQ ID NO:47) in the absence or presence of the enzyme Cleavase™ BN. Set two contains the reaction products from the incubation of the 157 nucleotide anti-sense strand fragment of the tyrosinase gene (SEQ ID NO:48) in the absence or presence of the enzyme Cleavase™ BN. Set three contains the reaction products from the incubation of the 165 base bottom strand fragment of the plasmid pGEM3Zf(+) (SEQ ID NO:49) in the absence or presence of the enzyme Cleavase™ BN. Set four contains the reaction products from the incubation of the 206 base top strand fragment of the plasmid pGEM3Zf(+) (SEQ ID NO:50) in the absence or presence of the enzyme Cleavase™ BN. Lanes marked "M" contain biotin-labeled molecular weight markers prepared as described above; the sizes of the marker fragments are indicated in FIG. 31. In the absence of the enzyme Cleavase™ BN, no cleavage of the substrates is observed. In the presence of the enzyme Cleavase™ BN, each substrate is cleaved generating a unique set of cleavage products. When these cleavage products are resolved on a polyacrylamide gel, a unique pattern or fingerprint is seen for each substrate DNA. Thus, although the four substrates are similar in size (157 to 206 bases), the enzyme Cleavase™ BN generates a unique collection of cleavage products from each substrate. These unique cleavage patterns result from the characteristic conformation each substrate DNA assumes.

The present invention contemplates the ability to generate a unique cleavage pattern for two or more DNA substrates of the same size as part of a method for the detection of genetic mutations. This method compares a normal (or wild type or non-mutated) substrate with a substrate from a patient suspected of having a mutation in that substrate. The two substrates would be of the same length and the cleavage reaction would be used to probe the patient DNA substrate for conformational changes relative to the pattern seen in the wild type control substrate.

EXAMPLE 11

Cleavage Directed By The Enzyme Cleavase™ BN Can Detect Single Base Changes In DNA Substrates The ability of the enzyme Cleavase™ BN to cleave DNA substrates of the same size but which contain single base changes between the substrates is herein demonstrated. The human tyrosinase gene was chosen as a model system because numerous single point mutations have been identified in exon 4 of this gene [Spritz, R. A. (1994) Human Molecular Genetics 3:1469]. Mutation of the tyrosinase gene leads to oculocutaneous albinism in humans.

Three single-stranded substrate DNAs were prepared; the substrates contain a biotin label at their 5' end. The wild type substrate comprises the 157 nucleotide fragment from the sense strand of the human tyrosinase gene [(SEQ ID NO:47); Geibel, L. B., et al. (1991) Genomics 9:435]. Two mutation-containing substrates were used. The 419 substrate (SEQ ID NO:54) is derived from the tyrosinase mutant G419R which contains a glycine (GGA) to arginine (AGA) substitution; this mutant differs from the wild-type exon 4 fragment by a single base change at nucleotide 2675 [King, R. A., et al. (1991) Mol. Biol. Med. 8:19]. The 422 substrate (SEQ ID NO:55) is derived from the tyrosinase mutant R422Q which contains an arginine (CGG) to glutamine (CAG) substitution; this mutant differs from the wild type exon 4 fragment by a single base change at nucleotide 2685 [Giebel, L. B., et al. (1991) J. Clin. Invest. 87:1119].

Single-stranded DNA containing a biotin label at the 5' end was generated for each substrate using asymmetric PCR as described in Example 10a with the exception that the single-stranded PCR products were recovered from the gel rather than the double-stranded products.

The following primer pair was used to amplify each DNA (the 419 and 422 mutations are located internally to the exon 4 fragment amplified by the primer pair thus the same primer pair can be used to amplify the wild type and two mutant templates). The primer listed as SEQ ID NO:42 (sense primer) contains a biotin label at the 5' end and was used in a 100-fold excess over the anti-sense primer of SEQ ID NO:43.

To generate the single stranded substrates the following templates were used. Ten ng of supercoiled plasmid DNA was used as the target to generate the wild-type (plasmid pcTYR-NlTyr) or 422 mutant (plasmid pcTYR-A422) 157 nucleotide fragments. Five microliters of the gel purified 339 bp PCR fragment (SEQ ID NO:44) derived from genomic DNA homozygous for the 419 mutation (described in Example 10a) was used as the target to generate the 157 nucleotide 419 mutant fragment (SEQ ID NO:54).

For each target DNA, the asymmetric PCR comprised 100 pmoles of SEQ ID NO:42 and 1 pmole of SEQ ID NO:43, 50 $\mu$M each dNTP, 20 mM Tris-Cl, pH 8.3, 1.5 mM MgCl$_2$, 50 mM KCl, with 0.05% Tween 20 and 0.05% Nonidet P-40. The reaction mixture (45 $\mu$l) was overlaid with two drops of light mineral oil and the tubes were heated to 95° C. for 5 sec then cooled to 70° C. Taq polymerase was then added as 1.25 units of enzyme in 5 $\mu$l of 20 mM Tris-Cl, pH 8.3, 1.5 mM MgCl$_2$, 50 mM KCl, with 0.05% Tween 20 and 0.05% Nonidet P-40. The tubes were heated to 95° C. for 45 sec, cooled to 50° C. for 45 sec, heated to 72° C. for 1 min 15 sec for 30 repetitions with a 5 min incubation at 72° C. after the last repetition. The single stranded PCR products were gel purified, precipitated and resuspended in 40 $\mu$l of TE buffer as described above.

Cleavage reactions were performed as follows. Each substrate DNA (100 fmoles) was placed in a 200 $\mu$l thin wall microcentrifuge tube (BioRad) in 5 $\mu$l of 1× CFLP™ buffer with 2 mM MnCl$_2$. A tube containing 33 fmoles of template DNA in 10 $\mu$l of 1× CFLP™ buffer and 1 MnCl$_2$ was prepared for each template and served as the no enzyme (or uncut) control. The solution was overlaid with one drop of light mineral oil. Tubes were brought to 95° C. for 5 seconds to denature the substrates and then the tubes were quickly cooled to 65° C.

Cleavage reactions were started immediately by the addition of a diluted enzyme mixture comprising 1 $\mu$l of the enzyme Cleavase™ BN [250 ng/$\mu$l in 1× dilution buffer (0.5% NP40, 0.5% Tween 20, 20 mM Tris-HCl, pH 8.0, 50 mM KCl, 10 $\mu$g/ml BSA)] in 5 $\mu$l of 1× CFLP™ buffer without MnCl$_2$. The enzyme solution was at room temperature before addition to the cleavage reaction. After 5 minutes at 65° C., the reactions were stopped by the addition of 8 $\mu$l of stop buffer. The samples were heated to 72° C. for 2 minutes and 7 $\mu$l of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10a. The DNA was transferred to the membrane and the membrane was dried, washed in 1.2× Sequenase Images Blocking Buffer, treated with 1× SAAP buffer and reacted with CDP-Star™ (Tropix) and exposed to X-ray film as described in Example 10a. The resulting autoradiograph is shown in FIG. 32.

Figure 32:
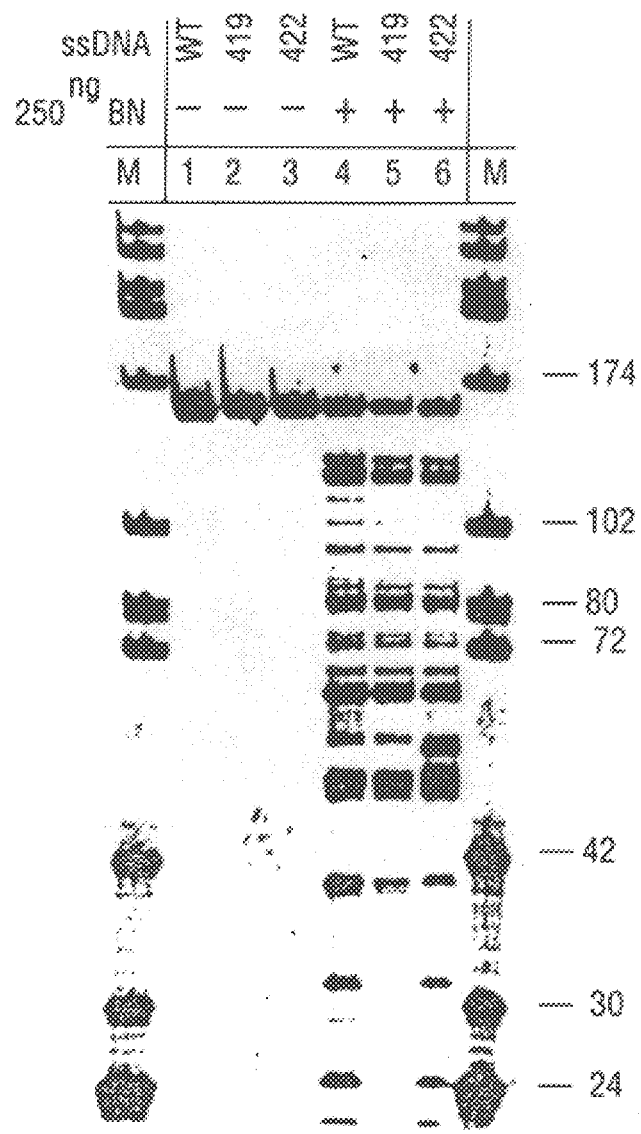
FIG. 32 shows an autoradiograph of a gel resolving the products of cleavage reactions run using a wild-type and two mutant tyrosinase gene substrates.

In FIG. 32, lanes marked "M" contain molecular weight markers prepared as described in Example 10. Lanes 1–3 contain the no enzyme control for the wild type (SEQ ID NO:47), the 419 mutant (SEQ ID NO:54) and the 422 mutant (SEQ ID NO:55) substrates, respectively. Lane 4 contains the cleavage products from the wild type template.

Lane 5 contains the cleavage products from the 419 mutant. Lane 6 contains the cleavage products from the 422 mutant.

FIG. 32 shows that a similar, but distinctly different, pattern of cleavage products is generated by digestion of the three template DNAs with the enzyme Cleavase™ BN. Note that in the digest of mutant 419, the bands below about 40 nucleotides are absent, when compared to wild-type, while in the digest of mutant 422 several new bands appear in the 53 nucleotide range.

Although the three template DNAs differed in only one of the 157 nucleotides, a unique pattern of cleavage fragments was generated for each. Thus a single base change in a 157 nucleotide fragment gives rise to different secondary structures which are recognized by the enzyme Cleavase™.

EXAMPLE 12

Single Base Changes In Large DNA Fragments Are Detected By The Enzyme Cleavase™ BN The previous example demonstrated that the 5' nuclease activity of the enzyme Cleavase™ BN could be used to detect single point mutations within a 157 nucleotide DNA fragment. The ability of the enzyme Cleavase™ BN to detect single point mutations within larger DNA fragments is herein demonstrated.

Increasingly larger fragments derived from the 422 tyrosinase mutant was compared to the same size fragments derived from the wild-type tyrosinase gene. Four sets of single-stranded substrates were utilized: 1) a 157 nucleotide template derived from the sense strand of exon 4 from the wild-type (SEQ ID NO:47) and 422 mutant (SEQ ID NO:55), 2) a 378 nucleotide fragment containing exons 4 and 5 from the wild-type (SEQ ID NO:56) and 422 mutant (SEQ ID NO:57), 3) a 1.059 kb fragment containing exons 1–4 from the wild-type (SEQ ID NO:58) and 422 mutant (SEQ ID NO:59) and 4) a 1.587 kb fragment containing exons 1-5 from the wild-type (SEQ ID NO:60) and 422 mutant (SEQ ID NO:61). The only difference between the wild type and 422 mutant templates is the G to A change in exon 4 regardless of the length of the template used. The G to A point mutation is located 27, 27, 929 and 1237 nucleotides from the labeled ends of the 157 base, 378 base, 1.059 kb and 1.6 kb substrate DNAs, respectively.

a) Preparation Of The Substrate DNA

A cDNA clone containing either the wild-type [pcTYR-N1Tyr, Bouchard, B., et al. (1989) J. Exp. Med. 169:2029] or 422 mutant [pcTYR-A422, Giebel, L. B., et al. (1991) 87:1119] tyrosinase gene was utilized as the target DNA in PCRs to generate the above substrate DNAs. The primer pair consisting of SEQ ID NOS:42 and 43 were used to generate a double stranded 157 bp DNA fragment from either the mutant of wild-type cDNA clone. The primer pair consisting of SEQ ID NO:42 and SEQ ID NO:62 was used to generate a double stranded 378 bp DNA fragment from either the wild-type or mutant cDNA clone. The primer pair consisting of SEQ ID NO:63 and SEQ ID NO:43 was used to generate a double stranded 1.059 kbp DNA fragment from either the wild-type or mutant cDNA clone. The primer pair consisting of SEQ ID NO:64 and SEQ ID NO:62 was used to generate a double stranded 1.587 kbp DNA fragment from either the wild-type or mutant cDNA clone. In each case the sense strand primer contained a biotin label at the 5' end.

The PCR reactions were carried out as follows. One to two ng of plasmid DNA from the wild-type or 422 mutant was used as the target DNA in a 100 µl reaction containing 50 µM of each dNTP, 1 µM of each primer in a given primer pair, 20 mM Tris-Cl, pH 8.3, 1.5 mM $MgCl_2$, 50 mM KCl, with 0.05% Tween 20 and 0.05% Nonidet P-40. Tubes containing the above mixture were overlaid with three drops of light mineral oil and the tubes were heated to 94° C. for 1 min, then cooled to 70° C. Taq polymerase was then added as 2.5 units of enzyme in 5 µl of 20 mM Tris-Cl, pH 8.3, 1.5 mM $MgCl_2$, 50 mM KCl, with 0.05% Tween 20 and 0.05% Nonidet P-40. The tube was heated to 93° C. for 45 sec, cooled to 52° C. for 2 min, heated to 72° C. for 1 min 45 sec for 35 repetitions, with a 5 min incubation at 72° C. after the last repetition.

Following the PCR, excess primers were removed using a QIA Quick-Spin PCR Purification kit (Qiagen, Inc. Chatsworth, Calif.) following the manufacturer's instructions; the DNA was eluted in 50 µl of 10 mM Tris-HCl, pH 8.0, 1 mM EDTA. The sense strand of each of the double-stranded fragments from the wild-type and 422 mutant gene were isolated as follows. Streptavidin-coated paramagnetic beads (Dynal M280 beads) [0.5 mg in 50 µl; pre-washed in 2× bind and wash (B&W) buffer (2M NaCl, 10 mM Tris-HCl, pH 7.5, 1 mM EDTA, 0.1% Tween 20)] were added to each purified PCR product. The samples were incubated at room temperature for 15 minutes with occasional shaking. The beads were removed from the supernatant by exposing the tube to a magnetic plate and the supernatant was discarded. The bead-DNA complexes were washed twice in 2× B&W buffer. One hundred microliters of 0.1M NaOH were added to the beads and the samples were incubated at room temperature for 15 minutes (for the 157, 378 bp DNAs); for DNA fragments larger than 1 kb, the beads were incubated at 47° C. for 30 minutes. After incubation, the beads were washed twice with 2× B&W buffer. Finally, the bead-ssDNA complexes were resuspended in 50 µl 2× B&W buffer and stored at 4° C.

b) Cleavage Reaction Conditions

The cleavage reactions were performed directly on the single-stranded DNA-bead complexes. Five to 10 µl of DNA-bead complex (about 100 fmoles of DNA) were placed in a 200 µl microcentrifuge tube and washed once with 10 µl of sterile $H_2O$. Seven and one half microliters of 1× CFLP™ buffer with 1.3 mM $MnCl_2$ (to yield a final concentration of 1 mM) was then added to each tube. The reaction tubes were prewarmed to 65° C. for 2 minutes and cleavage was initiated by the addition of 2.5 µl of the enzyme Cleavase™ BN (10–50 ng in 1× dilution buffer). The reaction was carried out at 65° C. for 5 min.

Immediately after this 5 min incubation, the beads were allowed to settle to the bottom of the tube and the supernatant was removed and discarded. Ten to forty microliters of stop buffer (95% formamide with 20 mM EDTA and 0,05% xylene cyanol and 0.05% bromophenol blue) was then added to the beads and the sample was incubated at 90° C. for 5–10 minutes. The formamide/EDTA solution releases the biotinylated DNA from the beads. The beads were allowed to settle to the bottom of the tube. The supernatant containing the cleavage products was collected. Two to eight microliters of the supernatant solution loaded onto 6% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 1 0a and allowed to transfer overnight. After transfer the membrane was dried, blocked, probed and washed as described in Example 10 a. The blot was reacted with CDP-Star™ (Tropix) and exposed to X-ray film as described in Example 10a. The resulting autoradiograph is shown in FIG. 33.

Figure 33:
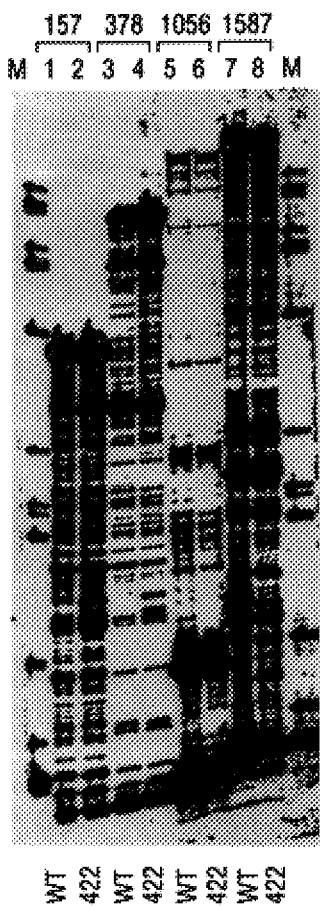
FIG. 33 shows an autoradiograph of a gel resolving the products of cleavage reactions run using either a wild-type or mutant tyrosinase substrate varying in length from 157 nucleotides to 1.587 kb.

In FIG. 33, lanes marked "M" contain molecular weight markers prepared as described in Example 10. Lanes 1, 3, 5 and 7 contain cleavage products using the 157, 378, 1056 or 1587 nucleotide sense strand fragment from the wild-type tyrosinase gene, respectively. Lanes 2, 4, 6 and 8 contain cleavage products using the 157, 378, 1056 or 1587 nucleotide sense strand fragment from the 422 mutant tyrosinase gene, respectively.

As shown in FIG. 33, the clear pattern of cleavages seen between the wild type and 422 mutant was not obscured when the single base change was located in longer DNA fragments. Thus, the cleavage reaction of the invention can be used to scan large fragments of DNA for mutations. Fragments greater than about 500 bp in length cannot be scanned using existing methodologies such as SSCP or DGGE analysis.

EXAMPLE 13

The Cleavase™ Reaction Is Insensitive To Large Changes In Reaction Conditions

The results shown above demonstrated that the enzyme Cleavase™ BN can be used to probe DNA templates in a structure-specific but sequence independent manner. These results demonstrated that the enzyme Cleavase™ BN could be used as an efficient way to recognize conformational changes in nucleic acids caused by sequence variations. This suggested that the 5' nuclease activity of the enzyme Cleaveseu BN could be used to develop a method to scan nucleic acid templates for sequence alterations relative to a wild-type template. The experiments below showed that this was the case. Furthermore it is demonstrated below that the method of the invention is relatively insensitive to large changes in conditions thereby making the method suitable for practice in clinical laboratories.

First, the effect of varying the concentration of $MnCl_2$ on the cleavage reaction was determined. Second, the effect of different amounts of salt (KCl) on the cleavage pattern was examined. Third, a time course was performed to investigate when complete cleavage was obtained. Fourth, a temperature titration was performed to determine the effect of temperature variations on the cleavage pattern. Next, the enzyme was titrated to determine the effect of a 50-fold variation in enzyme concentration on the cleavage reaction. The results of these experiments showed that the Cleavase™ reaction is remarkably robust to large changes in conditions.

a) $MnCl_2$ Titration

To determine the sensitivity of the cleavage reaction to fluctuations in the concentration of $MnCl_2$, a single template was incubated in the presence of a fixed amount of the enzyme Cleavase™ BN (250 ng) in a buffer containing 10 mM MOPS, pH 8.2 and various amount of $MnCl_2$. The cleavage reaction was performed as follows. One hundred fmoles of the 157 nucleotide sense strand fragment of the tyrosinase gene (SEQ ID NO:55; prepared by asymmetric PCR as described in Example 11) was placed in a 200 μl thin wall microcentrifuge tube (BioRad) in 5 μl of 1× CFLP™ buffer with 0, 2, 4, 8, 12 or 20 mM $MnCl_2$ (to yield a final concentration of either 0, 1, 2, 4, 6, 8 or 10 mM $MnCl_2$). A tube containing 100 finoles template DNA in 5 μl of IX CFLP™ buffer with 10 $MnCl_2$ was prepared and served as the no enzyme (or uncut) control. Each reaction mixture was overlaid with a drop of light mineral oil. The tubes were heated to 95° C. for 5 sec and then cooled to 65° C.

Cleavage reactions were started immediately by the addition of a diluted enzyme mixture comprising 1 μl of the enzyme Cleavase™ BN [250 ng/μl in 1× dilution buffer (0.5% NP40, 0.5% Tween 20, 20 mM Tris-HCl, pH 8.0, 50 mM KCl, 10 μg/ml BSA)] in 5 μl of 1× CFLP™ buffer without $MnCl_2$. The enzyme solution was at room temperature before addition to the cleavage reaction. After 5 minutes at 65° C., the reactions were stopped by the addition of 8 μl of stop buffer. Samples were heated to 72° C. for 2 minutes and 8 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega Corp., Madison WI) and exposed to X-ray film as described in Example 10. The resulting autoradiograph is shown in FIG. 34.

Figure 34:
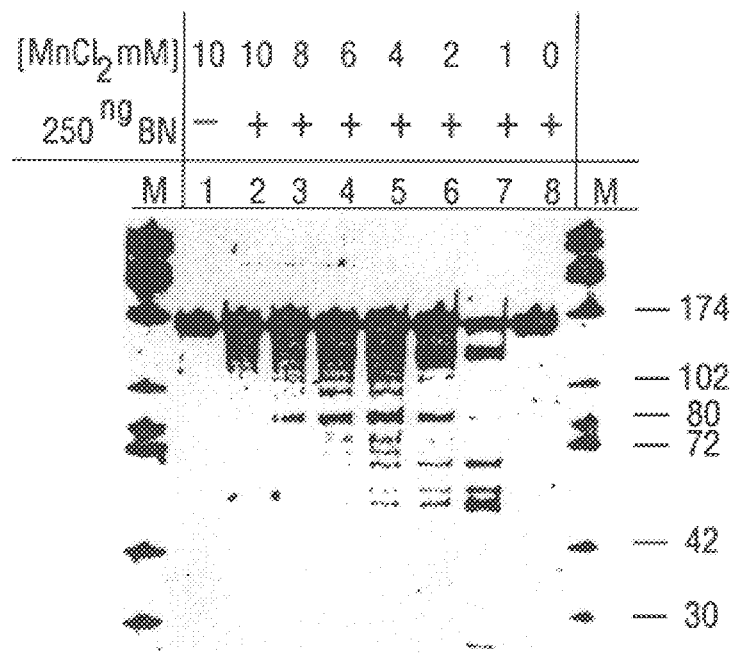
FIG. 34 shows an autoradiograph of a gel resolving the products of cleavage reactions run in various concentrations of $MnCl_2$.

In FIG. 34, lanes marked "M" contain molecular weight markers. Lane 1 contains the no enzyme control and shows the migration of the uncleaved template DNA. Lanes 2 through 8 contain reaction products incubated in the presence of the enzyme CleavaseTm BN in a buffer containing 10, 8, 6, 4, 2, 1, or 0 mM $MnCl_2$, respectively.

FIG. 34 shows that no cleavage occurs in the absence of divalent cations (lane 8, 0 mM $MnCl_2$). Efficient production of cleavage fragments was promoted by the inclusion of $MnCl_2$. The most distinct pattern of cleavage seen at 1 mM $MnCl_2$ (lane 7), but little change in the pattern was seen when the $Mn^{2+}$ concentration varied from 1 to 4 mM; High concentrations of $MnCl_2$ tend to suppress the cleavage reaction (concentrations above 6 mM). These results show that the cleavage reaction requires a divalent cation but that changes in the amount of divalent cation present have little effect upon the cleavage pattern.

b) Effect Of Salt Concentration On The Cleavage Reaction

To determine the effect of salt concentration upon the cleavage reaction, a single template was incubated in the presence of a fixed amount of the enzyme Cleavase™ BN (250 ng) in a buffer containing 10 mM MOPS, pH 8.2, 1 mM $MnCl_2$ and various amount of KCl.

One hundred fmoles of the 157 base fragment derived from the sense strand of exon 4 of the tyrosinase gene (SEQ ID NO:47; prepared as described in Example 10a) was placed in a 200 μl thin wall microcentrifuge tube (BioRad) in a buffer containing 10 mM MOPS, pH 8.2 and 1 mM $MnCl_2$. KCl was added to give a final concentration of either 0, 10, 20, 30, 40, or 50 mM KCl; the final reaction volume was 10 μl.

A tube containing 10 mM MOPS, pH 8.2, 1 mM $MnCl_2$, 33 fmoles template DNA and 50 mM KCl was prepared and served as the no enzyme (or uncut) control. Each reaction mixture was overlaid with a drop of light mineral oil. The tubes were heated to 95° C. for 5 seconds and then cooled to 65° C.

Cleavage reactions were started immediately by the addition of a diluted enzyme mixture comprising 1 μl of the enzyme Cleavase™ BN [250 ng/μl in 1× dilution buffer (0.5% NP40, 0.5% Tween 20, 20 mM Tris-HCl, pH 8.0, 50 mM KCl, 10 μg/ml BSA)] in 5 μl of 1× CFLP™ buffer without $MnCl_2$. The enzyme solution was at room temperature before addition to the cleavage reaction. After 5 minutes at 65° C., the reactions were stopped by the addition of 8 μl of stop buffer. Samples were heated to 72° C. for 2 minutes and 8 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega Corp., Madison Wis.) and exposed to X-ray film as described in Example 10. The resulting autoradiograph is shown in FIG. 35.

Figure 35:
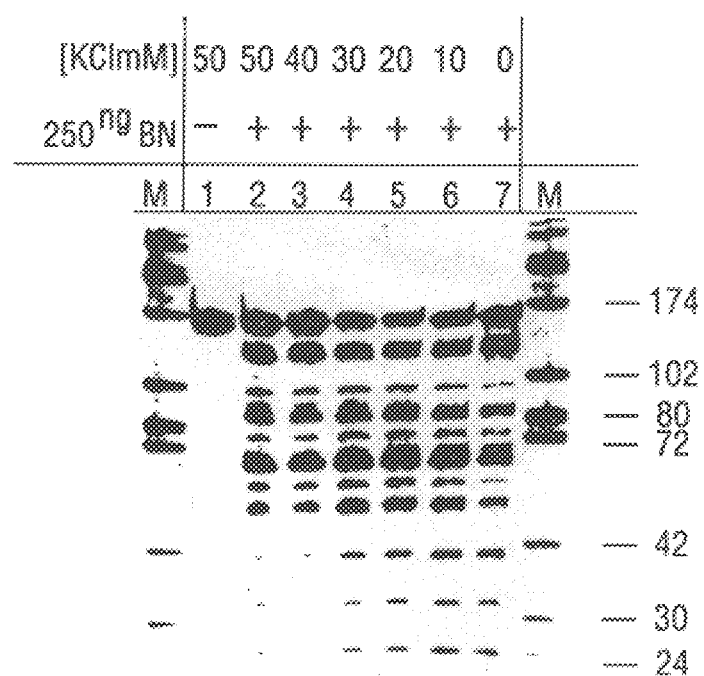
FIG. 35 shows an autoradiograph of a gel resolving the products of cleavage reactions run in various concentrations of KCl.

In FIG. 35, lanes marked "M" contain molecular weight markers. Lane 1 contains the no enzyme control and shows the migration of the uncleaved template DNA. Lanes 2 through 7 contain reaction products incubated in the presence of the enzyme Cleavase™ BN in a buffer containing 50, 40, 30, 20, 10 or 0 mM KCl, respectively.

The results shown in FIG. 35 show that the Cleavase™ reaction is relatively insensitive to variations in salt concentration. The same cleavage pattern was obtained when the 157 nucleotide tyrosinase DNA template (SEQ ID NO:47) was incubated with the enzyme Cleavase™ regardless of whether the KCl concentration varied from 0 to 50 mM.

c) Time Course Of The Cleavage Reaction

To determine how quickly the cleavage reaction is completed, a single template was incubated in the presence of a fixed amount of the enzyme Cleavase™ BN for various lengths of time. A master mix comprising 20 μl of a solution containing 1× CFLP™ buffer, 2 mM MnCl$_2$, and 400 fmoles of the 157 base fragment derived from the sense strand of exon 4 of the tyrosinase gene [(SEQ ID NO:47); prepared as described in Example 10b] was made. Five microliter aliquots were placed in 200 μl thin wall microcentrifuge tube (BioRad) for each time point examined. A no enzyme control tube was run; this reaction contained 33 fmoles of the template DNA in 1× CFLP™ buffer with 1 mM MnCl$_2$ (in a final reaction volume of 10μl). The solutions were overlaid with one drop of light mineral oil. The tubes were brought to 95° C. for 5 seconds to denature the templates and then the tubes were cooled to 65° C.

Cleavage reactions were started immediately by the addition of a diluted enzyme mixture comprising 1 μl of the enzyme Cleavase™ BN [250 ng per μl in 1× dilution buffer (0.5% NP40, 0.5% Tween 20, 20 mM Tris-HCl, pH 8.0, 50 mM KCl, 10 μg/ml BSA)] in 5 μl of 1× CFLP™ buffer without MnCl$_2$. Immediately at the indicated time points, the reaction was stopped by the addition of 8 μl of 95% formamide containing 20 mM EDTA and 0.05% each xylene cyanol and bromophenol blue. The no enzyme control was incubated at 65° C., for 10 minutes and treated in the same manner as the other reactions by the addition of 8 μl of stop buffer. Samples were heated to 72° C. for 2 minutes and 5 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega Corp., Madison Wis.) and exposed to X-ray film as described in Example 10b. The resulting autoradiograph is shown in FIG. 36.

In FIG. 36, lanes marked "M" contain molecular weight markers prepared as described in Example 10. Lane 1 contains the no enzyme control incubated for 10 minutes. Lanes 2–5 contain the cleavage products from reactions incubated for 0.1, 1, 5 or 10 minutes at 65° C. FIG. 36 shows that the cleavage reaction mediated by the enzyme Cleavase™ BN is very rapid. Cleavage is already apparent at less than 6 seconds (<0.1 min) and is complete within one minute. These results also show that the same pattern of cleavage is produced whether the reaction is run for 1 or 10 minutes.

d) Temperature Titration Of The Cleavase Reaction

To determine the effect of temperature variation on the cleavage pattern, the 157 base fragment derived from the sense strand of exon 4 of the tyrosinase gene (SEQ ID NO:47) was incubated in the presence of a fixed amount of the enzyme Cleavase™ BN for 5 minutes at various temperatures. One hundred fmoles of substrate DNA (prepared as described in Example 10b) was placed in a 200 μl thin wall microcentrifuge tube (BioRad) in 5 μl of 1× CFLP™ buffer with 2 mM MnCl$_2$. Two "no enzyme" test control tubes were set-up as above with the exception that these reactions contained 33 fmoles of substrate DNA in 10 μl of the above buffer with 1 mM MnCl$_2$. The solution was overlaid with one drop of light mineral oil. Tubes were brought to 95° C. for 5 seconds to denature the templates and then the tubes were cooled to the desired temperature.

Cleavage reactions were started immediately by the addition of a diluted enzyme mixture comprising 1 μl of the enzyme Cleavase™ BN [250 ng per μl in 1× dilution buffer (0.5% NP40, 0.5% Tween 20, 20 mM Tris-HCl, pH 8.0, 50 mM KCl, 10 μg/ml BSA)] in 5 μl of 1× CFLP™ buffer without MnCl$_2$. The tubes placed at either 55°, 60°, 65°, 70°, 75° or 80° C. After 5 minutes at a given temperature, the reactions were stopped by the addition of 8 μl of stop buffer.

Samples were heated to 72° C. for 2 minutes and 5 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega Corp., Madison Wis.) and exposed to X-ray film as described in Example 10. The resulting autoradiograph is shown in FIG. 37.

Figure 37:
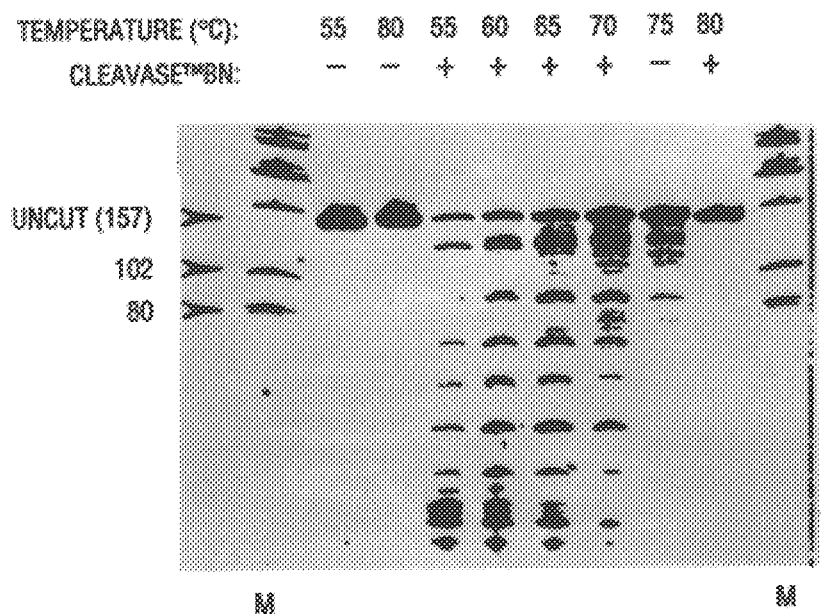
FIG. 37 shows an autoradiograph of a gel resolving the products of cleavage reactions run at different temperatures.
Figure 38:
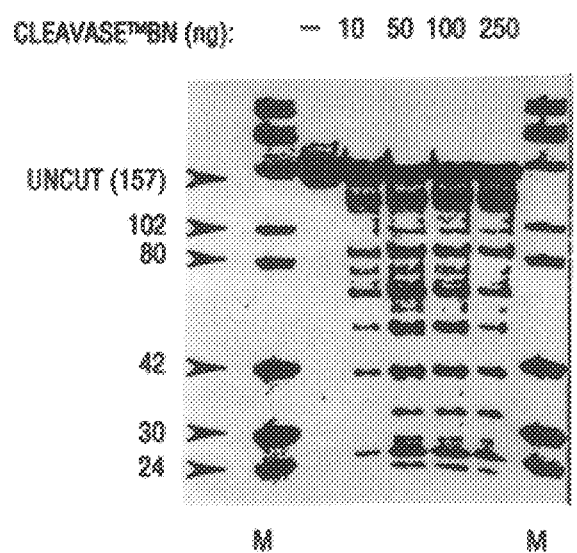

In FIG. 37, the lanes marker "M" contain molecular weight markers prepared as described in Example 10. Lanes 1 and 2 contain no enzyme controls incubated at 55° C. and 80° C., respectively. Lanes 3–8 contain the cleavage products from the enzyme Cleavase™-containing reactions incubated at 55° C., 60° C., 65° C., 70° C., 75° C. or 80° C., respectively.

FIG. 37 shows that the Cleavase™ reaction can be performed over a wide range of temperatures. The pattern of cleavages changed progressively in response to the temperature of incubation, in the range of 55° C. to 75° C. Some bands were evident only upon incubation at higher temperatures. Presumably some structures responsible for cleavage at the intermediate temperatures were not favored at the lower temperatures. As expected, cleavages became progressively less abundant in the high end of the temperature range tested as structures were melted out. At 80° C. cleavage was inhibited completely presumably due to complete denaturation of the template.

These results show that the cleavage reaction can be performed over a wide range of temperatures. The ability to run the cleavage reaction at elevated temperatures is important. If a strong (i.e., stable) secondary structure is assumed by the templates, a single nucleotide change is unlikely to significantly alter that structure, or the cleavage pattern it produces. Elevated temperatures can be used to bring structures to the brink of instability, so that the effects of small changes in sequence are maximized, and revealed as alterations in the cleavage pattern.within the target template, thus allowing the cleavage reaction to occur at that point.

e) Titration Of The Enzyme Cleavase™ BN

The effect of varying the concentration of the enzyme Cleavase™ BN in the cleavage reaction was examined. One hundred fmoles of the 157 base fragment derived from the sense strand of exon 4 of the tyrosinase gene (SEQ ID NO:47) was placed in 4 microcentrifuge tubes in 5 μl of 1× CFLP™ buffer with 2 mM $MnCl_2$. A no enzyme control tube was run; this reaction contained 33 fmoles of substrate DNA in 10 μl of 1× CFLP™ buffer containing 1 mM $MnCl_2$. The solutions were overlaid with one drop of light mineral oil. The tubes were brought to 95° C. for 5 seconds to denature the templates and then the tubes were cooled to 65° C.

Cleavage reactions were started immediately by the addition of a diluted enzyme mixture comprising 1 μl of the enzyme Cleavase™ BN in 1× dilution buffer such that 10, 50, 100 or 250 ng of enzyme was in the tubes in 5 μl of 1× CFLP™ buffer without $MnCl_2$. After 5 minutes at 65° C., the reactions were stopped by the addition of 8 μl of stop buffer. The samples were heated to 72° C. for 2 minutes and 7 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega Corp., Madison Wis.) and exposed to X-ray film as described in Example 10. The resulting autoradiograph is shown in FIG. 38.

Figure 38:
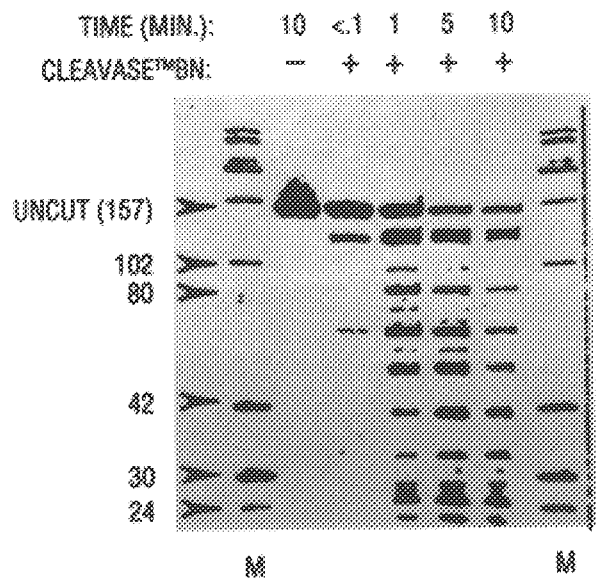
FIG. 38 shows an autoradiograph of a gel resolving the products of cleavage reactions run using different amounts of the enzyme Cleavase™ BN.

The lanes marked "M" in FIG. 38 contain molecular weight markers. Lane 1 contains the no enzyme control and shows the migration of the uncut substrate. Lanes 2–5 contain reaction products from reactions containing 10, 50, 100 or 250 ng of the enzyme Cleavase™ BN, respectively.

These results show that the same cleavage pattern was obtained using the 157 nucleotide tyrosinase DNA substrate regardless of whether the amount of enzyme used in the reaction varied over a 25-fold range. Thus, the method is ideally suited for practice in clinical laboratories where reactions conditions are not as controlled as in research laboratories.

f) Consistent Cleavage Patterns Are Obtained Using Different DNA Preparations

To demonstrate that the same cleavage pattern is consistently obtain from a given substrate, several different preparations of the 157 base fragment derived from the sense strand of exon 4 of the tyrosinase gene (SEQ ID NO:47) were generated. The substrate was generated as described in Example 10b. Three independent PCR reactions performed on separate days were conducted. One of these PCR samples was split into two and one aliquot was gel-purified on the day of generation while the other aliquot was stored at 4° C. overnight and then gel-purified the next day.

Cleavage reactions were performed as described in Example 10b. Samples were run on an acrylamide gel and processed as described in Example 10b. The resulting autoradiograph is shown in FIG. 39.

Figure 39:
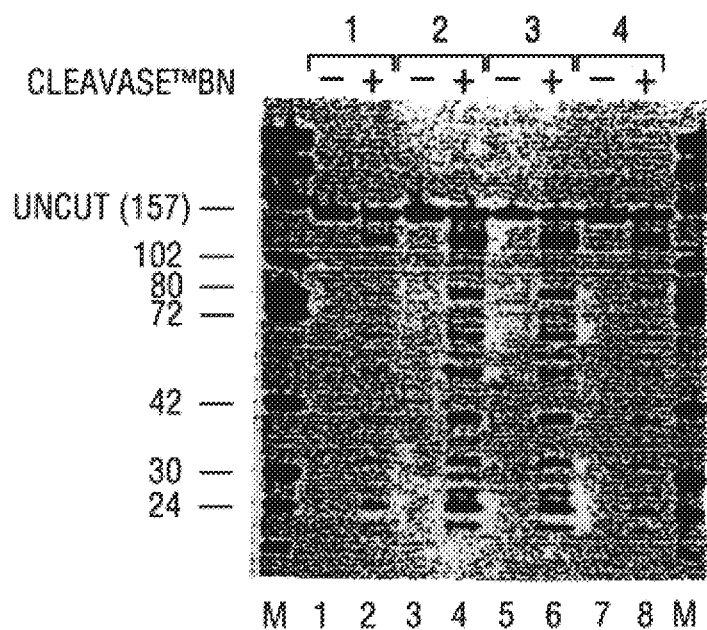
FIG. 39 shows an autoradiograph of a gel resolving the products of cleavage reactions run using four different preparations of the DNA substrate.

In FIG. 39, the lanes marked "M" contain biotinylated molecular weight markers. Set 1 contains the products from a cleavage reaction performed in the absence (−) or presence (+) of enzyme on preparation no. 1. Set 2 contains the products from a cleavage reaction performed in the absence (−) or presence (+) of enzyme on preparation no. 2. Set 3 contains the products from a cleavage reaction performed in the absence (−) or presence (+) of enzyme on preparation no. 3. Preparation no. 3 was derived from preparation 2 and is identical except that preparation no. 3 was gel-purified one day after preparation no. 2. Set 4 contains the products from a cleavage reaction performed in the absence (−) or presence (+) of enzyme on preparation no. 4. The same pattern of cleavage products is generated from these independently prepared substrate samples.

These results show that independently produced preparations of the 157 nucleotide DNA fragment gave identical cleavage patterns. Thus, the Cleavase™ reaction is not effected by minor differences present between substrate preparations.

EXAMPLE 14

Point Mutations Are Detected Using Either The Sense Or Anti-Sense Strand Of The Tyrosinase Gene The ability of the enzyme Cleavase™ to create a unique pattern of cleavage products (i.e., a fingerprint) using either the sense (coding) or anti-sense (non-coding) strand of a gene fragment was examined.

Single stranded DNA substrates corresponding to either the sense (SEQ ID NO:47) or anti-sense strand (SEQ ID NO:48) of the 157 nucleotide fragment derived from the wild-type tyrosinase gene were prepared using asymmetric PCR as described in Example 10a. The sense strand wild-type substrate contains a biotin label at the 5' end; the anti-sense strand contains a fluorescein label at the 5' end.

A single stranded DNA substrate corresponding to the sense strand of the 157 nucleotide fragment derived from the 419 mutant tyrosinase gene (SEQ ID NO:54) was prepared using asymmetric PCR as described in Example 11. The sense strand 419 mutant substrate contains a biotin label at the 5' end.

A single stranded DNA substrate corresponding to the anti-sense strand of the 157 nucleotide fragment derived from the 419 mutant tyrosinase gene (SEQ ID NO:65) was prepared using asymmetric PCR as described in Example 11 with the exception that 100 pmoles of the fluorescein-labeled anti-sense primer (SEQ ID NO:43) and 1 pmole of the biotin-labelled sense primer (SEQ ID NO:42) were used.

The resulting anti-sense strand 419 mutant substrate contains a fluorescein label at the 5' end.

A single stranded DNA substrate corresponding to the sense strand of the 157 nucleotide fragment derived from the 422 mutant tyrosinase gene (SEQ ID NO:55) was prepared using asymmetric PCR as described in Example 11. The sense strand 422 mutant substrate contains a biotin label at the 5' end.

A single stranded DNA substrate corresponding to the anti-sense strand of the 157 nucleotide fragment derived from the 422 mutant tyrosinase gene (SEQ ID NO:66) was prepared using asymmetric PCR as described in Example 11 with the exception that 100 pmoles of the fluorescein-labeled anti-sense primer (SEQ ID NO:43) and 1 pmole of the biotin-labelled sense primer (SEQ ID NO:42) were used. The resulting anti-sense strand 422 mutant substrate contains a fluorescein label at the 5' end.

Following asymmetric PCR, the single stranded PCR products were gel purified, precipitated and resuspended in 40 µl of TE buffer as described in Example 10.

Cleavage reactions were performed as described in Example 11. Following the cleavage reaction, the samples were resolved by electrophoresis as described in Example 10a. After electrophoresis, the gel plates were separated allowing the gel to remain flat on one plate. A 0.2 µm-pore positively-charged nylon membrane (Schleicher and Schuell, Keene, N.H.), pre-wetted in 0.5× TBE (45 mM Tris-Borate, pH 8.3, 1.4 mM EDTA), was laid on top of the exposed acrylamide gel. All air bubbles trapped between the gel and the membrane were removed. Two pieces of 3MM filter paper (Whatman) were then placed on top of the membrane, the other glass plate was replaced, and the sandwich was clamped with binder clips. Transfer was allowed to proceed overnight. After transfer, the membrane was carefully peeled from the gel and allowed to air dry. After complete drying, the membrane was washed twice in 1.5× Sequenase Images Blocking Buffer (United States Biochemical) for 30 minutes/wash. Three tenths of a ml of the buffer was used per cm$^2$ of membrane. The following reagents were added directly to the blocking solution: a streptavidin-alkaline phosphatase conjugate (SAAP, United States Biochemical) added at a 1:4000 final dilution and an anti-fluorescein antibody (Fab)-alkaline phosphatase conjugate (Boehringer Mannheim Biochemicals, Indianapolis, Ind.) added at a 1:20,000 final dilution. The membrane was agitated for 15 minutes. The membrane was rinsed briefly with H$_2$O and then washed 3 times (5 minutes/wash) in 1× SAAP buffer (100 mM Tris-HCl, pH 10; 50 mM NaCl) with 0.05% SDS and 0.025% Tween 20 using 0.5 ml buffer/cm$^2$ of the buffer, with brief H$_2$O rinses between each wash. The membrane was then washed once in 1× SAAP buffer without SDS or Tween 20, drained thoroughly and placed in a plastic heat-sealable bag. Using a sterile pipet tip, 0.05 ml/cm$^2$ of CDP-Star™ (Tropix, Bedford, Mass.) was added to the bag and distributed over the entire membrane for 5 minutes. The bag was drained of all excess liquid and air bubbles. The membrane was then exposed to X-ray film (Kodak XRP) for an initial 30 minutes. Exposure times were adjusted as necessary for resolution and clarity. The resulting autoradiograph is shown in FIG. 40.

Figure 40:
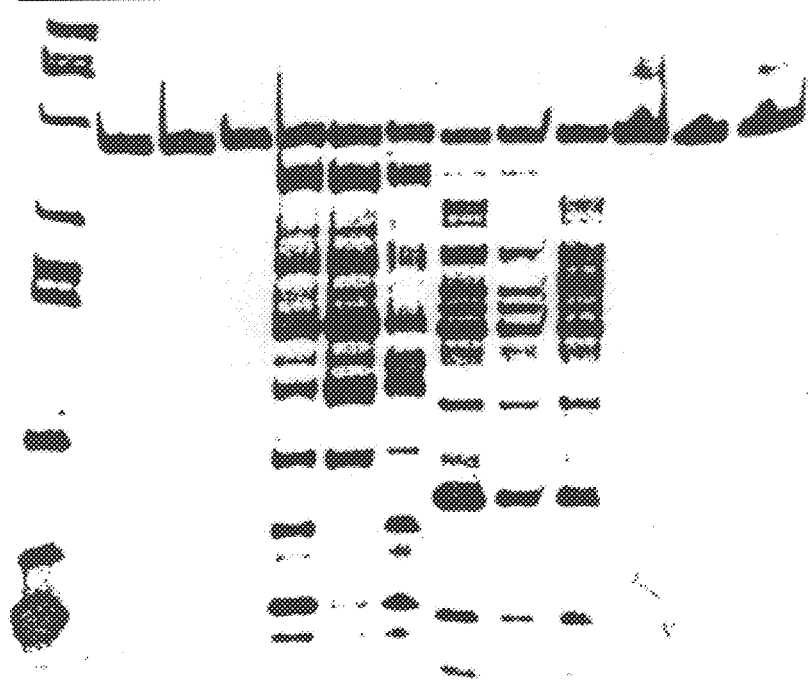
FIG. 40 shows an autoradiograph of a gel resolving the products of cleavage reactions run on either the sense or antisense strand of four different tyrosinase gene substrates.

In FIG. 40, lanes marked "M" contain biotinylated molecular weight markers prepared as described in Example 10. Lanes 1–6 contain biotinylated sense strand substrates from the wild-type, 419 and 422 mutant 157 nucleotide fragments. Lanes 1–3 contain no enzyme controls for the wild-type, 419 and 422 mutant fragments, respectively. Lanes 4–6 contain the reaction products from the incubation of the sense strand of the wild-type, 419 and 422 mutant fragments with the enzyme Cleavase™ BN, respectively. Lanes 7–12 contain fluoresceinated anti-sense strand substrates from the wild-type, 419 and 422 mutant 157 nucleotide fragments. Lanes 1–3 contain "no enzyme" controls for the wild-type, 419 and 422 mutant fragments, respectively. Lanes 4–6 contain the reaction products from the incubation of the anti-sense strand of the wild-type, 419 and 422 mutant fragments with the enzyme Cleavase™ BN, respectively.

As expected, distinct but unique patterns of cleavage products are generated for the wild-type, 419 and 422 mutant fragments when either the sense or anti-sense fragment is utilized. The ability to use either the sense or anti-sense strand of a gene as the substrate is advantageous because under a given set of reaction conditions one of the two strands may produce a more desirable banding pattern (i.e., the cleavage products are spread out over the length of the gel rather than clustering at either end), or may have a mutation more favorably placed to create a significant structural shift. This could be more important in the analysis of long DNA substrates which contain mutations closer to one end or the other. Additionally, detection on both strands serves as a confirmation of a sequence change.

EXAMPLE 15

Detection Of Mutations In The Human Beta-Globin Gene Using The Enzyme Cleavase™

The results shown in Examples 10–14 showed that the Cleavase™ reaction could be used to detect single base changes in fragments of the tyrosinase gene ranging from 157 nucleotides to 1.6 kb. To demonstrate that the Cleavase™ reaction is generally applicable for the detection of mutations, a second model system was examined.

The human β-globin gene is known to be mutated in a number of hemoglobinopathies such as sickle cell anemia and β-thalassemia. These disorders generally involve small (1 to 4) nucleotide changes in the DNA sequence of the wild type β-globin gene [Orkin, S. H. and Kazazian, H. H., Jr. (1984) Annu. Rev. Genet. 18:131 and Collins, F. S. and Weissman, S. M. (1984) Prog. Nucleic Acid Res. Mol. Biol. 31:315]. At least 47 different mutations in the β-globin gene have been identified which give rise to a β-thalassemia.

Three β-globin mutants were compared to the wild type β-globin gene [Lawn, R. M., et al. (1980) Cell 21:647] using the Cleavase™ reaction. Mutant 1 contains a nonsense mutation in codon 39; the wild-type sequence at codon 39 is CAG; the mutant 1 sequence at this codon is TAG [Orkin, S. H. and Goff, S. C. (1981) J. Biol. Chem. 256:9782]. Mutant 2 contains a T to A substitution in codon 24 which results in improper splicing of the primary transcript [Goldsmith, M. E., et al. (1983) Proc. Natl. Acad. Sci. USA 80:2318]. Mutant 3 contains a deletion of two A residues in codon 8 which results in a shift in the reading frame; mutant 3 also contains a silent C to T substitution in codon 9 [Orkin, S. H. and Goff, S. C. (1981) J. Biol. Chem. 256:9782].

a) Preparation Of Wild Type And Mutant β-Globin Gene Substrates

Single stranded substrate DNA was prepared from the above wild type and mutant β-globin genes as follows. Bacteria harboring the appropriate plasmids were streaked onto antibiotic plates and grown overnight at 37° C. (bacteria with the wild-type plasmid and the plasmid containing the mutant 3, were grown on tetracycline plates;

bacteria with the plasmids containing the mutant 1 and mutant 2 sequences were grown on ampicillin plates). Colonies from the plates were then used to isolate plasmid DNAs using the Wizard Minipreps DNA Purification System (Promega Corp., Madison, Wis.). The colonies were resuspended in 200 μl of "Cell Resuspension Buffer" from the kit. The DNA was extracted according to the manufacturers protocol. Final yields of approximately 2.5 μg of each plasmid were obtained.

A 536 (wild-type, mutants 1 and 2) or 534 (mutant 3) nucleotide fragment was amplified from each of the above plasmids in polymerase chain reactions comprising 5 ng of plasmid DNA, 25 pmoles each of 5'-biotinylated KM29 primer (SEQ ID NO:67) and 5'-fluorescein labeled RS42 primer (SEQ ID NO:68), 50 μM each dNTP and 1.25 units of Taq DNA Polymerase in 50 μl of 20 mM Tris-Cl, pH 8.3, 1.5 mM $MgCl_2$, 50 mM KCl with 0.05% each Tween-20 and Nonidet P-40. The reactions were overlaid with 2 drops of light mineral oil and were heated to 95° C. for 30 seconds, cooled to 55° C. for 30 seconds, heated to 72° C. for 60 seconds, for 35 repetitions in a thermocycler (MJ Research, Watertown, Mass.). The products of these reactions were purified from the residual dNTPs and primers by use of a Wizard PCR Cleanup kit (Promega Corp., Madison, Wis.), leaving the duplex DNA in 50 μl of 10 mM Tris-CL, pH 8.0, 0.1 mM EDTA.

To generate single stranded copies of these DNAs, the PCRs described above were repeated using 1 μl of the duplex PCR DNA as template, and omitting the RS42 primer. The products of this asymmetric PCR were loaded directly on a 6% polyacrylamide gel (29:1 cross-link) in a buffer of 45 mM Tris-Borate, pH 8.3, 1.4 mM EDTA, alongside an aliquot of the original PCR DNA to identify the location of the double-strand DNA product. After electrophoretic separation, the DNAs were visualized by staining with ethidium bromide and the single stranded DNAs, identified by altered mobility when compared to the duplex DNAs, were excised and eluted from the gel slices by passive diffusion overnight into a solution comprising 0.5M $NH_4OAc$, 0.1% SDS and 0.2 mM EDTA. The products were collected by ethanol precipitation and dissolved in 40 μl of 10 mM Tris-Cl, pH 8.0, 0.1 mM EDTA.

The sequence of the 536 nucleotide fragment from the wild-type β-globin gene is listed in SEQ ID NO:69. The sequence of the 534 nucleotide fragment from mutant 3 is listed in SEQ ID NO:70. The sequence of the 536 nucleotide fragment from mutant 1 is listed in SEQ ID NO:71. The sequence of the 536 nucleotide fragment from mutant 2 is listed in SEQ ID NO:72.

b) Optimization Of The Cleavage Reaction Using The Wild-Type Beta-Globin Substrate The optimal conditions (salt concentration, temperature) which produce an array of cleavage products having widely differing mobilities from the β-globin substrate were determined. Conditions which produce a cleavage pattern having the broadest spread array with the most uniform intensity between the bands were determined (the production of such an array of bands aids in the detection of differences seen between a wild-type and mutant substrate). This experiment involved running the cleavage reaction on the wild type β-globin substrate (SEQ ID NO:69) at several different temperatures in the presence of either no KCl or 50 mM KCl.

For each KCL concentration to be tested, 30 μl of a master mix containing DNA, CFLP™ buffer and salts was prepared. For the "0 mM KCl" reactions, the mix included approximately 500 fmoles of single-stranded, 5' biotinylated 536-mer PCR DNA from plasmid pHBG1 in 30 μl of 1× CFLP™ buffer (10 mM MOPS, pH 8.2) with 1.7 mM $MnCl_2$ (for 1 mM in the final reaction); the "50 mM KCl" mix included 83.3 mM KCl in addition to the above components. The mixes were distributed into labeled reaction tubes in 6 μl aliquots, and stored on ice until use. An enzyme dilution cocktail included 450 ng of the enzyme Cleavase™ BN in 1× CFLP™ buffer without $MnCl_2$.

Cleavage reactions were performed at 60° C., 65° C., 70° C. and 75° C. For each temperature to be tested, a pair of tubes with and without KCl were brought to 95° C. for 5 seconds, then cooled to the selected temperature. The reactions were then started immediately by the addition of 4 μl of the enzyme cocktail. In the 75° C. test, a duplicate pair of tubes was included, and these tubes received 4 μl of 1× CFLP™ buffer without $MnCl_2$ in place of the enzyme addition. No oil overlay was used. All reactions proceeded for 5 minutes, and were stopped by the addition of 8 μl of stop buffer. Completed and yet-to-be-started reactions were stored on ice until all reactions had been performed. Samples were heated to 72° C. for 2 minutes and 5 μl of each reaction was resolved by electrophoresis through a 6% polyacrylamide gel (19:1 cross-link), with 7M urea, in a buffer of 45 mM Tris-Borate, pH 8.3, 1.4 mM EDTA. After electrophoresis, the gel plates were separated allowing the gel to remain flat on one plate. A 0.2 μm-pore positively-charged nylon membrane (NYTRAN, Schleicher and Schuell, Keene, N.H.), pre-wetted in $H_2O$, was laid on top of the exposed gel. All air bubbles were removed. Two pieces of 3MM filter paper (Whatman) were then placed on top of the membrane, the other glass plate was replaced, and the sandwich was clamped with binder clips. Transfer was allowed to proceed overnight. After transfer, the membrane was carefully peeled from the gel and allowed to air dry. After complete drying the membrane was washed in 1.2× Sequenase Images Blocking Buffer (United States Biochemical) using 0.3 ml of buffer/$cm^2$ of membrane. The wash was performed for 30 minutes. A streptavidin-alkaline phosphatase conjugate (SAAP, United States Biochemical) was added to a 1:4000 dilution directly to the blocking solution, and agitated for 15 minutes. The membrane was rinsed briefly with $H_2O$ and then washed three times for 5 minutes per wash using 0.5 ml/$cm^2$ of 1× SAAP buffer (100 mM Tris-HCl, pH 10, 50 mM NaCl) with 0.1% sodium dodecyl sulfate (SDS). The membrane was rinsed briefly with $H_2O$ between each wash. The membrane was then washed once in 1× SAAP/1 mM $MgCl_2$ without SDS, drained thoroughly and placed in a plastic heat-sealable bag. Using a sterile pipet, 5 mls of either CSPD™ or CDP-Star™ (Tropix, Bedford, Mass.) chemiluminescent substrates for alkaline phosphatase were added to the bag and distributed over the entire membrane for 2–3 minutes. The CSPD™-treated membranes were incubated at 37° C. for 30 minutes before an initial exposure to XRP X-ray film (Kodak) for 60 minutes. CDP-Star™ treated membranes did not require preincubation, and initial exposures were for 10 minutes. Exposure times were adjusted as necessary for resolution and clarity. The results are shown in FIG. 41.

Figure 41:
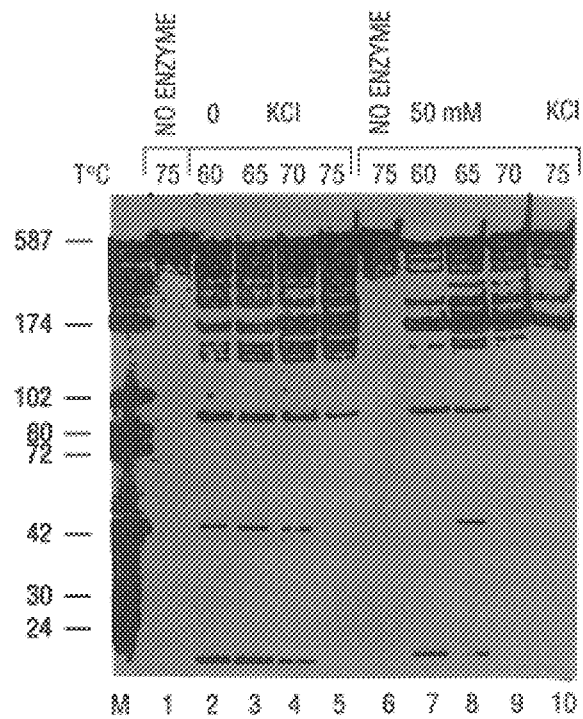
FIG. 41 shows an autoradiograph of a gel resolving the products of cleavage reactions run on a wild-type β-globin substrate in two different concentrations of KCl and at four different temperatures.

In FIG. 41, the lane marked "M" contains molecular weight markers. Lanes 1–5 contain reaction products from reactions run in the absence of KCl. Lane 1 contains the a reaction run without enzyme at 75° C. Lanes 2–5 contain reaction products from reactions run at 60° C., 65° C., 70° C. and 75° C., respectively. Lanes 6–10 contain reaction products from reactions run in the presence of 50 mM KCl. Lane 6 contains the a reaction run without enzyme at 75° C.

Lanes 7–10 contain reaction products from reactions run at 60° C., 65° C., 70° C. and 75° C., respectively.

In general, a preferred pattern of cleavage products was produced when the reaction included 50 mM KCl. As seen in Lanes 7–10, the reaction products are more widely spaced in the 50 mM KCL-containing reactions at every temperature tested as compared to the reactions run in the absence of KCL (lanes 2–5; more of the cleavage products are found clustered at the top of the gel near the uncut substrate). As seen in Lane 7 of FIG. 41, cleavage reactions performed in 50 mM KCl at 60° C. produced a pattern of cleavage products in which the products are maximally spread out, particularly in the upper portion of the gel, when compared to other reaction condition patterns.

From the results obtained in this experiment, the optimal cleavage conditions for the 536 nucleotide sense strand fragment derived from the wild-type β-globin gene (SEQ ID NO:69) were determined to be 1× CFLP™ buffer containing 1 mM MnCl$_2$ and 50 mM KCl at 60° C.

c) Optimization Of The Cleavage Reaction Using Two Mutant Beta-Globin Substrates From the results obtained above in a) and b), 60° C. was chosen as the optimum temperature for the cleavage reaction when a β-globin substrate was to be used. When the wild-type substrate was utilized, running the cleavage reaction in the presence of 50 mM KCl generate the optimal pattern of cleavage products. The effect of varying the concentration of KCl upon the cleavage pattern generated when both wild-type and mutant β-globin substrates were utilized was next examined to determine the optimal salt concentration to allow a comparison between the wild-type and mutant β-globin substrates.

Single stranded substrates, 536 nucleotides in length, corresponding to mutant 1 (SEQ ID NO:71) and mutant 2 (SEQ ID NO:72) mutations were prepared as described above in a). These two mutants each differ from the wild-type sequence by 1 nucleotide; they differ from each other by 2 nucleotides.

For each substrate tested, 39 μl of a master mix containing DNA, CFLP™ buffer and MnCl$_2$ was prepared. These mixes each included approximately 500 fmoles of single-stranded, 5' biotinylated 536 nucleotide substrate DNA, 39 μl of 1× CFLP™ buffer containing 1.54 mM MnCl$_2$ (giving a final concentration of 1 mM MnCl$_2$). The mixes were distributed into labeled reaction tubes in 6.5 μl aliquots. Each aliquot then received 0.5 μl of 200 mM KCl for each 10 mM final KCl concentration (e.g., 2.0 μl added to the 40 mM reaction tube) and all volumes were brought to 9 μl with dH$_2$O. No oil overlay was used. The reactions were brought to 95° C. for 5 seconds, then cooled to 65° C. The reactions were then started immediately by the addition of 50 ng of the enzyme Cleavase™ BN in 1 μl of enzyme dilution buffer (20 mM Tris-HC., pH 8.0, 50 mM KCl, 0.5% NP40, 0.5% Tween 20, 10 μg/ml BSA). All reactions proceeded for 5 minutes, and were stopped by the addition of 8 μl of stop buffer. Samples were heated to 72° C. for 2 minutes and 5 μl of each reaction was resolved by electrophoresis through a 6% polyacrylamide gel (19:1 cross-link), with 7M urea, in a buffer of 45 mM Tris-Borate, pH 8.3, 1.4 mM EDTA.

After electrophoresis, the gel plates were separated and overlaid with a nylon membrane as described above. The DNA was transferred to the membrane and the membrane was treated as described above in b) and then exposed to X-ray film. The resulting autoradiograph is shown in FIG. 42.

Figure 42:
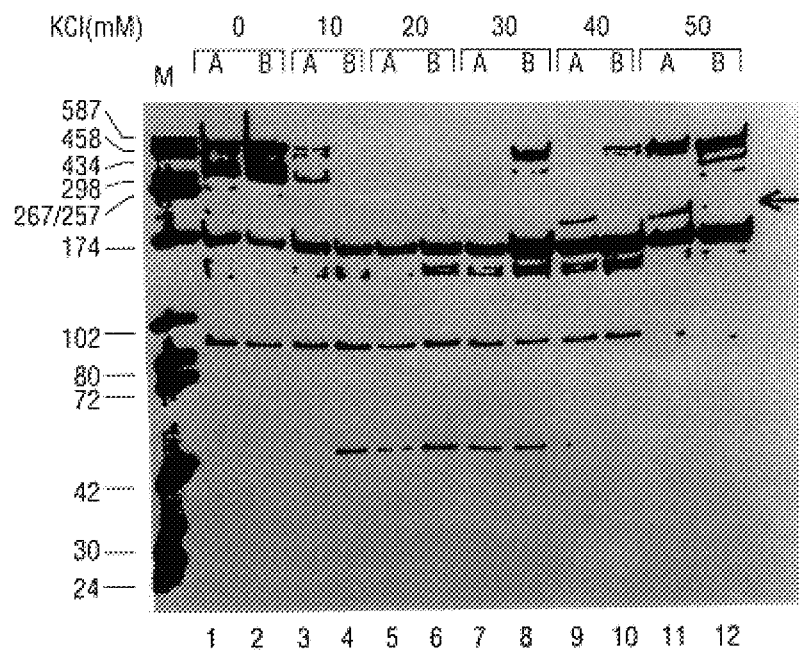
FIG. 42 shows an autoradiograph of a gel resolving the products of cleavage reactions run on two different mutant β-globin substrates in five different concentrations of KCl.

In FIG. 42, the lane marked "M" contains molecular weight markers. Lanes 1, 3, 5, 7, 9 and 11 contain reaction products from cleavage reactions using the mutant 1 substrate in the presence of 0, 10, 20, 30, 40 or 50 mM KCl, respectively. Lanes 2, 4, 6, 8, 10 and 12 contain reaction products from cleavage reactions using the mutant 2 substrate in the presence of 0, 10, 20, 30, 40 or 50 mM KCl, respectively.

FIG. 42 shows that while the pattern of cleavage products generated from each mutant changes as the KCl concentration is increased, distinct patterns are generated from each mutant and differences in banding patterns are seen between the two mutants at every concentration of KCl tested. In the mid-salt ranges (10 to 20 mM KCl), the larger cleavage bands disappear and smaller molecular weight bands appear (lanes 3–6). At higher salt concentrations (30 to 50 mM KCl), the larger molecular weight cleavage bands reappear with the cominant loss of the low molecular weight bands (lanes 7–12). Reaction conditions comprising the use of 50 mM KCl were chosen as optimal from the results show in FIG. 42. Clear differences in the intensities of a band appearing about 200 nucleotides (see arrow in FIG. 42) is seen between the two mutant substrates under these reaction conditions.

d) The Enzyme Cleavase™ Generates Unique Cleavage Products From Wild-Type And Mutant Beta-Globin Substrates From the experiments performed above, the optimal reaction conditions when the wild-type or mutant β-globin substrates were determined to be the use of 50 mM KCl and a temperature of 60° C. These conditions were then used to allow the comparison of the cleavage patterns generated when the wild-type substrate (SEQ ID NO:69) was compared to the mutant 1 (SEQ ID NO:71), mutant 2 (SEQ ID NO:72) and mutant 3 (SEQ ID NO:70) substrates.

Single-stranded substrate DNA, 534 or 536 nucleotides in length, was prepared for the wild-type, mutant 1, mutant 2 and mutant β-globin genes as described above in a). Cleavage reactions were performed as follows. Reaction tubes were assembled which contained approximately 100 fmoles of each DNA substrate in 9 μl of 1.1× CFLP™ buffer (1× final concentration) with 1.1 mM MnCl$_2$ (1 mM final concentration) and 55.6 mM KCl (50 mM final concentration). A "no enzyme" or uncut control was set up for each substrate DNA. The uncut controls contained one third as much DNA ( approximately 33 fmoles) as did the enzyme-containing reactions to balance the signal seen on the autoradiograph.

The tubes were heated to 95° C. for 5 sec, cooled to 60° C. and the reactions were started immediately by the addition of 1 μl of the enzyme Cleavase™ BN (50 ng per μl in 1× dilution buffer). The uncut controls received 1 μl of 1× dilution buffer.

Reactions proceeded for 5 min and then were stopped by the addition of 8 μl of stop buffer. The samples were heated to 72° C. for 2 min and 5 μl of each reaction was resolved by electrophoresis through a 6% polyacrylamide gel (19:1 cross-link), with 7M urea, in a buffer of 45 mM Tris-Borate, pH 8.3, 1.4 mM EDTA.

After electrophoresis, the gel plates were separated and overlaid with a nylon membrane as described above. The DNA was transferred to the membrane and the membrane was treated as described above in b) and then exposed to X-ray film. The resulting autoradiograph is shown in FIG. 43.

Figure 43:
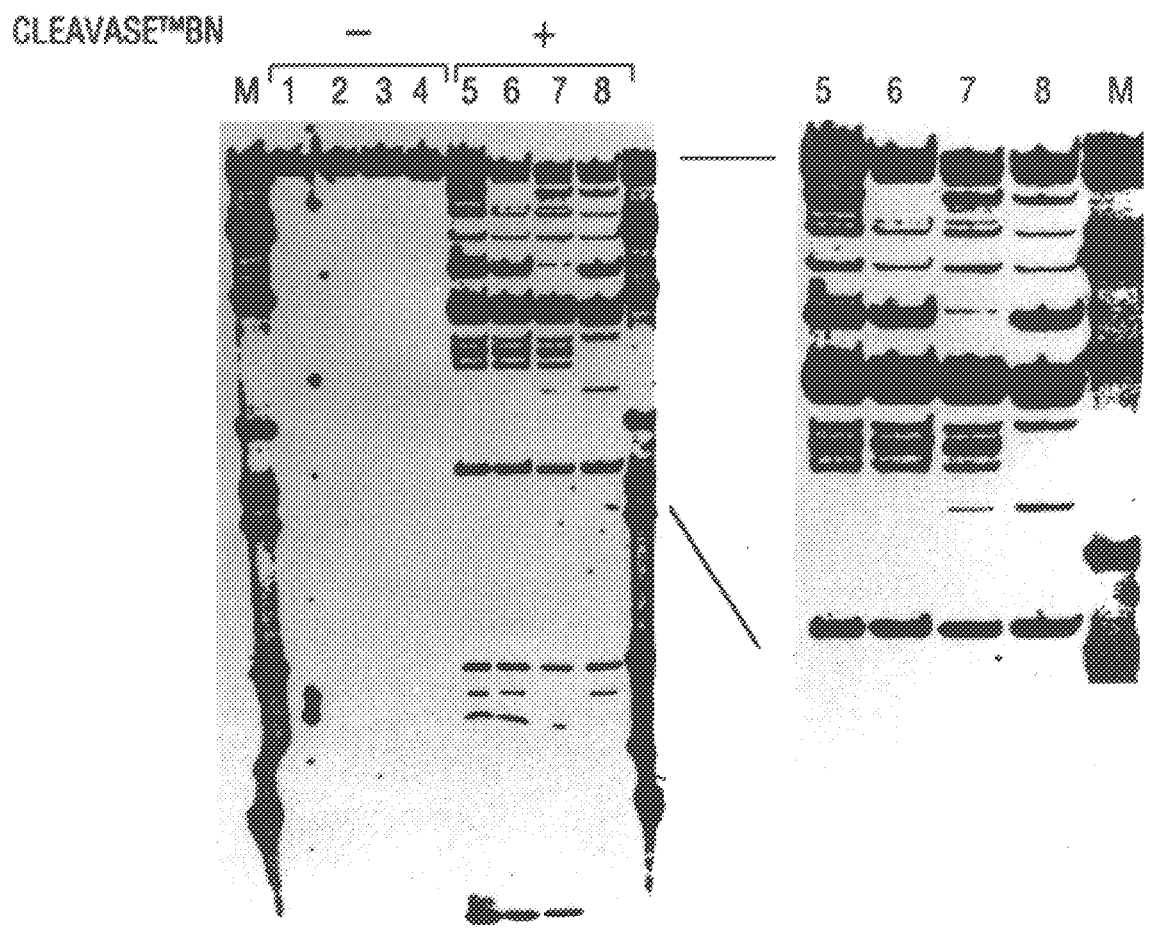
FIG. 43 shows an autoradiograph of a gel resolving the products of cleavage reactions run on a wild-type and three mutant β-globin substrates.

In FIG. 43, two panels are shown. The first panel shows the reaction products from the above cleavage reactions; the uncut controls are shown in lanes 1–4 and the cleavage products are shown in lanes 5–6. The second panel is a magnification of lanes 5–8 to better shown the different banding patterns seen between the substrate DNAs in the upper portion of the gel.

In FIG. 43, the lanes marked "M" contain biotinylated molecular weight markers prepared as described in Example 10. Lanes 1–4 contain the uncut controls for the wild-type, mutant 1, mutant 2 and mutant 3 β-globin substrates, respectively. Lanes 5–8 contain the cleavage products from the wild-type, mutant 1, mutant 2 and mutant 3 substrates, respectively.

From the results shown in FIG. 43, the enzyme Cleavase™ BN generates a unique pattern of cleavage products from each β-globin substrate tested. Differences in banding patterns are seen between the wild-type and each mutant; different banding patterns are seen for each mutant allowing not only a discrimination of the mutant from the wild-type but also a discrimination of each mutant from the others.

The results shown here for the β-globin gene and above for the tyrosinase gene demonstrate that the Cleavase™ reaction provides a powerful new tool for the detection of mutated genes.

EXAMPLE 16

Treatment Of RNA Substrates Generates Unique Cleavage Patterns

The present invention contemplates 5' nuclease cleavage of single- or double-stranded DNA substrates to generate a unique pattern of bands characteristic of a given substrate. The ability of the 5' nuclease activity of the enzyme Cleavase™ BN to utilize RNA as the substrate nucleic acid was next demonstrated. This experiment showed that RNA can be utilized as a substrate for the generation of a cleavage pattern using appropriate conditions (Lowering of the pH to 6.5 from 8.2 to reduce manganese-mediated degradation of the RNA substrate). The experiment was performed as follows.

An RNA transcript internally labelled with biotin was produced to serve as the substrate. The plasmid pGEM3Zf (Promega) was digested with EcoRI. EcoRI cuts the plasmid once generating a linear template. An RNA transcript 64 nucleotides in length (SEQ ID NO:73) was generated by SP6 transcription of the linearized template using a Riboprobe Gemini System kit from Promega, Corp.; the manufacturer's directions were followed with the exception that 25% of the UTP in the reaction was replaced with biotin-UTP (Boehringer Mannheim) to produce an internally labelled transcript. Following the transcription reaction (1 hour at 37° C.), the DNA template was removed by treatment with RQ1 RNase-free DNAse (from the Riboprobe kit and used according to the manufacturer's instructions) and the RNA was collected and purified by precipitating the sample twice in the presence of 2M NH$_4$OAc and ethanol. The resulting RNA pellet was rinsed with 70% ethanol, air dried and resuspended in 40 μl of 10 mM Tris-HCl, pH 8.0 and 1 mM EDTA.

Cleavage reactions contained 1 μl of the above RNA substrate and 50 ng of the enzyme Cleavase™ BN in 10 μl of 1× RNA-CFLP™ buffer (10 mM MOPS, pH 6.3) and 1 mM of either MgCl$_2$ or MnCl$_2$. The reactions were assembled with all the components except the enzyme and were warmed to 45° C. for 30 sec. Reactions were started by the addition of 50 ng of the enzyme Cleavase™ BN in 1 μl of dilution buffer (20 mM Tris-HCl, pH 8.0, 50 mM KCl, 0.5% NP40, 0.5% Tween 20, 10 μg/ml BSA). Reactions proceeded for 10 min and were stopped by the addition of 8 μl of stop buffer. The samples were heated to 72° C. for 2 minutes and 5 μl of each reaction were resolved by electrophoresis through a 10% polyacrylamide gel (19:1 crosslink), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1.2× Sequenase Images Blocking Buffer, treated with 1× SAAP buffer and reacted with Lumiphos-530 (United States Biochemical) or Quantum Yield Chemiluminescent Substrate (Promega) and exposed to X-ray film as described in Example 10b. The resulting autoradiograph is shown in FIG. 44.

Figure 44:
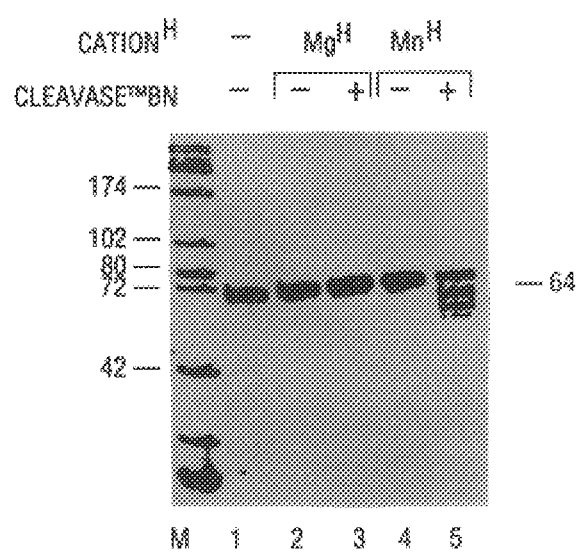
FIG. 44 shows an autoradiograph of a gel resolving the products of cleavage reactions run on an RNA substrate.

In FIG. 44, lanes marked "M" contain molecular weight markers. Lane 1 contains the no enzyme control and shows the migration of the uncut substrate. Lanes 2 and 3 contain reaction products from the incubation of the RNA substrate in a buffer containing MgCl$_2$ in the presence or absence of the enzyme Cleavase™ BN, respectively. Lanes 4 and 5 contain reaction products from the incubation of the RNA substrate in a buffer containing MnCl$_2$ in the presence or absence of the enzyme Cleavase™ BN, respectively. A pattern of cleavage products is seen when the enzyme is incubated with the RNA substrate in the presence of MnCl$_2$, (lane 5).

These results show that the enzyme Cleavase™ can be used to probe RNA substrates for changes in sequence (i.e., point mutations, deletions, substitutions). This capability enables the examination of genes which have very large introns (e.g., greater than 10 kb) interrupting the coding sequences. The spliced RNA transcript represents a simpler target for the scanning for mutations. In addition, the structural (i.e., folding) information gained by cleavage of the RNA would be useful in targeting of hybridization or ribozyme probes to unstructured regions of RNAs. Furthermore, because the cleavage reaction occurs so quickly, the enzyme Cleavase™ can be used to study various types of RNA folding and the kinetics with which this folding occurs.

EXAMPLE 17

The 5' Nuclease Activity From Both Cleavase™ BN And Taq Polymerase Generates Unique Cleavage Patterns Using Double-Stranded DNA Substrates The ability of both the enzyme Cleavase™ BN and Taq polymerase to generate cleavage patterns on single-stranded DNA templates was examined. The substrates utilized in this experiment were the 378 nucleotide fragment from either the wild-type (SEQ ID NO:56) or 422 mutant (SEQ ID NO:57) tyrosinase gene. These single-stranded substrates were generated as described in Example 12a.

Cleavage reactions were performed as described in Example 12b with the exception that half of the reactions were cut with the enzyme Cleavase™ BN as described and a parallel set of reaction was cut with Taq polymerase. The Taq polymerase reactions contained 1.25 units of Taq polymerase in 1× CFLP™ buffer. The reaction products were resolved by electrophoresis and the autoradiograph was generated as described in Example 12b. The autoradiograph is shown in FIG. 45.

Figure 45:
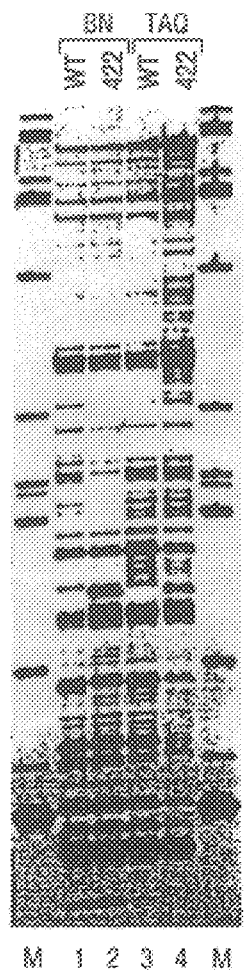
FIG. 45 shows an autoradiograph of a gel resolving the products of cleavage reactions run using either the enzyme Cleavase™ BN or Taq DNA polymerase as the 5' nuclease.

In FIG. 45, lanes marked "M" contain biotinylated molecular weight markers. Lanes 1 and 2 contain the wild-type or 422 mutant substrate cleaved with the enzyme Cleavase™ BN, respectively. Lanes 3 and 4 contain the wild-type or 422 mutant substrate cleaved with Taq polymerase, respectively.

FIG. 45 shows that both the enzyme Cleavase™ BN and Taq polymerase generate a characteristic set of cleavage bands for each substrate allowing the differentiation of the wild-type and 422 mutant substrates. The two enzyme produce similar but distinct arrays of bands for each template.

These results show that the 5' nuclease of both the enzyme Cleavase™ BN and Taq polymerase are useful for practicing the cleavage reaction of the invention. Cleavage with Taq polymerase would find application when substrates are generated using the PCR and no intervening purification step is employed other than the removal of excess nucleotides using alkaline phosphatase

EXAMPLE 18

Multiplex Cleavage Reactions

The above Examples show that the cleavage reaction can be used to generate a characteristic set of cleavage products from single-stranded DNA and RNA substrates. The ability of the cleavage reaction to utilize double-stranded DNA templates was examined. For many applications, it would be ideal to run the cleavage reaction directly upon a double-stranded PCR product without the need to isolate a single-stranded substrate from the initial PCR. Additionally it would be advantageous to be able to analyze multiple substrates in the same reaction tube ("multiplex" reactions).

Cleavage reactions were performed using a double-stranded template which was carried a 5' biotin label on the sense-strand and a 5' fluorescein label on the anti-sense strand. The double-stranded substrate was denatured prior to cleavage. The double-stranded substrate was cleaved using Taq polymerase. Taq polymerase was used in this experiment because it has a weaker duplex-dependent 5' to 3' exonuclease activity than does the enzyme Cleavase™ BN and thus Taq polymerase does not remove the 5' end label from the re-natured DNA duplexes as efficiently as does the enzyme Cleavase™ BN; therefore less signal is lost in the reaction.

The substrate utilized was a 157 bp fragment derived from either the wild-type (SEQ ID NO:47), 419 mutant (SEQ ID NO:54) or 422 mutant (SEQ ID NO:55) of the tyrosinase gene. The wild-type fragment was generated as described in Example 10a, the 419 mutant fragment was generated as described in Example 10a and the 422 mutant fragment was generated as described in Example 11 using PCR. The sense strand primer (SEQ ID NO:42) contains a 5' biotin label and the anti-sense primer (SEQ ID NO:43) contains a 5' fluorescein label resulting in the generation of a double-stranded PCR product label on each strand with a different label. The PCR products were gel purified as described in Example 10a.

The cleavage reactions were performed as follows. Reaction tubes were assembled with approximately 100 fmoles of the double-stranded DNA substrates in 5 µl of 1× CFLP™ buffer, 1 mM MnCl$_2$. The solutions were overlaid with a drop of mineral oil. The tubes were heated to 95° C. for 30 sec and 1 unit of Taq polymerase (Promega) was added. Uncut controls contained 33 fmoles of double-stranded DNA substrates in 5 µl of 1× CFLP™ buffer, 1 mM MnCl$_2$. The reactions were cooled to 65° C. and incubated at this temperature for 15 minutes. The reactions were stopped by the addition of 8 µl of stop buffer. The samples were heated to 72° C. for 2 min and 5 µl of reaction were resolved by electrophoresis through a 10% polyacrylamide gel (19:1 cross-link), with 7M urea in a buffer containing 45 mM Tris-Borate, pH 8.3, 1.4 mM EDTA. The entire set of reactions was loaded in duplicate on the gel such that duplicate nylon membranes containing the full set of reactions were created. After transfer to a nylon membrane (performed as described in Example 10a), the membrane was cut in half; one half was probed using a streptavidin-alkaline phosphatase conjugate to visualize the biotinylated sense-strand products (as described in Example 10a). The other half of the membrane was probed with an anti-fluorescein antibody-alkaline phosphatase conjugate to visualize the fluorescein-labelled anti-sense strand products (as described in Example 5). The blots were visualized using the chemiluminescent procedures described in Examples 10a and 5 for biotin-labeled or fluorescein-labeled DNA, respectively. The autoradiographs are shown side-by side in FIG. 46.

Figure 46:
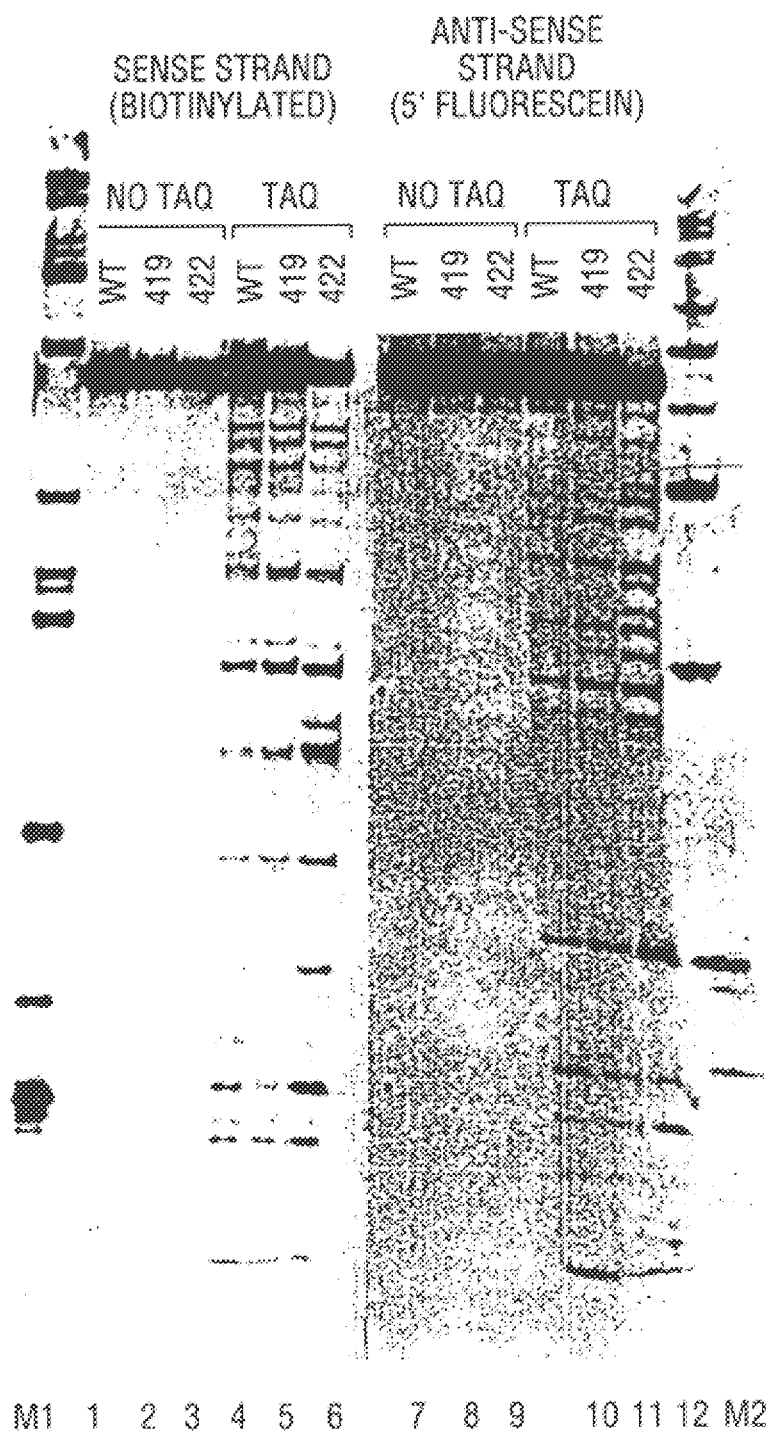
FIG. 46 shows an autoradiograph of a gel resolving the products of cleavage reactions run on a double-stranded DNA substrate to demonstrate multiplexing of the cleavage reaction.

In FIG. 46, the lane labeled "M1" contains biotinylated molecular weight markers prepared as described in Example 10a. The lane labeled "M2" contains molecular weight markers generated by digestion of pUC19 with MspI, followed by Klenow treatment to fill-in the ends. The blunt ends were then labeled with fluoresceinated dideoxynucleotides (Boehringer Mannheim) using terminal transferase (Promega). Lanes M1 and 1–6 were developed using the protocol for biotinylated DNA. Lanes 7–12 and M2 were developed using the protocol for fluorescein-labeled DNA. Note that in all lanes both strands of the substrate are present; only one strand is visualized in a given development protocol.

In FIG. 46, lanes 1–3 and 7–9 contain the "no enzyme" or uncut controls using the wild-type, 419 or 422 mutant substrates, respectively. Lanes 4–6 and 10–12 contain cleavage products from the wild-type, 419 or 422 mutant substrates, respectively. Unique patterns of cleavage products are seen for each strand of each of the three substrates examined. Thus, a single reaction allowed the generation of a unique fingerprint from either the sense or anti-sense strand of each of the three tyrosinase fragments tested.

The results shown in FIG. 46 demonstrate that a cleavage pattern can be generated from a double-stranded DNA fragment by denaturing the fragment before performing the cleavage reaction. Note that in FIG. 46 the cleavage patterns were generated in the course of a single round of heating to denature and cooling to cleave and that much of the substrate remains in an uncut form. This reaction would be amenable to performing multiple cycles of denaturation and cleavage in a thermocycler. Such cycling conditions would increase the signal intensity seen for the cleavage products. Substrates generated by the PCR performed in the standard PCR buffer (50 mM KCl, 10 mM Tris-Cl, pH 8.3, 1.5 mM MgCl$_2$, 0.01% gelatin) can be treated to remove remaining dNTPs (e.g., addition of alkaline phosphatase) and to provide Mn$^{2+}$. Under these conditions the cleavase reaction can be performed on both strands of one or more products generated in that PCR. Such a protocol reduces sample preparation to a minimum resulting in a savings of both time and expense.

The above example also demonstrates that two distinct substrates can be analyzed in a single reaction thereby allowing the "multiplexing" of the cleavage reaction.

EXAMPLE 19

Optimization Of Manganese Ion Concentration For Cleavage Of Double Stranded DNA Substrates As discussed above, it may be desirable to run the cleavage reaction on double-stranded DNA substrates such restriction fragments or segments generated by balanced or symmetric PCR. The effect of varying the concentration of $Mn^{2+}$ in cleavage reactions using double-stranded DNA substrates was investigated. The results shown below demonstrate that the optimal concentration of $Mn^{2+}$ is lower when a double-stranded DNA substrate is employed in the cleavage reaction as compared to single-stranded DNA substrates.

Two double-stranded (ds) DNA substrates, 157 bp in length, derived from the tyrosinase mutants 419 (SEQ ID NO:40) and 422 (SEQ ID NO:84) were prepared by PCR amplification of the exon 4 region of human tyrosinase gene as described above in Example 18. The sense strand of the 419 and 422 tyrosinase mutant substrates contained a biotin-labeled at the 5' end following the PCR. The PCR products were gel purified as described in Example 10a.

The cleavage reactions were performed as follows. Reaction tubes were assembled with approximately 40 fmoles of the ds DNA substrates in 10 μl of water. The tubes were brought to 95° C. for 10 seconds in a PTC-100™ Programmable Thermal Controller (MJ Research, Inc.) to denature the DNA. The cleavage reactions were started by the addition of 10 μl of 2× CFLP™ buffer (pH 8.2) containing 1 μl of the enzyme Cleavase™ BN (25 ng in 1× dilution buffer) and different concentrations of $MnCl_2$ such that the final concentration of $MnCl_2$ in reaction mixture (20 μl final volume) was either 0.5 mM, 0.25 mM, 0.15 mM, 0.1 mM, 0.05 mM and 0 mM. After mixing, the samples were immediately cooled to 65° C. and incubated at this temperature for 5 minutes. The reactions were terminated by placing the samples on ice and adding 10 μl of stop buffer. The samples were heated to 85° C. for 30 sec and 10 μl of each reaction were resolved by electrophoresis through a 10% polyacrylamide gel (19:1 cross-link), with 7M urea in a buffer containing 45 mM Tris-Borate, pH 8.3, 1.4 mM EDTA.

After electrophoresis, the gel plates were separated and overlaid with a nylon membrane as described in Example 10a. The DNA was transferred to the membrane and the membrane was dried, washed in 1× Sequenase Images Blocking Buffer (USB), treated with 1× SAAP buffer and reacted with CDP-Star™ (Tropix) and exposed to X-ray film as described in Example 10a. The resulting autoradiograph is shown in FIG. 47.

Figure 47:
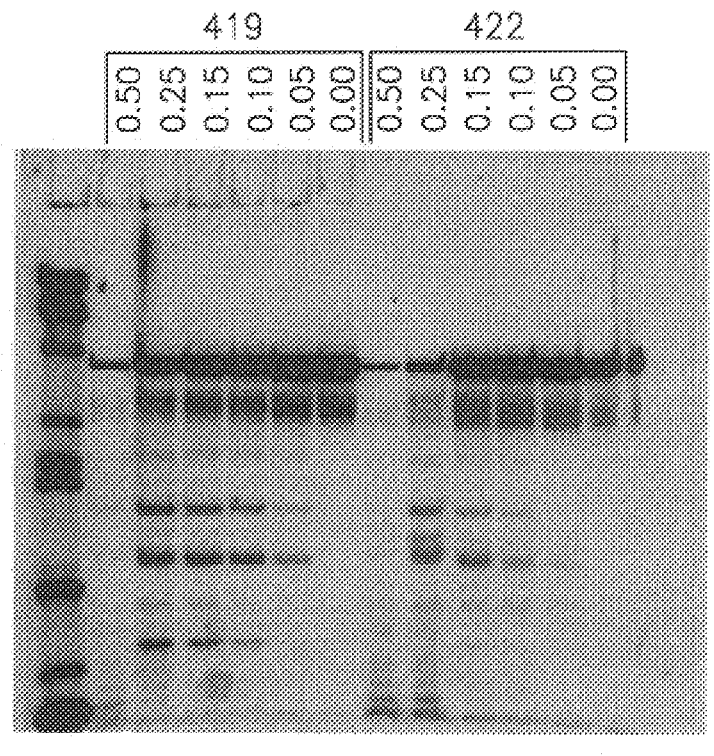
FIG. 47 shows an autoradiograph of a gel resolving the products of cleavage reactions run on double-stranded DNA substrates consisting of the 419 and 422 mutant alleles derived from exon 4 of the human tyrosinase gene in the presence of various concentrations of $MnCl_2$.

In FIG. 47, the lane marked "M" contains molecular weight markers prepared as described in Example 10. Lanes 1–6 contain the cleavage products generated by cleavage of the 419 mutant and lanes 7–12 contain the cleavage products generated by cleavage of the 422 mutant. The reaction products generated by cleavage of the ds DNA substrates in 1× CFLP™ buffer containing 0.5 mM (lanes 1,7); 0.25 mM (lanes 2,8); 0.15 mM (lanes 3,9); 0.1 mM (lanes 4,10); 0.05 mM (lanes 5,11) and 0 mM $MnCl_2$ (lanes 6,12) are shown.

The results shown in FIG. 47 show no cleavage is seen in the absence of divalent cations as is also the case for cleavage of ss DNA substrates [see Example 13(a) and FIG. 34]. Optimal cleavage (i.e., production of the most distinct pattern of clevage fragments) of ds DNA substrates was seen in the presence of 0.25 mM $MnCl_2$. This optimum is considerably lower than that obtained using ss DNA substrates [Example 13 and FIG. 34 show that cleavage of ss DNA substrates was optimal in 1 mM $MnCl_2$.]. FIG. 47 shows that the efficiency of cleavage of ds DNA substrates decreases as the concentration of $MnCl_2$ is lowered; this effect is likely due to the lower efficiency of the enzyme in decreasing concentrations of $MnCl_2$.

FIG. 47 shows that the cleavage pattern for dsDNA substrates apparently disappears when high concentrations of $MnCl_2$ (0.5 mM, lanes 1 and 7) are employed in the cleavage reaction. This result is in contrast to the results obtained when cleavage reactions are performed on single-stranded DNA (ssDNA) substrates. Example 13(a) showed that efficient cleavage of ss DNA substrates were obtained in 1 mM $MnCl_2$ and little change in the cleavage pattern was seen when the $Mn^{2+}$ concentration varied from 1 to 4 mM.

The loss of the signal seen when ds DNA substrates are cleaved in buffers containing high concentrations of $MnCl_2$ may be explained as follows. The presence of high concentrations of divalent ions promotes the reannealling of the DNA strands of the ds substrate during the course of the cleavage reaction. The enzyme Cleavase™ BN can nibble ds DNA substrates from the 5' end (ie., the enzyme removes short DNA fragments from the 5' end in an exonucleolytic manner; see Example 6). This nibbling results in the apparent removal of the label from the substrate DNA (as the DNA contains a 5' end label). Very short DNA fragments which contain the 5' end label are not visualized as they run out of the gel or are not efficiently transferred to the membrane.

EXAMPLE 20

Detection of Cleavage Patterns Can Be Automated

The ability to detect the characteristic genetic fingerprint of a nucleic acid substrate generated by the cleavage reaction using fluorescently labelled substrates in conjunction with automated DNA sequencing instrumentation would facilitate the use of the CFLP™ method in both clinical and research applications. This example demonstrates that differently labelled isolates (two different dyes) can be cleaved in a single reaction tube and can be detected and analyzed using automated DNA sequencing instrumentation.

Double-stranded DNA substrates, which contained either the N-hydroxy succinimidyl ester JOE-NHS (JOE) or FAM-NHS (FAM) on the sense-strand, were generated using the PCR and primers labelled with fluorescent dyes. The anti-sense strand contained a biotin label. The substrates utilized in this experiment were the 157 bp fragments from the wild-type (SEQ ID NO:40) and 422 mutant (SEQ ID NO:55) of exon 4 of the tyrosinase gene.

The wild-type and 422 mutant tyrosinase gene substrates were amplified from cDNA plasmid clones containing either the wild-type [pcTYR-N1Tyr, Bouchard, B., et al. (1989) J. Exp. Med. 169:2029] or the 422 mutant [pcTYR-A422, Giebel, L. B., et al. (1991) 87:1119] forms of the tyrosinase gene. Each double-stranded substrate was amplified and the 5' ends labelled with either a biotin moiety or a fluorescent dye by using the following primer pairs in the PCR. The anti-sense primer of SEQ ID NO:43 containing a 5'-biotin moiety was obtained from Integrated DNA Technologies, Inc. (IDT, Coralville, Iowa). The biotinylated anti-sense primer was used to prime the synthesis of both the wild-type and 422 mutant substrates. The sense primer of SEQ ID NO:42 labelled with JOE was used to prime synthesis of the wild-type tyrosinase gene. The sense primer of SEQ ID NO:42 labelled with FAM was used to prime synthesis of the 422 mutant tyrosinase gene. The JOE and FAM-labelled primers were obtained from Genset (Paris, France).

The PCR reactions were carried out as follows. One to two nanograms of plasmid DNA from the wild-type or 422 mutant were used as the target DNA in a 100 μl reaction containing 50 μM of each dNTP, 1 μM of each primer in a given primer pair, 20 mM Tris-Cl, pH 8.3, 1.5 mM $MgCl_2$, 50 mM KCl, 0.05% Tween 20 and 0.05% Nonidet P-40. Tubes containing the above mixture were overlaid with 70 $\mu$l Chill Out 14™ liquid wax (MJ Research, Watertown, Mass.). The tubes were heated to 95° C. for 1 min and then cooled to 70° C. Taq DNA polymerase (Perkin-Elmer) was then added as 2.5 units of enzyme in 5 $\mu$l of a solution containing 20 mM Tris-Cl, pH 8.3, 1.5 mM $MgCl_2$, 50 mM KCl, 0.05% Tween 20 and 0.05% Nonidet P-40. The tubes were heated to 95° C. for 45 sec, cooled to 50° C. for 45 sec, heated to 72° C. for 1 min and 15 sec for 35 repetitions. Following the last repetition, the tubes were incubated at 72° C. for 5 min.

The PCR products were gel purified as follows. The products were resolved by electrophoresis through a 6% polyacrylamide gel (29:1 cross-link) in a buffer containing 45 mM Tris-Borate, pH 8.3, 1.4 mM EDTA. The DNA was visualized by ethidium bromide staining and the 157 bp fragments were excised from the gel. The DNA was eluted from the gel slices by passive diffusion overnight into a solution containing 0.5M $NH_4OAc$, 0.1% SDS and 0.1M EDTA. The DNA was then precipitated with ethanol in the presence of 4 pg of glycogen carrier. The DNA was pelleted and resuspended in 30 $\mu$l of $H_2O$.

The cleavage reactions were performed as follows. Approximately 100 fmoles of each double-stranded DNA substrate (1–3 $\mu$l of each gel purified DNA) in a total volume of 6 $\mu$l in $H_2O$ was placed in a 500 $\mu$l thin wall microcentrifuge tube (Perkin-Elmer). The tube was heated to 95° C. for 10 seconds to denature the substrates and then the tube was quickly cooled to 50° C. (this step allows the DNA to assume its unique secondary structure by allowing the formation of intra-strand hydrogen bonds between complimentary bases). The cleavage reaction was started by adding 2 $\mu$l of 50 mM MOPS (pH 7.2), 1 $\mu$l of 1 mM $MnCl_2$ and 1 $\mu$l of Cleavase™ BN (50 ng/$\mu$l). The cleavage reaction was performed in a thermocycler (Perkin-Elmer DNA Thermal Cycler 480, Norwalk, Conn.) programmed to heat to 95° C. for 10 seconds and then cooled immediately to 50° C. The reaction was then incubated at 50° C. for 5 minutes and stopped by the addition of 1 $\mu$l of 10 mM EDTA.

Following the cleavage reaction, the sample was resolved by gel electrophoresis using an ABI 373A DNA Sequencer (Foster City, Calif.). Prior to loading, the sample was denatured by adding 5 $\mu$l of a solution containing 95% formamide and 10 mM EDTA and heating to 90° C. for 2 minutes. Five microliters of the sample was resolved by electrophoresis through a 6% polyacrylamide gel (19:1 cross-link), with 6M urea, in 1× TBE buffer (89 mM Tris-Borate, pH 8.3, 2 mM EDTA). The gel was run at 30 watts for 14 hours. Signals from four wavelength channels were collected using the Applied Biosystem Data Collection program on a Macintosh computer. The raw data was analyzed with the BaseFinder program [Giddings, M., et al. (1993) Nucl. Acids Res. 21:4530] which corrects for the fluorescent spectrum overlap in the four channel signals and mobility shifts caused by the use of different dye labels.

Figure 48:
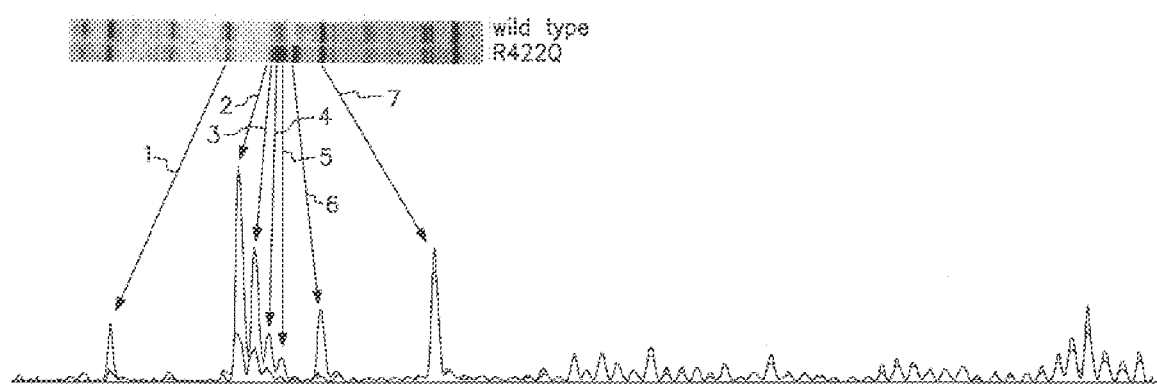
FIG. 48 displays two traces representing two channel signals (JOE and FAM fluorescent dyes) for cleavage fragments derived from a cleavage reaction containing two differently labelled substrates (the wild-type and 422 mutant substrates derived from exon 4 of the tyrosinase gene). The thin lines represent the JOE-labelled wild-type substrate and the thick lines represent the FAM-labelled 422 mutant substrate. Above the tracing is an autoradiograph of a gel resolving the products of cleavage reactions run on double-stranded DNA substrates consisting of the wild-type and 422 mutant alleles derived from exon 4 of the tyrosinase gene.

The results are shown in FIG. 48. FIG. 48 shows two traces representing the two channel signals for the wild-type and mutant samples. The wild-type sample, which was labeled with JOE dye, is shown by the thin lines. The mutant sample (R422Q), which was labeled with FAM dye, is shown by the thick lines. For comparison, a photograph of a high resolution polyacrylamide gel (10% gel with 19:1 crosslink) containing the resolved cleavage products is shown above the traces (the top lane contains cleavage fragments produced by clevage of the wild-type substrate; the bottom lane contains cleavage fragments produced by clevage of the R422Q mutant substrate). The cleavage products shown in the gel, which contain biotin labels at the 5' end of the sense strand, were generated, transferred to a nylon membrane and visualized as described in Example 10a. Arrows point from selected bands seen upon cleavage of the 422 mutant substrate to the corresponding peaks in the trace generated by the automated DNA sequencer (the arrows are labelled 1 through 7 beginning with the left-hand side of FIG. 48).

Comparison of the two traces shows that differences in the cleavage patterns generated from the cleavage of the wild-type and 422 mutant substrates in the same reaction are detected using automated DNA sequencing instrumentation. For example, cleavage of the 422 substrate generates a cleavage product of approximately 56 nucleotides which is not seen when the wild-type substrate is cleaved. This 56 nucleotide product is seen as the peak depicted by arrow 6 in FIG. 48. FIG. 48 shows that not only are new cleavage products generated by cleavage of the mutant substrate, but that the cleavage of certain structures is enhanced in the mutant substrate as compared to the wild-type substrate (compare the intensity of the peaks corresponding to arrows 2–5 in the wild-type and mutant traces). In addition, certain cleavage products are shared between the two substrates and serve as reference markers (see arrows 1 and 7).

The above results show that automated DNA sequencing instrumentation can be used to detect the characteristic genetic fingerprint of a nucleic acid substrate generated by the cleavage reaction. The results also demonstrate that the cleavage reaction can be run as a multiplex reaction. In this experiment both the wild-type and the mutant ds DNA substrates were cleaved in the same reaction (i.e., a multiplex reaction) and then were resolved on the same electrophoretic run using an automated DNA sequencer.

EXAMPLE 21

Identification of Viral Strains Using the Cleavase™ Reaction

The above examples demonstrate that the Cleavase™ reaction could be used to detect single base changes in fragments of varying size from the human β-globin and tyrosinase genes. These examples showed the utility of the Cleavase™ reaction for the detection and characterization of mutations in the human population. The ability of the Cleavase™ reaction to detect sequence variations characteristic of different strains of a virus was next examined.

The simian immunodeficiency virus (SIV) infection of monkeys is a widely used animal model for the transmission of human immunodeficiency virus type-1 (HIV) in humans. Biological isolates of SIV contain multiple virus strains. When a monkey is infected with a biological isolate of SIV, unique subsets of the virus stock are recovered from the infected animals (specific strains are also able to infect tissue culture cells). Different genotypes of the virus are isolated from infected animals depending on the route of infection [Trivedi, P. et al. Journal of Virology 68:7649 (1994)]. The SIV long terminal repeat (LTR) contains sequences which vary between the different viral strains and can be used as a marker for the identification of the viral genotype.

In order to develop a rapid method for the identification of viral strain(s) in a sample (e.g., a clinical isolate), the Cleavase™ reaction was used to characterized SIV genotypes isolated after infection of cultured cells in vitro or after infection of rhesus monkeys by either intravenous or intrarectal inoculation with uncloned biological SIV stocks. Six clones generated from viral DNA isolated following in vitro infection of the CEM×174 cell line (L.CEM/251/12 clone), after intravenous inoculation of monkeys (Li00.8-1 clone), after intrarectal low-dose inoculation of monkeys (L46.16-10 and L46.16-12 clones) and after intrarectal high-dose inoculation of monkeys (L19.16-3 and L36.8-3 clones) were obtained from C. David Pauza (Wisconsin Primate Research Center, Madison, Wis.). These clones were generated as described by Trivedi, P. et al. Journal of Virology 68:7649 (1994). These plasmid clones contained viral LTR sequences and were utilized to generate double-stranded DNA (ds DNA) substrates for the cleavage reaction.

a) Preparation Of The Substrate DNA

The six SIV plasmids were utilized as templates in PCRs in order to generate dsDNA substrates for the cleavage reaction. The primer pair utilized spans the U3-R boundary in the SIV LTR and amplifies an approximately 350 bp fragment. This portion of the SIV LTR contains recognition sequences for transcription factors (including Sp1 and NF-KB) as well as the TATA box for transcription initiation and is polymorphic in different viral strains [Trivedi, P. et al., supra].

The primer pair consisting of SEQ ID NOS:74 and 75 was used to amplify the SIV LTR clones in the PCR. SEQ ID NO:74 primes synthesis of the (+) strand of the SIV LTR and comprises 5'-GGCTGACAAGAAGGAAACTC-3'. SEQ ID NO:75 primes synthesis of the (−) strand of the SIV LTR and comprises 5'-CCAGGCGGCG GCTAGGAGAGATGGG-3'. To visualize the cleavage pattern generated by cleavage of the (+) strand of the LTR, the PCR was performed using the primer consisting of SEQ ID NO: 74 containing a biotin label at 5' end and unlabeled primer consisting of SEQ ID NO:75. To visualize the cleavage pattern generated by clevage of the (−) strand of the viral LTR, the PCR was performed using the primer pair consisting of SEQ ID NO:75 containing a biotin label at the 5' end and unlabeled primer SEQ ID NO:74.

The PCR reactions were carried out as follows. Ten to twenty nanograms of plasmid DNA from each of the above 6 SIV LTR clones was used as the target DNA in separate 100 µl reactions containing 60 µM of each DNTP, 0.2 µM of each primer in a given primer pair, 10 mM Tris-Cl, pH 9.0 (at 25° C.), 2 mM MgCl$_2$, 50 mM KCl, with 0.1% Triton X-100. Tubes containing the above mixture were overlaid with two drops of light mineral oil and the tubes were heated to 96° C. for 3 min and Taq DNA polymerase (Perkin-Elmer) was then added as 2.5 units of enzyme in 0.5 µl of 20 mM Tris-HCl, pH 8.0, 100 mM KCl, 0.1 mM EDTA, 1 mM DTT, 50% glycerol and 0.5% Tween 20 and 0.5% Nonidet P-40. The tubes were heated to 96° C. for 45 seconds, cooled to 60° C. for 45 seconds, heated to 72° C. for 1 minute for 35 repetitions. Following the PCR, the reaction mixture was separated from the mineral oil and 5 µl of 5M NaCl, 4 µl of 10 mg/ml glycogen and 250 µl of 100% ethanol were added to the aqueous PCR samples. After incubation at −20° C. for 1 hour, the DNA was pelleted by centrifugation in a Marathon Micro A centrifuge (Fisher Scientific) at maximum speed for 5 minutes and resuspended in 40 µl of 10 mM Tris-HCl, pH 8.0, 0.1 mM EDTA.

The PCR products were gel purified as follows. The DNA was mixed with 0.5 volume of loading buffer (95% formamide, 5mM EDTA, 0.02% bromphenol blue, 0.02% xylene cyanol) and heated to 75° C. for 2 minutes. The products were resolved by electrophoresis through a 6% polyacrylamide denaturing gel (19:1 cross-link) in a buffer containing 7M urea, 45 mM Tris-Borate, pH 8.3, 1.4 mM EDTA. The DNA was visualized by ethidium bromide staining and the product bands were excised from the gel. The DNA was eluted from the gel slices by passive diffusion overnight into a solution containing 0.5M NH$_4$OAc, 0.1% SDS and 0.1M EDTA. The DNA was then precipitated with ethanol in the presence of 4 µg of tRNA carrier. The DNA was pelleted and resuspended in 50 µl of 0.2M NaCl, 10 mM Tris-HCl, pH8.0, 0.1 mM EDTA. The DNA was precipitated with ethanol and resuspended in 50 µl of 10 mM Tris-HCl, pH 8.0, 0.1 mM EDTA. The final DNA concentration was estimated to be 40 fmole/µl for each double-stranded SIV LTR PCR product.

b) DNA Sequence Analysis Of The SIV LTR PCR Products

The DNA sequence of the six PCR fragments generated in section a) above was determined using the fmol™ DNA Sequencing System (Promega) according to the manufacturer's instructions. For each set of the sequencing reactions 0.2 pmoles of the PCR product and 2 pmoles of one of the two 5'-biotinylated PCR primers SEQ ID NOS:74 and 75 was used (i.e., both strands of the PCR fragments were sequenced). Following the sequencing reactions, the sequencing products were resolved by electrophoresis. After electrophoresis, the DNA bands were visualized following transfer to a nylon membrane as described in Example 19 with the following modification. A solution containing 0.2% Blocking reagent (Boehringer-Mannheim) and 0.2% SDS in TBS buffer (100 mM Tris-HCl, pH7.4; 68 mM NaCl) was used in place of the 1× Sequenase Images Blocking Buffer (USB).

The sequence of the 351 bp fragment derived from the L100.8-1 LTR clone is listed in SEQ ID NO:76. The sequence of the 340 bp fragment from the L46.16-10 LTR clone is listed in SEQ ID NO:77. The sequence of the 340 bp fragment derived from the L46.16-12 LTR clone is listed in SEQ ID NO:78. The sequence of the 351 bp fragment from the L19.16-3 LTR clone is listed in SEQ ID NO:79. The sequence of the 351 bp fragment derived from the LCEM/251/12 LTR clone is listed in SEQ ID NO:80. The sequence of the 351 bp fragment derived from the L36.8-3 LTR clone is listed in SEQ ID NO:81.

Analysis of sequenced LTR fragments shows that they have multiple substitutions and a deletion relative to the LlOO.8-1 LTR sequence (SEQ ID NO:76); the L100.8-1 LTR sequence was chosen as a reference to permit comparisons between the six LTR clones. For the ease of discussion, the first or 5'-terminal nucleotide of the (+) strand of L100.8-1 LTR sequence (SEQ ID NO:76) is defined as number 1 and the last or 3'-terminal nucleotide of this sequence is defined as number 351.

FIG. 49 displays the nucleotide sequence of the six LTR clones. The reference clone, L.100.8-1 (SEQ ID NO:76), is shown on the top line. Sequences appearing in bold type represent sequence changes relative to the sequence of clone L.100.8-1 (SEQ ID NO:76). The sequences outlined by the brackets in FIG. 49 represent palindromic sequences which can form a very stable hairpin structure having a stem of 14 base pairs (12/14 bases in the stem are complementary) and a loop of 7 nucleotides in the reference clone L.100.8-1 (SEQ ID NO:76). This hairpin structure is present in all six LTR clones although the sequence of the stem and loop structures varies between the clones.

In comparison with L100.8-1 sequence (SEQ ID NO:76), the L46.16-10 sequence (SEQ ID NO:77) has seven substitutions and one 11 nucleotide deletion corresponding to nucleotides 65–75 of SEQ ID NO:76. The substitutions are: C to T in position 28 (C28T), C57T, G90A, C97T, G238A, G242A and G313A. The L46.16-12 sequence (SEQ ID NO:78) has seven substitutions and one 11 nucleotide deletion corresponding to nucleotides 65–75 of SEQ ID NO:76. The substitutions are: C28T, C57T, G9OA, C97T, A103G, G242A and G313A. L19.16-3 sequence (SEQ ID NO:79) has two substitutions: A94C and A317T. LCEM/251/12 sequence (SEQ ID NO:80) has seven substitutions: G26A, G72A, C97T, G258A, A281C, G313A and C316T. L36.8-3 sequence (SEQ ID NO:81) has six substitutions: G60A, G172A, G207A, G221A, T256C and C316T.

c) Cleavage Reaction Conditions And CFLP™ Analysis Of The (−) Strand Of The SIV LTR Double-stranded substrates corresponding to the SIV LTR sequences listed in SEQ ID NOS:76–81 were labelled on the (−) strand using the PCR and the primer pair corresponding to SEQ ID NO: 74 and 75. The primer of SEQ ID NO:75 [the (−) strand primer]contained a biotin label at the 5' end. The PCR was performed and the reaction products were isolated as described in section a).

The cleavage reactions were performed as follows. Reaction tubes were assembled with approximately 60 fmoles of the ds DNA substrates in 6 µl of water. The following reagents were added to the DNA: 2 µl of 5× CFLP™ buffer (pH 7.2) containing 150 mM KCl (to yield a final concentration of 30 mM KCl) and 1 µl of the Cleavase™ BN enzyme (25 ng in 1× dilution buffer). A reaction tube containing the above components with the exception that 1 µl of H$_2$O was added in place of the Cleavase™ BN enzyme was prepared and run as the uncut or no enzyme control. The tubes were brought to 95° C. for 10 seconds in a PTC-100™ Programmable Thermal Controller (MJ Research, Inc.) to denature the DNA. Following the denaturation step, the tubes were immediately cooled to 40° C. The cleavage reaction was immediately started by the addition of 1 µl of 2 mM MnCl$_2$ (to achieve a final concentration of 0.2 mM). The tubes were incubated at 40° C. for 5 minutes. The reactions were terminated by adding 6 µl of stop buffer. The samples were heated to 85° C. for 30 sec and 5 µl of each reaction were resolved by electrophoresis through a 12% polyacrylamide gel (19:1 cross-link), with 7M urea in a buffer containing 45 mM Tris-Borate, pH 8.3, 1.4 mM EDTA.

After electrophoresis, the gel plates were separated and overlaid with a nylon membrane as described in Example 10a. The DNA was transferred to the membrane and the membrane was dried, washed in 0.2% Blocking reagent (Boehringer Mannheim); 0.2% SDS in 100 mM Tris-HCl, pH 7.4; 68 mM NaCl, treated with 1× SAAP buffer and reacted with CDP-Star™ (Tropix) and exposed to X-ray film as described in Example 10a. The resulting autoradiograph is shown in FIG. 50.

Figure 50:
FIG. 50 shows an autoradiograph of a gel resolving the products of cleavage reactions run on six different double-stranded SIV LTR substrates which contained a biotin label on the 5' end of the (−) strand.

FIG. 50 shows the cleavage patterns which correspond to the cleavage of the (−) strand of the double-stranded LTR substrates. In FIG. 50, the lane marked "M" contains molecular weight markers (prepared as described in Example 10). Lanes 1–6 contain the cleavage products generated by cleavage of the L100.8-1, L46.16-10, L46.16-12, L19.16-3, LCEM/251/12 and L36.8-3 LTR PCR fragments, respectively. Lanes 7–12 contain the uncut controls of each of the 6 LTR substrates in the same order as that described for Lanes 1–6.

The results shown in FIG. 50 show that the cleavage or CFLP™ pattern for each LTR substrate contains multiple bands which range in size from approximately 350 nucleotides (the uncut substrate) to less than 24 nucleotides. The bands located below about 100 nucleotides in length show differences between the six clones which reflect nucleotide changes characteristic of the different SIV LTR isolates. Examination of the CFLP™ patterns revealed that the reaction detected five unique cleavage patterns among the six SIV LTR isolates. From the DNA sequence data, it was known that all six LTR clones were unique. However, the CFLP™ pattern appeared to be identical for the clones shown in lanes 2 and 3.

The CFLP™ patterns generated by cleavage of the (−) strand from all six substrates contain a strong band which corresponds to a fragment of approximately 100 nucleotides in length. This band corresponds to cleavage of all six LTR substrates at the long palindromic sequence located 97 nucleotides from the 5' end of the (−) strand (see the bracketed region in FIG. 49). This palindromic sequence forms a very stable hairpin structure in single-stranded DNA and provides an optimal substrate for the Cleavase™ BN enzyme. Cleavage of this hairpin structure is predicted to generate a fragment of approximately 100 nucleotides.

The LTR substrates, L46.16-10 (SEQ ID NO:77) and L46.16-12 (SEQ ID NO:78), shown in lanes 2 and 3 were generated from the same animal using the same route of infection [Trivedi, P. et al., supra]. These substrates have identical sequences in the region corresponding to the detectable cleavage sites (i.e., below 100 nucleotides) with the exception of a single base; the L46.16-10 clone (SEQ ID NO:77) contains a G to A change at position 239 (G239A) relative to the reference sequence listed in SEQ ID NO:76. Examination of the DNA sequence of these two clones reveals that this substitution is located in the loop region of a strong hairpin structure (see the palindromic region bracketed in FIG. 49). Because the single base difference between these two sequences is located in the loop region of the hairpin structure, it may not change DNA secondary structure of the two substrates sufficiently to generate different CFLP™ patterns under the conditions utilized here. It may be possible to detect this single base difference between these two clones by varying the reaction conditions in a way that destablizes the strong hairpin structure.

The results shown in FIG. 50 demonstrate that the CFLP™ reaction can be used to detect the majority (⅚ or 83%) of the sequence variations present in the six SIV LTR clones studied. In addition, FIG. 50 demonstrates that the CFLP™ reaction is a sensitive means for probing the secondary structure of single strands of nucleic acids.

d) Cleavage Reaction Conditions And CFLP™ Analysis Of The (+) Strand Of The SIV LTR Double-stranded substrates corresponding to the SIV LTR sequences listed in SEQ ID NOS:76–81 were labelled on the (+) strand using the PCR and the primer pair corresponding to SEQ ID NO: 74 and 75. The primer of SEQ ID NO:74 [the (+) strand primer]contained a biotin label at the 5' end. The PCR was performed and the reaction products were isolated as described in section a). The cleavage reactions, electrophoresis and DNA visualization were performed as described above in section c). The resulting autoradiograph is shown in FIG. 51.

Figure 51:
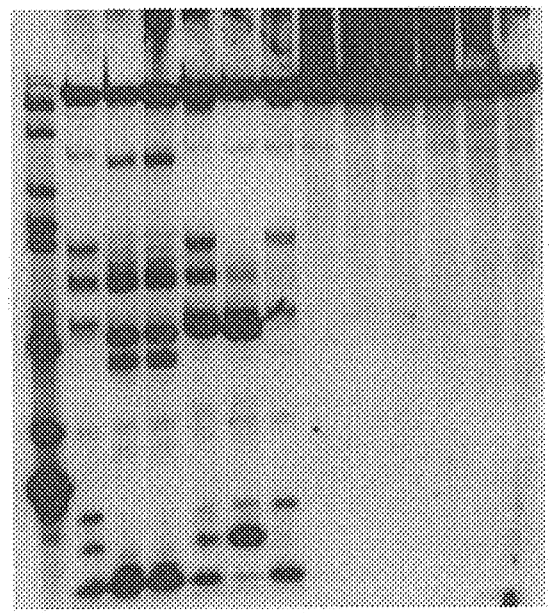
FIG. 51 shows an autoradiograph of a gel resolving the products of cleavage reactions run on six different double-stranded SIV LTR substrates which contained a biotin label on the 5' end of the (+) strand.

FIG. 51 shows the resulting pattern corresponding to the cleavage products of the (+) strand of six SIV LTR fragments. The lane marked "M" contains molecular weight markers (prepared as described in Example 10). Lanes 1–6 contain the cleavage products generated by cleavage of the L100.8-1, L46.16-10, L46.16-12, L19.16-3, LCEM/251/12 and L36.8-3 LTR PCR fragments, respectively. Lanes 7–12 contain the uncut controls of each of the 6 LTR substrates in the same order as that described for Lanes 1–6.

As was shown for cleavage of the (−) strand of the LTR clones, the CFLP™ pattern for each (+) strand of the SIV LTR substrates contains unique features that characterize the majority of specific nucleotide substitutions. For example, deletion of 11 nucleotides can be easily detected for L46.16-10 (SEQ ID NO:77) and L46.16-12 (SEQ ID NO:78) (FIG. 51, lanes 2 and 3). This deletion removes one of the three Sp1 binding sites and is a change characteristic of the genotype of SIV which predominates in animals which are infected using low-doses of virus stock via intrarectal inoculation [Trivedi, P. et al., supra]. The CFLP™ pattern generated by cleavage of the (+) strand of the substrates derived from clones L46.16-10 and L46.16-12 again were identical under these reaction conditions.

The results shown above demonstrate that the CFLP™ reaction can be used as a means to rapidly identify different strains (i.e., genotypes) of virus. The ability to rapidly identify the particular strain of virus or other pathogenic organism in a sample is of clinical importance. The above results show that the CFLP™ reaction can be used to provide a fast method of strain or species identification.

EXAMPLE 22

The Effects Of Alterations In Salt Conditions In Cleavage Reactions Using A Single-Stranded DNA Substrate In Example 13 it was shown that the Cleavase™ reaction is insensitive to large changes in reactions conditions when a single-stranded DNA is employed as the substrate. Example 13 showed that the cleavage reaction can be performed using a range of salt concentrations (0 to 50 mM KCl) in conjunction with single-stranded substrates. In this example, the effect of substituting other salts in place of KCl was examined in cleavage reactions using single-stranded DNA substrates.

a) Effect Of Substituting NaCl For KCl In Cleavage Reactions Using A Single-Stranded Template To determine the effect of substituting NaCl in place of KCl upon the cleavage pattern created by 5' nuclease activity on a single-stranded DNA substrate, the following experiment was performed. A single template was incubated in the presence of a fixed amount of the Cleavase™ BN enzyme (50 ng) in a buffer containing 10 mM MOPS, pH 8.2, 1 mM $MnCl_2$ and various amounts of NaCl.

Approximately 100 fmoles of the 157 nucleotide fragment derived from the sense strand of exon 4 of the tyrosinase gene (SEQ ID NO 47; prepared as described in example 10b) were placed in a 500 μl thin wall microcentrifuge tubes (Perkin Elmer, Norwalk, Conn.) in 1× CFLP™ buffer, pH 8.2 and 1.33 mM $MnCl_2$ (to yield a final concentration of 1 mM $MnCl_2$) in a volume of 15 μl. NaCl was added to yield a final concentration of 0, 10, 20, 30, 40, 50, 75 or 100 mM. The final reaction volume was 20 μl.

A tube containing 1× CFLP™ buffer, pH 8.2, 1 mM $MnCl_2$ and 100 fmoles substrate DNA was prepared and served as the no salt, no enzyme control (sterile distilled water was substituted for Cleavase™ BN and all reaction components were added prior to denaturation at 95° C.).

The tubes were heated to 95° C. for 20 seconds and then rapidly cooled to 65° C. The cleavage reaction was started immediately by the addition of 5 μl of a diluted enzyme mixture comprising 1 μl of Cleavase™ BN [50 ng/μl in 1× dilution buffer (0.5% NP40, 0.5% Tween 20, 20 mM Tris-HCl, pH 8.0, 50 mM KCl, 10 μg/ml BSA)] in 1× CFLP™ buffer, pH 8.2 without $MnCl_2$.

After 5 minutes at 65° C., reactions were stopped by the addition of 16 μl of stop buffer (95% formamide, 10 mM EDTA, 0.05% bromophenol blue, 0.05% xylene cyanol). Samples were heated to 72° C. for 2 minutes and 7 μl of each reaction were resolved by electrophoresis through a 10% polyacrylamide gel (19:1 cross-link), with 7M urea, in a buffer containing 45 mM Tris-Borate, pH 8.3, 1.4 MM EDTA, as described in Example 10a.

After electrophoresis, the gel plates were separated and overlaid with a nylon membrane, as described in example 10a. The DNA was transferred to the membrane and the membrane was dried, blocked in 1× I-Block (Tropix, Bedford, Mass.), conjugated with streptavidin-alkaline phosphatase (United States Biochemical), washed, reacted with CDP-Star™ (Tropix, Bedford, Mass.) as described in Example 10a with the exception that 0.01 ml CDP-Star™ was added per $cm^2$ of membrane. The membrane was exposed to X-ray film as described in Example 10a. The results are shown in FIG. 52.

Figure 52:
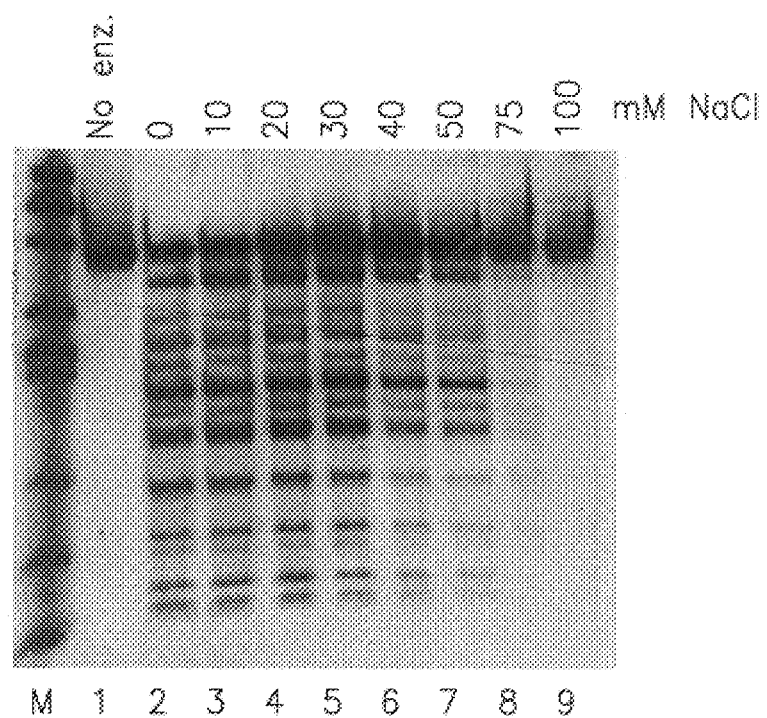
FIG. 52 shows an autoradiograph of a gel resolving the products of single-stranded cleavage reactions run in various concentrations of NaCl.

In FIG. 52, the lane marked "M" contains molecular weight markers as described in example 10a. Lane 1 contains the no salt, no enzyme control and shows the mobility of the uncleaved template DNA. Lanes 2 through 9 contain reaction products incubated in the presence of Cleavase™ BN enzyme in a buffer containing 0, 10, 20, 30, 40, 50 75 or 100 mM NaCl, respectively.

The results shown in FIG. 52 demonstrate that the substitution of NaCl in place of KCl has little or no effect upon the cleavage pattern generated using the 157 nucleotide tyrosinase DNA substrate (SEQ ID NO:47). Essentially the same dependence of the cleavage pattern on salt concentration was observed using this single-stranded DNA substrate when either KCl (See example 13b, FIG. 35) or NaCl (FIG. 52) was employed in the cleavage reaction.

b) Effect Of Substituting $(NH_4)_2SO_4$ For KCl In Cleavage Reactions Using A Single-Stranded Template In an approach similar to that described in above in section a), the effect of substituting $(NH_4)_2SO_4$ in place of KCl upon the cleavage pattern created by 5' nuclease activity on a single-stranded DNA substrate was tested. Cleavage reactions were set up exactly as described in section a) with the exception that variable amounts of $(NH_4)_2SO_4$ were used in place of the NaCl.

Approximately 100 fmoles of the 157 nucleotide fragment derived from the sense strand of exon 4 of the tyrosinase gene (SEQ ID NO 47; prepared as described in example 10a) were placed in 500 μl thin wall microcentrifuge tubes (Perkin Elmer, Norwalk, Conn.) in 1× CFLP™ buffer, pH 8.2 and 1.33 mM $MnCl_2$ (to yield a final concentration of 1 mM) in a volume of 15 μl. $(NH_4)_2SO_4$ was added to yield a final concentration of 0, 10, 20, 30, 40, 50, 75 or 100 mM. The final reaction volume was 20 μl.

A tube containing 1× CFLP™ buffer, pH 8.2, 1 mM $MnCl_2$ and 100 fmoles substrate DNA was prepared and served as the no salt, no enzyme control (sterile distilled water was substituted for Cleavase™ BN and all reaction components were added prior to denaturation at 95° C.).

The tubes were heated to 95° C. for 20 seconds and then rapidly cooled to 65° C. The cleavage reaction was started immediately by the addition of 5 μl of a diluted enzyme mixture comprising 1 μl of Cleavase™ BN [50 ng/ml in 1× dilution buffer (0.5% NP40, 0.5% Tween 20, 20 mM Tris-HCl, pH 8.0, 50 mM KCl, 10 μg/ml BSA)] in 1× CFLP™ buffer, pH 8.2 without $MnCl_2$.

After 5 minutes at 65° C., reactions were stopped by the addition of 16 μl of stop buffer (95% formamide, 10 mM EDTA, 0.05% bromophenol blue, 0.05% xylene cyanol). Samples were heated to 72° C. for 2 minutes and 7 μl of each reaction were resolved by electrophoresis through a 10% polyacrylamide gel (19:1 cross-link), with 7M urea, in a buffer containing 45 mM Tris-Borate, pH 8.3, 1.4 mM EDTA, as described in Example 10a.

After electrophoresis, the DNA was transferred to a membrane and the detected as described in section a) above. The resulting autoradiograph is shown in FIG. 53.

Figure 53:
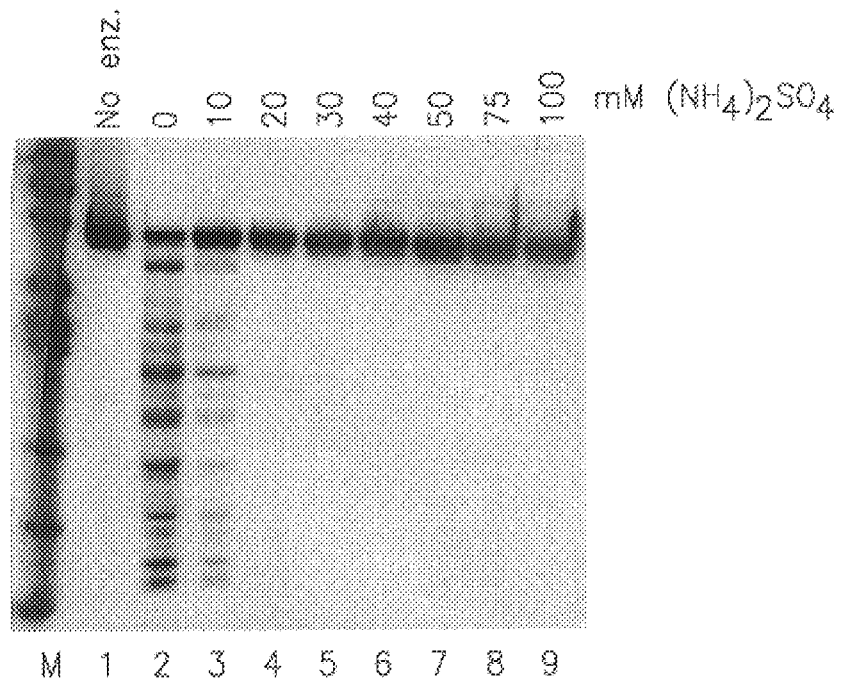
FIG. 53 shows an autoradiograph of a gel resolving the products of single-stranded cleavage reactions run in various concentrations of $(NH_4)_2SO_4$.

In FIG. 53, the lane marked "M" contains molecular weight markers as described in example 10a. Lane 1 contains the no enzyme control and shows the mobility of the uncleaved template DNA. Lanes 2 through 9 contain reaction products incubated in the presence of Cleavase™ BN enzyme in a buffer containing 0, 10, 20, 30, 40, 50 75 or 100 mM $(NH_4)_2SO_4$, respectively.

The results shown in FIG. 53 demonstrate that the cleavage reaction is severely inhibited by the presence of $(NH_4)_2SO_4$. The reaction is completely inhibited by as little as 20 mM $(NH_4)_2SO_4$; the extent of the cleavage reaction in 10 mM $(NH_4)_2SO_4$ is comparable to that obtained in 50 mM KCl or NaCl and is significantly reduced relative that obtained at 0 mM $(NH_4)_2SO_4$. The pattern of cleavage obtained at 10 mM $(NH_4)_2SO_4$, however, is identical to that observed when the 157 nucleotide template (SEQ ID NO:47) incubated in the absence of $(NH_4)_2SO_4$ or in KCl or NaCl. This indicates that the choice of salt included in the cleavase reaction has no effect on the nature of the sites recognized as substrates by the Cleavase™ BN enzyme (ie., the inhibitory effect seen is due the effect of $(NH_4)_2SO_4$ upon enzyme activity not upon the formation of the cleavage structures).

c) Effect of Increasing KCl Concentration on the Cleavage of Single-Stranded Substrates The effect of increasing the concentration of KCl in cleavage reactions using a single-stranded DNA substrate was examined by performing the cleavage reaction in concentrations of KCl which varied from 0 to 100 mM. The cleavage reactions were performed as described in section a) with the exception that KCl was added to yield final concentrations of 0, 25, 50, 75 or 100 mM and 200 fmoles of the substrate were used in the reaction; additionally the substrate DNA was denatured by incubation at 95° C. for 5 seconds.

Following the cleavage reaction, the samples were electrophoresed, transferred to a membrane and detected as described in section a) above. The resulting autoradiograph is shown in FIG. 54.

Figure 54:
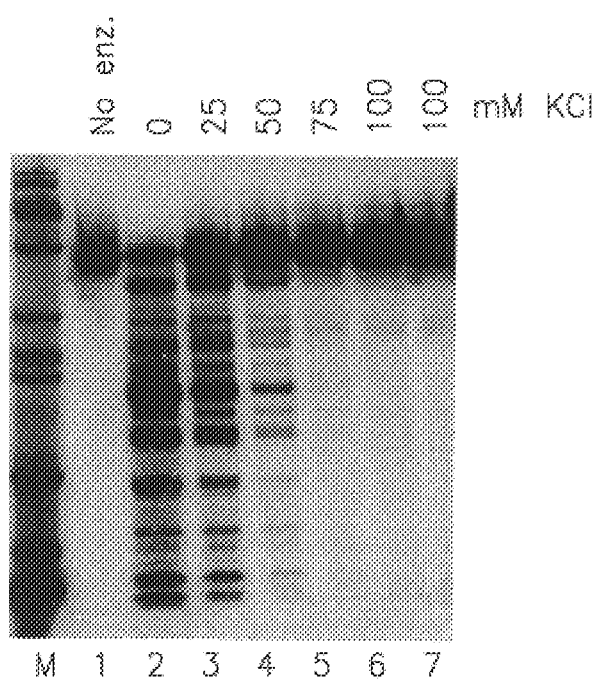
FIG. 54 shows an autoradiograph of a gel resolving the products of single-stranded cleavage reactions run in increasing concentrations of KCl.

In FIG. 54, the lanes marked "M" contains molecular weight markers as described in Example 10a. Lane 1 is the no enzyme control; Lanes 2–7 contain reactions carried out in the presence of 0, 25, 50, 75, 100 or 100 mM KCl (the 100 mM sample was repeated twice), respectively.

The results shown in FIG. 54 demonstrate that the extent of cleavage in the cleavage reaction decreased as a function of increasing KCl concentration (although residual cleavage was detectable at 100 mM KCl). Furthermore, the pattern of fragments generated by cleavage of single-stranded substrates with Cleavase™ BN is unaffected by the concentration of KCl present in the reactions.

d) Effect Of High KCl Concentrations On Cleavage Reactions Using A Single-Stranded Substrate The ability of the Cleavase™ reaction to be carried out at relatively high concentrations of KCl was tested by performing the cleavage reaction in the presence of variable concentrations of KCl in excess of 100 mM. The reactions were performed using the 157 nucleotide fragment from exon 4 of the tyrosinase gene (SEQ ID NO:47) as described above in section c), with the exception that KCl was added to yield a final concentration of 0, 100, 150, 200, 250 or 300 mM.

Following the cleavage reaction, the samples were electrophoresed, transferred to a membrane and detected as described in section a) above. The results (data not shown) indicated that the cleavage reaction was severely inhibited by KCl concentrations in excess of 100 mM. Some residual cleavage did, however, persist at these elevated salt concentrations, up to and including 300 mM KCl.

e) Effect Of KCl Concentration On The Stability Of The Cleavage Pattern During Extended Incubation Periods The results presented above demonstrate that the Cleavase™ reaction is inhibited by elevated concentrations (i.e., above 50 mM) of either KCl or NaCl. To determine whether this inhibition would effectively result in the stabilization of the cleavage pattern after extended reaction times (ie., due to inhibition of enzyme activity), reactions were examined at varying extended time points at both 0 and 50 mM KCl.

Approximately 100 fmoles of the 157 nucleotide fragment derived from the sense strand of exon 4 of the tyrosinase gene (SEQ ID NO 47; prepared as described in example 10a) were placed in 200 μl thin wall microcentrifuge tubes (BioRad, Richmond, Calif.) in 1× CFLP™ buffer, pH 8.2, 1.33 mM $MnCl_2$ (to yield a final concentration of 1 mM) and KCl to yield a final concentration of 0 or 50 mM KCl. The final reaction volume was 20 μl.

Control reactions which lacked enzyme were set up in parallel for each time point examined; these no enzyme controls were prepared as described above with the exception that sterile distilled water was substituted for Cleavase™ BN and all reaction components were added prior to denaturation at 95° C.

The tubes were heated to 95° C. for 20 seconds and then rapidly cooled to 65° C. The cleavage reaction was started immediately by the addition of 5 μl of a diluted enzyme mixture comprising 1 μl of Cleavase™ BN [50 ng/ml in 1× dilution buffer (0.5% NP40, 0.5% Tween 20, 20 mM Tris-HCl, pH 8.0, 50 mM KCl, 10 μg/ml BSA)] in 1× CFLPυ buffer, pH 8.2 without $MnCl_2$. Twenty microliters of Chill Out 14™ (MJ Research, Watertown, Mass.) were added to each tube after the addition of the enzyme. The reactions were allowed to proceed at 65° C. for 5 min, 30 min, 1 hour, 2 hours, 4 hours and 17 hours.

At the desired time point, the reactions were stopped by the addition of 16 μl of stop buffer (95% formamide, 10 mM EDTA, 0.05% bromophenol blue, 0.05% xylene cyanol). Samples were heated to 72° C. for 2 minutes and 7 μl of each reaction were resolved by electrophoresis through a 10% polyacrylamide gel (19:1 cross-link), with 7M urea, in a buffer containing 45 mM Tris-Borate, pH 8.3, 1.4 mM EDTA, as described in Example 10a.

After electrophoresis, the DNA was transferred to a membrane and the detected as described in section a) above. The resulting autoradiograph is shown in FIG. 55.

Figure 55:
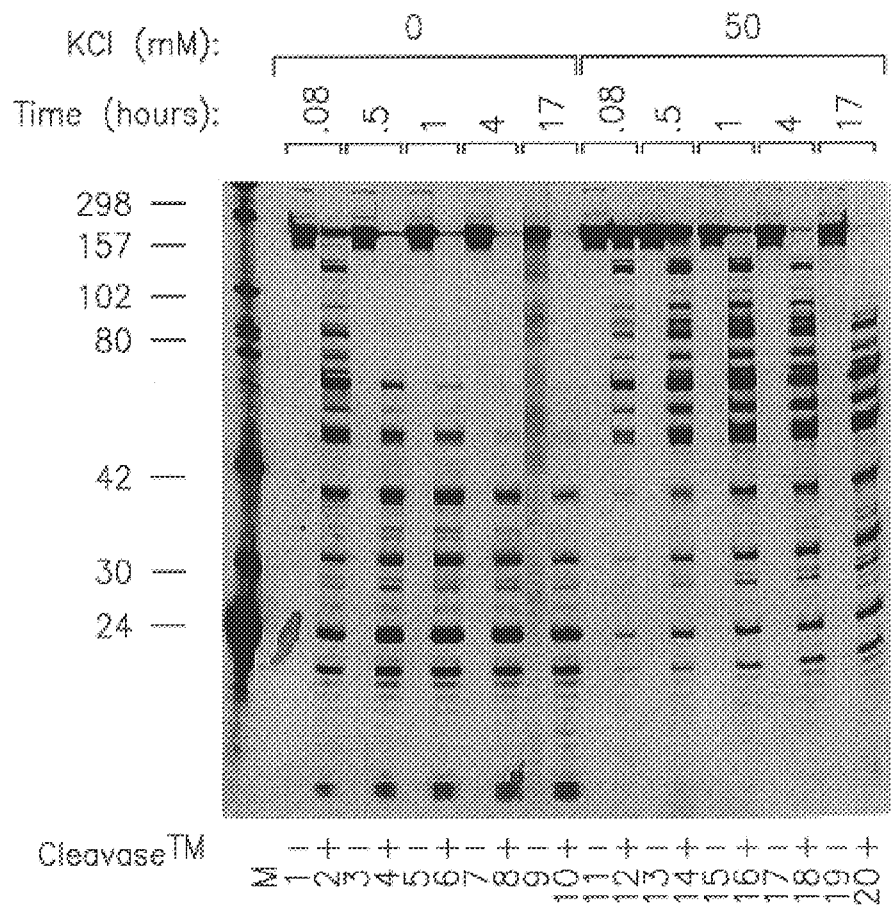
FIG. 55 shows an autoradiograph of a gel resolving the products of single-stranded cleavage reactions run in two concentrations of KCl for various periods of time.

In FIG. 55, the lane marked "M" contains molecular weight markers as described in example 10a. Lanes 1–10 contain products from reactions carried out in the absence of KCl; lanes 11–20 contain products from reactions carried out in the presence of 50 mM KCl. Lanes 1, 3, 5, 7, and 9 contain no enzyme controls incubated for 5 minutes, 30 minutes, 1 hour, 2 hours, 4 hours and 17 hours, respectively.

Lanes 2, 4, 6, 8, and 10 contain the reaction products from reactions incubated at 65° C. for 5 minutes, 30 minutes, 1 hour, 2 hours, 4 hours and 17 hours, respectively. Lanes 11, 13, 15, 17, and 19 contain no enzyme controls incubated in 50 mM KCl for 5 minutes, 30 minutes, 1 hour, 2 hours, 4 hours and 17 hours, respectively. Lanes 12, 14, 16, 18 and 20 contain reaction products from CFLP™ reactions incubated in 50 mM KCl at 65° C. for 5 minutes, 30 minutes, 1 hour, 2 hours, 4 hours and 17 hours, respectively.

The results indicated that cleavage was retarded in the presence of 50 mM KCl which resulted in a significant stabilization of the cleavage pattern (i.e., the cleavage pattern remained the same over time because the rate of cleavage was dramatically slowed and thus the larger cleavage fragments are not further cleaved to produce smaller fragments). Note that at the extended incubation times, the reactions carried out in the absence of KCl were significantly overdigested; after 1 hour at 65° C., essentially no large fragments remain, and there is substantial accumulation of small cleavage products. In contrast, the reactions carried out at 50 mM KCl were essentially static between 30 minutes and 4 hours; overdigestion was only apparent at the longest time point and was not as extensive as that observed in the absence of KCl.

EXAMPLE 23

Comparison Of The Patterns Of Cleavage Generated By Cleavage-Of-Single-Stranded And Double-Stranded DNA Substrates In Cleavase™ BN-mediated primer-independent cleavage of double-stranded DNA substrates, the two strands of DNA are separated in a denaturation step prior to the addition of enzyme. Therefore, the patterns generated by cleaving double-stranded templates should be identical to those generated by cleaving single-stranded template. This assumption was verified by the experiment described below.

The single-stranded substrate comprising the 157 nucleotide fragment derived from the sense strand of exon 4 of the tyrosinase gene (SEQ ID NO:47) was prepared as described in example 10b with the following modification. After gel purification and precipitation in the presence of glycogen carrier, the PCR products were resuspended in TE (10 MM Tris-Cl, pH 8.0, 1 mM EDTA) and then reprecipitated with 2M $NH_4OAc$ and 2.5 volumes of ethanol. The DNA was then resuspended in 400 μl of 10 mM Tris-HCl, pH 8.0, 0.1 mM EDTA.

Approximately 50 or 100 fmoles of the single-stranded 157 nucleotide fragment (SEQ ID NO: 47) were placed in a 200 μl centrifuge tube (BioRad, Richmond, Calif.) in 1× CFLP™ buffer, pH 8.2 and 1.33 mM $MnCl_2$ (final concentration was 1 mM $MnCl_2$) in a volume of 15 μl. The final reaction volume was 20 μl. A 20 μl no salt, no enzyme control was set up in parallel; this reaction contained sterile distilled water in place of the Cleavase™ BN enzyme and all reaction components were added prior to denaturation at 95° C.

The reaction tubes were heated to 95° C. for 5 seconds and then rapidly cooled to 65° C. The cleavage reactions were started immediately by the addition of 5 μl of a diluted enzyme mixture comprising 1 μl of Cleavase™ BN [50 ng/μl in 1× dilution buffer (0.5% NP40, 0.5% Tween 20, 20 mM Tris-HCl, pH 8.0, 50 mM KCl, 10 μg/ml BSA)] in 1× CFLP™ buffer, pH 8.2 without $MnCl_2$. After 5 minutes at 65° C., reactions were stopped by the addition of 16 μl of stop buffer (95% formamide, 10 mM EDTA, 0.05% bromophenol blue, 0.05% xylene cyanol).

A double stranded form of the 157 nucleotide substrate was cleaved with Cleavase™ BN in the same experiment. This double-stranded substrate (SEQ ID NO:40) was generated as described in Example 10b with the following modifications. After gel purification and precipitation in the presence of glycogen carrier, the PCR products were resuspended in TE (10 mM Tris-Cl, pH 8.0, 1 mM EDTA) and then reprecipitated with 2M $NH_4OAc$ and 2.5 volumes of ethanol. The DNA was then resuspended in 400 μl of 10 mM Tris-HCl, pH 8.0, 0.1 mM EDTA.

Approximately 33 or 66 fmoles of the double-stranded 157 bp fragment (SEQ ID NO:40) were placed in a 200 μl thin walled microcentrifuge tube (BioRad, Richmond, Calif.). Sterile distilled water was added to a volume of 15 μl.

The reaction tubes were heated to 95° C. for 5 seconds and then rapidly cooled to 65° C. The cleavage reactions were started immediately by the addition of 5 μl of a diluted enzyme mixture comprising 4× CFLP™ buffer, pH 8.2, 0.8 mM $MnCl_2$ (to yield a final concentration of 1× CFLP™ buffer and 0.2 mM $MnCl_2$) and 0.5 μl of Cleavase™ BN [50 ng/μl in 1× dilution buffer (0.5% NP40, 0.5% Tween 20, 20 mM Tris-HCl, pH 8.0, 50 mM KCl, 10 μg/ml BSA)]. A 20 μl no salt, no enzyme double-stranded substrate control was set up in parallel; this reaction contained sterile distilled water in place of the Cleavase™ BN enzyme.

After 5 minutes at 65° C., the reactions were stopped by the addition of 16 μl of stop buffer (95% formamide, 10 mM EDTA, 0.05% bromophenol blue, 0.05% xylene cyanol). The samples were then heated to 72° C. for 2 minutes and the reaction products were resolved by electrophoresis through a 10% polyacrylamide gel (19:1 cross-link), with 7M urea, in a buffer containing 45 mM Tris-Borate, pH 8.3, 1.4 mM EDTA, as described in Example 10a.

After electrophoresis, the gel plates were separated and overlaid with a nylon membrane, as described in example 10a. The DNA was transferred to the membrane and the membrane was dried, blocked in 1× I-Block (Tropix, Bedford, Mass.), conjugated with streptavidin-alkaline phosphatase (United States Biochemical), washed, reacted with CDP-Star (Tropix, Bedford, Mass.), and exposed to X-ray film as described in Example 22a. The resulting autoradiograph is shown in FIG. 56.

Figure 56:
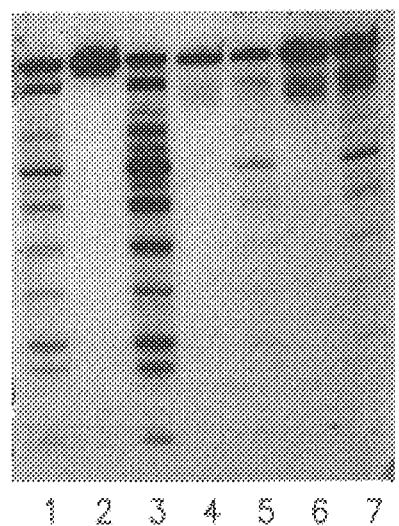
FIG. 56 shows an autoradiograph of a gel resolving the products of cleavage reactions run on either the single-stranded or double-stranded form of the same substrate.

In FIG. 56, lanes 1–3 contain reaction products derived from reactions containing the single-stranded substrate; lanes 4–7 contain reaction products derived from reactions containing the double-stranded substrate. Lanes land 3 contain 7.0 μl of the reaction products derived from the cleavage reactions which contained either 50 or 100 fmoles of the single-stranded substrate, respectively. Lane 2 contains 7.0 μl of the uncut single-stranded substrate control reaction. Lanes 4 and 6 contain 7.0 μl of the uncut double-stranded control reactions which contained either 33 or 66 fmoles of the substrate, respectively. Lanes 5 and 7 contain 7.0 μl of the reaction products derived from cleavage reactions which contained either 33 or 66 fmoles of the double-stranded substrate, respectively. Note that the uncut double-stranded control shows a doublet underneath the prominent band containing the 157 bp substrate; it is believed that this doublet represents alternative structures which migrate with an altered mobility rather than degradation products. This doublet does not appear in experiments performed using double-stranded DNA purified from a denaturing gel (See Example 24)

Comparison of the cleavage patterns generated by cleavage of either the single-stranded or double-stranded substrate shows that identical patterns are generated.

EXAMPLE 24

The Cleavase™ Reaction Using A Double Stranded DNA Template Is Sensitive to Large Changes In Reaction Conditions The results presented in Example 13 demonstrated that the Cleavase™ reaction is relatively insensitive to significant changes in numerous reaction conditions including, the concentration of $MnCl_2$ and KCl, temperature, the incubation period, the amount of Cleavase™ BN enzyme added and DNA preparation. The results shown in Example 13 demonstrated that when the Cleavase™ reaction is performed using a single-stranded substrate, the reaction is remarkably robust to large changes in conditions. The experiments shown below show that the cleavage of double-stranded substrates is restricted to a somewhat narrower range of reaction conditions.

a) Generation Of The Double-Stranded 157 bp Fragment Of Exon 4 Of The Tyrosinase Gene The following experiments examine the effect of changes in reaction conditions when double-stranded DNA templates are used in the Cleavase™ reaction. The double-stranded substrate utilized was the 157 bp fragment of the wild type tyrosinase gene (SEQ ID NO:40). This 157 bp fragment was generated using symmetric PCR as described in Example 10b. Briefly, approximately 75 fmoles of double-stranded substrate DNA were incubated with 50 pmoles of the primer 5' biotin-GCCTTATTTTACTTTAAAAAT-3' (SEQ ID NO: 45), 50 pmoles of the primer 5' fluorescein-TAAAGTTTTGTGTTATCTCA-3' (SEQ ID NO:46), 50 mM of each dNTP, 20 mM Tris-Cl, pH 8.3, 1.5 mM $MgCl_2$, 50 mM KCl, with 0.05% Tween 20 and 0.05% Nonidet P-40 (NP40). Tubes containing 95 µl of the above mixture were heated to 95° C. for 5 seconds and cooled to 70° C. Five microliters of enzyme mix containing 1.25 units of Taq DNA polymerase in 20 mM Tris-Cl, pH 8.3, 1.5 mM $MgCl_2$, 50 mM KCl, with 0.05% Tween 20 and 0.05% Nonidet P-40 were then added. Each tube was overlaid with 50 µl of Chill Out 14™ (MJ Research, Watertown, Mass.).

The tubes were heated to 95° C. for 45 seconds, cooled to 50° C. for 45 seconds, heated to 72° C. for 75 seconds for 30 repetitions with a 5 minute incubation at 72° C. after the last repetition. The reactions were then ethanol precipitated to reduce the volume to be gel purified. NaCl was added to a final concentration of 400 mM and glycogen (in distilled water) was added to a final concentration of 200 µg/ml. Two and one-half volumes of 100% ethanol were added to each tube, and the tubes were chilled to -70° C. for two and one-half hours. The DNA was pelleted and resuspended in one-fifth the original volume of sterile distilled water.

The PCR products were gel purified as follows. An equal volume of stop buffer (95% formamide, 0.05% bromophenol blue, 0.05% xylene cyanol) was added to each tube and the tubes were heated to 72° C. for 2 minutes. The products were resolved by electrophoresis through a 6% denaturing polyacrylamide gel (19:1 cross-link) and 7M urea in a buffer containing 45 mM Tris-Borate, pH 8.3 and 1.4 mM EDTA. The DNA was visualized by ethidium bromide staining and the 157 bp fragment was excised from the gel. The DNA was eluted from the gel slice by passive diffusion as described in Example 10a with the exception that diffusion was allowed to occur over two days at room temperature. The DNA was then precipitated with ethanol in the presence of 200 mM NaCl and no added carrier molecules. The DNA was pelleted and resuspended in 150 µl TE (10 mM Tris-Cl, pH 8.0, 0.1 mM EDTA).

b) Effect Of KCl Concentration On The Double-Stranded Cleavage Reaction

To determine the effect of salt concentration upon the cleavage reaction when a double-stranded substrate was utilized, a single substrate was incubated in the presence of a fixed amount of the enzyme Cleavase™ BN (25 ng) in a buffer containing 10 mM MOPS, pH 7.5, 0.2 mM $MnCl_2$ and varying concentrations of KCl from 0 to 100 mM.

Approximately 100 fmoles of the 157 bp fragment derived from the exon 4 of the tyrosinase gene (SEQ ID NO:40; prepared as described above in section a) were placed in 200 µl thin wall microcentrifuge tubes (BioRad, Richmond, Calif.) in sterile distilled water in a volume of 6.25 µl (the final reaction volume was 10 µl). The tubes were heated to 95° C. for 15 seconds and then rapidly cooled to 45° C. The cleavage reactions were started by the addition of 3.75 µl of an enzyme mix containing 2.7× CFLP™ buffer, pH 7.5 (to yield a final concentration of 1×), 0.53 mM $MnCl_2$ (to yield a final concentration of 0.2 mM), 0.5 µl Cleavase™ BN [50 ng/µl in 1× dilution buffer (0.5% NP40, 0.5% Tween 20, 20 mM Tris-HCl, pH 8.0, 50 mM KCl, 10 µg/ml BSA)], and KCl to yield a final concentration of 0, 2.5, 5, 10, 15, 20, 25, 30, 50 or 100 mM. The final reaction volume was 10 µl. The enzyme solution was brought to room temperature before addition to the cleavage reaction. No enzyme (i.e., uncut) controls were set up in parallel at either 0 or 100 mM KCl, with the difference that sterile distilled water was substituted for the Cleavase™ BN.

After 5 minutes at 45° C., the reactions were stopped by the addition of 8 µl of stop buffer (95% formamide, 10 mM EDTA, 0.05% bromophenol blue, 0.05% xylene cyanol). Samples were heated to 72° C. for 2 minutes and 4 µl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiograph is shown in FIG. 57.

Figure 57:
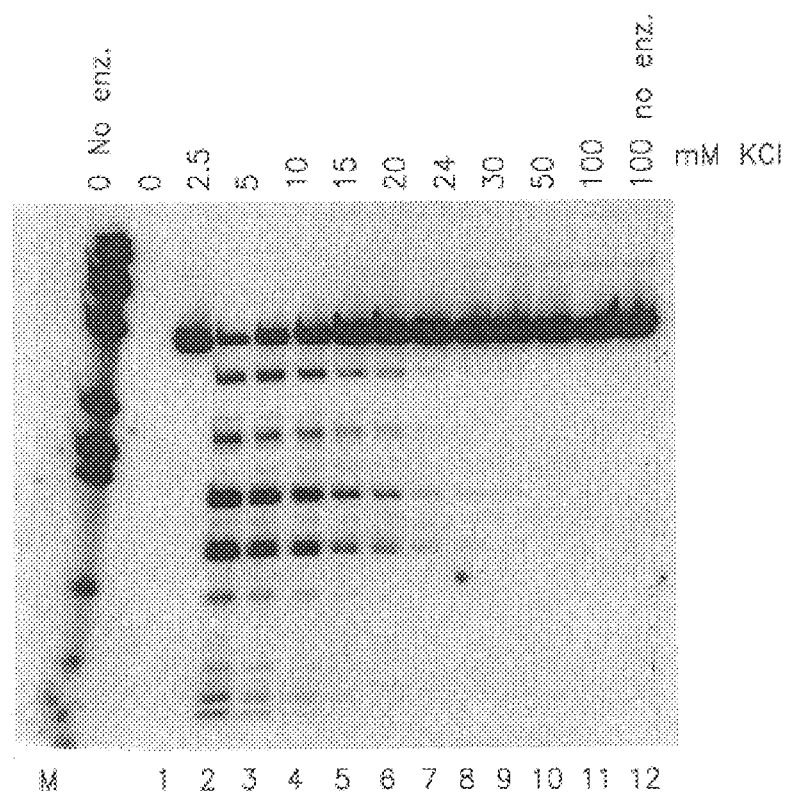
FIG. 57 shows an autoradiograph of a gel resolving the products of double-stranded cleavage reactions run in various concentrations of KCl.

In FIG. 57, the lane marked "M" contains molecular weight markers. Lane 1 contains the uncut control in 0 mM KCl and shows the mobility of the uncleaved template DNA. Lanes 2 through 11 contain reaction products generated by incubation of the substrate in the presence of Cleavase™ BN enzyme in a buffer containing 0, 2.5, 5, 10, 15, 20, 25, 30, 50, or 100 mM KCl, respectively. Lane 12 contains the uncut control incubated in a buffer containing 100 mM KCl.

The results shown in FIG. 57 demonstrate that the Cleavase™ reaction carried out on double-stranded DNA template was sensitive to variations in salt concentration. Essentially no cleavage was detected in reactions containing greater than 30 mM KCl. The same cleavage pattern was obtained when the 157 bp tyrosinase DNA substrate (SEQ ID NO:40) was incubated with the Cleavase™ BN enzyme regardless of whether the concentration of KCl was varied from 0 to 30 mM.

c) Effect Of NaCl On The Double-Stranded Cleavage Reaction

The effect of substituting NaCl in place of KCl upon the cleavage pattern created by 5' nuclease activity on a double-stranded DNA substrate was examined. Approximately 100 fmoles of the 157 bp fragment derived from exon 4 of the tyrosinase gene (SEQ ID NO 40; prepared as described in Example 24a) were placed in 200 μl thin wall microcentrifuge tubes (BioRad, Richmond, Calif.) in sterile distilled water in a volume of 6.25 μl and were heated to 95° C. for 15 seconds. The tubes were cooled to 45° C. The cleavage reaction was started by the addition of 3.75 μl of an enzyme mix containing 2.7× CFLP™ buffer, pH 7.5 (to yield a final concentration of 1×), 0.53 mM MnCl$_2$ (to yield a final concentration of 0.2 nM), 0.5 μl Cleavase™ BN [50 ng/μl in 1× dilution buffer (0.5% NP40, 0.5% Tween 20, 20 mM Tris-HCl, pH 8.0, 50 mM KCl, 10 pg/ml BSA)], and NaCl to yield a final concentration of 0, 2.5, 5, 10, 15, 20, 25, 30, 50 or 100 mM. The final reaction volume was 10 μl. No enzyme (ie., uncut) controls were set up in parallel at either 0 or 100 mM NaCl, with the difference that sterile distilled water was substituted for the Cleavase™ BN.

The reactions were incubated at 45° C. for 5 minutes and were stopped by the addition of 8 μl of stop buffer (95% formamide, 10 mM EDTA, 0.05% bromophenol blue, 0.05% xylene cyanol). Samples were heated to 72° C. for 2 minutes and 4 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a with the exception that the distilled water washes were omitted. The resulting autoradiograph is shown in FIG. 58.

Figure 58:
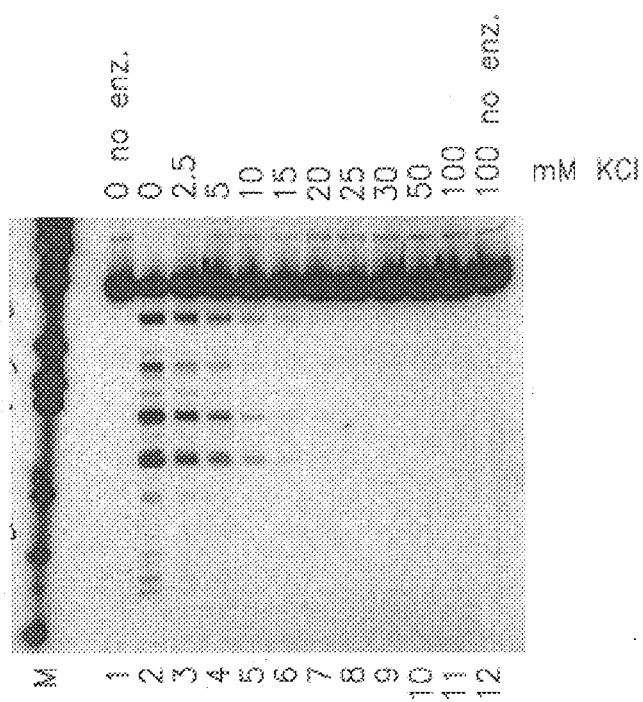
FIG. 58 shows an autoradiograph of a gel resolving the products of double-stranded cleavage reactions run in various concentrations of NaCl.

In FIG. 58, the lane marked "M" contains molecular weight markers. Lane 1 contains the no enzyme control incubated in a buffer containing 0 mM NaCl and shows the mobility of the uncleaved template DNA. Lanes 2 through 11 contain reaction products generated by cleavage of the 157 bp substrate (SEQ ID NO:40) with the Cleavase™ BN enzyme in a buffer containing 0, 2.5, 5, 10, 15, 20, 25, 30, 50, or 100 mM NaCl, respectively. Lane 12 contains the no enzyme control incubated in a buffer containing 100 mM NaCl.

The results shown in FIG. 58 demonstrate that the Cleavase™ reaction carried out on a double-stranded DNA template was sensitive to variations in NaCl concentration. Essentially no cleavage was detected above 20 mM NaCl. The same cleavage pattern was obtained when the 157 bp tyrosinase DNA template (SEQ ID NO:40) was incubated with the Cleavase™ BN enzyme regardless of whether the NaCl concentration was varied from 0 to 20 mM.

d) Effect Of Substituting (NH$_4$)$_2$SO$_4$ For KCl In Cleavage Of Double-Stranded Template In an approach similar to that described in Example 22b, the ability of (NH$_4$)$_2$SO$_4$ to substitute for KCl in the cleavage reaction when double-stranded substrates were utilized was tested. Cleavage reactions were set up exactly as described in Examples 24b and c with the exception that variable amounts of (NH$_4$)$_2$SO$_4$ were substituted for the KCl or NaCl.

Approximately 100 fmoles of the 157 bp fragment derived exon 4 of the tyrosinase gene (SEQ ID NO 40; prepared as described above in section a) were placed in 200 μl thin wall microcentrifuge tubes (BioRad, Richmond, Calif.) in sterile distilled water in a volume of 6.25 μl and were heated to 95° C. for 15 seconds. The tubes were cooled to 45° C.

Cleavage reactions were started by the addition of 3.75 μl of an enzyme mix containing 2.7× CFLP™ buffer, pH 7.5 (to yield a final concentration of 1×), 0.53 mM MnCl$_2$ (to yield a final concentration of 0.2 mM MnCl$_2$), 0.5 μl Cleavase™ BN [50 ng/μl in 1× dilution buffer (0.5% NP40, 0.5% Tween 20, 20 mM Tris-HCl, pH 8.0, 50 mM KCl, 10 μg/ml BSA)], and (NH$_4$)$_2$SO$_4$ to yield a final concentration of 0, 2.5, 5, 10, 15, 20, 25, 30, 50 or 100 mM. The final reaction volume was 10 μl. No enzyme (i.e., uncut) controls were set up in parallel at either 0 or 100 mM (NH$_4$)$_2$SO$_4$, with the difference that sterile distilled water was substituted for the Cleavase™ BN.

The reactions were incubated at 45° C. for 5 minutes and were stopped by the addition of 8 μl of stop buffer (95% formamide, 10 mM EDTA, 0.05% bromophenol blue, 0.05% xylene cyanol). Samples were heated to 72° C. for 2 minutes and 4 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiograph is shown in FIG. 59.

Figure 59:
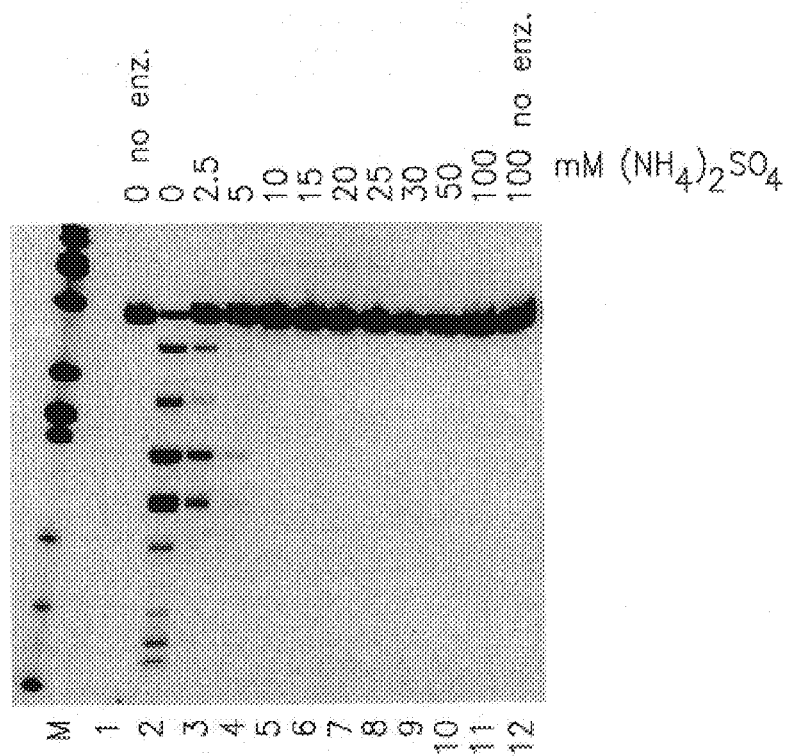
FIG. 59 shows an autoradiograph of a gel resolving the products of double-stranded cleavage reactions run in various concentrations of $(NH_4)_2SO_4$.

In FIG. 59, the lane marked "M" contains molecular weight markers. Lane 1 contains the no enzyme control incubated in a buffer containing 0 mM (NH$_4$)$_2$SO$_4$ and shows the migration of the uncleaved substrate DNA. Lanes 2 through 11 contain reaction products generated by incubation of the substrate in the presence of Cleavase™ BN enzyme in a buffer containing 0, 2.5, 5, 10, 15, 20, 25, 30, 50, or 100 mM (NH$_4$)$_2$SO$_4$, respectively. Lane 12 contains the no enzyme control incubated in a buffer containing 100 mM (NH$_4$)$_2$SO$_4$.

The results shown in FIG. 59 demonstrate that the Cleavase™ reaction was severely inhibited by the presence of (NH$_4$)$_2$SO$_4$. The reaction was completely inhibited by as little as 15 mM (NH$_4$)$_2$SO$_4$; the extent of the cleavage reaction in 5 mM (NH$_4$)$_2$SO$_4$ was comparable to that obtained in 20 mM KCl and was significantly reduced relative to that obtained in 0 mM (NH$_4$)$_2$SO$_4$. The pattern of cleavage obtained using 5 mM (NH$_4$)$_2$SO$_4$, however, was identical to that observed when the 157 bp substrate was incubated in the absence of (NH$_4$)$_2$SO$_4$ or in KCl or NaCl, indicating that the choice of salt included in the Cleavase™ reaction has no effect on the nature of the sites recognized by the enzyme.

e) Time Course Of The Double-Stranded Cleavage Reaction

To determine how quickly the double-stranded cleavage reaction is completed, a single substrate was incubated in the presence of a fixed amount of Cleavase™ BN enzyme for various lengths of time. Approximately 100 fmoles of the double-stranded 157 bp fragment of exon 4 of the tyrosinase gene (SEQ ID NO 40; prepared as described above in Example 24a) were placed in sterile distilled water in 200 μl thin walled centrifuge tubes (BioRad, Richmond, Calif.) in a volume of 6.25 μl. The tubes were heated to 95° C. for 15 seconds, as described in section b), and cooled to 45° C.

Cleavage reactions were started by the addition of 3.75 μl of an enzyme mix containing 2.7× CFLP™ buffer, pH 7.5 (to yield a final concentration of 1×), 0.53 mM MnCl$_2$ (to yield a final concentration of 0.2 mM MnCl$_2$), 0.5 μl Cleavase™ BN [50 ng/μl in 1× dilution buffer (0.5% NP40, 0.5% Tween 20, 20 mM Tris-HCl, pH 8.0, 50 mM KCl, 10 μg/ml BSA)]. The final reaction volume was 10 μl. No enzyme (i.e., uncut)

controls were set up in parallel and stopped after either 5 minutes or 120 minutes, with the difference that sterile distilled water was substituted for the Cleavase™ BN enzyme.

The cleavage reactions were stopped by the addition of 8 μl of stop buffer (95% formamide, 10 mM EDTA, 0.05% bromophenol blue, 0.05% xylene cyanol) at the following times: 5 seconds, 1, 2, 5, 10, 15, 20, 30, 60 or 120 minutes. Samples were heated to 72° C. for 2 minutes and 4 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a with the exception that the distilled water washes were omitted. The resulting autoradiograph is shown in FIG. 60.

Figure 60:
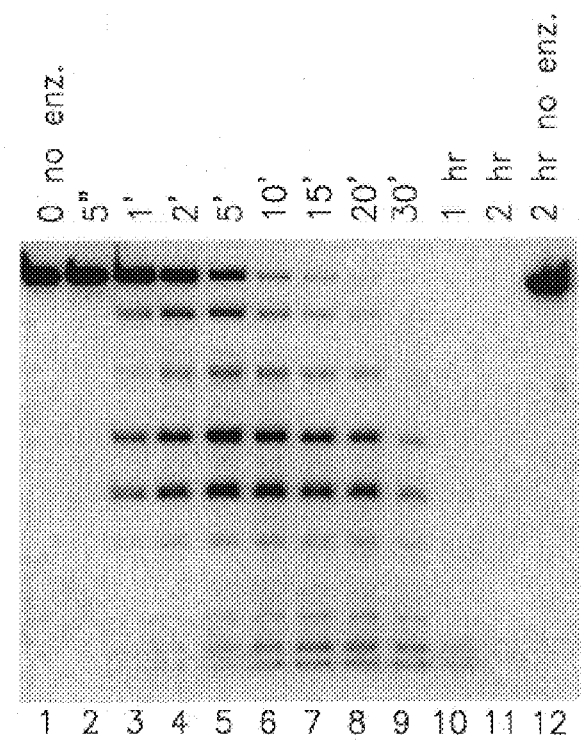
FIG. 60 shows an autoradiograph of a gel resolving the products of double-stranded cleavage reactions run for various lengths of time.

In FIG. 60, lane 1 contains the no enzyme control after a 5 minute incubation at 45° C. and shows the mobility of the uncleaved template DNA. Lanes 2–10 contain cleavage fragments derived from reactions incubated in the presence of Cleavase™ BN for 5 sec, 1, 2, 5, 10, 15, 20, 30, 60 (i hr), or 120 minutes (2 hr), respectively. Lane 11 contains the no enzyme control after a 120 minute incubation at 45° C.

FIG. 60 shows that the cleavage of a double-stranded DNA template mediated by the Cleavase™ BN enzyme was rapid. A full cleavage pattern was apparent and essentially complete within one minute. Unlike the example of cleavage of a single-stranded DNA template (Example 13c), very little cleavage is detectable after 5 seconds. This reaction contained one-tenth the amount of enzyme used in the reaction described in Example 13c. In addition, whereas incubation of single-stranded cleavage reactions for extended periods generated a pattern of increasingly truncated fragments (Example 22e), extended incubation of the double-stranded cleavage reaction resulted in a complete loss of signal (FIG. 60, lane 10); this result is probably due to nibbling by the enzyme of the 5' biotin moiety from the reannealed strands. It is important to note that these results show that the same pattern of cleavage was produced for cleavage of double-stranded DNA, as for single-stranded, whether the reaction is run for 1 or 30 minutes. That is, the full representation of the cleavage products (i.e., bands) is seen over a 30-fold difference in time of incubation; thus the double-stranded CFLP™ reaction need not be strictly controlled in terms of incubation time.

Figure 61:
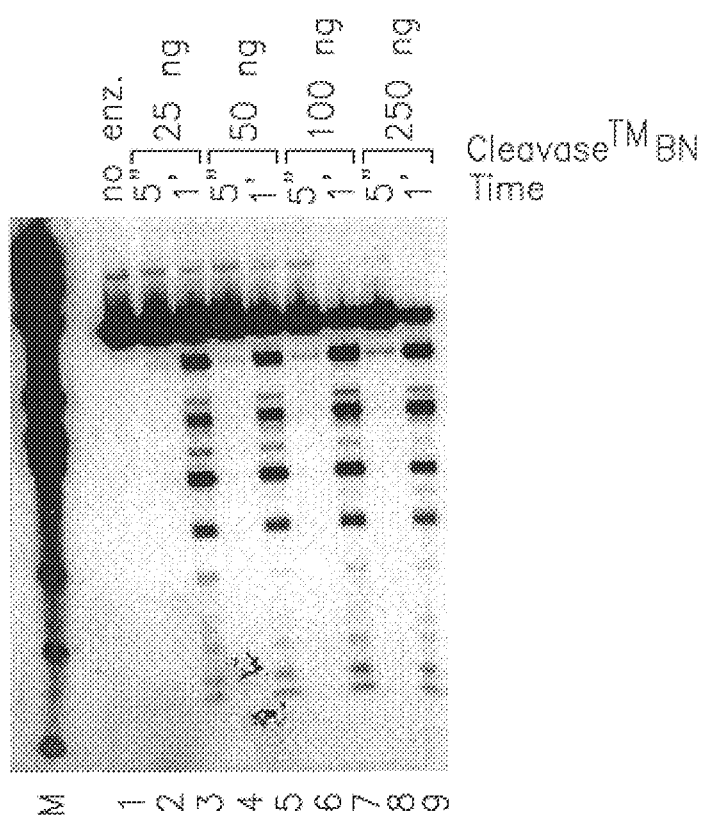
FIG. 61 shows an autoradiograph of a gel resolving the products of double-stranded cleavage reactions run using various amounts of Cleavase™ BN enzyme for either 5 seconds or 1 minute.

The results shown in FIG. 61 contain short time courses of cleavage reactions performed at a variety of enzyme concentrations. Approximately 100 fmoles of the double-stranded 157 bp fragment of exon 4 of the tyrosinase gene (SEQ ID NO:40) were placed in sterile distilled water in 200 μl thin walled centrifuge tubes (BioRad, Richmond, Calif.) in a volume of 6.25 μl. The tubes were heated to 95° C. for 15 seconds, as described in Example 24b, and cooled to 45° C. Cleavage reactions were started by the addition of 3.75 μl of an enzyme mix containing 2.7× CFLP™ buffer, pH 7.5 (to yield a final concentration of 1×), 0.53 mM MnCl$_2$ (to yield a final concentration of 0.2 mM MnCl$_2$), 0.5 μl Cleavase™ BN [at either 50, 100, 200, or 500 ng/μl in 1× dilution buffer (0.5% NP40, 0.5% Tween 20, 20 mM Tris-HCl, pH 8.0, 50 mM KCl, 10 μg/ml BSA) to yield a final amount of enzyme of 25, 50, 100, or 250 ng]. The final reaction volume was 10 μl. A no enzyme control was set up in parallel, with the difference that sterile distilled water was substituted for the Cleavase™ BN enzyme, and stopped after 1 minute at 45° C.

The cleavage reactions were stopped by the addition of 8 μl of stop buffer (95% formamide, 10 mM EDTA, 0.05% bromophenol blue, 0.05% xylene cyanol) after either 5 seconds or 1 minute. Samples were heated to 72° C. for 2 minutes and 4 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiograph is shown in FIG. 61.

In FIG. 61, lane "M" contains molecular weight markers as described in Example 10a. Lane 1 contains the no enzyme control. Lanes 2 and 3 each contain reaction products generated by incubation of the substrate in the presence of 25 ng of Cleavase™ BN; the reaction in lane 2 was stopped after 5 seconds, that in lane 3, after 1 minute. Lanes 4 and 5 contain reaction products generated by cleavage of the substrate in the presence of 50 ng of Cleavase™ BN; the reaction in lane 4 was stopped after 5 seconds, that in lane 5, after 1 minute. Lanes 6 and 7 contain reaction products generated by cleavage of the substrate in the presence of 100 ng of Cleavase™ BN enzyme; the reaction in lane 6 was stopped after 5 seconds, that in lane 7, after 1 minute. The reactions shown in lanes 8 and 9 each contain 250 ng of Cleavase™ BN; that in lane 8 was stopped after 5 seconds, that in lane 9, after 1 minute.

The results presented in FIG. 61 indicate that the rate of cleavage of double-stranded DNA increased with increasing enzyme concentration. Note that as the concentration of enzyme was increased, there was a corresponding reduction in the amount of uncut DNA that remained after 1 minute. As was demonstrated below, in FIG. 63, the concentration of enzyme included in the cleavage reaction had no effect on the cleavage pattern generated. Comparison of the 250 ng reaction (shown in FIG. 61, lanes 8 and 9) to the short time point digestion described in Example 13c, indicates that the amount of enzyme rather than the double-stranded or single-stranded nature of the substrate controls the extent of cleavage in the very early time points.

f) Temperature Titration Of The Double-Stranded Cleavage Reaction

To determine the effect of temperature variation on the cleavage pattern, the 157 bp fragment of exon 4 of the tyrosinase gene (SEQ ID NO:40) was incubated in the presence of a fixed amount of Cleavase™ BN enzyme for 5 minutes at various temperatures. Approximately 100 fmoles of substrate DNA (prepared as described in Example 24a) were placed in sterile distilled water in 200 μl thin walled centrifuge tubes (BioRad, Richmond, Calif.) in a volume of 6.25 μl. The tubes were heated to 95° C. for 15 seconds and cooled to either 37, 40, 45, 50, 55, 60, 65, 60, 75, or 80° C. Cleavage reactions were started by the addition of 3.75 μl of an enzyme mix containing 2.7× CFLP™ buffer, pH 7.5 (to yield a final concentration of 1×), 0.53 mM MnCl$_2$ (to yield a final concentration of 0.2 mM MnCl$_2$), 0.5 μl Cleavase™ BN [50 ng/μl in 1× dilution buffer (0.5% NP40, 0.5% Tween 20, 20 mM Tris-HCl, pH 8.0, 50 mM KCl, 10 μg/ml BSA)]. The enzyme mix was kept on ice throughout the duration of the experiment, but individual aliquots of the enzyme mix were allowed to come to room temperature before being added to the reactions. A second reaction was run at 37° C. at the end of the experiment to control for any loss of enzyme activity that may have occurred during the course of the experiment. No enzyme controls were set up in parallel and incubated at either 37° C. or 80° C., with the difference that sterile distilled water was substituted for the Cleavase™ BN. The reactions were stopped by the addition of 8 μl of stop buffer (95% formamide, 10 mM EDTA, 0.05% bromophenol blue, 0.05% xylene cyanol).

Samples were heated to 72° C. for 2 minutes and 5 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiograph is shown in FIG. 62.

Figure 62:
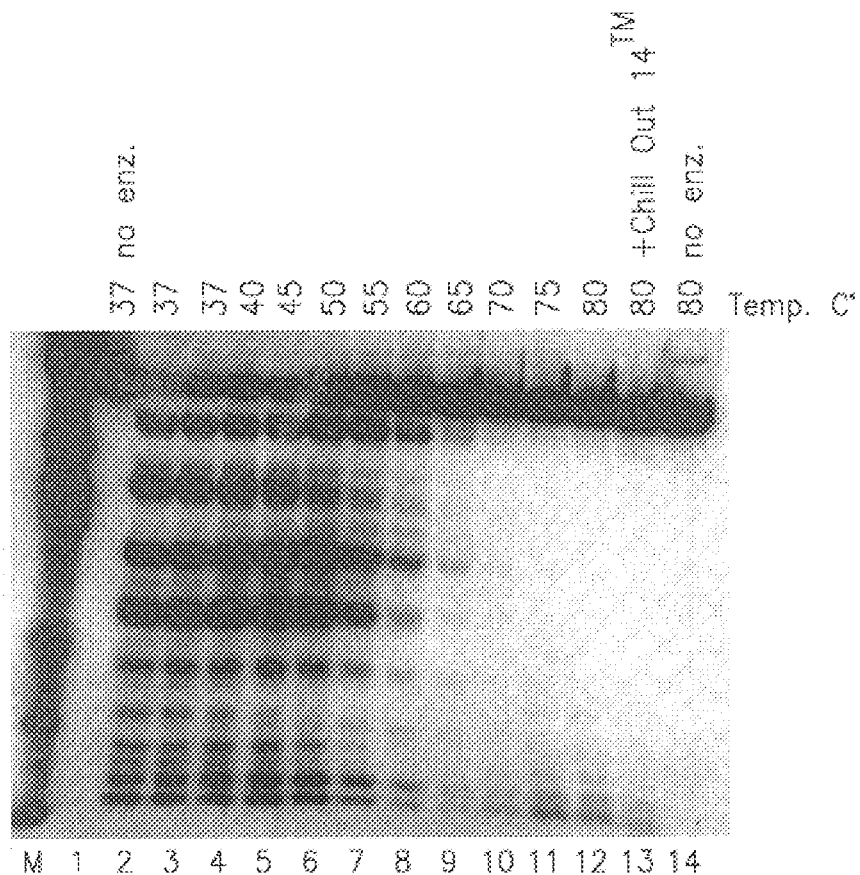
FIG. 62 shows an autoradiograph of a gel resolving the products of double-stranded cleavage reactions run at various temperatures.

In FIG. 62, the lane marked "M" contains molecular weight markers, prepared as described in Example 10a. Lane 1 contains the no enzyme control after a 5 minute incubation at 37° C. Lanes 2 and 3 contain reactions incubated at 37° C., run at the beginning and end of the experiment, respectively. Lanes 4–13 contain reactions incubated at 40, 45, 50, 55, 60, 65, 70, 75, or 80° C. [there are two 80° C. samples; the first was not covered with Chill Out 14™ (MJ Research, Watertown, Mass.), the second was overlaid with 20 μl Chill Out 14™ after the addition of the enzyme mix], respectively. Lane 14 contains a no enzyme control incubated at 80° C. for 5 minutes.

FIG. 62 shows that cleavage of double-stranded DNA substrates proceeded most effectively at lower temperatures. The distribution of signal and pattern of cleavage changed smoothly in response to the temperature of incubation over the range of 37° C. to 60° C. Some cleavage products were evident only upon incubation at higher temperatures, whereas others were far more predominant at lower temperatures. Presumably, certain structures that are substrates for the Cleavase™ BN enzyme at one end of the temperature range are not favored at the other. As expected, the production of cleavage fragments became progressively less abundant in the high end of the temperature range as the cleavage structures were melted out. Above 70° C., the cleavage products were restricted to small fragments, presumably due to extensive denaturation of the substrate. When longer DNAs (350 to 1000 nucleotides) are used, it has been found that useful patterns of cleavage are generated up to 75° C.

These results show that the cleavage reaction can be performed over a fairly wide range of temperatures using a double-stranded DNA substrate. As in the case of the single-stranded cleavage reaction, the ability to cleave double-stranded DNA over a range of temperatures is important. Strong secondary structures that may dominate the cleavage pattern are not likely to be destabilized by single-base changes and may therefore interfere with mutation detection. Elevated temperatures can then be used to bring these persistent structures to the brink of instability, so that the effects of small changes in sequence are maximized and revealed as alterations in the cleavage pattern. This also demonstrates that within the useful temperature range, small changes in the reaction temperature due to heating block drift or similar device variations will not cause radical changes in the cleavage pattern.

g) Titration Of The Cleavase™ BN Enzyme In Double-Stranded Cleavage Reactions

The effect of varying the concentration of the Cleavase™ BN enzyme in the double-stranded cleavage reaction was examined. Approximately 100 fmoles of the 157 bp fragment of exon 4 of the tyrosinase gene (SEQ ID NO:40; prepared as described in Example 24a) were placed in sterile distilled water in 200 μl thin walled centrifuge tubes (BioRad, Richmond, Calif.) in a total volume of 6.25 μl. These tubes were heated to 95° C. for 15 seconds and then rapidly cooled to 45° C.

Cleavage reactions were started immediately by the addition of 3.75 μl of a diluted enzyme mix containing 2.7× CFLP™ buffer, pH 7.5 (to yield a final concentration of 1×), 0.53 mM MnCl$_2$ (to yield a final concentration of 0.2 mM MnCl$_2$), 0.5 μl Cleavase™ BN [2, 10, 20, 50, 100, 200, 500 ng/μl in 1× dilution buffer (0.5% NP40, 0.5% Tween 20, 20 mM Tris-HCl, pH 8.0, 50 mM KCl, 10 μg/ml BSA) such that 1, 5, 10, 25, 50, 100 or 250 ng of enzyme was added to the reactions]. No enzyme controls were set up in parallel, with the difference that IX dilution buffer was substituted for the Cleavase™ BN. After 5 minutes at 45° C., the reactions were stopped by the addition of 8 μl of stop buffer (95% formamide, 10 mM EDTA, 0.05% bromophenol blue, 0.05% xylene cyanol). The samples were heated to 72° C. for 2 minutes and 4 μl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiograph is shown in FIG. 63.

Figure 63:
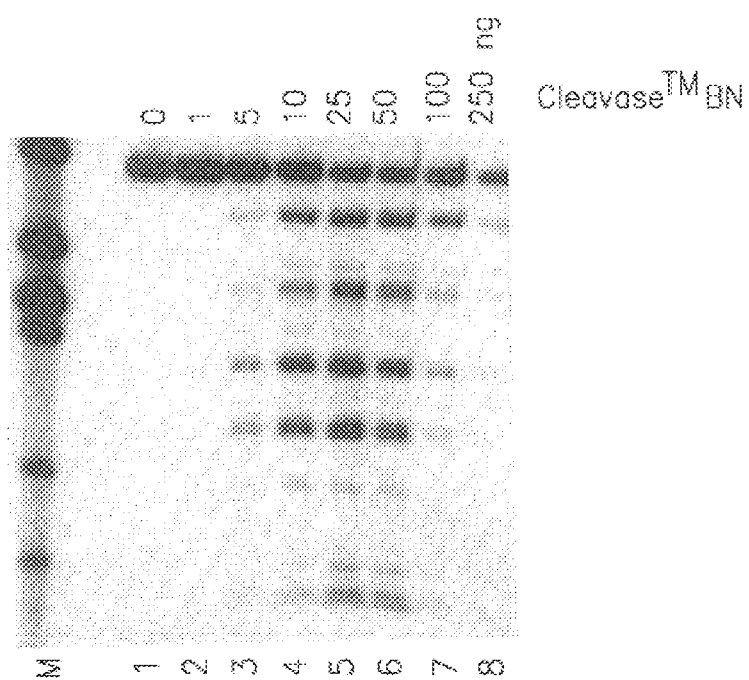
FIG. 63 shows an autoradiograph of a gel resolving the products of double-stranded cleavage reactions run using various amounts of Cleavase™ BN enzyme.

The lane marked "M" in FIG. 63 contains molecular weight markers. Lane 1 contains the no enzyme control and shows the migration of the uncut substrate. Lanes 2–8 contain cleavage products derived from reactions containing 1, 5, 10, 25, 50, 100 or 250 ng of the Cleavase™ BN enzyme, respectively.

These results show that the same cleavage pattern was obtained using the 157 bp tyrosinase DNA substrate (SEQ ID NO:40) regardless of whether the amount of enzyme used in the reaction varied over a 50-fold range. Thus, the double-stranded cleavage reaction is ideally suited for practice in clinical laboratories where reaction conditions are not as controlled as in research laboratories. Note, however, that there is a distinct optimum for cleavage at intermediate enzyme concentrations for a double-stranded template, in marked contrast to what was observed on single-stranded substrates (Example 13e). The progressive loss of signal in the double-stranded reactions at increasing concentrations of Cleavase™ BN is likely due to the nibbling of the 5' biotin label off the end of the reannealed double-stranded template.

EXAMPLE 25

Determination Of The pH Optimum For Single-Stranded And Double-Stranded Cleavage Reactions In order to establish optimal pH conditions for the two types of primer-independent cleavage reactions (i.e., single-stranded and double-stranded cleavage reactions), the Cleavase™ reaction buffer was prepared at a range of different pHs.

a) Establishment Of A pH Optimum For The Single-Stranded Cleavage Reaction

The effect of varying the pH of the Cleavase™ reaction (i.e., CFLP™) buffer upon the cleavage of single-stranded substrates was examined. Several 10× buffer solutions were made with 0.5M MOPS at pH 6.3, 7.2, 7.5, 7.8, 8.0 and 8.2 by titrating a 1M solution of MOPS at pH 6.3 with 6N NaOH. The volume was then adjusted to yield a 0.5M solution at each pH.

Approximately 100 fmoles of a single-stranded substrate prepared from the sense strand of exon 4 of the tyrosinase gene (SEQ ID NO:47; prepared as described in Example 10a), were placed in 200 µl thin walled centrifuge tubes (BioRad, Richmond, Calif.) in 15 µl of 1× CFLP™ buffer, at varying pH, and 1.33 mM $MnCl_2$ (to yield a final concentration of 1 mM). The final reaction volume was 20 µl. The reaction mixes were heated to 95° C. for 5 seconds and rapidly cooled to 65° C. The reactions were started by the addition of 5 µl of diluted enzyme mix containing 1 µl of Cleavase™ BN [50 ng/µl in 1× dilution buffer (0.5% NP40, 0.5% Tween 20, 20 mM Tris-HCl, pH 8.0, 50 mM KCl, 10 pg/ml BSA)] in 1× CFLP™ buffer (without $MnCl_2$), again at the appropriate pH. A 20 µl no salt, no enzyme control was set up in parallel and incubated at 65° C. for each of the indicated pHs, with the difference that sterile distilled water was substituted for Cleavase™ BN and all reaction components were added prior to denaturation. Reactions were stopped by the addition of 16 µl of stop buffer (95% formamide, 10 mM EDTA, 0.05% bromophenol blue, 0.05% xylene cyanol) after 5 minutes.

Samples were heated to 72° C. for 2 minutes and 7 µl of each reaction were resolved by electrophoresis through a 10% polyacrylamide gel (19:1 cross-link), with 7M urea, in a buffer containing 45 mM Tris-Borate, pH 8.3, 1.4 mM EDTA, as described in Example 10a.

After electrophoresis, the gel plates were separated and overlaid with a nylon membrane, as described in Example 10a. The DNA was transferred to the membrane and the membrane was dried, blocked in 1× I-Block (Tropix, Bedford, Mass.), conjugated with streptavidin-alkaline phosphatase (United States Biochemical), washed, reacted with CDP-Star™ (Tropix, Bedford, Mass.), and exposed to X-ray film as described in Example 22a, except that the distilled water washes were omitted. The results are presented in FIG. 64.

Figure 64A:
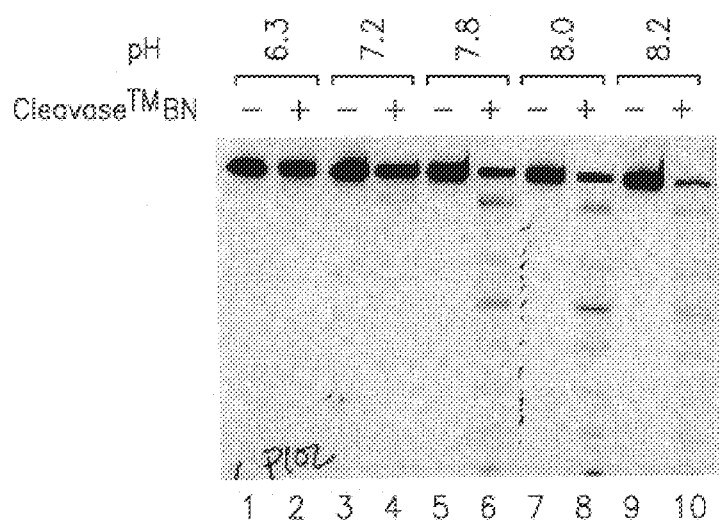
FIG. 64A shows an autoradiograph of a gel resolving the products of single-stranded cleavage reactions run in buffers having various pHs.
Figure 64B:
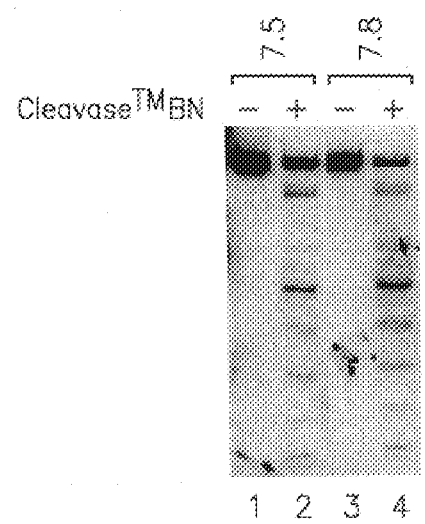
FIG. 64B shows an autoradiograph of a gel resolving the products of single-stranded cleavage reactions run in buffers having a pH of either 7.5 or 7.8.

In FIG. 64, panels A and B contain reactions which used single-stranded DNA substrates. In panel A, 5 pairs of reactions are presented. In each case, the first lane of the pair is the no enzyme control and the second is the single-stranded cleavage reaction. Lanes 1 and 2 depict reaction products obtained using a reaction buffer at pH 6.3; lanes 3 and 4, at pH 7.2; lanes 5 and 6, pH 7.8; lanes 7 and 8, pH 8.0; lanes 9 and 10, at pH 8.2. Panel B contains the results of a separate experiment comparing cleavage reactions performed using a reaction buffer at pH 7.5 (lanes 1 and 2, uncut and cut, respectively) and at pH 7.8 (lanes 3 and 4, uncut and cut, respectively).

The results shown in FIG. 64, panels A and B, indicate that the cleavage of the single-stranded DNA template was sensitive to relatively small changes in pH. There was a pH optimum for the reaction between pH 7.5 and 8.0. Because the $pK_a$ of MOPS is 7.2, the pH closest to that value which supported cleavage, pH 7.5, was determined to be optimal for the single-stranded cleavage reaction.

b) Establishment Of A pH Optimum For The Double-Stranded Cleavage Reaction

The effect of varying the pH of the Cleavase™ reaction (i.e., CFLP™) buffer upon the cleavage of double-stranded substrates was examined. Several 10× buffer solutions were made with 0.5M MOPS at pH 7.2, 7.5, 7.8, and 8.0, as described above in section a). Approximately 100 fmoles of the double-stranded 157 bp fragment of exon 4 of the tyrosinase gene (SEQ ID NO:40; prepared as described in Example 10) were placed in 200 µl thin walled centrifuge tubes (BioRad, Richmond, Calif.) in a total volume of 6.25 µl. The tubes were heated to 95° C. for 15 seconds and cooled to 45° C. The clevage reactions were started by the addition of 3.75 µl of diluted enzyme mix containing 2.7× CFLP™ buffer, pH 7.5 (to yield a final concentration of 1×), 0.53 mM $MnCl_2$ (to yield a final concentration of 0.2 mM $MnCl_2$), 0.5 µl of Cleavase™ BN [50 ng/µl in 1× dilution buffer (0.5% NP40, 0.5% Tween 20, 20 mM Tris-HCl, pH 8.0, 50 mM KCl, 10 µg/ml BSA)].

The cleavage reactions were incubated for 5 minutes and then were terminated by the addition of 8 µl of stop buffer (95% formamide, 10 mM EDTA, 0.05% bromophenol blue, 0.05% xylene cyanol).

Samples were heated to 72° C. for 2 minutes and 4 µl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in Example 10b. The DNA was transferred to the membrane and the membrane was dried, washed in 1× I-Block Blocking Buffer, washed and exposed to X-ray film as described in Example 22a, except that the distilled water washes were omitted. The resulting autoradiographs are shown in FIG. 65, panels A and B.

Figures 65A, 65B:
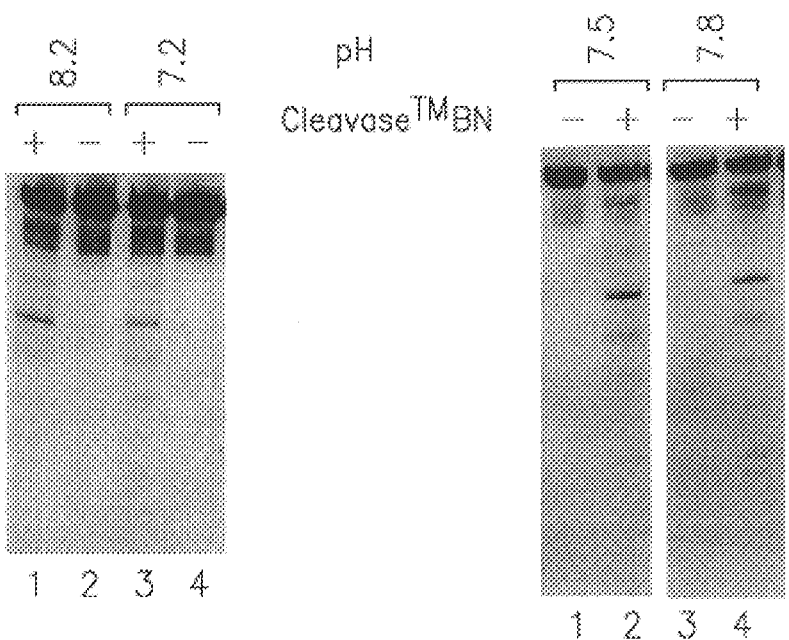
FIG. 65A shows an autoradiograph of a gel resolving the products of double-stranded cleavage reactions run in buffers having a pH of either 8.2 or 7.2.
FIG. 65B shows an autoradiograph of a gel resolving the products of double-stranded cleavage reactions run in buffers having a pH of either 7.5 or 7.8.

In FIG. 65, panel A, lanes 1 and 2 contain cleavage products from reactions run in a buffer at pH 8.2 (lane 1 contains the cleavage reaction; lane 2 is the uncut control). Lanes 3 and 4 contain cleavage products from reactions run in a buffer at pH 7.2 (lane 3 contains the cleavage reaction; lane 4 is the uncut control). In panel B, lanes 1 and 2 contain cleavage products from reactions run in a buffer at pH 7.5 (lane 1 is the uncut control; lane 2 contains the cleavage reaction). Lanes 3 and 4 contain cleavage products from reactions run in a buffer at pH 7.8 (lane 3 contains the uncut control; lane 4 contains the cleavage reaction).

The results in FIG. 65, panels A and B, demonstrate that the cleavage of double-stranded DNA was not sensitive to changes in pH over the range of buffer conditions tested. Because the cleavage of single-stranded DNA, however, was sensitive to changes in pH, the buffer conditions that were determined to be optimal for the single-stranded cleavage reaction were chosen for subsequent double-stranded cleavage experiments.

EXAMPLE 26

The Presence Of Competitor DNA Does Not Alter The Cleavage Pattern

The effect of the presence of competitor (ie., non-labelled substrate) DNA upon the cleavage reaction was examined. The cleavage reaction was run using the 157 nucleotide fragment from the sense strand of the human tyrosinase gene (SEQ ID NO:47) and human genomic DNA. The results shown below demonstrate that the presence of non-substrate DNA has no effect on the CFLP™ pattern obtained in the cleavage reaction.

a) Preparation Of The Substrate DNA And The Cleavage Reactions

The 157 nucleotide single-stranded wild type tyrosinase substrate (SEQ ID NO:47) containing a biotin label on the 5' end was prepared as described in Example 11. Human genomic DNA (Promega) present at 235 µg/ml in Tris-HCl, pH 8.0; 1 mM EDTA was ethanol precipitated and resuspended in Tris-HCl, pH 8.0; 0.1 mM EDTA to final concentration 400 µg/ml. This DNA was used as a competitor in standard CFLP™ single-stranded reactions (described in Example 11). Tyrosinase DNA substrate (SEQ ID NO:47) and human genomic DNA were mixed in H$_2$O in final volume of 6 µl. Samples were heated at 95° C. for 10 seconds to denature the DNA, cooled to the target temperature of 65° C., and mixture of 2 µl 5× CFLP™ buffer, pH 7.5, 1 µl 10 mM MnCl$_2$ and 1 µl (25 ng) the enzyme Cleavase™ BN in dilution buffer was added. After 5 minutes at 65° C., 6 µl of stop buffer was added to terminate reaction and 5 µl of each sample was separated on a 10% denaturing polyacrylamide gel. Membrane transfer and DNA visualization were performed as described in Example 21.

b) The Presence Of Genomic DNA Does Not Alter The CFLP™ Pattern

Figure 66:
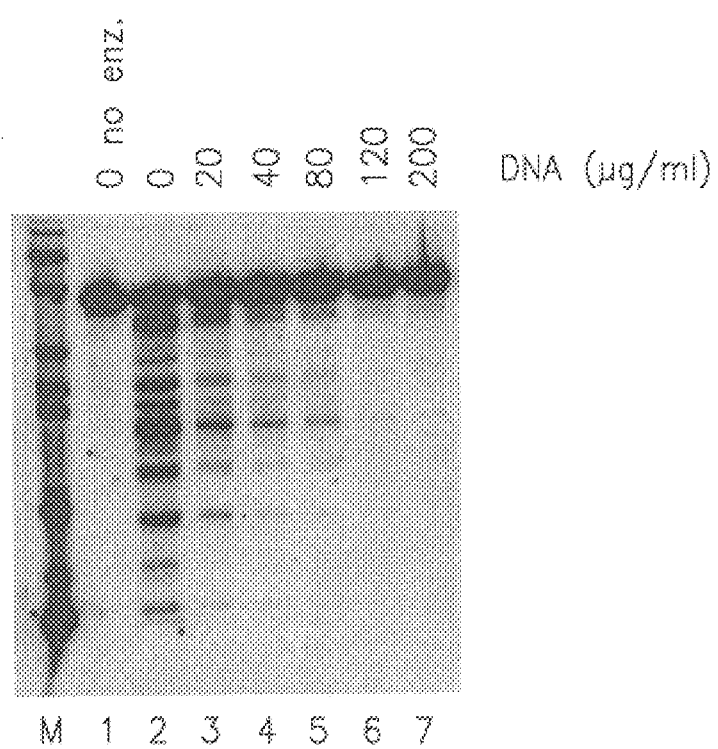
FIG. 66 shows an autoradiograph of a gel resolving the products of single-stranded cleavage reactions run in the presence of various amounts of human genomic DNA.

FIG. 66 shows the resulting pattern corresponding to the cleavage products of the sense strand of the wild type tyrosinase substrate (SEQ ID NO:47) in the presence of 0 µg/ml (lane 2), 20 µg/ml (lane 3), 40 µg/ml (lane 4), 80 µg/ml (lane 5), 120 µg/ml (lane 6) and 200 µg/ml (lane 7) unlabeled human genomic DNA. Lane 1 shows an uncut control in the absence of the enzyme Cleavase™ BN and lane marked "M" contains the molecular weight markers prepared as described in Example 10.

FIG. 66 shows that the presence of genomic DNA in the cleavage reaction did not change either the position or the relative intensity of the product bands produced. Increasing the amount of nonspecific DNA in the reaction did, however, decrease the efficiency of the cleavage reaction and reduced the overall intensity of the pattern. These results can be explained by the binding of the Cleavase™ BN enzyme to the nonspecific DNA which has the effect of decreasing the effective enzyme concentration in the reaction. This effect became significant when the concentration of genomic DNA in the reaction was equal to or greater than 120 µg/ml [FIG. 66, lanes 6 (120 µg/ml) and 7 (200 µg/ml)]. Under these conditions, the genomic DNA was present at more than a 20,000-fold excess relative to the specific substrate DNA; nonetheless the CFLP™ pattern could still be recognized under these conditions. The observed stability of the CFLP™ pattern in the presence of genomic DNA ruled out the possibility that nonspecific DNA could significantly change the structure of the substrate DNA or alter the interaction of the Cleavase™ BN enzyme with the substrate.

EXAMPLE 27

The CFLP™ Reaction Can Be Practiced Using A Variety of Enzymes

The above Examples demonstrated the ability of Cleavase™ BN, a 5' nuclease derived from Taq DNA polymerase, to generate a characteristic set of cleavage fragments from a nucleic acid substrate. The following experiments demonstrate that a number of other enzymes can be used to generate a set of cleavage products which are characteristic of a given nucleic acid. These enzymes are not limited to the class of enzymes characterized as 5' nucleases.

a) Cleavage Patterns Generated by Other DNA Polymerases From The Genus Thermus

To determine whether 5' nuclease activity associated with DNA polymerases (DNAPs) other than Taq DNAP could generate a distinct cleavage pattern from nucleic acid substrates, DNAPs from two species of Thermus were examined. The DNAP of *Thermus flavus* ["Tfl", Kaledin et al., Biokhimiya 46:1576 (1981); obtained from Promega Corp., Madison, Wis.] and the DNAP of *Thermus thermophilus*["Tth", Carballeira et al., Biotechniques 9:276 (1990); Myers et al., Biochem. 30:7661 (1991); obtained from U.S. Biochemicals, Cleveland, Ohio] were examined for their ability to generate suitable cleavage patterns (i.e., patterns which can be used to characterize a given nucleic acid substrate).

The ability of these other enzymes to cleave nucleic acids in a structure-specific manner was tested using the single-stranded 157 nucleotide fragment of the sense strand of exon 4 of the tyrosinase gene (SEQ ID NO:47) under conditions reported to be optimal for the synthesis of DNA by each enzyme.

Approximately 100 fmoles of the 157 nucleotide fragment derived from the sense strand of exon 4 of the tyrosinase gene (SEQ ID NO 47; prepared as described in example 10a) were placed in 200 µl thin wall microcentrifuge tubes (BioRad, Richmond, Calif.) in 1× CFLP™ buffer, pH 8.2 and 1.33 mM MnCl$_2$ (to yield a final concentration of 1 mM) and KCl to yield a final concentration of either 0 or 50 mM. Final reaction volumes were 20 µl. Samples were heated to 95° C. for 5 seconds and then cooled to 65° C. A 20 µl no salt, no enzyme control was set up in parallel, with the differences that sterile distilled water was substituted for Cleavase™ BN and all reaction components were added prior to denaturation at 95° C.

The cleavage reactions were started by the addition of 5 µl of a diluted enzyme mix containing either 1.25 units or 5 units of the indicated enzyme (see below) in 1× CFLP™ buffer, pH 8.2. After 5 minutes, reactions were stopped by the addition of 16 µl of stop buffer (95% formamide, 10 mM EDTA, 0.05% bromophenol blue, 0.05% xylene cyanol).

Samples were heated to 72° C. for 2 minutes and 7 µl (in the case of the samples digested with Tfl) or 5 µl (in the case of the samples digested with Tth) were electrophoresed through a 10% polyacrylamide gel (19:1 cross-link), with 7M urea, in a buffer containing 45 mM Tris-Borate, pH 8.3, 1.4 mM EDTA, as described in Example 10a.

After electrophoresis, the gel plates were separated and overlaid with a nylon membrane, as described in Example 10a. The DNA was transferred to the membrane and the membrane was dried, blocked in 1× I-Block (Tropix, Bedford, Mass.), conjugated with streptavidin-alkaline phosphatase (United States Biochemical, Cleveland, Ohio), washed, reacted with CDP-Star™ (Tropix, Bedford, Mass.), and exposed to X-ray film as described in Example 22a, except that the distilled water washes were omitted. The results are presented in FIGS. 67 and 68.

Figure 67:
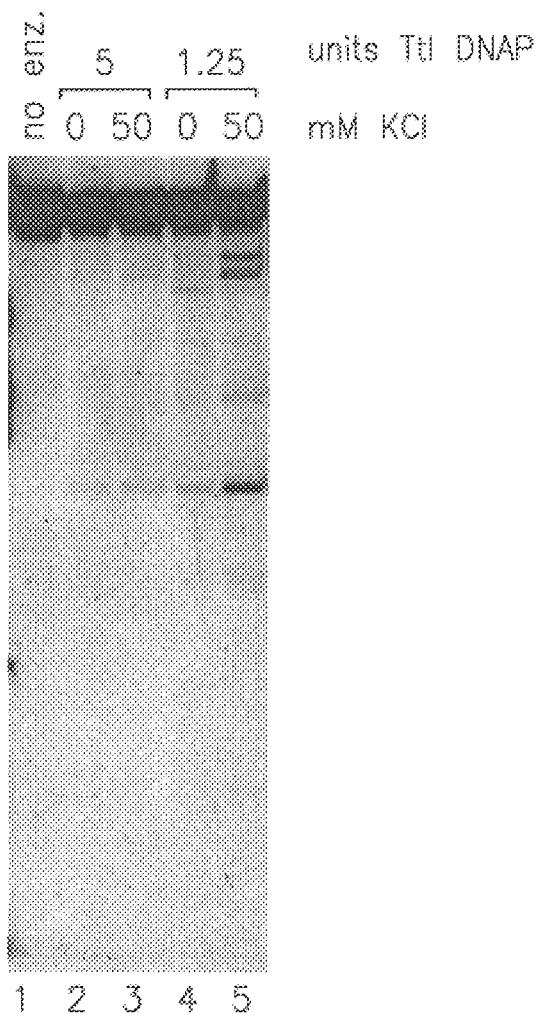
FIG. 67 shows an autoradiograph of a gel resolving the products of single-stranded cleavage reactions run using the Tfi DNA polymerase in two different concentrations of KCl.

In FIG. 67, lane 1 contains the no enzyme control and indicates the migration of the uncut DNA. Lanes 2–5 contain cleavage products derived from reactions incubated with Tfl DNAP. The reactions represented in lane 2 and 3 each contained 5 units of Tfl DNAP; the sample in lane 2 was incubated in a reaction buffer containing 0 mM KCl, while the sample in lane 3 was incubated in a reaction buffer containing 50 mM KCl. The reactions in lanes 4 and 5 each contained 1.25 units of Tfl DNAP; the sample in lane 4 was incubated in a reaction buffer containing 0 mM KCl; that in lane 5 was incubated in a reaction buffer containing 50 mM KCl.

Figure 68:
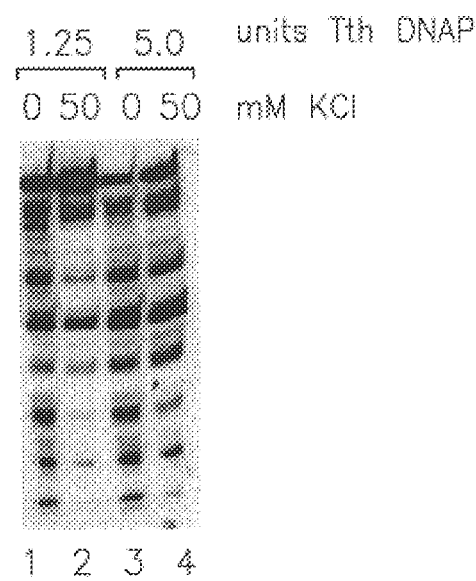
FIG. 68 shows an autoradiograph of a gel resolving the products of single-stranded cleavage reactions run using the Tth DNA polymerase in two different concentrations of KCl.

In FIG. 68, lanes 1 and 2 each contain cleavage products derived from reactions incubated with 1.25 units of Tth DNAP. The sample in lane 1 was incubated in a reaction buffer containing 0 mM KCl; that in lane 2 was incubated in a reaction buffer containing 50 mM KCl. Lanes 3 and 4 contain cleavage products derived from reactions incubated with 5 units of Tth DNAP. The sample shown in lane 3 was incubated in a reaction buffer containing 0 mM KCl; that in lane 4 was incubated in a reaction buffer containing 50 mM KCl.

FIGS. 67 and 68 demonstrates that both Tth DNAP and Tfl DNAP display structure specific endonuclease activity similar in nature to that seen in the Cleavase™ BN enzyme. A comparison of the results shown in FIGS. 67 and 68 showed that the Tth DNAP was more efficient at generating a cleavage pattern under the reaction conditions tested. Comparison of the cleavage patterns generated by Tth DNAP with those generated by the Cleavase™ BN enzyme the indicates that essentially the same structures are recognized by these two enzymes [compare FIG. 69, lane 2 (Cleavase™ BN) with FIG. 68 (Tth DNAP)].

b) Enzymes Characterized As 3' Nucleases Can be Used To Generate Distinct Clevage Patterns To determine whether enzymes possessing 3' nucleolytic activity could also generate a distinct cleavage pattern, enzymes other than DNAPs (which possess 5' nuclease activity) were tested in the cleavage reaction. Exonuclease III from *Escherichia coli* (*E. coli* Exo III) was tested in a cleavage reaction using the 157 nucleotide fragment prepared from the sense strand of exon 4 of the tyrosinase gen (SEQ ID NO:47). As a comparison, a reaction containing this substrate (SEQ ID NO:47) and Cleavase™ BN was also prepared.

Approximately 100 fmoles of the 157 nucleotide fragment prepared from the sense strand of exon 4 of the tyrosinase gene (SEQ ID NO:47; prepared as described in Example 10a) were placed in 200 μl thin wall microcentrifuge tubes (BioRad, Richmond, Calif.) in 1× CFLP™ buffer, pH 8.2 and 1.33 mM $MnCl_2$ (to yield a final concentration of 1 mM) and KCl to yield a final concentration of either 0 or 50 mM in a volume of 15 μl. Final reaction volumes were 20 μl.

The samples were heated to 95° C. for 5 seconds and then rapidly cooled to 37° C. A 20 μl no salt, no enzyme control was set up in parallel, with the differences that sterile distilled water was substituted for Cleavase™ BN and all reaction components were added prior to denaturation at 95° C.

A reaction tube containing 100 fmoles of the 157 nucleotide fragment (SEQ ID NO:47) and 50 ng of Cleavase™ BN in a buffer containing 0 mM KCl was prepared and treated as described in Example 23 (i.e., denatured by incubation at 95° C. for 5 seconds followed by cooling to 65° C. and the addition of the enzyme and incubation at 65° C. for 5 minutes).

The cleavage reactions were started by the addition of 5 μl of a diluted enzyme mix containing either 1.25 units or 200 units of Exo III (United States Biochemical, Cleveland, Ohio) in 1× CFLP™ buffer, pH 8.2 (without $MnCl_2$) were added to the 15 μl reactions, and the reactions were incubated for 5 minutes. After 5 minutes at 37° C., the reactions were stopped by the addition of 16 μl of stop buffer (95% formamide, 10 mM EDTA, 0.05% bromophenol blue, 0.05% xylene cyanol).

The samples were heated to 72° C. for 2 minutes and 5 μl were electrophoresed through a 10% polyacrylamide gel (19:1 cross-link), with 7M urea, in a buffer containing 45 mM Tris-Borate, pH 8.3, 1.4 mM EDTA, as described in Example 10a.

After electrophoresis, the gel plates were separated and overlaid with a nylon membrane, as described in example 10a. The DNA was transferred to the membrane and the membrane was dried, blocked in 1× I-Block (Tropix, Bedford, Mass.), conjugated with streptavidin-alkaline phosphatase (United States Biochemical, Cleveland, Ohio), washed, reacted with CDP-Star™ (Tropix, Bedford, Mass.), and exposed to X-ray film as described in Example 22a, except that the distilled water washes were omitted. The results are presented in FIG. 69.

Lane 1 in FIG. 69 contains the no enzyme control and indicates the mobility of the uncut DNA. Lane 2 contains cleavage fragments generated by incubation of the substrate with Cleavase™ BN enzyme and provides a comparison of the patterns generated by the two different enzymes. Lanes 3–6 contain cleavage fragments generated by incubation of the substrate with Exo III. Lanes 3 and 4 each contain reaction products generated in reactions which contained 200 units of Exo III; the reaction in lane 3 was run in a buffer containing 0 mM KCl, that in lane 4 was run in a buffer containing 50 mM KCl. Lanes 5 and 6 each contain reaction products generated in reactions which contained 1.25 units of Exo III; the reaction in lane 5 was run in a buffer containing 0 mM KCl, that in lane 6 was run in a buffer containing 50 mM KCl.

The results presented in FIG. 69 demonstrate that Exo III generated a distinct cleavage pattern when incubated with a single-stranded DNA substrate. The pattern generated by Exo III was entirely distinct from that generated by the Cleavase™ BN enzyme. The results shown in FIG. 69 also show that significant differences in the cleavage pattern generated by Exo III were observed depending on the concentrations of both the enzyme and KCl included in the reactions.

c) Ability Of Alternative Enzymes To Identify Single Base Changes

In sections and a) and b) above it was shown that enzymes other than Cleavase™ BN could generate a distinct pattern of cleavage fragments when incubated in the presence of a nucleic acid substrate. Because both Tth DNAP and *E. coli* Exo III generated distinct cleavage patterns on single-stranded DNA, the ability of these enzymes to detect single base changes present in DNA substrates of the same size was examined. As in Example 11, the human tyrosinase gene was chosen as a model system because numerous single point mutations have been identified in exon 4 of this gene.

Three single-stranded substrate DNAs were prepared; all three substrates contained a biotin label at their 5' end. The wild type substrate comprises the 157 nucleotide fragment from the sense strand of the human tyrosinase gene (SEQ ID NO:47). Two mutation-containing substrates were used. The 419 substrate (SEQ ID NO:54) and the 422 substrate (SEQ ID NO:55), both of which are described in Example 11. Single-stranded DNA containing a biotin label at the 5' end was generated for each substrate using asymmetric PCR as described in Example 10a with the exception that the single-stranded PCR products were recovered from the gel rather than the double-stranded products.

Cleavage reactions were performed as follows. Each substrate DNA (approximately 100 fmoles) was placed in a 200 μl thin wall microcentrifuge tubes (BioRad, Richmond, Calif.) in 5 μl of 1× CFLP™ buffer with 1.33 mM $MnCl_2$ (to yield a final concentration of 1 mM). A no enzyme control was set up with the wild type DNA fragment in parallel and incubated at 65° C. for each of the indicated time points, with the differences that sterile distilled water was substituted for Cleavase™ BN and all reaction components were added prior to denaturation at 95° C. The reaction tubes were brought to 95° C. for 5 seconds to denature the substrates and then the tubes were quickly cooled to 65° C. for the reactions containing Tth DNAP and 37° C. for the reactions containing Exo III.

Cleavage reactions were started immediately by the addition of a diluted enzyme mixture containing 1.25 units of the enzyme either Tth DNAP or Exo III in 5 µl of 1× CFLP™ buffer without MnCl$_2$. The enzyme solution was brought to room temperature before addition to the cleavage reaction. After 5 minutes at 65° C., the reactions were stopped by the addition of 8 µl of stop buffer (95% formamide, 10 mM EDTA, 0.05% bromophenol blue, 0.05% xylene cyanol). The samples were heated to 72° C. for 2 minutes and 7 µl of each reaction were resolved by electrophoresis through a 10% polyacrylamide gel (19:1 cross-link), with 7M urea, in a buffer containing 45 mM Tris-Borate, pH 8.3, 1.4 mM EDTA.

After electrophoresis, the gel plates were separated and overlaid with a nylon membrane, as described in example 10a. The DNA was transferred to the membrane and the membrane was dried, blocked in 1× I-Block (Tropix, Bedford, Mass.), conjugated with streptavidin-alkaline phosphatase (United States Biochemical), washed, reacted with CDP-Star™ (Tropix, Bedford, Mass.), and exposed to X-ray film as described in Example 22a with the exception that the distilled water washes were omitted. The results are presented in FIG. 70.

In FIG. 70, lanes 1–3 contain cleavage fragments generated by incubation of either the wild-type, mutant 419 and mutant 422 alleles of the tyrosinase gene, respectively, with Tth DNAP. Lanes 4–6 contain cleavage fragments generated by incubation of either the wild type, mutant 419 and mutant 422 substrates, respectively, with Exo III in a buffer containing 0 mM KCl. Lanes 7–9 contain cleavage fragments generated by incubation of either the wild type, mutant 419 and mutant 422 substrates, respectively, incubated with Exo III in a buffer containing 50 mM KCl. Lane 10 contains cleavage fragments generated by incubation of the wild type DNA substrate with Cleavase™ BN in a buffer containing 0 mM KCl; this reaction provides a comparison of the patterns generated by the three different enzymes (i.e., Cleavase™ BN, Tth DNAP and Exo III). Lane 11 contains the no enzyme control with the wild type DNA substrate incubated in the presence of 50 mM KCl.

The results shown in FIG. 70 demonstrate that both Tth DNAP and Exo III were able to detect single base changes in a single-stranded DNA substrate relative to a wild-type DNA substrate. The patterns generated by Tth DNAP were comparable to those generated by Cleavase™ BN for all three DNA substrates (See FIG. 32 for a comparison of the pattern generated by Cleavase™).

The patterns generated by Exo III were entirely distinct from those generated by enzymes derived from the genus Thermus (i.e., Cleavase™ BN and Tth DNAP). Furthermore, the pattern produced by cleavage of the DNA substrates by Exo III were distinct depending on which concentration of KCl was employed in the reaction (FIG. 70). A distinct pattern change was evident for the 419 mutant at both KCl concentrations. As shown in FIG. 70, at 0 mM KCl, a band appears in the 40 nucleotide range in the 419 mutant (lane 5); at 50 mM KCl, the 419 mutant contains an additional band in the 70 nucleotide range (lane 8). Pattern changes were not discernable for the 422 mutant (relative to the wild-type) in the Exo III digestions; this difference in the ability of the E. coli Exo III enzyme to detect single base changes could relate to the relative positions of the changes with respect to secondary structures that act as substrates for the structure specific cleavage reaction, and the position of the label (5' or 3' end) relative to the preferred cleavage site (5' or 3'), FIG. 71.

d) The Drosophila RrpI Enzyme Can Be Used to Generate Cleavage Patterns

Another protein in the Exo III family of DNA repair endonucleases, RrpI from *Drosophila melanogaster* (Nugent, M, Huang, S. -M., and Sander, M. *Biochemistry*, 1993: 32, pp. 11445–11452), was tested for its ability to generate a distinct cleavage pattern on a single-stranded DNA template. Because its characteristics in the cleavage assay were unknown, this enzyme was tested under a variety of buffer conditions. Varying amounts of this enzyme (1 ng or 30 ng) were incubated with approximately 100 fmoles of the 157 nucleotide fragment 3of the sense strand of exon 4 of the tyrosinase gene (SEQ ID NO: 47) in either 1 mM MnCl$_2$ or 5 mM MgCl$_2$ and either 1× CFLP™ buffer, pH 8.2 or 1× CFLP™ buffer, pH 7.8, with 10 mM NaCl. Samples were heated to 95° C. and begun by the addition of a diluted enzyme mix containing either 1 or 30 ng of RrpI in 1× CFLP™ buffer. Reactions were carried out at 30° C. for either 5 or 30 minutes. The results (data not shown) indicated that this enzyme generates a weak, but distinct cleavage pattern on a single-stranded DNA template.

e) The Rad1/Rad10 Complex Can Be Used To Generate Cleavage Patterns

The Rad1-Rad10 endonuclease (Rad1/10) from *S. cerevisiae* is a specific 3' endonuclease which participates in nucleotide excision repair in yeast. This enzyme is a heterodimer consisting of two proteins, Rad1 and Rad10. Rad1 and Rad10 alone do not have enzymatic activity. Rad1/10 recognizes structures comprising a bifurcated DNA duplex and cleaves the single-stranded 3' arm at the end of the duplex [Bardwell, A. J et al. (1994) Science 265:2082]. In this sense Rad1/10 shares the same substrate specificity as does the Cleavase™ BN enzyme. However, the cleavage products produced by Rad1/10 and Cleavase™ BN differ as the Rad1/10 cleaves on the 3' single-stranded arm of the duplex while Cleavase™ BN cuts on the 5' single-stranded arm.

FIG. 71 provides a schematic drawing depicting the site of cleavage by these two enzymes on a bifurcated DNA duplex (formed by the hairpin structure shown). In FIG. 71, the hairpin structure at the top shows the site of cleavage by a 5' nuclease (e.g., Cleavase™ BN). The hairpin structure shown at the bottom of FIG. 71 shows the site of cleavage by an enzyme which cleaves at the 3' single-stranded arm (e.g., Rad1/10). Enzymes which cleave on the 5' single-stranded arm are referred to as Cleavase™ 5' enzymes; enzymes which cleave on the 3' single-stranded arm are referred to as Cleavase™ 3' enzymes.

In order to determine whether the Rad1/10 protein is able to detect single base changes in DNA substrates, the cleavage patterns created by cleavage of DNA substrates by the Rad1/10 and Cleavase™ BN enzymes were compared. In this comparison the following substrates were used. The 157 nucleotide fragment from the wild type (SEQ ID NO:47), the 419 mutant (SEQ ID NO:54) and the 422 mutant (SEQ ID NO:55) alleles derived from the sense strand of exon 4 of the human tyrosinase gene was generated containing a biotin label at the 5' end as described in Example 11.

The Rad1 and Rad10 proteins were generously provided by Dr. Errol C. Friedberg (The University of Texas Southwestern Medical Center, Dallas). The Rad1/10 complex was prepared by mixing Rad1 and Rad10 proteins in 1× dilution buffer (0.5% NP40, 0.5% Tween 20, 20 mM Tris-HCl, pH 8.0, 50 mM KCl, 10 μg/ml BSA) to achieve a final concentration of 0.1 mM of each protein.

Cleavage reactions using the Rad1/10 endonuclease were performed as follows. The substrate DNA and 15 ng (0.1 pmole) of Rad1/10 complex in 1 μl of 1× dilution buffer were mixed on ice in 10 μl of 1× CFLP™ buffer pH 7.8, 1 mM $MnCl_2$. The reaction was then incubated at 37° C. for 5 minutes. The cleavage reaction was stopped by addition of 6 μl of stop buffer.

Cleavage reactions using the Cleavase™ BN enzyme were done exactly as described above for the Rad1/10 cleavages with the exception that 10 ng of the Cleavase™ BN enzyme was added and the incubation at 37° C. was performed for 3 minutes. Uncut or no enzyme controls were run for each substrate DNA and were prepared as described for the reactions containing enzyme with the exception that sterile water was added in place of the enzyme (data not shown).

The cleavage products (3 μl each) were separated by electrophoresis through a 10% denaturing polyacrylamide gel, transferred to a membrane and visualized as described in Example 21. The resulting autoradiograph is shown in FIG. 72.

Figures 72, 73:
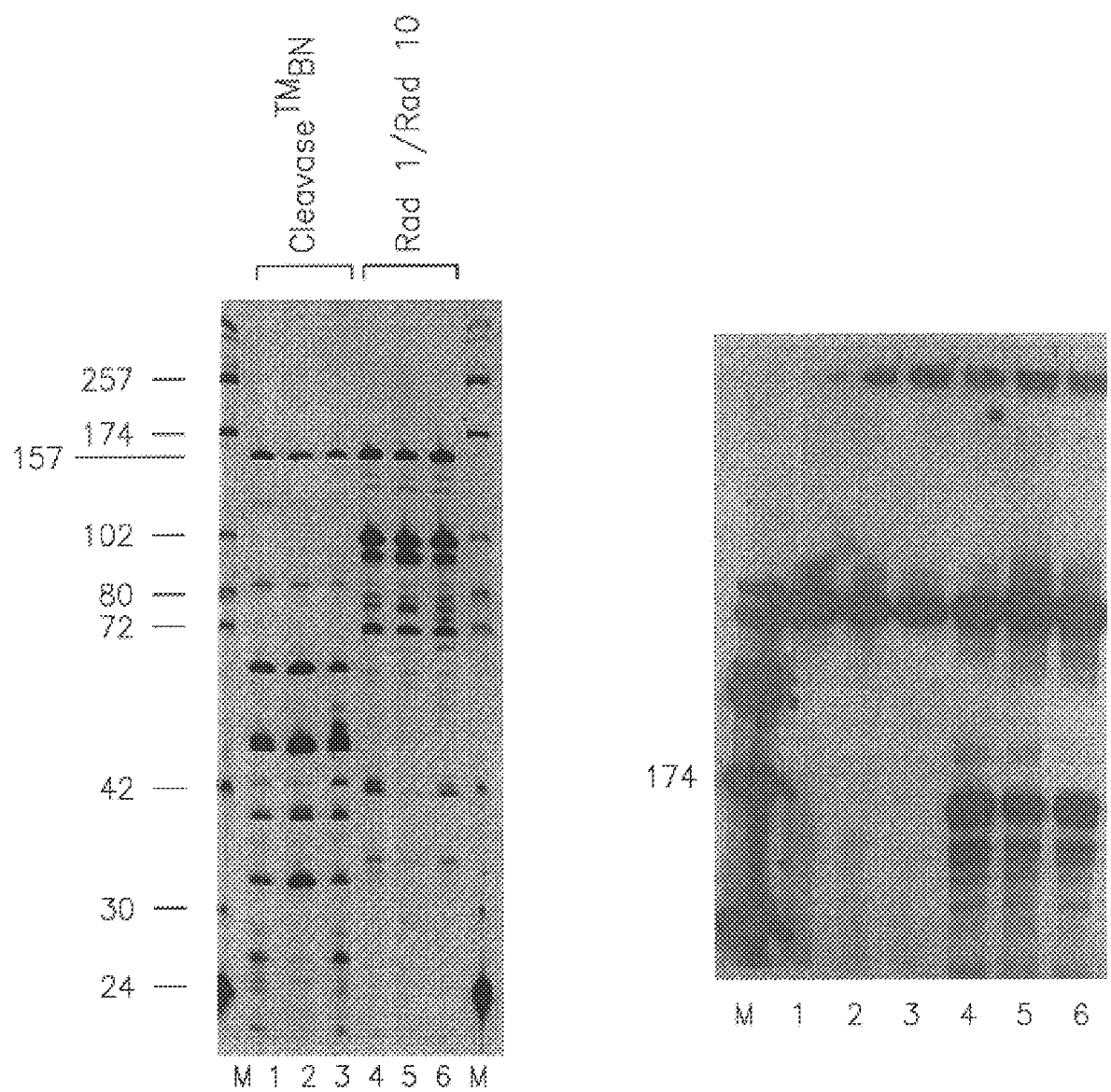
FIG. 72 shows an autoradiograph of a gel resolving the products of single-stranded cleavage reactions run on three different tyrosinase gene substrates (SEQ ID NOS:47, 54 and 55) using either Cleavase™ BN or the Rad1/Rad10 complex.
FIG. 73 shows an autoradiograph of a gel resolving the products of double-stranded cleavage reactions run on a wild-type and two mutant β-globin substrates.

FIG. 72 shows the resulting patterns corresponding to the cleavage products of the sense strand of the wild type tyrosinase substrate (SEQ ID NO:47) (lanes 1 and 4), the 419 mutant (SEQ ID NO:54) (lanes 2 and 5) and the 422 mutant (SEQ ID NO:55) (lanes 3 and 6). Lanes 1–3 show the cleavage pattern created by incubation of the three substrate DNAs with the Cleavase™ BN enzyme and lanes 4–6 show cleavage patterns created by incubation of the three substrate DNAs with the Rad1/10 enzyme. Lanes marked "M" contain molecular weight markers prepared as described in Example 10.

The results shown in FIG. 72 demonstrate that the Rad1/10 enzyme was able to produce distinctive cleavage patterns from the substrate DNAs (lanes 4–6); the average product length produced by cleavage of the substrate was longer than that produced by Cleavase™ BN. Importantly, the results shown in FIG. 72 demonstrate that the single base substitutions found in the mutant tyrosinase substrates resulted in the production of specific changes in the otherwise similar cleavage patterns of tyrosinase substrates (compare lanes 5 and 6 with lane 4). Note that in the digestion of the mutant 419 substrate with Rad1/10, the bands below about 40 nucleotides have lower intensity and one band is absent, when compared to wild-type, while in the digest of the mutant 422 substrate several new bands appear in the range of 42–80 nucleotides. Since both enzymes were tested using the same reaction conditions, these results show that Rad1/10 was able to detect the same differences in DNA secondary structure that were recognized by Cleavase™ BN. Rad1/10 generates a different cleavage pattern relative to that produced by Cleavase™ BN, since cleavage takes place at the 3' end of DNA hairpins producing inherently longer fragments when the substrate contains a 5' end label.

EXAMPLE 28

Detection Of Mutations In The Human β-Globin Gene Using Double-Stranded DNA Substrates The results shown in Example 15 demonstrated that single base changes in fragments of the β-globin gene can be detected by cleavage of single-stranded DNA substrates with the Cleavase™ BN enzyme. In this example it is shown that mutations in the β-globin gene can be detected by cleavage of double-stranded DNA substrates using the Cleavase™ BN enzyme.

Double-stranded substrate DNA comprising 536 bp fragments derived from the wild-type β-globin gene (SEQ ID NO:69), mutant 1 (SEQ ID NO:71) and mutant 2 (SEQ ID NO:72) were generated containing a 5' biotin label on the sense strand using the PCR. PCR amplification of these substrates was done as described in Example 15a. Gel purification and isolation of double-stranded fragments was performed as described in Example 21a.

The cleavage reactions were performed as described in Example 21c. Briefly, 2 μl of stock DNA (80 ng) in 10 mM Tris-HCl pH 8.0, 0.1 mM EDTA was mixed with 3 μl $H_2O$ and denatured at 95° C. for 20 seconds. The denatured DNA was cooled to 70° C. and a mixture consisting of 2 μl of 5× CFLP™ buffer pH 7.5, 2 μl of 2 mM $MnCl_2$ and 1 μl (25 ng) of the enzyme Cleavase™ BN in dilution buffer was added to start the cleavage reaction. The cleavage reactions were stopped after 1 minute by the addition of 6 μl of stop buffer. Control uncut reactions were performed as described above with the exception that of 1 μl of $H_2O$ was used in place of 1 μl of the Cleavase™ BN enzyme. The cleavage products (5 μl each) were separated by electrophoresis through a 6% denaturing polyacrylamide gel, transferred to a membrane and visualized as described in Example 21. The resulting autoradiograph is shown in FIG. 73.

FIG. 73 shows the cleavage patterns which correspond to the cleavage of the sense strand of the wild type β-globin 536 bp fragment (lane 4), mutant 1 fragment (lane 5) and mutant 2 fragment (lane 6). Lanes 1–3 show the uncut controls for wild-type, mutant 1 and mutant 2 substrates, respectively. The lane marked "M" contains biotinylated molecular weight markers prepared as described in Example 10.

As shown in FIG. 73, the base substitution present in mutant 1 results in a reduction in the intensity of a band which migrates close to the uncut DNA (lane 5), when compared to wild-type cleavage pattern. The base substitution present in mutant 2 results in the disappearance of the band present in the region just above major product band (approximately 174 nucleotides), when compared to the wild-type cleavage pattern.

For the double-stranded cleavage reactions described above, different reaction conditions were used than those employed for the cleavage of the single-stranded β-globin DNA substrates described in Example 15. The conditions employed for the cleavage of the double-stranded substrates used a lower $MnCl_2$ concentration, no KCl was added, a higher temperature and shorter time course relative to the conditions used in Example 15. Although the cleavage patterns generated by cleavage of the double-stranded and single-stranded P-globin DNA were slightly different, the positions of the pattern changes for mutants 1 and 2 are similar to those demonstrated in Example 15, and it was possible to detect the base substitutions in both double-stranded cases. These results show that the subtle changes in DNA secondary structure caused by single base substitutions in larger DNA substrates can be detected by the Cleavase™ BN enzyme whether a single- or double-stranded form of the DNA substrate is employed.

EXAMPLE 29

Identification Of Mutations In The Human β-Globin Gene CFLP™ Patterns Of Unknowns By Comparison To An Existing Library of Patterns The results shown in Examples 15 demonstrated that Cleavase™ BN enzyme generates a unique pattern of cleavage products from each β-globin substrate tested. Differences in banding patterns were seen between the wild-type and each mutant; different banding patterns were seen for each mutant allowing not only a discrimination of the mutants from the wild-type but also a discrimination of each mutant from the others. To demonstrate that the products of the Cleavase™ reaction can be compared to previously characterized mutants for purposes of identification and classification, a second set of β-globin mutants were characterized and the CFLP™ patterns, by comparison to the set analyzed in Example 15, were used to determine if the mutants in the second set were the same as any in the first set, or were unique to the second set. Although these isolates have all been described previously (specific references are cited for of these isolates at the end of this example), the experiment was performed "blind", with the samples identified only by a number.

Five β-globin mutants were compared to the CFLP™ patterns from the first set: the wild type β-globin gene (SEQ ID NO:69) or mutant 1 (SEQ ID NO:71), mutant 2 (SEQ ID NO:72)or mutant 3 (SEQ ID NO:70). Plasmids for containing these 5 new isolates were grown and purified, and single-stranded substrate DNA, 534 or 536 nucleotides in length, was prepared for each of the 5 β-globin genes as described above in Example 15a. Cleavage reactions were performed and reaction products were resolved as described in Example 15; the resulting autoradiograph is shown in FIG. 74.

Figures 74A, 74B:
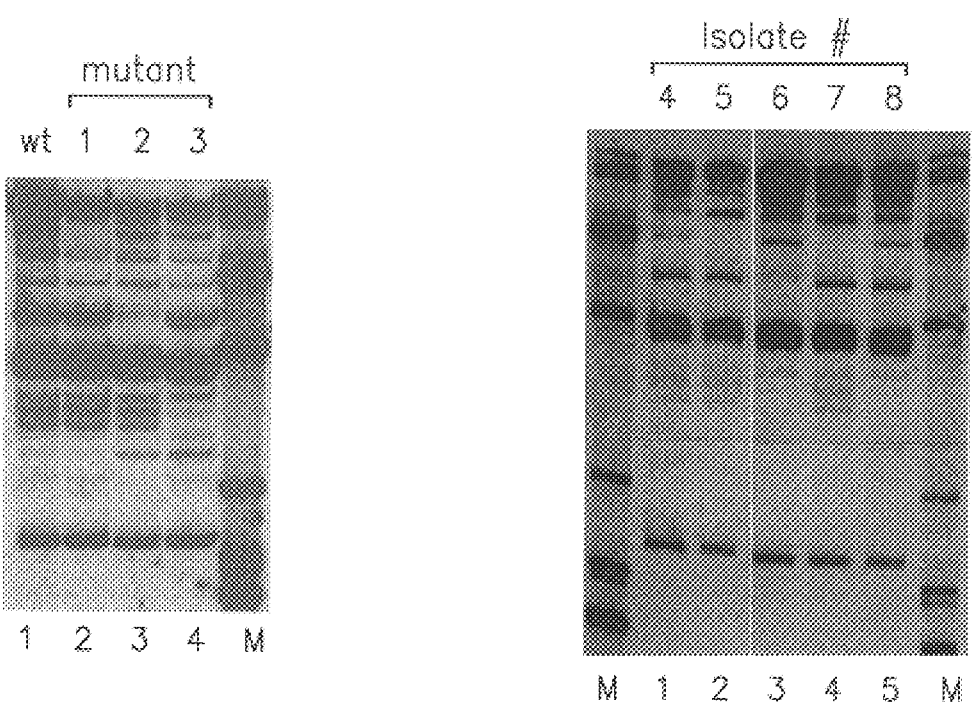
FIG. 74A shows an autoradiograph of a gel resolving the products of single-stranded cleavage reactions run on a wild-type and three mutant β-globin substrates.
FIG. 74B shows an autoradiograph of a gel resolving the products of single-stranded cleavage reactions run on five mutant β-globin substrates.

In FIG. 74, two panels are shown. Panel A shows the reaction products from the β-globin isolates described in Example 15 (and as seen in FIG. 43). Panel B shows the reaction products of the five additional isolates, numbered 4, 5, 6, 7 and 8.

The lanes marked "M" contain biotinylated molecular weight markers prepared as described in Example 10.

By comparison to the CFLP™ patterns shown in Panel A, the isolates shown in Panel B can be characterized. It can be seen that the banding pattern of isolate 4 (Panel B, lane 1) is the same as was seen for the wild-type P-globin substrate shown in Panel A (lane 1); isolate 8 (Panel B, lane 5) is comparable to the previously characterized mutant 3 (Panel A, lane 4); isolate number 6 (Panel B, lane 3) has changes in two areas of the pattern and appears to have features of both isolates 2 (Panel A, lane 3)and 3 (Panel A, lane 4); isolates 5 and 7 (Panel B, lanes 2 and 4, respectively) appear to be identical, and they show a pattern not seen in panel A.

To confirm the relationships between the different isolates, the identities of the mutations were then determined by primer extension sequencing using the fmole™ DNA Sequencing System (Promega Corp., Madison, Wis.) using the PCR primers [5'-biotinylated KM29 primer (SEQ ID NO:67) and 5'-biotinylated RS42 primer (SEQ ID NO:68)], according to the manufacturer's protocol. The sequencing reactions were visualized by the same procedures used for the β-globin CFLP™ reactions, as described in Example 15b.

The two isolates that matched members of the original set by CFLP™ pattern analysis matched by sequence also. Isolate 4 is identical to the wild type sequence (SEQ ID NO: 69); isolate 8 is a duplicate of mutant 3 (SEQ ID NO: 70).

Isolate 6 appears by CFLP™ pattern to have changes similar to both mutant 2 and mutant 3 of the original set. The sequence of mutant 6 (SEQ ID NO:82) reveals that it shares a one base change with mutant 3, a silent C to T substitution in codon 3. Mutant 6 also has a G-to-A substitution in codon 26, only 4 bases downstream of that found in mutant 2 (SEQ ID NO: 72). This mutation has been shown to enhance a cryptic splice site causing a fraction of the mRNA to encode a nonfunctional protein [Orkin, S. H., et al. (1982) Nature, 300:768]. It is worthy of note that while mutant 6 and mutant 2 both showed alteration in the band that migrates at about 200 nucleotides (e.g., the band is missing or weak in mutant 2 but appears to be split into 3 weak bands in mutant 6) these changes are not of identical appearance. These CFLP™ changes, caused by mutations four nucleotides apart, are distinguishable from each other.

The last two isolates, 5 and 7, had the same sequence (SEQ ID NO:83), and revealed a single base substitution within the first intron, at IVS position 110. This mutation is associated with abnormal splicing leading to premature termination of translation of the β-globin protein [R. A. Spritz et al. (1981) Proc. Natl. Acad. Sci. USA, 78:2455]. It is worthy of note that the band that disappears in the CFLP™ patterns for these mutants (at approximately 260 nucleotides, as compared to the size markers) is between the indicative bands in the mutant 1 (at approximately 400 nucleotides) and mutant 2 (at approximately 200 nucleotides) CFLP™ patterns, and the actual mutation (at nucleotide 334 from the labeled 5' end) is between those of mutants 1 and 2, at nucleotides 380 and 207, respectively. Thus, the CFLP™ analysis not only indicated the presence of a change, but also gave positional information as well.

From the results shown in FIG. 74, the unique pattern of cleavage products generated by Cleavase™ BN from each of the first four (wild type plus three variants) β-globin substrates tested was used as reference to characterize additional β-globin isolates. The banding patterns show an overall "familial" similarity, with subtle differences (e.g., missing or shifted bands) associated with each particular variant. Differences in banding patterns were seen between the wild-type and each mutant; different banding patterns were seen for each mutant allowing not only a discrimination of the mutant from the wild-type but also a discrimination of each mutant from the others.

EXAMPLE 30

Effect Of The Order Of Addition Of The Reaction Components On The Double-Stranded Cleavage Pattern The cleavage reaction using a double-stranded DNA substrate can be considered a two-step process. The first step is the denaturation of the DNA substrate and the second step is the initiation of the cleavage reaction at the target temperature. As it is possible that the resulting cleavage pattern may differ depending on the conditions present during denaturation (e.g., whether the DNA is denatured in water or in a buffer) as well as on the conditions of reaction initiation (e.g., whether the cleavage reaction is started by the addition of enzyme or $MnCl_2$) the following experiment was performed.

To study the effect of the addition of the reaction components on the resulting cleavage pattern, all possible mixing combinations for 4 reaction components (i.e., DNA, CFLP™ buffer, $MnCl_2$ and the Cleavase™ BN enzyme) were varied. A single DNA substrate was used which comprised the 536 bp fragment derived from the wild-type β-globin gene (SEQ ID NO:69). The substrate DNA contained a biotin label at the 5' end of the sense strand and was prepared as described in Example 28.

The substrate was cut in 8 different cleavage reactions which employed different combinations for the addition of the reaction components at the denaturing and initiation steps. These reactions are described below.

Figure 75:
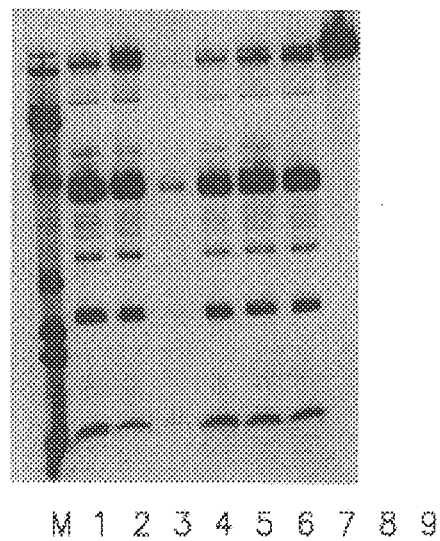
FIG. 75 shows an autoradiograph of a gel resolving the products of double-stranded cleavage reactions which varied the order of addition of the reaction components.

FIG. 75 shows the resulting patterns generated by cleavage of the sense strand of the wild-type β-globin 536-bp substrate (SEQ ID NO:69). In lane 1, the substrate DNA (40 fmoles of DNA in 1 μl of 10 mM Tris-HCl, pH 8.0, 0.1 mM EDTA mixed with 5 μl H$_2$O) was denatured at 95° C. for 10 seconds, cooled to 55° C. and the reaction was started by the addition of a mixture containing 2 μl of 5× CFLP™ buffer with 150 mM KCl, 1 μl of 2 mM MnCl$_2$ and 1 μl (50 ng) of the Cleavase™ BN enzyme. In lane 2, the DNA was denatured in the presence of 2 μl of 5× CFLP™ buffer and reaction was started at 55° C. by the addition of 1 μl MnCl$_2$ and 1 μl (50 ng) of the Cleavase™ BN enzyme. In lane 3, the DNA was denatured in the presence of MnCl$_2$ and the reaction was started with addition of the buffer and the enzyme. In lane 4, the denaturation mixture included the substrate DNA and the enzyme and the reaction was started with addition of the buffer and MnCl$_2$. In lane 5, the substrate DNA was denatured in the presence of CFLP™ buffer and MnCl$_2$ and then the enzyme was added at 55° C. In lane 6, the substrate DNA was denatured in the presence of CFLP™ buffer and the enzyme and then MnCl$_2$ was added at 55° C. Lane 7 shows the uncut control. In lane 8, the DNA was denatured in the presence of the enzyme and MnCl$_2$ and then the buffer was added at 55° C. In lane 9, the substrate DNA was denatured in the presence of the enzyme, MnCl$_2$ and the CFLP™ buffer and then the mixture was incubated at 55° C. for 5 minutes. The lane marked "M" contains biotinylated molecular weight markers prepared as described in Example 10.

In all cases reaction was stopped by addition of 6 μl of stop buffer. The reaction products (5 μl each) were resolved by electrophoresis through a 10% denaturing polyacrylamide gel and the DNA was transferred to a membrane and visualized as described in Example 21. The resulting autoradiograph is shown in FIG. 75.

The results shown in FIG. 75 demonstrate that most of denaturation-initiation protocols employed generated identical cleavage patterns with the exception of the reaction shown in lane 3. In the reaction shown in lane 3, the DNA was denatured in the presence of MnCl$_2$ and in the absence of CFLP™ buffer. In the cases where the enzyme and MnCl$_2$ were added before the denaturation step (lanes 8,9) no labeled material was detected. In these cases the label was released in a form of short DNA fragments which were produced as a result of nibbling (i.e., the exonucleolytic removal) of the label from the 5' end of the double-stranded DNA template.

The results shown in FIG. 75 demonstrate that the order of addition of the reaction components has little effect upon the cleavage pattern produced with the exception that 1) the DNA should not be denatured in the presence of MnCl$_2$ but in the absence of any buffering solution and 2) the Cleavase™ BN enzyme and MnCl$_2$ should not be added together to the DNA prior to the denaturation step. Under these two exceptional conditions, the 5' label was removed from the 5' end of the substrate by the enzyme resulting in a loss of the signal.

We claim:

1. A method for treating nucleic acid, comprising:
   a) providing:
      i) a 5' nuclease derived from a thermostable DNA polymerase altered in amino acid sequence such that it exhibits reduced DNA synthetic activity from that of the wild-type DNA polymerase but retains substantially the same 5' nuclease activity of the wild-type DNA polymerase; and
      ii) a nucleic acid substrate;
   b) treating said nucleic acid substrate under conditions such that said substrate forms one or more cleavage structures; and
   c) reacting said 5' nuclease with said cleavage structures so that one or more cleavage products are produced.

2. The method of claim 1, wherein said nuclease is selected from the group consisting of Cleavase™ BN, *Thermus aquaticus* DNA polymerase, and *Thermus thermophilus* DNA polymerase.

3. The method of claim 1, wherein said nucleic acid of step (a) is substantially single-stranded.

4. The method of claim 1, wherein said nucleic acid is RNA.

5. The method of claim 1, wherein said nucleic acid is DNA.

6. The method of claim 1, wherein said nucleic acid of step (a) is double stranded.

7. The method of claim 6, wherein said treating of step (b) comprises:
   i) rendering said double-stranded nucleic acid substantially single-stranded; and
   ii) exposing said single-stranded nucleic acid to conditions such that said single-stranded nucleic acid has secondary structure.

8. The method of claim 7, wherein said double-stranded nucleic acid is rendered substantially single-stranded by increased temperature.

9. The method of claim 1, further comprising the step of detecting said one or more cleavage products.

10. A method for treating nucleic acid, comprising:
    a) providing
       i) an enzymatic cleavage means; and
       ii) a nucleic acid substrate;
    b) treating said nucleic acid substrate with increased temperature such that said substrate is substantially single-stranded;
    c) reducing said temperature under conditions such that said single-stranded substrate forms one or more cleavage structures, said cleavage structures formed by intrastrand hydrogen bonding in the absence of a primer oligonucleotide;
    d) reacting said cleavage means with said cleavage structures so that one or more cleavage products are produced; and
    e) detecting said one or more cleavage products.

11. The method of claim 10, wherein said enzymatic cleavage means is a nuclease.

12. The method of claim 11, wherein said nuclease is selected from the group consisting of Cleavase™ BN, *Thermus aquaticus* DNA polymerase, *Thermus thermophilus* DNA polymerase, *Escherichia coli* Exo III, and the *Saccharomyces cerevisiae* Rad1/Rad10 complex.

13. The method of claim 10, wherein said nucleic acid is RNA.

14. The method of claim 10, wherein said nucleic acid is DNA.

15. The method of claim 10, wherein said nucleic acid of step (a) is double stranded.

16. The method of claim 10, wherein said cleavage means is provided in a solution containing manganese.

17. A nucleic acid treatment kit, comprising:

a) an enzyme capable of reacting with secondary structures that are cleavage structures so as to generate cleavage products; and b) a solution containing manganese.

18. The kit of claim 17, further comprising reagents for detecting said cleavage products.

* * * * *

UNITED STATES PATENT AND TRADEMARK OFFICE
CERTIFICATE OF CORRECTION

PATENT NO. : 5,888,780
DATED : 03/30/99
INVENTOR(S): James E. Dahlberg et al.

It is certified that error appears in the above-identified patent and that said Letters Patent is hereby corrected as shown below:

In Column 15, line 22, please delete "Tfi" and insert --Tfl--.
In Column 17, line 62, please delete "finctional" and insert --functional--.
In Column 33, line 64, please delete "finoles" and insert --fmoles--.
In Column 40, line 67, please delete "CleavaseTm" and insert --Cleavase™--.
In Column 46, line 29, please delete "1.4 MM EDTA" and insert --1.4 mM EDTA--.
In Column 61, line 48, please delete "washibind" and insert --wash/bind--.
In Column 63, line 26, please delete "CleavaseTm" and insert --Cleavase™--.
In Column 65, line 36, please delete "(Le.," and insert --(i.e.,--.
In Column 74, line 61-62, please delete "10a" and insert --10A--.
In Column 74, line 64, please delete "10 a" and insert --10a--.
In Column 75, line 28-29, please delete "Cleavase$v$" and insert --Cleavase™--.
In Column 75, line 61, please delete "finoles" and insert --fmoles--.
In Column 75, line 61, please delete "IX" and insert --1x--.
In Column 76, line 26, please delete "CleavaseTm" and insert --Cleavase™--.
In Column 77, line 35, please delete "finoles" and insert --fmoles--.
In Column 84, line 50, please delete "CSPDTM" and insert --CSPD™--.

UNITED STATES PATENT AND TRADEMARK OFFICE
CERTIFICATE OF CORRECTION

PATENT NO. : 5,888,780
DATED : 03/30/99
INVENTOR(S) : James E. Dahlberg *et al.*

It is certified that error appears in the above-identified patent and that said Letters Patent is hereby corrected as shown below:

In Column 84, line 51, please delete "StarTm" and insert --Star™--.
In Column 84, line 54, please delete "CSPDTm" and insert --CSPD™--.
In Column 86, line 36, please insert --3-- between "mutant" and "β-globin".
In Column 89, line 49, please delete "10a" and insert --10a--.
In Column 93, line 23, please delete "pg" and insert --µg--.
In Column 95, line 4, please delete "Li00.8-1" and insert --L100.8-1--.
In Column 95, line 21, please delete "NF-KB" and insert --NF-κB--.
In Column 95, line 29, please delete the space between "G" and "C".
In Column 96, line 46, please delete "L100.8-1" and insert --L100.8-1--.
In Column 97, line 6, please delete "G90A" and insert --G90A--.
In Column 102, line 44, please delete "CFLPϑ" and insert --CFLP™--.
In Column 103, line 43, please delete "10MM" and insert --10mM--.
In Column 107, line 10, please delete "pg/ml" and insert --µg/ml--.
In Column 112, line 22, please delete "IX" and insert --1x--.
In Column 113, line 23, please delete "pg/ml" and insert --µg/ml--.

UNITED STATES PATENT AND TRADEMARK OFFICE
CERTIFICATE OF CORRECTION

PATENT NO. : 5,888,780
DATED : 03/30/99
INVENTOR(S) : James E. Dahlberg et al.

It is certified that error appears in the above-identified patent and that said Letters Patent is hereby corrected as shown below:

In Column 122, line 53, please delete "P-globin" and insert --β-globin--.
In Column 123, line 40, please delete "P-globin" and insert --β-globin--.
In Column 23, line 8, please delete "V" and insert --I--.
In Column 1, line 1, please insert --The U.S. Government has a paid-up license in this invention and the right in limited circumstances to require the patent owner to license others on reasonable terms as provided for by the terms of Cooperative Agreement No. 70NANB5H1030 awarded by ATP.--.
In Column 57, line 53, please delete "ph" and insert --pH--.
In Column 58, line 46, please delete "um" and insert --μm--.

In Column 79, line 18, please delete "pattern.within" and insert --pattern within--.
In Column 84, line 67, please delete "a".
In Column 120, line 18, please delete "3".

Signed and Sealed this

Fourth Day of July, 2000

Q. TODD DICKINSON

Attest:

Attesting Officer

Director of Patents and Trademarks